US012729243B2

(12) United States Patent
Lundberg et al.

(10) Patent No.: US 12,729,243 B2
(45) Date of Patent: Sep. 8, 2026

(54) DOSING FOR TREATMENT WITH ANTI-CD20/ANTI-CD3 BISPECIFIC ANTIBODY

(71) Applicant: Hoffmann-La Roche Inc., Little Falls, NJ (US)

(72) Inventors: Linda Lundberg, Binningen (CH); Peter N. Morcos, Marlboro, NJ (US); Martin Weisser, Penzberg (DE); Axel Boehnke, Muenchenstein (CH); David Carlile, Princes Risborough (GB); Nassim Djebli, Rixheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 1089 days.

(21) Appl. No.: 17/733,909

(22) Filed: Apr. 29, 2022

(65) Prior Publication Data

US 2022/0372156 A1 Nov. 24, 2022

Related U.S. Application Data

(60) Provisional application No. 63/226,962, filed on Jul. 29, 2021, provisional application No. 63/182,398, filed on Apr. 30, 2021.

(51) Int. Cl.

| | |
|---|---|
| ***C07K 16/28*** | (2006.01) |
| ***A61K 31/475*** | (2006.01) |
| ***A61K 31/573*** | (2006.01) |
| ***A61K 31/664*** | (2006.01) |
| ***A61K 31/704*** | (2006.01) |
| ***A61K 39/00*** | (2006.01) |
| ***A61K 39/395*** | (2006.01) |
| ***A61P 35/00*** | (2006.01) |

(52) U.S. Cl.

CPC ........ *C07K 16/2887* (2013.01); *A61K 31/475* (2013.01); *A61K 31/573* (2013.01); *A61K 31/664* (2013.01); *A61K 31/704* (2013.01); *A61K 39/3955* (2013.01); *A61P 35/00* (2018.01); *C07K 16/2809* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/31* (2013.01); *C07K 2317/52* (2013.01); *C07K 2317/522* (2013.01); *C07K 2317/55* (2013.01); *C07K 2317/56* (2013.01); *C07K 2319/30* (2013.01); *C12N 2320/35* (2013.01)

(58) Field of Classification Search

None

See application file for complete search history.

(56) References Cited

U.S. PATENT DOCUMENTS

| | | | |
|---|---|---|---|
| 5,571,894 | A | 11/1996 | Wels et al. |
| 5,587,458 | A | 12/1996 | King et al. |
| 5,591,828 | A | 1/1997 | Bosslet et al. |
| 5,731,168 | A | 3/1998 | Carter et al. |
| 5,821,337 | A | 10/1998 | Carter et al. |
| 5,869,046 | A | 2/1999 | Presta et al. |
| 6,248,516 | B1 | 6/2001 | Winter et al. |
| 6,737,056 | B1 | 5/2004 | Presta |
| 6,809,185 | B1 | 10/2004 | Schoonjans et al. |
| 7,332,581 | B2 | 2/2008 | Presta |
| 7,695,936 | B2 | 4/2010 | Carter et al. |
| 8,227,577 | B2 | 7/2012 | Klein et al. |
| 8,236,308 | B2 | 8/2012 | Kischel et al. |
| 8,242,247 | B2 | 8/2012 | Klein et al. |
| 8,642,742 | B2 | 2/2014 | Hofer et al. |
| 8,703,132 | B2 | 4/2014 | Imhof-Jung et al. |
| 8,709,421 | B2 | 4/2014 | Heiss et al. |
| 8,796,424 | B2 | 8/2014 | Croasdale et al. |
| 8,846,042 | B2 | 9/2014 | Zhou |
| 8,895,702 | B2 | 11/2014 | Williams et al. |
| 8,969,526 | B2 | 3/2015 | Baehner et al. |
| 9,068,008 | B2 | 6/2015 | Mossner et al. |
| 9,206,260 | B2 | 12/2015 | Hofer et al. |
| 9,266,938 | B2 | 2/2016 | Ast et al. |
| 9,266,967 | B2 | 2/2016 | Klein et al. |
| 9,382,323 | B2 | 7/2016 | Brinkmann et al. |
| 9,447,159 | B2 | 9/2016 | Ast et al. |
| 9,526,797 | B2 | 12/2016 | Gerdes et al. |
| 9,714,291 | B2 | 7/2017 | Niwa et al. |
| 9,914,776 | B2 | 3/2018 | Ast et al. |
| 10,357,571 | B2 | 7/2019 | Williams et al. |

(Continued)

FOREIGN PATENT DOCUMENTS

| | | | |
|---|---|---|---|
| CA | 2853230 | A1 | 5/2013 |
| CA | 2884307 | A1 | 3/2014 |

(Continued)

OTHER PUBLICATIONS

Bannerji, et al., Blood, 2019, 134, 1-7 (Year: 2019).*

(Continued)

*Primary Examiner* — Misook Yu

*Assistant Examiner* — Samantha Lake Hopkins

(74) *Attorney, Agent, or Firm* — Clark & Elbing LLP; Karen L. Elbing

(57) ABSTRACT

The present invention relates to methods of treating a B-cell proliferative disorder by administering an anti-CD20/anti-CD3 bispecific antibody, and methods for reduction of adverse effects in response to the administration of the anti-CD20/anti-CD3 bispecific antibody. The present invention further relates to combination treatment methods of treating a B-cell proliferative disorder.

24 Claims, 17 Drawing Sheets

Specification includes a Sequence Listing.

(56) References Cited

U.S. PATENT DOCUMENTS 10,611,840 B2 4/2020 Ast et al.
10,611,841 B2 4/2020 Ast et al.
2002/0004587 A1 1/2002 Miller et al.
2007/0071675 A1 3/2007 Wu et al.
2007/0111281 A1 5/2007 Sondermann et al.
2007/0219133 A1 9/2007 Lazar et al.
2008/0241152 A1 10/2008 Alitalo et al.
2009/0252683 A1 10/2009 Kischel et al.
2009/0304719 A1 12/2009 Daugherty et al.
2010/0015133 A1 1/2010 Igawa et al.
2010/0150918 A1 6/2010 Kufer et al.
2010/0316645 A1 12/2010 Imhof-Jung et al.
2011/0178279 A1 7/2011 Williams et al.
2011/0293613 A1 12/2011 Brinkmann et al.
2012/0225071 A1 9/2012 Klein et al.
2012/0276125 A1 11/2012 Ast et al.
2013/0022601 A1 1/2013 Brinkmann et al.
2013/0058936 A1 3/2013 Bruenker et al.
2013/0058937 A1 3/2013 Auer et al.
2013/0060011 A1 3/2013 Bruenker et al.
2013/0078249 A1 3/2013 Ast et al.
2013/0171095 A1 7/2013 Bernett et al.
2013/0266568 A1 10/2013 Brinkmann et al.
2014/0088295 A1 3/2014 Smith et al.
2014/0112914 A1 4/2014 Nezu et al.
2014/0154254 A1 6/2014 Kannan et al.
2014/0242079 A1 8/2014 Bacac et al.
2014/0242080 A1 8/2014 Jaeger et al.
2014/0288275 A1 9/2014 Moore et al.
2014/0294823 A1 10/2014 Moore et al.
2014/0294833 A1 10/2014 Desjarlais et al.
2014/0302064 A1 10/2014 Moore
2014/0322217 A1 10/2014 Moore et al.
2014/0363426 A1 12/2014 Moore et al.
2014/0370013 A1 12/2014 Desjarlais et al.
2014/0377270 A1 12/2014 Moore et al.
2015/0166661 A1 6/2015 Chen et al.
2015/0266966 A1 9/2015 Smith et al.
2015/0274845 A1 10/2015 Bruenker et al.
2015/0315296 A1 11/2015 Schaefer et al.
2015/0368351 A1 12/2015 Vu et al.
2015/0376287 A1 12/2015 Vu et al.
2016/0075785 A1 3/2016 Ast et al.
2016/0130347 A1 5/2016 Bruenker et al.
2016/0145354 A1 5/2016 Bacac et al.
2016/0152711 A1 6/2016 Williams et al.
2016/0159906 A1 6/2016 Sun et al.
2016/0175397 A1 6/2016 Umana et al.
2016/0194399 A1 7/2016 Irving et al.
2016/0208017 A1 7/2016 Ast et al.
2016/0208019 A1 7/2016 Bacac et al.
2016/0263240 A1 9/2016 Ast et al.
2016/0297881 A1 10/2016 Vu et al.
2016/0368985 A1 12/2016 Hotzel et al.
2017/0008971 A1 1/2017 Dennis et al.
2017/0096485 A1 4/2017 Bacac et al.
2017/0096495 A1 4/2017 Bacac et al.
2017/0114146 A1 4/2017 Klein et al.
2017/0174786 A1 6/2017 Bacac et al.
2017/0190783 A1 7/2017 Bacac et al.
2017/0209573 A1 7/2017 Bacac et al.
2017/0218074 A1 8/2017 Williams et al.
2017/0253670 A1 9/2017 Klein et al.
2017/0267783 A1 9/2017 Nezu et al.
2017/0306018 A1 10/2017 Vu et al.
2017/0306036 A1 10/2017 Vu et al.
2017/0306044 A1 10/2017 Vu et al.
2017/0327579 A1 11/2017 Vu et al.
2017/0327580 A1 11/2017 Vu et al.
2018/0134798 A1 5/2018 Chu et al.
2018/0148508 A1 5/2018 Wang et al.
2018/0193479 A1 7/2018 Williams et al.
2020/0164077 A1 5/2020 Williams et al.
2020/0172627 A1 6/2020 Bacac et al.
2020/0199578 A1 6/2020 Short et al.
2020/0325238 A1 10/2020 Bacac et al.
2024/0132613 A1 4/2024 Chu et al.
2024/0376223 A1 11/2024 Chu et al.
2025/0171552 A1 5/2025 Chu et al.

FOREIGN PATENT DOCUMENTS

CN 102369218 A 3/2012
CN 102373214 A 3/2012
CN 102892779 A 1/2013
CN 103429737 A 12/2013
CN 103748114 A 4/2014
CN 103764681 A 4/2014
CN 103889452 A 6/2014
CN 104245738 A 12/2014
CN 104640881 A 5/2015
CN 105143258 A 12/2015
CN 105934253 A 9/2016
CN 106029696 A 10/2016
CN 106164095 A 11/2016
EP 0404097 B1 9/1996
EP 1870459 A1 12/2007
EP 1870459 A4 9/2010
EP 2578230 A1 4/2013
EP 2647707 A1 10/2013
EP 2647707 A4 4/2014
EP 1870459 B1 6/2016
EP 3177643 B1 5/2019
JP 2011508604 A 3/2011
JP 2015-509951 A 4/2015
JP 2015-509952 A 4/2015
JP 2018527887 A 9/2018
JP 2020-517640 A 6/2020
RU 2539112 C2 1/2015
SG 10201803384 T 6/2018
TW 201508008 A 3/2015
WO WO-91/03493 A1 3/1991
WO WO-93/01161 A1 1/1993
WO WO-93/16185 A2 8/1993
WO WO-96/01126 A1 1/1996
WO WO-96/27011 A1 9/1996
WO WO-96/40210 A1 12/1996
WO WO-98/50431 A2 11/1998
WO WO-98/50431 A3 1/1999
WO WO-02/09573 A2 2/2002
WO WO-03/074679 A2 9/2003
WO WO-2005/044859 A2 5/2005
WO WO-2005/083431 A2 9/2005
WO WO-2006/082515 A2 8/2006
WO WO-2007/005874 A2 1/2007
WO WO-2007/024715 A2 3/2007
WO WO-2007/042261 A2 4/2007
WO WO-2007/075270 A2 7/2007
WO WO-2007/110205 A2 10/2007
WO WO-2007/146968 A2 12/2007
WO WO-2007/147901 A1 12/2007
WO WO-2007/024715 A3 10/2008
WO WO-2008/119566 A2 10/2008
WO WO-2008/119567 A2 10/2008
WO WO-2007/024715 A9 4/2009
WO WO-2009/070642 A1 6/2009
WO WO-2009/080251 A1 7/2009
WO WO-2009/080252 A1 7/2009
WO WO-2009/080253 A1 7/2009
WO WO-2009/080254 A1 7/2009
WO WO-2009/089004 A1 7/2009
WO WO-2009/106321 A1 9/2009
WO WO-2009118142 A1 10/2009
WO WO-2010/114940 A1 10/2010
WO WO-2010/115589 A1 10/2010
WO WO-2010/129304 A2 11/2010
WO WO-2010/136172 A1 12/2010
WO WO-2010/145792 A1 12/2010
WO WO-2010/145793 A1 12/2010
WO WO-2010/129304 A3 2/2011
WO WO-2011/028945 A1 3/2011
WO WO-2011/028952 A1 3/2011
WO WO-2011/090754 A1 7/2011
WO WO-2011/090762 A1 7/2011

(56) References Cited

FOREIGN PATENT DOCUMENTS

WO WO-2011/103242 A1 8/2011
WO WO-2011/121110 A1 10/2011
WO WO-2011/143545 A1 11/2011
WO WO-2012/025525 A1 3/2012
WO WO-2012/058768 A1 5/2012
WO WO-2012/058768 A8 6/2012
WO WO-2012/073985 A1 6/2012
WO WO-2012/117002 A1 9/2012
WO WO-2012/130831 A1 10/2012
WO WO-2012/143524 A2 10/2012
WO WO-2012/158818 A2 11/2012
WO WO-2012/162067 A2 11/2012
WO WO-2013/012414 A1 1/2013
WO WO-2013/026831 A1 2/2013
WO WO-2013/026832 A1 2/2013
WO WO-2013/026833 A1 2/2013
WO WO-2013/026837 A1 2/2013
WO WO-2013/026839 A1 2/2013
WO WO-2013/096291 A2 6/2013
WO WO-2013/128027 A1 9/2013
WO WO-2013/128194 A1 9/2013
WO WO-2013/150043 A1 10/2013
WO WO-2013/157953 A1 10/2013
WO WO-2013/157954 A1 10/2013
WO WO-2014/022540 A1 2/2014
WO WO-2014/028560 A2 2/2014
WO WO-2014/039855 A1 3/2014
WO WO-2014/047231 A1 3/2014
WO WO-2014/054804 A1 4/2014
WO WO-2014/056783 A1 4/2014
WO WO-2014/028560 A3 5/2014
WO WO-2014/081955 A1 5/2014
WO WO-2014/122143 A1 8/2014
WO WO-2014/122144 A1 8/2014
WO WO-2014/122251 A2 8/2014
WO WO-2014/131712 A1 9/2014
WO WO-2014/141152 A2 9/2014
WO WO-2014/144722 A2 9/2014
WO WO-2014/150877 A2 9/2014
WO WO-2014/153002 A1 9/2014
WO WO-2014/122251 A3 10/2014
WO WO-2014/167022 A1 10/2014
WO WO-2014/141152 A3 12/2014
WO WO-2014/191113 A1 12/2014
WO WO-2014/210064 A1 12/2014
WO WO-2014/191113 A8 2/2015
WO WO-2015/095392 A1 6/2015
WO WO-2015/095418 A1 6/2015
WO WO-2015/150447 A1 10/2015
WO WO-2016/019969 A1 2/2016
WO WO-2016/020065 A1 2/2016
WO WO-2016/020309 A1 2/2016
WO WO-2016/020332 A1 2/2016
WO WO-2016/036678 A1 3/2016
WO WO-2016/055592 A1 4/2016
WO WO-2016/055593 A1 4/2016
WO WO-2016/079081 A1 5/2016
WO WO-2016/079177 A1 5/2016
WO WO-2016/081490 A1 5/2016
WO WO-2016/087531 A1 6/2016
WO WO-2016/090210 A1 6/2016
WO WO-2016/110576 A1 7/2016
WO WO-2016/179003 A1 11/2016
WO WO-2016/205520 A1 12/2016
WO WO-2017/021450 A1 2/2017
WO WO-2018/093821 A1 5/2018
WO WO-2018/114748 A1 6/2018
WO WO-2018/193105 A1 10/2018
WO WO-2018/220099 A1 12/2018
WO WO-2022/098648 A2 5/2022
WO WO-2023201291 A1 * 10/2023 ......... C07K 16/2809

OTHER PUBLICATIONS

Patel, et al., Blood, 2019, 134, 1-4 (Year: 2019).*

Rudikoff, et al., PNAS, 1982, 79, 1979-1983 (Year: 1982).*

Brinkmann, et al., MABS, 2017, 9, 182-212 (Year: 2017).*

Janeway, et al., Immunobiology: The Immune System in Health and Disease, 5th edition, 2001 (Year: 2001).*

Morschhauser, et al., Blood, 2019, 134, 1584 (Year: 2019).*

Ghosh, Nilanjan et al., Prospective Therapeutic Trials "Glofitamab Plus R-CHOP Induces High Response Rates with Minimal Cytokine Release Syndrome (CRS) in Patients (pts) with Relapsed/Refractory (R/R) Non-Hodgkin Lymphoma (NHL) and Previously Untreaed (1L) Diffuse Large B-Cell Lymphoma (DLBCL): Preliminary Results from a Dose-Escalation and Safety Run-in Phase Ib Study", Blood. 63rd ASH Annual Meeting Abstracts Poster Abstracts 626. Aggressive Lymphomas, vol. 138(Supplement 1): 2479-2482 (Nov. 2021).

Hanel et. al., "Emerging therapies in mantle cell lymphoma". Journal of Hematology & Oncology. 13(79): 1-18 (Jun. 2020).

Hutchings et. al., "Glofitamab, a Novel, Bivalent CD20 Targeting T-cell Engaging Bispecific Antibody, Induces Durable Complete Remissions in Relapsed/Refractory B-cell Lymphoma: a Phase I Trial," Data Supplement, J Clin Oncol. pp. 1-34 (Jun. 2021).

Li et al., "Exposure-response analyses indicate a promising benefit/risk profile of mosunetuzumab in relapsed and refractory non-Hodgkin lymphoma," Blood. 134(Supplement 1):1285 (Nov. 2019) (8 pages).

Melchardt et al., "Feasibility and Safety of the First-in-Human Chemotherapy-Light Combination of Rituximab, Polatuzumab Vedotin and Glofitamab in Previously Untreated Aggressive B-Cell Lymphoma Patients Above 60 Years of Age Ineligible for a Fully Dosed R-CHOP-R-Pola-Glo/Ifk-t062, a Study of the Austrian Group for Medical Tumor Therapy (AGMT-NHL-16) and the German Lymphoma Alliance (GLA2022-10)," Blood. 142(Supplement 1):1734-1736 (Nov. 2, 2023).

Phillips et al., "Glofitamab Step-up Dosing Induces High Response Rates in Patients (pts) with Relapsed or Refractory (R/R) Mantle Cell Lymphoma (MCL), Most of Whom Had Failed Prior Bruton's Tyrosine Kinase Inhibitor (BTKi) Therapy," Blood Journal. 138(Supp. 1): 130-133 (Nov. 2021).

Sehn, Laurie H et al., "The revised International Prognostic Index (R-IPI) is a better predictor of outcome than the standard IPI for patients with diffuse large B-cell lymphoma treated with R-CHOP," Blood. 109(5): 1857-1861 (Mar. 2007).

"Purified Mouse Anti-Human CD3-epsilon Clone SP34," BD Biosciences, <https://www.bdbiosciences.com/US/reagents/research/antibodies-buffers/immunology-reagents/anti-non-human-primate-antibodies/cell-surface-antigens/purified-mouse-anti-human-cd3-sp34/p/556610>, retrieved on Jan. 4, 2021 (4 pages).

BBE23702, GenomeQuest Keyword Search Report, dated May 1, 2017 (2 pages).

BBE23705, GenomeQuest Keyword Search Report, dated May 1, 2017 (2 pages).

BBF28771, GenomeQuest Keyword Search Report, dated May 1, 2017 (2 pages).

BBF28775, GenomeQuest Keyword Search Report, dated May 1, 2017 (2 pages).

Beckman et al., "Antibody constructs in cancer therapy: protein engineering strategies to improve exposure in solid tumors," Cancer. 109(2):170-9 (2007).

Booy et al., "Monoclonal and bispecific antibodies as novel therapeutics," Arch Immunol Ther Exp (Warsz). 54(2):85-101 (2006).

Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).

(56) References Cited

OTHER PUBLICATIONS

Budde et al., "Ongoing Phase 1B/2 Trials of Mosunetuzumab Investigating Novel Treatment Regimens for Patients with B-Call Non-Hodgkin Lymphoma (NHL)," Hematol Oncol. 37(52):564-566 (2019) (4 pages).
Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).
Carter, "Bispecific human IgG by design," J Immunol Methods. 248(1-2):7-15 (2001).
Chan et al., "Variable region domain exchange in human IgGs promotes antibody complex formation with accompanying structural changes and altered effector functions," Mol Immunol. 41(5):527-38 (2004).
Conaghan et al., "Targeted killing of colorectal cancer cell lines by a humanised IgG1 monoclonal antibody that binds to membrane-bound carcinoembryonic antigen," Br J Cancer. 98(7):1217-25 (2008).
Desnoyers et al., "Tumor-specific activation of an EGFR-targeting probody enhances therapeutic index," Sci Transl Med. 5(207):207ra144 (2013) (2 pages) (Abstract only).
Diefenbach et al., "An individualized risk mitigation approach for safety: experience from the mosunetuzumab (CD20/CD3 bispecific antibody) development program in relation to neurotoxicity risk," 61st Ash Annual Meeting & Exposition 10 (2019).
Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).
Edelman et al., "The covalent structure of an entire gammaG immunoglobulin molecule," Proc Natl Acad Sci U S A. 63(1):78-85 (1969).
Edwards et al., "The remarkable flexibility of the human antibody repertoire; isolation of over one thousand different antibodies to a single protein, BLyS," J Mol Biol. 334(1):103-18 (2003).
Erster et al., "Site-specific targeting of antibody activity in vivo mediated by disease-associated proteases," J Control Release. 161(3): 804-12 (2012) (2 pages) (Abstract only).
Gaston et al., "Intracellular delivery of therapeutic antibodies into specific cells using antibody-peptide fusions," Sci Rep. 9(1):18688 (2019) (12 pages).
Ghosh et al., "Glofitamab Plus R-CHOP Induces High Response Rates with Minimal Cytokine Release Syndrome (CRS) in Patients (pts) with Relapsed/Refractory (R/R) Non-Hodgkin Lymphoma (NHL) and Previously Untreated (1L) Diffuse Large B-Cell Lymphoma (DLBCL): Preliminary Results from a Dose-Escalation and Safety Run-in Phase Ib Study," Blood. 138(Supplement 1):2479 (2021) (Abstract only).
Gonzales et al., "Minimizing the Immunogenicity of Antibodies for Clinical Application," Tumor Biol. 26(1):31-43 (2005) (Abstract only).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Han et al., "Masked Chimeric Antigen Receptor for Tumor-Specific Activation," Mol Ther. 25(1):274-84 (2017).
Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).
Holliger et al., "'Diabodies': small bivalent and bispecific antibody fragments," Proc Natl Acad Sci USA. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival, New York USA, (pp. 4) (2016).
Hosseini et al., "Mitigating The Risk Of Cytokine Release Syndrome In A Phase I Trial Of CD20/CD3 Bispecific Antibody Mosunetuzumab In NHL: Impact Of Translational System Modeling," NPJ Syst Biol Appl. 6(1):28 (2020) (11 pages).
Huang, "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Hutchings et al., "Glofitamab (Glofit) in Combination with Polatuzumab Vedotin (Pola): Phase Ib/II Preliminary Data Support Manageable Safety and Encouraging Efficacy in Relapsed/Refractory (R/R) Diffuse Large B-Cell Lymphoma (DLBCL)" Blood. 138(Supplement 1):525 (2021) (Abstract only).
Hutchings et al., "Glofitamab, a Novel, Bivalent CD20-Targeting T-Cell-Engaging Bispecific Antibody, Induces Durable Complete Remissions in Relapsed or Refractory B-Cell Lymphoma: A Phase I Trial," J Clin Oncol. 39(18):1959-70 (2021) (13 pages).
Jaksic et al., "High Dose Chlorambucil versus Binet's Modified Cyclophosphamide Doxorubicin, Vincristine, and Prednisone Regimen in the Treatment of Patients with Advanced B-Cell Chronic Lymphocytic Leukemia. Results of an International Multicenter Randomized Trial," Cancer. 79(11):2107-14 (1997).
Kipriyanov et al., "Bispecific Tandem Diabody for Tumor Therapy with Improved Antigen Binding and Pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Leabman et al., "Effects of altered FcgammaR binding on antibody pharmacokinetics in cynomolgus monkeys," MAbs. 5(6):896-903 (2013).
Lee et al., "Current concepts in the diagnosis and management of cytokine release syndrome," Blood. 124(2):188-95 (2014) (18 pages).
Li et al., "Exposure-response analyses indicate a promising benefit/risk profile of mosunetuzumab in relapsed and refractory non-Hodgkin lymphoma," 61st Ash Annual Meeting & Exposition (2019) (1 page).
Lloyd et al., "Modelling the human immune response: performance of a $10^{11}$ human antibody repertoire against a broad panel of therapeutically relevant antigens". Protein Eng Des Sel. 22(3):159-68 (2009).
Lord et al., "Structure-based engineering to restore high affinity binding of an isoform-selective anti-TGFβ1 antibody," MAbs. 10(3):444-452 (2018) (10 pages).
Lu et al., "Tetravalent anti-CD20/CD3 bispecific antibody for the treatment of B cell lymphoma," Biochem Biophys Res Commun. 473(4):808-813 (2016) (3 pages) (Abstract only).
Lund et al., "Multiple interactions of IgG with its core oligosaccharide can modulate recognition by complement and human Fc gamma receptor I and influence the synthesis of its oligosaccharide chains," J Immunol. 157(11):4963-9 (1996) (8 pages).
MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).
Mariuzza et al., "The structural basis of antigen-antibody recognition," Annu Rev Biophys Biophys Chem. 16:139-159 (1987) (2 pages) (Abstract only).

(56) References Cited

OTHER PUBLICATIONS

Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Minson et al., "Trial in Progress: A Multicentre, Parallel Arm, Open-Label Trial of Frontline R-CHOP/Polatuzumab Vedotin-RCHP and Glofitamab in Younger Patients with Higher Risk Diffuse Large B Cell Lymphoma (COALITION)," Blood. 138(Supplement 1):3571 (2021) (Abstract only).
Montoto et al., "Risk and Clinical Implications of Transformation of Follicular Lymphoma to Diffuse Large B-Cell Lymphoma," J Clin Oncol. 25(17):2426-33 (2007) (9 pages).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
NIH/NCI, "anti-PD-1 fusion protein AMP-224," dated Jul. 10, 2015, accessed Jul. 31, 2019 (1 page).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Paino et al., "Reply to 'Response to "CD20 Positive Cells Are Undetectable in the Majority of Multiple Myeloma Cell Lines and Are Not Associated With a Cancer Stem Cell Phenotype,"'" Haematologica. 97(7):1110-1114 (2012) (1 page).
Peng et al., "The CEA/CD3-bispecific antibody MEDI-565 (MT111) binds a nonlinear epitope in the full-length but not a short splice variant of CEA," PLoS One. 7(5):e36412 (2012) (14 pages).
Pessano et al., "The T3/T cell receptor complex: antigenic distinction between the two 20-kd T3 (T3-delta and T3-epsilon) subunits," EMBO J. 4(2):337-44 (1985).
Pluckthun, Chapter 11: Antibodies from *Escherichia coli. The Pharmacology of Monoclonal Antibodies*. Martin Rosenberg & Gordon P. Moore (eds.), 269-315 (1994) (26 pages).
Polu et al., "Probody therapeutics for targeting antibodies to diseased tissue," Expert Opin Biol Ther. 14(8):1049-53 (2014).
Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-90 (2006) (9 pages).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Rudnick et al., "Affinity and avidity in antibody-based tumor targeting," Cancer Biother Radiopharm. 24(2):155-61 (2009).
Salmerón et al., "A conformational epitope expressed upon association of CD3-epsilon with either CD3-delta or CD3-gamma is the main target for recognition by anti-CD3 monoclonal antibodies," J Immunol. 147(9):3047-52 (1991) (2 pages) (Abstract only).
Schaefer et al., "Immunoglobulin domain crossover as a generic approach for the production of bispecific IgG antibodies," Proc Natl Acad Sci U S A. 108(27):11187-92 (2011).
Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015) (13 pages).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Sen et al., "Use of Anti-CD3 x Anti-HER2/neu Bispecific Antibody for Redirecting Cytotoxicity of Activated T Cells Toward HER2/neu+ Tumors," J Hematother Stem Cell Res. 10(2):247-60 (2001).
Seung et al., "Immunotherapy with long-lived anti-CD20 x anti-CD3 bispecific antibodies stimulates potent t cell-mediated killing of human b cell lines and of circulating and lymphoid b cells in monkeys: a potential therapy for b cell lymphomas and leukemias," 56th ASH Annual Meeting and Exposition, Dec. 6-9, San Francisco, CA. 124(21):3111 (2014).
Shi et al., "Margin-Infiltrating $CD20^+$ B Cells Display an Atypical Memory Phenotype and Correlate with Favorable Prognosis in Hepatocellular Carcinoma," Clin Cancer Res. 19(21):5994-6005 (2013) (13 pages).
Somasundaram et al., "Will Engineered T Cells Expressing CD20 scFv Eradicate Melanoma?" Mol Ther. 19(4):638-40 (2011).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stewart et al., "Humanisation and characterisation of PR1A3, a monoclonal antibody specific for cell-bound carcinoembryonic antigen," Cancer Immunol Immunother. 47(6):299-306 (1999).
Stieglmaier et al., "Utilizing the BiTE (bispecific T-cell engager) platform for immunotherapy of cancer," Expert Opin Biol Ther. 15(8):1093-1099 (2015) (8 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Trabolsi et al., "T Cell-Activating Bispecific Antibodies in Cancer Therapy," J Immunol. 203(3):585-592 (2019) (9 pages).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wakefield et al., "Addition of a C-terminal extension sequence to transforming growth factor-beta 1 interferes with biosynthetic processing and abolishes biological activity," Growth Factors. 5(3):243-53 (1991) (2 pages) (Abstract only).
Wells et al., "Reaching for high-hanging fruit in drug discovery at protein-protein interfaces," Nature. 450(7172):1001-9 (2007).
Wolf et al., "BiTEs: bispecific antibody constructs with unique anti-tumor activity," Drug Discov Today. 10(18):1237-44 (2005).
Wu et al., "Humanization of a Murine Monoclonal Antibody by Simultaneous Optimization of Framework and CDR Residues," J Mol Biol. 294(1):151-162 (1999).
Yang et al., "Generation and characterization of a target-selectively activated antibody against epidermal growth factor receptor with enhanced anti-tumor potency," MAbs. 7(2):440-50 (2015).
Yu et al., "Interaction between bevacizumab and murine VEGF-A: a reassessment," Invest Ophthalmol Vis Sci. 49(2):522-7 (2008).
Zhu et al., "Identification of heavy chain residues in a humanized anti-CD3 antibody important for efficient antigen binding and T cell activation," J Immunol. 155(4):1903-10 (1995).
"History of Changes for Study: NCT02500407: A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).

(56) References Cited

OTHER PUBLICATIONS

Chu et al., "Immunotherapy with long-lived anti-CD20 x anti-CD3 bispecific antibodies stimulates potent T cell-mediated killing of Human B cell lines and of circulating and lymphoid B cells in monkeys: a potential therapy for B cell lymphomas and leukemias," Blood. 124(21):3111 (2014) (1 page).
Djebli et al., "Population Pharmacokinetics and Exposure-Response Analyses for Glofitamab in Relapsed/Refractory B-Cell Non-Hodgkin Lymphoma (R/R NHL): Confirmation of Efficacy and CRS Mitigation in Patients with Step-up Dosing," Blood. 136(Supplemental 1) (Nov. 2020) (4 pages).
Heini et al., "Experiences with Glofitamab Administration following CAR T Therapy in Patients with Relapsed Mantle Cell Lymphoma," Cells 11:2747 (Sep. 2022).
Hutchings et al., "Glofitamab Plus Polatuzumab Vedotin Continues to Demonstrate Frequent and Durable Responses and Has a Manageable Safety Profile in Patients with 2L Relapsed/Refractory DLBCL, Including HGBCL, and in Patients with Prior CAR T-Cell Therapy: Updated Results from a Phase Ib/II Study," Blood. 142(Supplement 1):4460 (Nov. 2, 2023) (6 pages).
Hutchings et al., "Glofitamab Step-up Dosing Induces High Response Rates in Patients with Hard-to-Treat Refractory or Relapsed Non-Hodgkin Lymphoma" Blood. 136(Supplement 1):46 (Nov. 5, 2020) (6 pages).
Xiong et al., "Study of specific targeting cytotoxicity mediated by anti-CD3/anti-CD20 Diabody," Chin J Hematol. 22(7):359-362 (2001) (8 pages).
Xu et al., "Production of bispecific antibodies in 'knobs-into-holes' using a cell-free expression system," MAbs. 7(1):231-42 (Jan. 14, 2015) (13 pages).
Yuraszeck et al., "A quantitative systems pharmacology (QSP) model to assess the action of blinatumomab in NHL patients (pts)," Journal of Clinical Oncology 34(15_suppl) Abstract e14511 (May 20, 2016) (3 pages).
Bacac et al., "CD20-TCB with Obinutuzumab Pretreatment as Next-Generation Treatment of Hematologic Malignancies," Clin Cancer Res. 24(19):4785-4797 (Oct. 2018) (13 pages).
Cairo et al., "Prospective randomized trial between two doses of granulocyte colony-stimulating factor after ifosfamide, carboplatin, and etoposide in children with recurrent or refractory solid tumors: a children's cancer group report," J Pediatric Hematology/Oncology 23(1) (Jan. 2001) (9 pages).
Coiffier et al., "Diffuse large B-cell lymphoma: R-CHOP failure-what to do?" Hematology Am Soc Hematol Educ Program (1):366-378 (Dec. 2016) (13 pages).
FDA drug label for Actemera (tocilizumab), version Aug. 2017, https://www.accessdata.fda.gov/drugsatfda_docs/label/2017/125276s114lbl.pdf (43 pages).
FDA drug label for Gazyva® (obinutuzumab), version Feb. 2016, https://www.accessdata.fda.gov/drugsatfda_docs/label/2016/125486s013lbl.pdf (25 pages).
FDA drug label for ifosfamide, version Jul. 2018, https://www.accessdata.fda.gov/drugsatfda_docs/label/2018/019763s020lbl.pdf (35 pages).
FDA drug label for Rituxan (rituximab), version Oct. 2012, https://www.accessdata.fda.gov/drugsatfda_docs/label/2012/103705s5367s5388lbl.pdf (40 pages).
FDA drug label for SOLU-MEDROL (methylprednisolone), version Oct. 2011, https://www.accessdata.fda.gov/drugsatfda_docs/label/2011/ 011856s103s104lbl.pdf (18 pages).
Griffin et al., "A study of rituximab and ifosfamide, carboplatin, and etoposide chemotherapy in children with recurrent/refractory B-cell (CD20+) non-Hodgkin lymphoma and mature B-cell acute lymphoblastic leukemia: a report from the Children's Oncology Group," Pediatric Blood Cancer 52(2):177-181 (Feb. 2009) (12 pages).
Hendrayana et al., "Anticancer Dose Adjustment for Patients with Renal and Hepatic Dysfunction: From Scientific Evidence to Clinical Application," Sci Pharm. 85(1):8 (Feb. 2017) (16 pages).
IWK Health, Dexamethasone, Website: www.dir.iwk.nshealth.ca/Home/DDGDetails/aed57259-168d-e911-80f2-005056b200d2?PatientPopulation=Ped, published on Jun. 12, 2019 (2 pages).
Jannin et al., "Rectal route in the 21st Century to treat children," Adv Drug Delivery Reviews 73:34-49 (May 2014) (16 pages).
Kewalramani et al., "Rituximab and ICE as second-line therapy before autologous stem cell transplantation for relapsed or primary refractory diffuse large B-cell lymphoma," Blood 103(10):3684-8 (May 2004) (5 pages).
Lu et al., WikiEM diphenhydramine, Website: wikem.org/wiki/Diphenhydramine, last updated on Mar. 7, 2021 (4 pages).
Rampotas et al., "Integration of cell therapies and bispecific antibodies into the treatment pathway of relapsed diffuse large B-cell lymphoma," Ther Adv Hematol. 12:1-12 (Oct. 2021) (12 pages).
Salvaris et al., "Bispecific Antibodies: A Review of Development, Clinical Efficacy and Toxicity in B-Cell Lymphomas," J Pers Med.11(5):355 (Apr. 2021) (15 pages).
Sapkota et al., "Non-Hodgkin Lymphoma," [Updated Feb. 24, 2023]. In: StatPearls [Internet]. Treasure Island (FL): StatPearls Publishing, Available from: https://www.ncbi.nlm.nih.gov/books/NBK559328 (15 pages).
Singh et al., "Overcoming the challenges associated with CD3+ T-cell redirection in cancer," British Journal of Cancer 124(6):1037-1048 (Jan. 2021) (12 pages).
Temrikar et al., "Pharmacokinetics and Clinical Pharmacology of Monoclonal Antibodies in Pediatric Patients," Pediatric Drugs 22:199-216 (Apr. 2020) (18 pages).
Van Rongen et al., "An Update on the Use of Allometric and Other Scaling Methods to Scale Drug Clearance in Children: Towards Decision Tables," Expert Opin Drug Metabolism & Toxicology 18(2):99-113 (Feb. 2022) (16 pages).
Vose et al., "Outpatient regimen rituximab plus ifosfamide, carboplatin and etoposide (R-ICE) for relapsed non-Hodgkin's lymphoma," Annals of Oncology 14(Supplement 1):i17-i20 (May 2003)/15(3):541 (Mar. 2004) (6 pages).
Xu et al., "Model-Aided Adults-to-Children Pharmacokinetic Extrapolation and Empirical Body Size-Based Dosing Exploration for Therapeutic Monoclonal Antibodies-Is Allometry a Reasonable Choice?" J Clin Pharmacol. 60(12):1573-1584 (Dec. 2020) (8 pages).
Yang et al. "Evaluation of Weight Thresholds for Pediatric Patients to Use Adult Dosage of Therapeutic Monoclonal Antibodies," J Clin Pharmacol. 59(10):1309-1318 (Oct. 2019) (10 pages).

* cited by examiner

FIG. 3
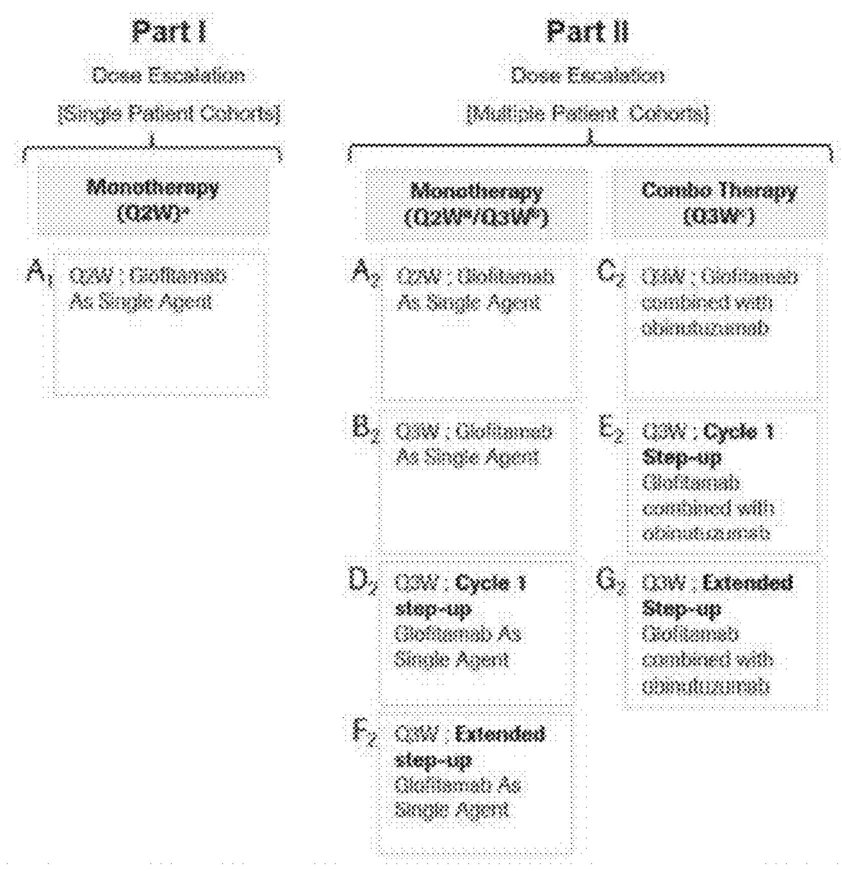
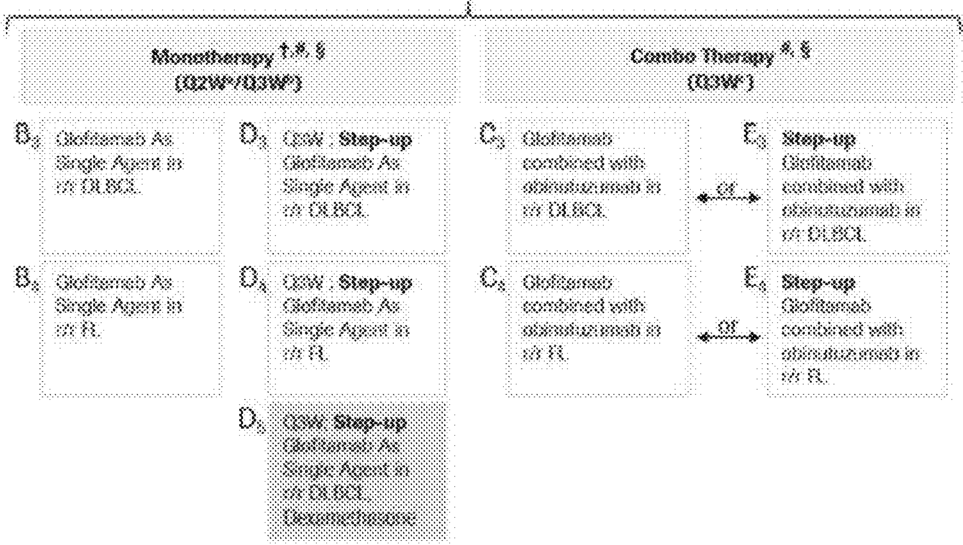

FIG. 7

| Characteristic | All Glofitamab Cohorts* (N = 171) | RP2D Glofitamab † (N = 35) |
|---|---|---|
| Age — years | | |
| Median | 64 | 66 |
| Range | 22–85 | 44–85 |
| Male gender — no. (%) | 100 (52.6) | 17 (48.6) |
| ECOG performance status — no. (%) | | |
| 0 | 87 (51.2) | 19 (54.3) |
| 1 | 83 (48.8) | 16 (45.7) |
| Ann Arbor staging — no. (%) | | |
| I | 10 (5.8) | 0 |
| II | 28 (16.4) | 3 (8.6) |
| III | 38 (22.2) | 10 (28.6) |
| IV | 95 (55.6) | 22 (62.9) |
| Bulky disease >5 cm — no. (%) | 86 (50.3) | 12 (34.3) |
| Sum of products of lesion diameters — $mm^2$ | | |
| Number of evaluable patients‡ | 171 | 35 |
| Median | 2996 | 2788 |
| Range | 256 - 20635 | 256 - 10816 |
| Histology subtype — no. (%) | | |
| DLBCL | 73 (42.7) | 5 (14.3) |
| FL grades 1 to 3A | 44 (25.7) | 21 (60.0) |
| DLBCL arising from FL | 29 (17.0%) | 3 (8.6) |
| Richter's transformation | 10 (5.8%) | 2 (5.7) |
| PMBCL | 3 (1.8%) | 0 |
| Other | 12 (7.0%) | 4 (11.4) |
| Prior autologous stem cell transplant — no. (%) | 41 (24.0) | 9 (25.7) |
| Prior CAR-T therapy — no. (%) | 3 (1.8) | 1 (2.9) |
| Prior lines of therapy — no. | | |
| Median | 3 | 3 |
| Range | 1–13 | 1–12 |
| Refractory to any prior therapy — no. (%) | | |
| Refractory | 155 (90.6) | 29 (82.9) |
| Relapsed | 16 (9.4) | 6 (17.1) |
| Refractory to any line of prior CD20 therapy — no. (%) | | |
| Refractory | 144 (84.2) | 25 (71.4) |
| Relapsed | 27 (15.8) | 10 (28.6) |
| Time since last prior therapy to first study treatment — mo | | |
| Number of evaluable patients‡ | 161 | 34 |
| Median | 2.4 | 4.6 |
| Range | 0.6–128.8 | 0.9–53.2 |
| Time since last anti-CD20 therapy to first study treatment — mo | | |
| Number of evaluable patients‡ | 157 | 34 |
| Median | 5.8 | 12.7 |
| Range | 0.6–146.7 | 2.2–85.7 |

FIG. 8

| Number of Patients (%) | All Glofitamab Cohorts (N = 171) | RP2D Glofitamab Cohort (N = 35) |
|---|---|---|
| Any adverse event | 168 (98.2) | 34 (97.1) |
| Adverse event related to glofitamab | 143 (83.6) | 32 (92.14) |
| Adverse event related to obinutuzumab | 68 (39.8) | 14 (40.0) |
| Adverse event leading to withdrawal from glofitamab | 5 (2.9) | 2 (5.7) |
| Adverse event leading to glofitamab dose interruption | 53 (31.0) | 17 (48.6%) |
| Adverse event leading to glofitamab dose reduction | 2 (1.2) | 0 |
| Grade ≥ 3 adverse event | 97 (56.7) | 19 (54.3) |
| Grade ≥ 3 adverse event related to glofitamab | 53 (31.0) | 15 (42.9) |
| Grade ≥ 3 adverse event related to obinutuzumab | 24 (14.0) | 5 (14.3) |
| Common (≥ 5% of patients) grade ≥ 3 adverse events by preferred term | | |
| Neutropenia‡ | 43 (25.1) | 9 (25.7) |
| Thrombocytopenia | 14 (8.2) | 3 (8.6) |
| Anemia | 13 (7.6) | 0 |
| CRS | 6 (3.5) | 2 (5.7) |
| Gamma-glutamyltransferase increased | 5 (2.9) | 2 (5.7) |
| Pneumonia | 5 (2.9) | 2 (5.7) |
| Febrile neutropenia | 5 (2.9) | 2 (5.7) |
| Serious adverse event | 100 (58.5) | 21 (60.0) |
| Serious adverse event related to glofitamab | 77 (45.0) | 18 (51.4) |
| Serious adverse event related to obinutuzumab | 10 (5.8) | 3 (8.6) |
| Common (≥ 3% of patients) serious adverse events by preferred term | | |
| Cytokine release syndrome | 61 (35.7) | 13 (37.1) |
| Pyrexia | 22 (12.9) | 3 (8.6) |
| Infusion-related reaction | 6 (3.5) | 2 (5.7) |
| Tumor flare | 2 (1.2) | 2 (5.7) |
| Adverse events of special interest (all grades) | | |
| Cytokine release syndrome | 86 (50.3) | 25 (71.4) |
| Infections and infestations | 88 (51.5) | 15 (42.9) |
| Neurologic adverse event | 74 (43.3) | 11 (31.4) |
| ICANS-like event | 31 (18.1) | 4 (11.4) |
| Febrile neutropenia | 5 (2.9) | 2 (5.7) |
| Grade 5 (fatal) adverse event | 2 (1.2) | 0 |

‡Includes the terms 'neutropenia' and 'neutrophil count decreased'.

FIG. 9

| | All Histologies | aNHL* | DLBCL | trFL | FL (Gr 1–3A) |
|---|---|---|---|---|---|
| **All cohorts** | **171** | **127** | **73** | **29** | **44** |
| Overall response rate† | | | | | |
| No. (%) | 92 (53.8) | 61 (48.0) | 30 (41.4) | 16 (55.2) | 31 (70.5) |
| 95% CI | 46.0, 61.4 | 39.1, 57.1 | 29.7, 53.2 | 35.7, 73.6 | 54.8, 83.2 |
| Complete response | | | | | |
| No. (%) | 63 (36.8) | 42 (33.1) | 21 (28.8) | 10 (34.5) | 21 (47.7) |
| 95% CI | 29.6, 44.5 | 25.0, 42.0 | 18.8, 40.6 | 17.9, 54.3 | 32.5, 63.3 |
| Partial response | | | | | |
| No. (%) | 29 (17.0) | 19 (15.0) | 9 (12.3) | 6 (20.7) | 10 (22.7) |
| 95% CI | 11.7, 23.4 | 9.3, 22.4 | 5.8, 22.1 | 8.0, 39.7 | 11.5, 37.8 |
| **≥10 mg cohorts** | **98** | **69** | **38** | **14** | **29** |
| Overall response rate† | | | | | |
| No. (%) | 62 (63.3) | 42 (60.9) | 21 (55.3) | 9 (64.3) | 20 (69.0) |
| 95% CI | 52.9, 72.8 | 48.4, 72.4 | 38.3, 71.4 | 35.1, 87.2 | 49.2, 84.7 |
| Complete response | | | | | |
| No. (%) | 51 (52.0) | 34 (49.3) | 16 (42.1) | 9 (64.3) | 17 (58.6) |
| 95% CI | 41.7, 62.2 | 37.0, 61.6 | 26.3, 59.2 | 35.1, 87.2 | 38.9, 76.5 |
| Partial response | | | | | |
| No. (%) | 11 (11.2) | 8 (11.6) | 5 (13.2) | 0 | 3 (10.3) |
| 95% CI | 5.7, 19.2 | 5.1, 21.6 | 4.4, 28.1 | | |
| **RP2D** | **35** | **14** | **5** | **3** | **21** |
| Objective response rate† | | | | | |
| No. (%) | 23 (65.7) | 10 (71.4) | 3 (60.0) | 3 (100.0) | 13 (61.9) |
| 95% CI | 47.8, 80.9 | 41.9, 91.6 | | | 38.4, 81.9 |
| Complete response | | | | | |
| No. (%) | 20 (57.1) | 9 (64.3) | 2 (40.0) | 3 (100.0) | 11 (52.4) |
| 95% CI | 39.4, 73.7 | 35.1, 87.2 | | | 29.8, 74.3 |
| Partial response | | | | | |
| No. (%) | 3 (8.6) | 1 (7.1) | 1 (20.0) | 0 | 2 (9.5) |
| 95% CI | 1.8, 23.1 | 0.2, 33.9 | | | 1.2, 30.4 |

†Investigator-assessed best response by PET-CT and standard Lugano criteria.

Figure 14:
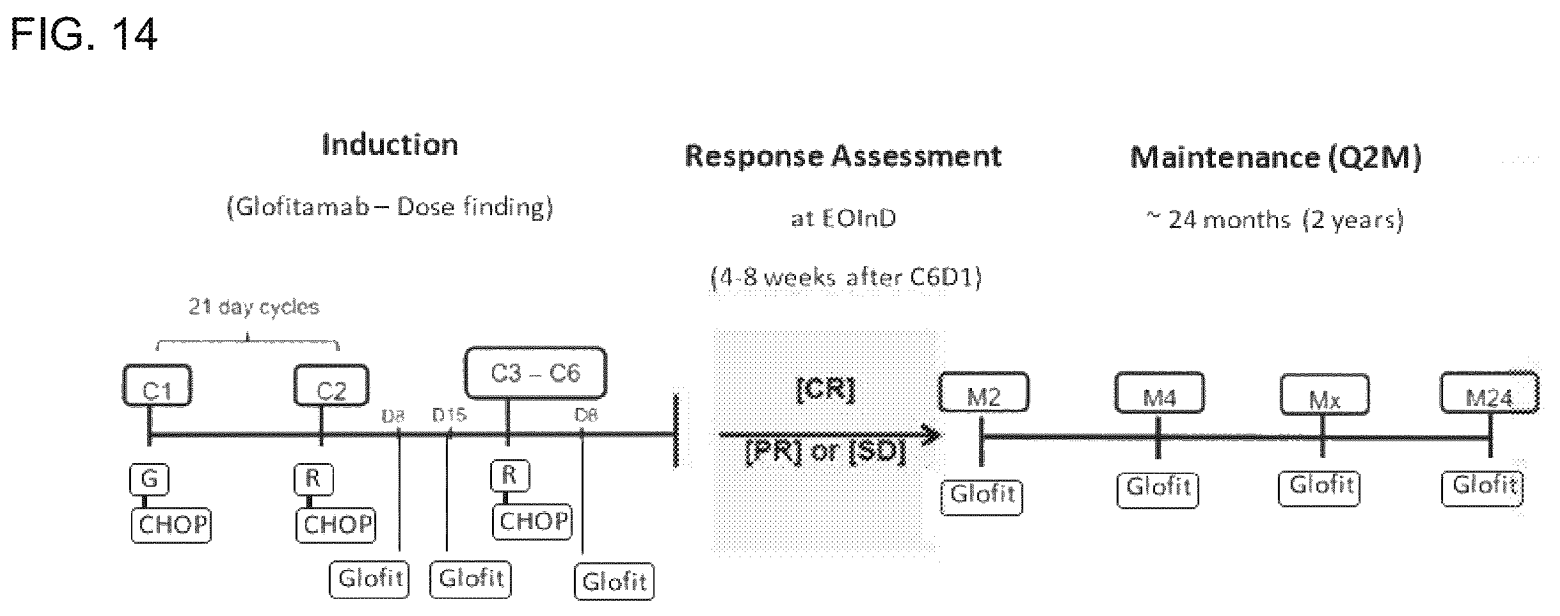

Induction
(Glofitamab – Dose finding)
21 day cycles
C1
G
CHOP
C2
R
CHOP
D8
Glofit
D15
Glofit
C3 – C6
R
CHOP
D8
Glofit Response Assessment
at EOInD
(4-8 weeks after C6D1)
[CR]
[PR] or [SD]

Maintenance (Q2M)
~ 24 months (2 years)
M2
Glofit
M4
Glofit
Mx
Glofit
M24
Glofit

FIG. 15

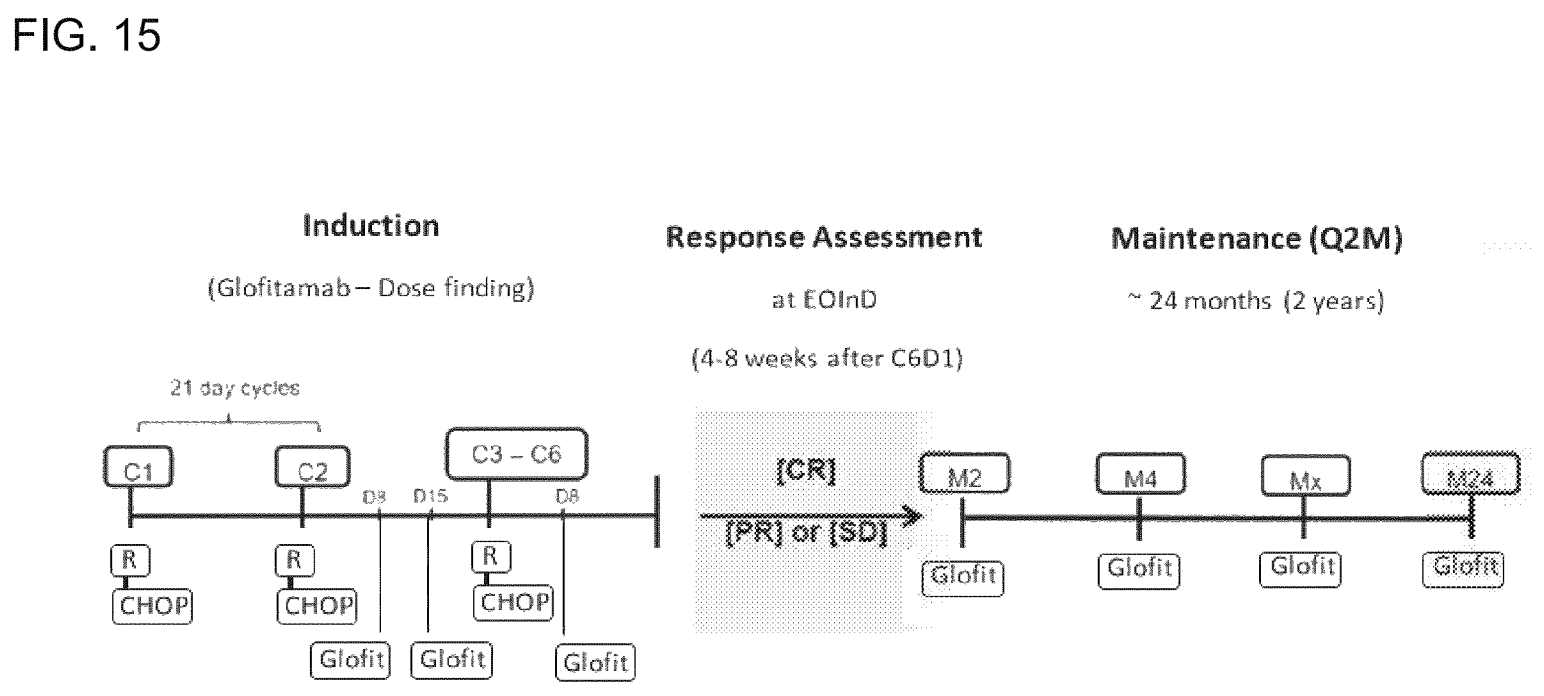

Induction
(Glofitamab – Dose finding)
21 day cycles
C1
R
CHOP
C2
R
CHOP
D8
Glofit
D15
Glofit
C3 – C6
R
CHOP
D8
Glofit Response Assessment
at EOInD
(4-8 weeks after C6D1)
[CR]
[PR] or [SD]

Maintenance (Q2M)
~ 24 months (2 years)
M2
Glofit
M4
Glofit
Mx
Glofit
M24
Glofit

FIG. 16

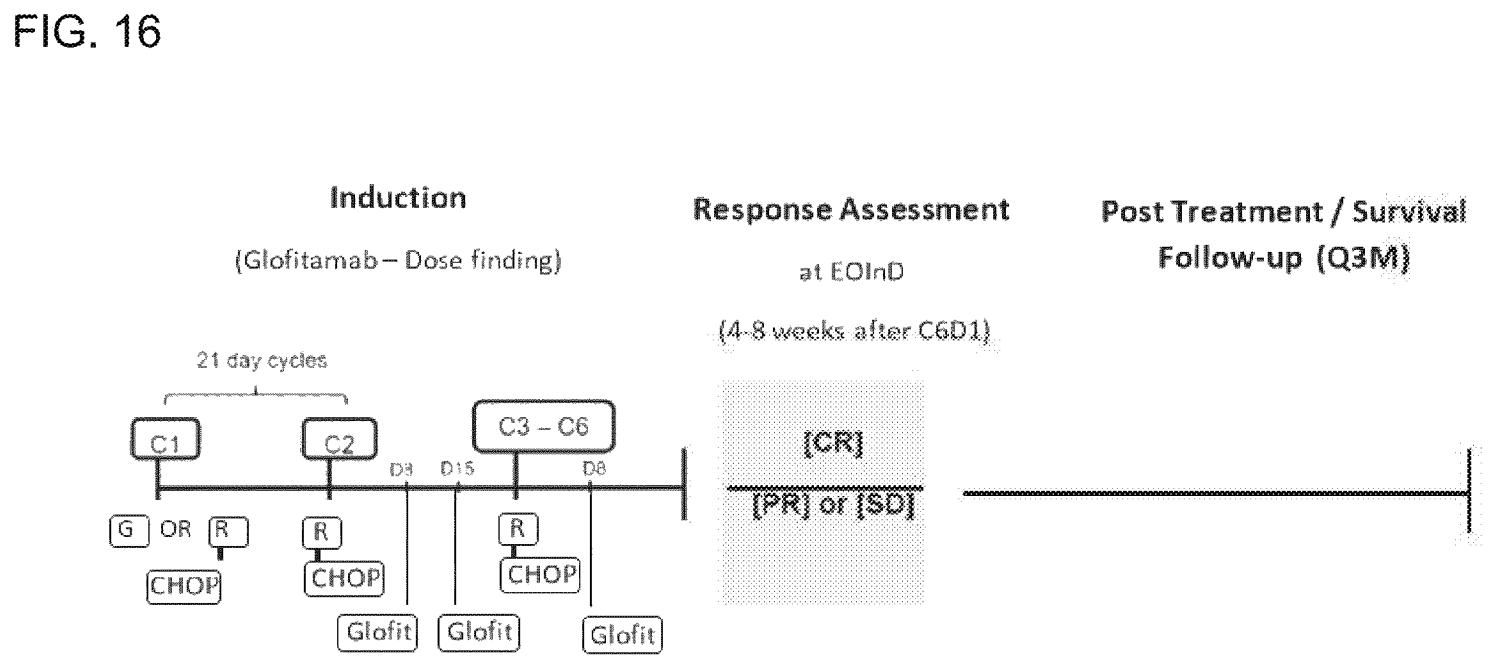

Induction (Glofitamab – Dose finding)

21 day cycles

C1

C2

C3 – C6

D8 D15 D8

G OR R

CHOP

R

CHOP

R

CHOP

Glofit Glofit Glofit

Response Assessment at EOInD (4-8 weeks after C6D1)

[CR]

[PR] or [SD]

Post Treatment / Survival Follow-up (Q3M)

DOSING FOR TREATMENT WITH ANTI-CD20/ANTI-CD3 BISPECIFIC ANTIBODY

CROSS-REFERENCE TO RELATED APPLICATIONS

This application claims benefit of priority to U.S. Provisional Application No. 63/182,398, filed on Apr. 30, 2021, U.S. Provisional Application No. 63/226,962, filed on Jul. 29, 2021, and PCT Application No. PCT/EP2021/080300, filed on Nov. 2, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 26, 2022, is named 51177-036004_Sequence_Listing_4_26_22_ST25 and is 31,375 bytes in size.

FIELD OF THE INVENTION

The present invention relates to methods of treating a disease, particularly a B-cell proliferative disorder by administering an anti-CD20/anti-CD3 bispecific antibody, and methods for reduction of adverse effects in response to the administration of the anti-CD20/anti-CD3 bispecific antibody.

BACKGROUND

B-cell proliferative disorders describe a heterogeneous group of malignancies that include both leukemias and lymphomas. Lymphomas develop from lymphatic cells and include two main categories: Hodgkin lymphomas (HL) and the non-Hodgkin lymphomas (NHL). In the United States, lymphomas of B cell origin constitute approximately 80-85% of all non-Hodgkin lymphoma cases, and there is considerable heterogeneity within the B-cell subset, based upon genotypic and phenotypic expression patterns in the B-cell of origin. For example, B cell lymphoma subsets include the slow-growing indolent and incurable diseases, such as Follicular lymphoma (FL) or chronic lymphocytic leukemia (CLL), as well as the more aggressive subtypes, mantle cell lymphoma (MCL) and diffuse large B cell lymphoma (DLBCL). Diffuse large B-cell lymphoma (DLBCL) is the most common type of NHL accounting for approximately 30%-40% of all NHL diagnosis, followed by follicular lymphoma (FL; 20%-25% of all NHL diagnosis) and mantle cell lymphoma (MCL; 6%-10% of all NHL diagnosis). B-cell chronic lymphocytic leukemia (CLL) is the most common leukemia in adults, with approximately 15,000 new cases per year in the United States (American Cancer Society 2015).

Bispecific antibodies are capable of simultaneously binding cell surface antigens on cytotoxic cells (e.g., T cells, via binding to cluster of differentiation 3 (CD3)) and cancer cells (e.g., B cells, via binding to CD20), with the intent that the bound cytotoxic cell will destroy the bound cancer cell. Glofitamab is a T cell bispecific (TCB) antibody targeting CD20 expressed on B cells and CD3 epsilon chain (CD3ε) present on T cells.

However, immunotherapies with anti-CD20/anti-CD3 bispecific antibodies like glofitamab can be limited by unwanted effects, including cytokine driven toxicities (e.g., cytokine release syndrome (CRS)), infusion-related reactions (IRRs), severe tumor lysis syndrome (TLS), and central nervous system (CNS) toxicities.

Thus, there is an unmet need in the field for the development of efficacious methods of dosing of an anti-CD20/anti-CD3 bispecific antibody (e.g., glofitamab) for the treatment of CD20-positive B cell proliferative disorders (e.g., non-Hodgkin's lymphoma, NHL) that achieve a more favorable benefit-risk profile.

SUMMARY OF THE INVENTION

The present invention is based on the finding that cytokine release related side effects associated with administration of an anti-CD20/anti-CD3 bispecific antibody (e.g., glofitamab) to a subject can be significantly reduced by a specific dosing regimen, while achieving clinical efficacy.

In one aspect, the invention features a method of treating a subject having a CD20-positive B cell proliferative disorder comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In one embodiment the single dose of the second dosing cycle (C2D1) comprises 30 mg of the anti-CD20/anti-CD3 bispecific antibody.

In one embodiment the first dose (C1D1) is administered on day 1 of the first dosing cycle and the second dose (C1D2) is administered on day 8 of the first dosing cycle.

In one embodiment the single dose of the second dosing cycle (C2D1) is administered on day 1 of the second dosing cycle.

In one embodiment the method of treating a subject having a CD20-positive B cell proliferative disorder comprises 1 to 10 additional dosing cycles (C3 to C12). In one such embodiment the 1 to 10 additional dosing cycles (C3 to C12) each comprises a single dose (C3D1 to C12D1) of either 16 or 30 mg of the anti-CD20/anti-CD3 bispecific antibody. In one embodiment the single dose of each of the additional dosing cycles (C3D1 to C12D1) comprises 30 mg of the anti-CD20/anti-CD3 bispecific antibody. In one embodiment the single dose of the additional dosing cycles (C3D1 to C12D1) is administered on day 1 of the respective additional dosing cycle.

In one embodiment the method of treating a subject having a CD20-positive B cell proliferative disorder comprises 12 dosing cycles in total.

In one embodiment, one treatment cycle comprises 14 days or 21 days. In one embodiment, one treatment cycle comprises 21 days.

In one embodiment, the CD20-positive B cell proliferative disorder is a non-Hodgkin's lymphoma (NHL). In one embodiment the B cell proliferative disorder is relapsed or refractory NHL. In one embodiment, the NHL is indolent NHL (iNHL) or aggressive NHL (aNHL). In one embodiment the NHL is a diffuse large B cell lymphoma (DLBCL), high grade B cell lymphoma (HGBCL), primary mediastinal large B-cell lymphoma (PMBCL), or marginal zone lymphoma (MZL). In one embodiment the DLBCL is a Richter's transformation. In one embodiment the NHL is a mantle cell lymphoma (MCL). In one embodiment, the MCL is a relapsed or refractory (R/R) MCL. In one embodiment the subject suffering from R/R MCL has received at least one prior systemic treatment regimen comprising a Bruton tyrosine kinase inhibitor (BTKi). In one embodiment, the BTKi comprises ibrutinib, acalabrutinib, or zanubrutinib.

In one embodiment, the NHL is a follicular lymphoma (FL). In one embodiment, the FL is Grade 1, 2, or 3a FL. In one embodiment, the FL is a transformed FL. In one embodiment, the FL is a relapsed or refractory (R/R) FL. In one embodiment the subject suffering from FL is a high-risk subject who:

(a) has relapsed after or is refractory to at least two prior therapies;
(b) has relapsed after or is refractory to treatment with a phosphoinositide 3-kinase (PI3K) inhibitor;
(c) experiences progression of disease within 24 months of frontline treatment; and/or
(d) has lesions, wherein the sum of the product of the lesion diameters is ≥3,000 $mm^2$.

In one embodiment, the population of subjects having the CD20-positive B cell proliferative disorder exhibits cytokine release syndrome after administering the anti-CD20/anti-CD3 bispecific antibody, and wherein the rate of the cytokine release syndrome of a grade of 3 or greater (as defined by the American Society for Transplantation and Cellular Therapy, 2019; ASTCT) is less than or about 5%.

In one embodiment, administration of the anti-CD20/anti-CD3 bispecific antibody to a plurality of subjects results in a complete response rate of at least about 70%.

In one embodiment, administration of the anti-CD20/anti-CD3 bispecific antibody to a plurality of subjects results in a complete response rate of at least about 70% in subjects suffering from iNHL. In one embodiment, administration of the anti-CD20/anti-CD3 bispecific antibody to a plurality of subjects results in a complete response rate of at least about 70% in subjects suffering from aNHL.

In one embodiment, administration of the anti-CD20/anti-CD3 bispecific antibody to a plurality of subjects results in an overall response rate of at least about 80% in subjects suffering from MCL. In one embodiment, administration of the anti-CD20/anti-CD3 bispecific antibody to a plurality of subjects results in a complete response rate of at least about 65% in subjects suffering from MCL. In one embodiment, the MCL is a relapsed or refractory (R/R) MCL. In one embodiment the subject suffering from R/R MCL has received at least one prior systemic treatment regimen comprising a Bruton tyrosine kinase inhibitor (BTKi). In one embodiment, the BTKi comprises ibrutinib, acalabrutinib, or zanubrutinib.

In one embodiment, administration of the anti-CD20/anti-CD3 bispecific antibody to a plurality of subjects results in an overall response rate of at least about 80% in subjects suffering from FL.

In one embodiment, the FL is Grade 1, 2, or 3a FL. In one embodiment, the FL is a transformed FL. In one embodiment, the FL is a relapsed or refractory (R/R) FL.

In one embodiment, administration of the anti-CD20/anti-CD3 bispecific antibody to a plurality of subjects results in a complete metabolic response rate of at least about 40% in subjects suffering from high-risk FL who:

(a) have relapsed after or are refractory to at least two prior therapies;
(b) have relapsed after or are refractory to treatment with a phosphoinositide 3-kinase (PI3K) inhibitor;
(c) experience progression of disease within 24 months of frontline treatment; and/or
(d) have lesions, wherein the sum of the product of the lesion diameters is ≥3,000 $mm^2$.

In a second aspect, a method of treating a subject having Follicular lymphoma (FL) is provided, comprising administering to the subject an anti-CD20/anti-CD3 bispecific antibody in a dosing regimen comprising at least a first dosing cycle, a second dosing cycle and a third dosing cycle, wherein:

(i) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody
(ii) the second dosing cycle comprises a single dose (C2D1) of 10 mg of the anti-CD20/anti-CD3 bispecific antibody, and
(iii) the third dosing cycle comprises a single dose (C3D1) of 16 or 30 mg of the anti-CD20/anti-CD3 bispecific antibody.

In one embodiment, the single dose of the third dosing cycle (C3D1) comprises 30 mg of the anti-CD20/anti-CD3 bispecific antibody.

In one embodiment, the first dose (C1D1) is administered on day 1 of the first dosing cycle and the second dose (C1D2) is administered on day 8 of the first dosing cycle.

In one embodiment, the single dose of the second dosing cycle (C2D1) is administered on day 1 of the second dosing cycle.

In one embodiment, the single dose of the third dosing cycle (C3D1) is administered on day 1 of the third dosing cycle.

In one embodiment, the method of treating a subject having Follicular lymphoma (FL) comprises 1 to 9 additional dosing cycles (C4 to C12). In one embodiment, the 1 to 9 additional dosing cycles (C4 to C12) each comprises a single dose (C4D1 to C12D1) of either 16 or 30 mg of the anti-CD20/anti-CD3 bispecific antibody. In one embodiment, the single dose of each of the additional dosing cycles (C4D1 to C12D1) comprises 30 mg of the anti-CD20/anti-CD3 bispecific antibody. In one embodiment, the single dose of the additional dosing cycles (C4D1 to C12D1) is administered on day 1 of the respective additional dosing cycle.

In one embodiment, the method of treating a subject having Follicular lymphoma (FL) comprises 12 dosing cycles in total.

In one embodiment one treatment cycle comprises 14 days or 21 days. In one embodiment one treatment cycle comprises 21 days.

In one embodiment the FL is Grade 1, 2, or 3a FL. In one embodiment, the FL is a transformed FL. In one embodiment, the FL is a relapsed or refractory (R/R) FL. In one embodiment the subject suffering from FL is a high-risk subject who:

(a) has relapsed after or is refractory to at least two prior therapies;
(b) has relapsed after or is refractory to treatment with a phosphoinositide 3-kinase (PI3K) inhibitor;
(c) experiences progression of disease within 24 months of frontline treatment; and/or
(d) has lesions, wherein the sum of the product of the lesion diameters is ≥3,000 mm2.

In one embodiment, administration of the anti-CD20/anti-CD3 bispecific antibody to a plurality of subjects results in an overall response rate of at least about 80% in subjects suffering from FL. In one embodiment, the subjects are high-risk subjects having R/R FL, and administration of the anti-CD20/anti-CD3 bispecific antibody to a plurality of subjects results in a complete response rate of at least about 40%. In one embodiment, the population of subjects having FL exhibits cytokine release syndrome after administering the anti-CD20/anti-CD3 bispecific antibody, and wherein the rate of the cytokine release syndrome of a grade of 3 or greater (as defined by the American Society for Transplantation and Cellular Therapy, 2019; ASTCT) is about 3%.

In one embodiment, the method of treating a subject having a CD20-positive B cell proliferative disorder is combined with administration of obinutuzumab or rituximab. In one embodiment, the method of treating a subject having Follicular lymphoma (FL) is combined with administration of obinutuzumab or rituximab. In one embodiment, the method of treating a subject having MCL is combined with administration of obinutuzumab or rituximab. In one embodiment, the subject suffers from MCL and has received at least two prior systemic therapies.

In one embodiment obinutuzumab or rituximab is administered 7 days before the first dose of the anti-CD20/anti-CD3 bispecific antibody (C1D1). In one embodiment, obinutuzumab is administered at one single dose of 1000 mg. In one embodiment, obinutuzumab is administered at a first and a second dose of each 1000 mg obinutuzumab. In one embodiment, the first and second dose of obinutuzumab are administered on the same day.

In one embodiment, 2000 mg of obinutuzumab is administered 7 days before the first dose (C1D1) of the anti-CD20/anti-CD3 bispecific antibody.

In one embodiment, the first and second dose of obinutuzumab are administered on different days.

In one embodiment, the first dose of obinutuzumab is administered 7 days before the first dose (C1D1) of the anti-CD20/anti-CD3 bispecific antibody and the second dose of obinutuzumab is administered one day before the first dose (C1D1) of the anti-CD20/anti-CD3 bispecific antibody.

In one embodiment, the subject suffers from mantle cell lymphoma (MCL) and has received at least two prior systemic therapies.

In one embodiment, obinutuzumab or rituximab is administered on the first day of the second dosing cycle (C2) and on the first day of any subsequent dosing cycle.

In one embodiment, obinutuzumab or rituximab is administered on the first day of the second dosing cycle (C2) and on the first day of the third (C3) to twelfth dosing cycle (C12) In one embodiment, obinutuzumab is administered at a dose of 1000 mg.

In one embodiment, the patient receives corticosteroid premedication prior to the anti-CD20/anti-CD3 bispecific antibody.

In one embodiment, the corticosteroid premedication comprises prednisolone and methylprednisolone, and/or dexamethasone.

In one embodiment, the corticosteroid premedication is given prior to the first dose (C1D1) of the anti-CD20/anti-CD3 bispecific antibody.

In one embodiment, treatment is stopped after a total of 12 treatment cycles.

In one embodiment, the patient is retreated with a method described herein if a relapse occurs and/or if disease progresses.

In a third aspect, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, corticosteroid, and anti-CD20/anti-CD3 bispecific antibody to a plurality of humans results in a complete response in at least about 60%, at least about 70% or at least about 80% of the humans in the plurality after treatment with the anti-CD20 antibody, cyclophosphamide, doxorubicin, corticosteroid, and anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, corticosteroid, and anti-CD20/anti-CD3 bispecific antibody to a plurality of humans results in an overall response in at least about 80%, at least about 85% or at least about 90% of the humans in the plurality after treatment with the anti-CD20 antibody, cyclophosphamide, doxorubicin, corticosteroid, and anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, corticosteroid, and anti-CD20/anti-CD3 bispecific antibody to the human does not result in Grade 2 or higher CRS.

In one embodiment, the method comprises a dosing regimen comprising at least a first dosing cycle, a second dosing cycle and a third dosing cycle, wherein:

(a) the first dosing cycle comprises a first dose (C1D1) of the anti-CD20 antibody, cyclophosphamide, doxorubicin and corticosteroid, and no dose of the anti-CD20/anti-CD3 bispecific antibody;

(b) the second dosing cycle comprises a second dose (C2D1) of the anti-CD20 antibody, cyclophosphamide, doxorubicin and corticosteroid, and a first dose (C2D1) and second dose (C2D2) of the anti-CD20/anti-CD3 bispecific antibody, wherein the C2D1 of the anti-CD20/anti-CD3 bispecific antibody is about 2.5 mg and the C2D2 of the anti-CD20/anti-CD3 bispecific antibody is about 10 mg;

(c) the third dosing cycle comprises a third dose (C3D1) of the anti-CD20 antibody, cyclophosphamide, doxorubicin and corticosteroid, and a third dose (C3D1) of the anti-CD20/anti-CD3 bispecific antibody, wherein the C3D1 of the anti-CD20/anti-CD3 bispecific antibody is about 30 mg.

In one embodiment, the anti-CD20 antibody, cyclophosphamide, doxorubicin, and corticosteroid is administered on day 1 of each dosing cycle. In one embodiment, the first dose (C2D1) of the anti-CD20/anti-CD3 bispecific antibody is administered on day 8 of the second dosing cycle and the second dose (C2D2) of the anti-CD20/anti-CD3 bispecific antibody is administered on day of the second dosing cycle.

In one embodiment, the third dose of the of the anti-CD20/anti-CD3 bispecific antibody (C3D1) is administered on day 8 of the third dosing cycle.

In one embodiment, the method comprises 1 to 5 additional dosing cycles (C4 to C8). In one embodiment, the 1 to 5 additional dosing cycles (C4 to C8) each comprises a single dose of anti-CD20 antibody, cyclophosphamide, doxorubicin, corticosteroid, and a single dose (C4D1 to C8D1) of 30 mg of the anti-CD20/anti-CD3 bispecific antibody. In one embodiment, the single dose of each of the anti-CD20 antibody, cyclophosphamide, doxorubicin, and corticosteroid is administered on day 1 and the single dose (C4D1 to C8D1) of the anti-CD20/anti-CD3 bispecific antibody is administered on day 8 of the respective additional dosing cycle (C4 to C8).

In one embodiment, the corticosteroid is prednisone and the anti-CD20 antibody is rituximab. In one embodiment, a method of treating a subject having a CD20-positive B cell proliferative disorder is provided, comprising administering to the subject rituximab, cyclophosphamide, doxorubicin, vincristine, and prednisone (R-CHOP) and anti-CD20/anti-CD3 bispecific antibody in a dosing regimen comprising at least a first dosing cycle, a second dosing cycle and a third dosing cycle, wherein:

(a) the first dosing cycle comprises a first dose (C1D1) of rituximab, cyclophosphamide, doxorubicin, vincristine, and prednisone (R-CHOP), and no dose of the anti-CD20/anti-CD3 bispecific antibody;

(b) the second dosing cycle comprises a second dose (C2D1) of the R-CHOP and a first dose (C2D1) and second dose (C2D2) of the anti-CD20/anti-CD3 bispecific antibody, wherein the C2D1 of the anti-CD20/anti-CD3 bispecific antibody is about 2.5 mg and the C2D2 of the anti-CD20/anti-CD3 bispecific antibody is about 10 mg;

(c) the third dosing cycle comprises a third dose (C3D1) of the R-CHOP and a third dose (C3D1) of the anti-CD20/anti-CD3 bispecific antibody, wherein the C3D1 of the anti-CD20/anti-CD3 bispecific antibody is about 30 mg.

In one embodiment, R-CHOP is administered on day 1 of each dosing cycle. In one embodiment, the first dose (C2D1) of the anti-CD20/anti-CD3 bispecific antibody is administered on day 8 of the second dosing cycle and the second dose (C2D2) of the anti-CD20/anti-CD3 bispecific antibody is administered on day 15 of the second dosing cycle. In one embodiment, the third dose of the of the anti-CD20/anti-CD3 bispecific antibody (C3D1) is administered on day 8 of the third dosing cycle. In one embodiment, the method comprises 1 to additional dosing cycles (C4 to C8). In one embodiment, the 1 to 5 additional dosing cycles (C4 to C8) each comprises a single dose of R-CHOP and a single dose (C4D1 to C8D1) of 30 mg of the anti-CD20/anti-CD3 bispecific antibody. In one embodiment, the single dose of the R-CHOP is administered on day 1 and the single dose (C4D1 to C8D1) of the anti-CD20/anti-CD3 bispecific antibody is administered on day 8 of the respective additional dosing cycle (C4 to C8). In one embodiment, rituximab is replaced by obinutuzumab in the first dosing cycle.

In one embodiment, the method comprises 6 dosing cycles in total. In one embodiment, one treatment cycle comprises 14 days or 21 days. In one embodiment, one treatment cycle comprises 21 days. In one embodiment, the CD20-positive B cell proliferative disorder is previously untreated DLBCL. In one embodiment, the subject to be treated has international prognostics indicator [IPI] 2-5.

In one embodiment, the anti-CD20/anti-CD3 bispecific antibody is administered intravenously.

In one embodiment, the subject is human. In one embodiment, the human is a high-risk subject.

In one embodiment, the anti-CD20/anti-CD3 bispecific antibody comprises at least one antigen binding domain that specifically binds to CD20, comprising a heavy chain variable region comprising (i) an HVR-H1 comprising the amino acid sequence of SEQ ID NO: 1;

(ii) an HVR-H2 comprising the amino acid sequence of SEQ ID NO: 2;

(iii) an HVR-H3 comprising the amino acid sequence of SEQ ID NO:3;

and a light chain variable region comprising (i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6.

In one embodiment, the anti-CD20/anti-CD3 bispecific antibody comprises at least one antigen binding domain that specifically binds to CD20 comprising a VH domain comprising an amino acid sequence of SEQ ID NO: 7 and a VL domain comprising an amino acid sequence of SEQ ID NO: 8.

In one embodiment, the anti-CD20/anti-CD3 bispecific antibody comprises at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10;

(iii) an HVR-H3 comprising the amino acid sequence of SEQ ID NO:11; and a light chain variable region comprising (i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

In one embodiment, the anti-CD20/anti-CD3 bispecific antibody comprises at least one antigen binding domain that specifically binds to CD3 comprising a VH domain comprising an amino acid sequence of SEQ ID NO: 15 and a VL domain comprising an amino acid sequence of SEQ ID NO: 16.

In one embodiment, the anti-CD20/anti-CD3 bispecific antibody comprises an antigen binding domain that specifically binds to CD3 and is a cross-Fab molecule wherein the variable domains or the constant domains of the Fab heavy and light chain are exchanged.

In one embodiment, the anti-CD20/anti-CD3 bispecific antibody comprises an IgG1 Fc domain comprising one or more amino acid substitutions that reduce binding to an Fc receptor and/or effector function.

In one embodiment, the anti-CD20/anti-CD3 bispecific antibody comprises an IgG1 Fc domain comprising the amino acid substitutions L234A, L235A, and P329G (numbering according to Kabat EU index).

In one embodiment, the anti-CD20/anti-CD3 bispecific antibody comprises at least one Fab molecule comprising an antigen binding domain that specifically binds to CD20, wherein in the constant domain CL of the Fab molecule the amino acid at position 124 is substituted by lysine (K) (numbering according to Kabat) and the amino acid at position 123 is substituted by arginine (R) or lysine (K) (numbering according to Kabat), and wherein in the constant domain CH1 of the Fab molecule the amino acid at position 147 is substituted by glutamic acid (E) (numbering according to Kabat EU index) and the amino acid at position 213 is substituted by glutamic acid (E) (numbering according to Kabat EU index).

In one embodiment, the anti-CD20/anti-CD3 bispecific antibody comprises two antigen binding domains that specifically bind to CD20 and one antigen binding domain that specifically binds to CD3.

In one embodiment, the anti-CD20/anti-CD3 bispecific antibody is bivalent for CD20 and monovalent for CD3.

In one embodiment, the anti-CD20/anti-CD3 bispecific antibody comprises (i) an antigen binding domain that specifically binds to CD3 which is fused at the C-terminus of the Fab heavy chain to the N-terminus of the first subunit of the Fc domain;

(ii) a first antigen binding domain that specifically binds to CD20 which is fused at the C-terminus of the Fab heavy chain to the N-terminus of the Fab heavy chain of the antigen binding domain that specifically binds to CD3; and (iii) a second antigen binding domain that specifically binds to CD20 which is fused at the C-terminus of the Fab heavy chain to the N-terminus of the second subunit of the Fc domain.

In one embodiment, the anti-CD20/anti-CD3 bispecific antibody is glofitamab (WHO Drug Information (International Nonproprietary Names for Pharmaceutical Substances), Recommended INN: List 83, 2020, vol. 34, no. 1, p. 39).

In one embodiment an anti-CD20/anti-CD3 bispecific antibody for use in a method of treating a subject having a CD20-positive B cell proliferative disorder is provided, said method comprising administering to the subject the anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In one embodiment an anti-CD20/anti-CD3 bispecific antibody for use in a method of treating a subject having Follicular lymphoma (FL) is provided, said method comprising administering to the subject the anti-CD20/anti-CD3 bispecific antibody in a dosing regimen comprising at least a first dosing cycle, a second dosing cycle and a third dosing cycle, wherein:

(i) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody, (ii) the second dosing cycle comprises a single dose (C2D1) of 10 mg of the anti-CD20/anti-CD3 bispecific antibody, and (iii) the third dosing cycle comprises a single dose (C3D1) of 16 or 30 mg of the anti-CD20/anti-CD3 bispecific antibody.

In one embodiment, an anti-CD20/anti-CD3 bispecific antibody for use in a method of treating a subject having a CD20-positive cell proliferative disorder is provided, said method comprising administering to the subject an anti-CD20 antibody, cyclophosphamide, doxorubicin, a corticosteroid, and the anti-CD20/anti-CD3 bispecific antibody.

In one embodiment, use of an anti-CD20/anti-CD3 bispecific antibody in the manufacture of a medicament for the treatment of a CD20-positive cell proliferative disorder is provided, said treatment comprising administering to the subject the anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In one embodiment, use of an anti-CD20/anti-CD3 bispecific antibody in the manufacture of a medicament for the treatment of a CD20-positive cell proliferative disorder is provided, said treatment comprising administering to the subject the anti-CD20/anti-CD3 bispecific antibody in a dosing regimen comprising at least a first dosing cycle, a second dosing cycle and a third dosing cycle, wherein:

(i) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody, (ii) the second dosing cycle comprises a single dose (C2D1) of 10 mg of the anti-CD20/anti-CD3 bispecific antibody, and (iii) the third dosing cycle comprises a single dose (C3D1) of 16 or 30 mg of the anti-CD20/anti-CD3 bispecific antibody.

In one embodiment, use of an anti-CD20/anti-CD3 bispecific antibody in the manufacture of a medicament for the treatment of a CD20-positive cell proliferative disorder is provided, said treatment comprising administering to the subject an anti-CD20 antibody, cyclophosphamide, doxorubicin, a corticosteroid, and the anti-CD20/anti-CD3 bispecific antibody.

BRIEF DESCRIPTION OF THE DRAWINGS

FIG. 1A-FIG. 1N. Configurations of the anti-CD20/anti-CD3 bispecific antibody. An antibody with a single antigen binding moiety capable of specific binding to a target cell antigen is shown in FIG. 1A, FIG. 1D, FIG. 1G, FIG. 1H, FIG. 1K, and FIG. 1L. An antibody comprising two antigen binding moieties specific for a target cell antigen is shown in FIG. 1B, FIG. 1C, FIG. 1E, FIG. 1F, FIG. 1I, FIG. 1J, FIG. 1M, and FIG. 1N. FIG. 1A, FIG. 1D, FIG. 1H, and FIG. 1L show an antibody where the second Fab molecule is fused at the C-terminus of the Fab heavy chain to the N-terminus of the first or second subunit of the Fc domain. FIG. 1G and FIG. 1K show antibodies where the second Fab molecule is fused at the C-terminus of the Fab heavy chain to the N-terminus of the Fab heavy chain of the first Fab molecule. FIG. 1B, FIG. 1C, FIG. 1E, and FIG. 1F show antibodies where the third Fab molecule is a conventional Fab molecule and identical to the second Fab molecule. FIG. 1I, FIG. 1J, FIG. 1M, and FIG. 1N show antibodies where the third Fab molecule is a crossover Fab molecule.

FIG. 3. Study Design Overview: Glofitamab Monotherapy and Combination Therapy in r/r NHL Dose—Escalation and Dose Expansion Cohorts. (Q2W)$^a$ Monotherapy schedule; (Q2W$^a$/Q3W$^b$) Monotherapy schedule; (Q3W$^c$) Combination schedule; †Patients in Part III dose expansion monotherapy cohorts may receive glofitamab on a Q2W or Q3W dosing schedule with fixed dosing or Q3W with step-up dosing (Cycle 1 Step-up or Extended Step-up), if supported by emerging data and/or recommended by the IMC. # Based on determined MTD/OBD, both or one expansion cohort may be selected for monotherapy B3 and/or D3, B4 and/or D 4, while C3 or E3 and C4 or E4 may be selected. § Mandatory paired fresh baseline (cycle 1, day −7) and on-treatment tumor biopsies (cycle 1, day 9) are collected in a subset of patients. Abbreviations: Q2W=every 2 weeks; Q3W=every 3 weeks; SoA=Schedule of Assessments.

Abbreviations: AE, adverse event; NCI-CTCAE, National Cancer Institute-Common Terminology Criteria for Adverse Events.

Figure 6:
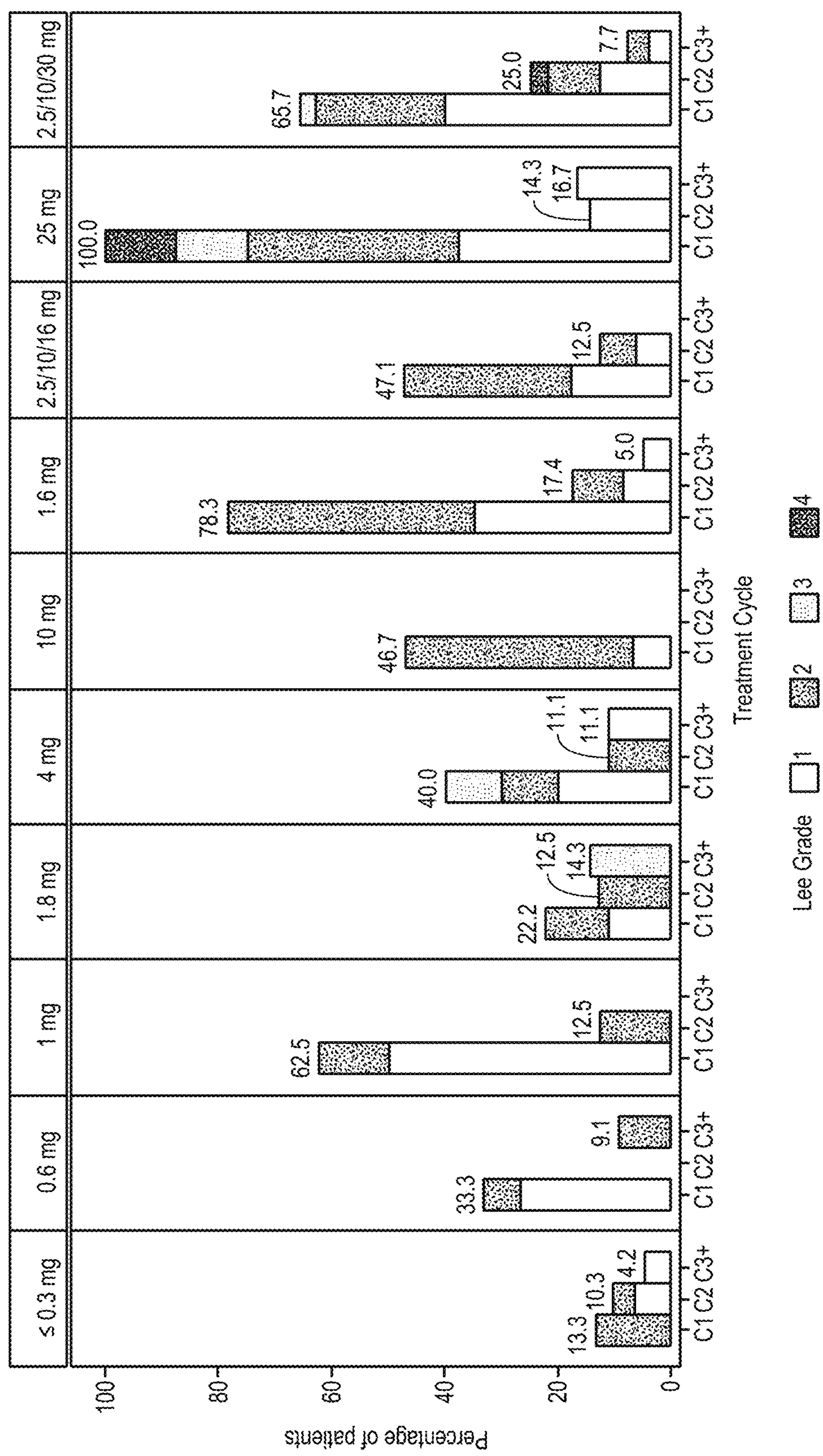

FIG. 6. Incidence of cytokine release syndrome by cycle and dose (Lee grade). Cytokine release syndrome events were predominantly confined to cycle 1 and 2. Step-up dosing of glofitamab allowed the administration of a high target dose (30 mg). Abbreviations: C, cycle.

FIG. 7. Patient Demographics and Baseline Disease Characteristics in Patients who Received Glofitamab at any dose and at the RP2D (Safety-Evaluable Patients). Abbreviations: CAR-T, chimeric antigen receptor T-cell; DLBCL, diffuse large B-cell lymphoma; FL, follicular lymphoma; ECOG, Eastern Cooperative Oncology Group; PMBCL, primary mediastinal B-cell lymphoma; RP2D, recommended phase II dose. ‡Data not available for all patients by cutoff date. § Includes FL Grade 3B (n=1), mantle cell lymphoma (n=1), DLBCL transformed from MZL (n=1), DLBCL transformed from isolated cervical immunoblastic lymphoma (n=1) and DLBCL transformed from Waldenström/Immunocytoma (n=1).

FIG. 8. Summary of Adverse Events in Patients Receiving Glofitamab at any dose and at the RP2D (Safety-Evaluable Patients). Abbreviations: ICANS, immune effector cell-associated neurotoxicity syndrome; RP2D, recommended phase II dose. $Includes the terms ‘neutropenia’ and ‘neutrophil count decreased’.

FIG. 9. Summary of Efficacy Data in Patients Receiving Glofitamab by Dose Level and Histology Abbreviations: aNHL, aggressive non-Hodgkin lymphoma; CI, confidence interval; CT, computer tomography; DLBCL, diffuse large B-cell lymphoma; FL, follicular lymphoma; Gr, grade; MCL, mantle cell lymphoma; PET, positron emission tomography; PMBCL, primary mediastinal B-cell lymphoma; RP2D, recommended phase II dose; trFL, transformed follicular lymphoma; trMZL, transformed marginal zone lymphoma. *aNHL includes FL (Gr 3B), DLBCL, trFL, PMBCL, MCL, trMZL, Richter’s transformation, and DLBCL transformed from other histologies.

Figure 10:
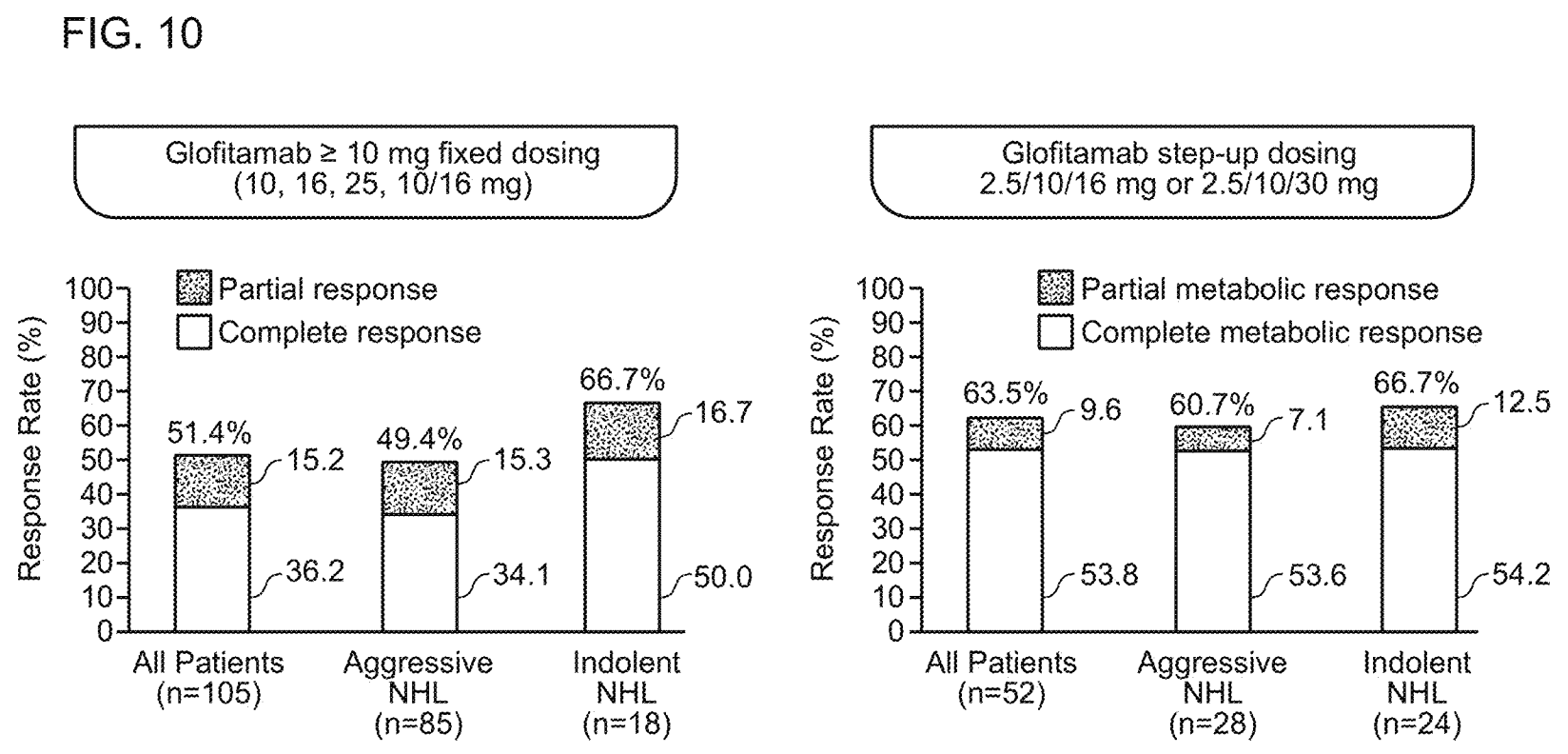

FIG. 10. High response to glofitamab was maintained with step up dosing. Complete response was usually achieved early, at first or second response assessment (Cycle 3: ~44 days after obinutuzumab pretreatment, Cycle 6: ~107 days after obinutuzumab pretreatment Efficacy population includes all patients who have been on study long enough to have their first mandatory response assessment (Lugano criteria). Patients with missing or no response assessment are included as non-responders. Two aNHL and six iNHL patients did not have a response assessment reported at time of clinical cut off date, CCOD.)

Figure 11A:
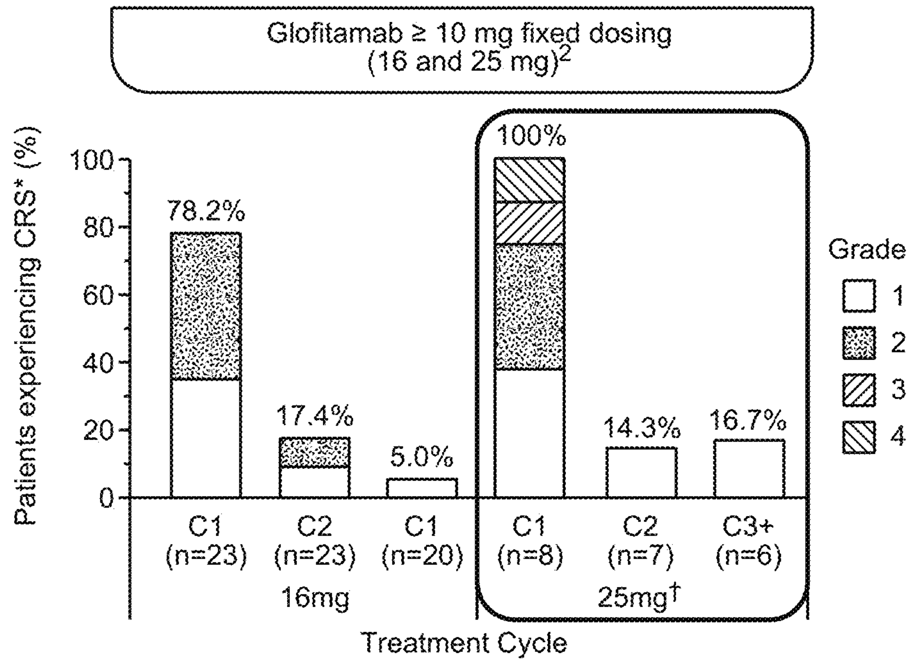
Figure 11B:
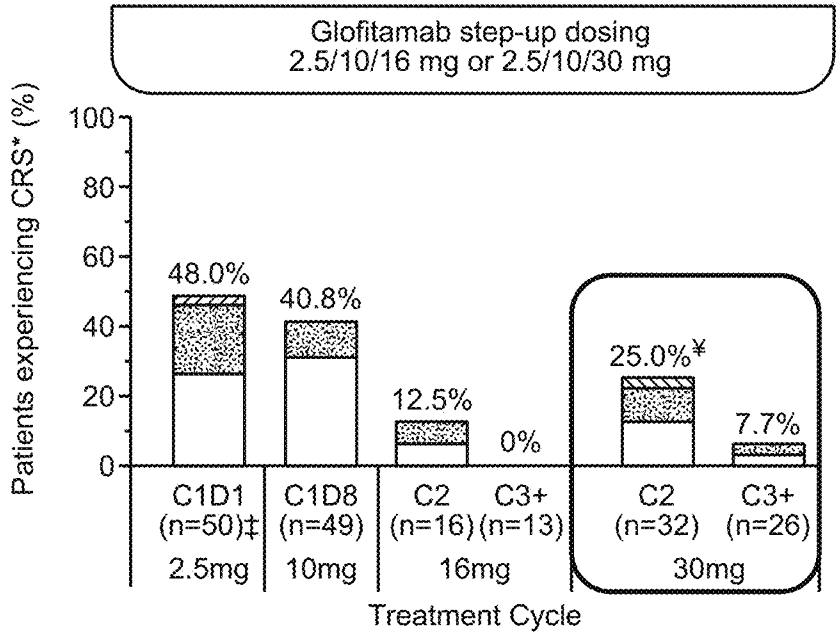

FIG. 11A and FIG. 11B. CRS frequency/severity: FIG. 11A: Glofitamab unchanging, set dosing. FIG. 11B: Glofitamab Step up dosing. Step up dosing allows administration of a high target dose of glofitamab. While the overall CRS rates were similar between the fixed dosing and step up dosing cohorts, step up dosing reduced the frequency of high grade CRS (Grade 2; 36.3% in the 10 mg fixed dosing versus 30.7% in the step up dosing cohort). *Multiple occurrences of CRS are counted at the highest grade. †Based on observed events, 25 mg as first C1 dose on fixed dosing schedule was determined to exceed maximum tolerated dose. % Two patients had not reached their first dose of glofitamab at CCOD. ¥Patient who experienced Grade 4 CRS received 30 mg of glofitamab as part of step-up dosing regimen following a long treatment delay.

Figure 12:
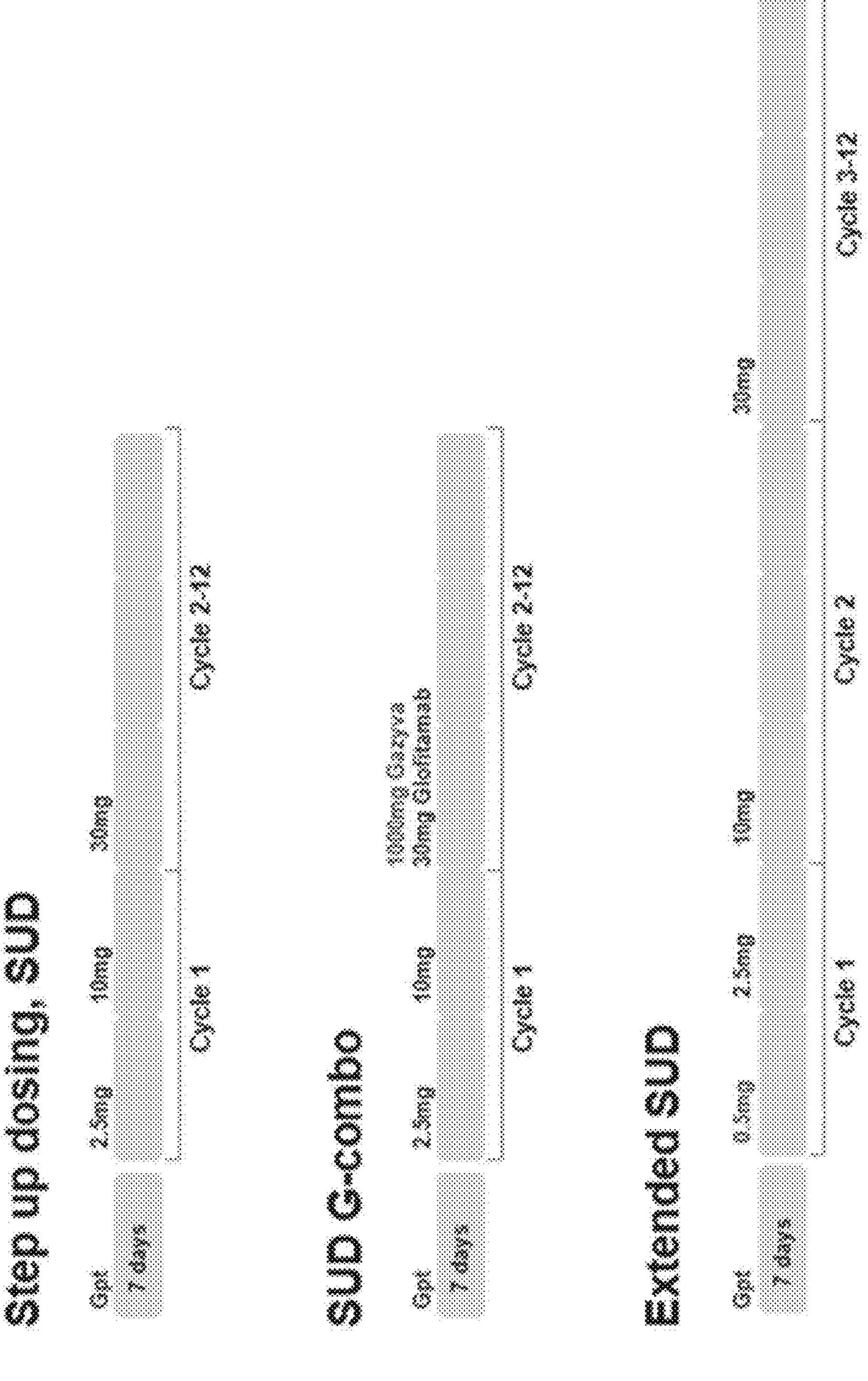

FIG. 12. Overview of glofitamab Step-up dosing schedule for the FL1-3A patient cohort. In the extended step-up (eSUD) dosing for FL1-3A patients, an initial lower dose of glofitamab (0.5 mg) was administered on day 1 of dosing cycle 1, 2.5 mg of glofitamab was administered on day 8 of dosing cycle 1, followed by an intermediate dose of 10 mg in Cycle 2 (day 1 of dosing cycle 2) and the first administration of the target treatment dose (30 mg) is in Cycle 3 (day 1 of dosing cycle 3). Data was compared to a FL1-3A patient cohort which received glofitamab monotherapy in step-up dosing (SUD) with 2.5 mg at day 1 of dosing cycle 1, 10 mg at day 8 of dosing cycle 1 and 16 or 30 mg at day 1 of dosing cycle 2 and with a FL1-3A patient cohort which received glofitamab step-up dosing (SUD) with 2.5 mg at day 1 of dosing cycle 1, 10 mg at day 8 of dosing cycle 1 and 30 mg at day 1 of dosing cycle 2 in combination with 1000 mg GAZYVA® as of C2D1 (“G-Combo). All cohorts received GAZYVA® pretreatment of 1000 mg GAZYVA® 7 days before the start of the first dosing cycle.

Figure 13:
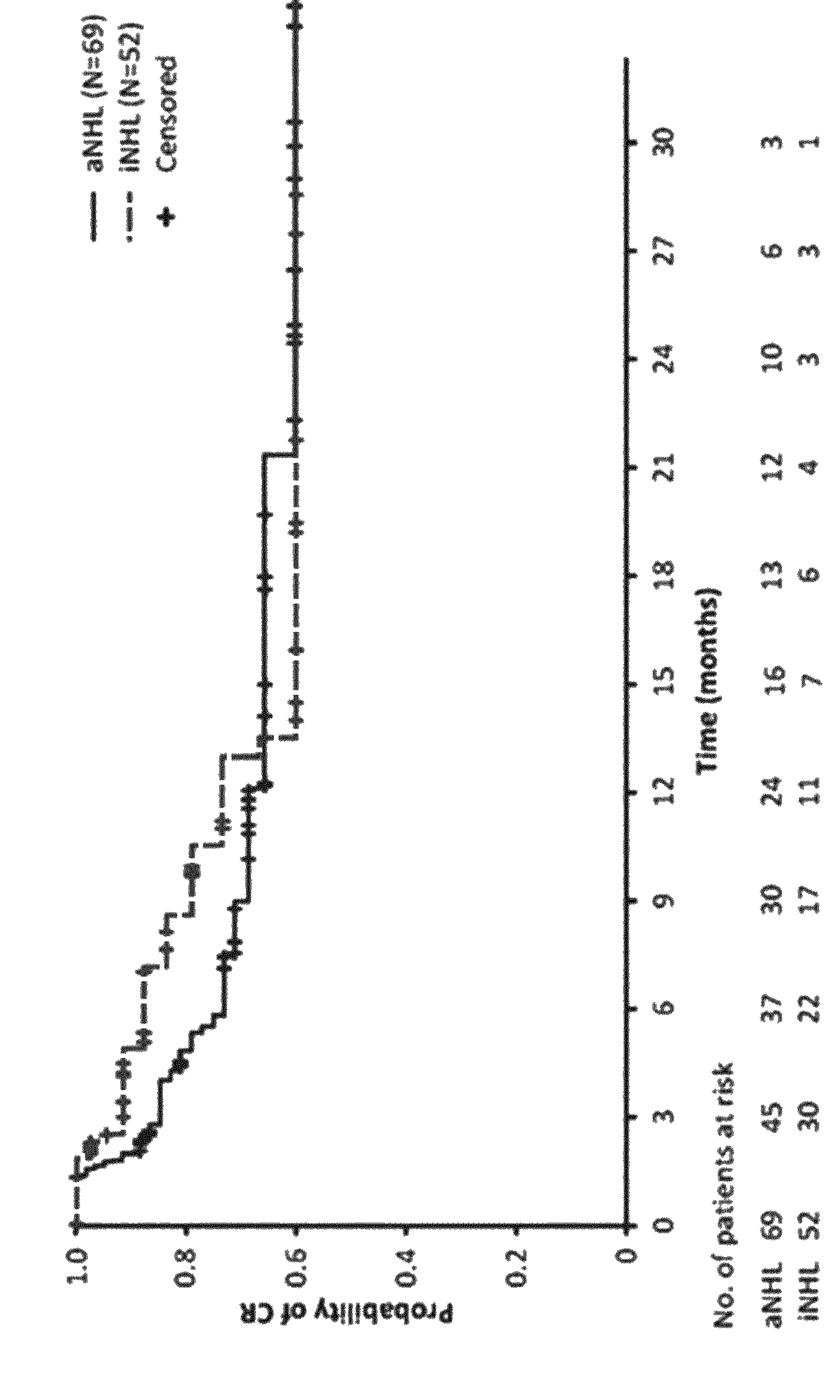

FIG. 13. Kaplan-Meier plot to determine duration of complete response of efficacy evaluable population in aggressive non-Hodgkin lymphoma (aNHL) and indolent non-Hodgkin lymphoma (iNHL) patients who received glofitamab step-up dosing (SUD). The efficacy population includes all pts who have a response assessment performed, or who are still on treatment at the time of their first scheduled response assessment. aNHL, aggressive non-Hodgkin lymphoma; CI, confidence interval; CR, complete response; iNHL, indolent non-Hodgkin lymphoma; RP2D, recommended Phase II dose.

FIG. 14. Schematic overview of the Study Design of NP40126, Part I Participants with Relapsed/Refractory Non-Hodgkin Lymphoma and the Use of Obinutuzumab for Cycle 1. Abbreviations: C=cycle; CHOP=cyclophosphamide (C), doxorubicin (H), vincristine (O), and prednisone (P); CR=complete response; d/c=discontinued; D=day; DLT=dose-limiting toxicity; EOInd=end of induction; EOT=end of treatment; G=obinutuzumab; IMC=Internal Monitoring Committee; IV=intravenously; M=month; PR=partial response; Q2M=every 2 months; Q3M=every 3 months; R=rituximab; SD=stable disease.

FIG. 15. Schematic overview of the Study Design of NP40126, Part I Participants with Relapsed/Refractory Non-Hodgkin Lymphoma and the Use of Rituximab for Cycle 1.

Abbreviations: C=cycle; CHOP=cyclophosphamide (C), doxorubicin (H), vincristine (O), and prednisone (P); CR=complete response; d/c=discontinued; D=day; DLT=dose-limiting toxicity; EOInd=end of induction; EOT=end of treatment; G=obinutuzumab; IMC=Internal Monitoring Committee; IV=intravenously; M=month;

PR=partial response; Q2M=every 2 months; Q3M=every 3 months; R=rituximab; SD=stable disease.

FIG. 16. Schematic overview of the Study Design of NP40126, Part II Participants with Untreated Diffuse Large B-Cell Lymphoma and the Use of Either Rituximab or Obinutuzumab for Cycle 1. Participants with untreated DLBCL may be offered the choice of consolidation therapy with glofitamab (to be administered for up to 6 cycles). Abbreviations: C=cycle; CHOP=cyclophosphamide (C), doxorubicin (H), vincristine (O), and prednisone (P); CR=complete response; d/c=discontinued; D=day; DLT=dose-limiting toxicity; EOInd=end of induction; EOT=end of treatment; G=obinutuzumab; IMC=Internal Monitoring Committee; IV=intravenously; M=month; PR=partial response; Q2M=every 2 months; Q3M=every 3 months; R=rituximab; SD=stable disease.

DETAILED DESCRIPTION OF THE INVENTION

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

II. Definitions

Terms are used herein as generally used in the art, unless otherwise defined in the following.

CD20 (also known as B-lymphocyte antigen CD20, B-lymphocyte surface antigen B1, Leu-16, Bp35, BM5, and LF5; the human protein is characterized in UniProt database entry P11836) is a hydrophobic transmembrane protein with a molecular weight of approximately 35 kD expressed on pre-B and mature B lymphocytes (Valentine, M. A. et al., J. Biol. Chem. 264 (1989) 11282-11287; Tedder, T. F., et al., Proc. Natl. Acad. Sci. U.S.A. 85 (1988) 208-212; Stamenkovic, I., et al., J. Exp. Med. 167 (1988) 1975-1980; Einfeld, D. A., et al., EMBO J. 7 (1988) 711-717; Tedder, T. F., et al., J. Immunol. 142 (1989) 2560-2568). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The term "CD20" as used herein, refers to any native CD20 from any vertebrate source, including mammals such as primates (e.g., humans) and rodents (e.g., mice and rats), unless otherwise indicated. The term encompasses "full-length," unprocessed CD20 as well as any form of CD20 that results from processing in the cell. The term also encompasses naturally occurring variants of CD20, e.g., splice variants or allelic variants. In one embodiment, CD20 is human CD20.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., Blood 103 (2004) 2738-2743; Cragg et al., Blood 101 (2003) 1045-1052, Klein et al., mAbs 5 (2013), 22-33, and summarized in Table 1 below.

TABLE 1

Properties of type 1 and type II anti-CD20 antibodies

| type I anti-CD20 antibodies | type II anti-CD20 antibodies |
|---|---|
| Bind class I CD20 epitope | Bind class II CD20 epitope |
| Localize CD20 to lipid rafts | Do not localize CD20 to lipid rafts |
| High CDC * | Low CDC * |
| ADCC activity * | ADCC activity * |
| Full binding capacity to B cells | Approx, half binding capacity to B cells |
| Weak homotypic aggregation | Homotypic aggregation |
| Low cell death induction | Strong cell death induction |

* if $IgG_1$ isotype

Examples of type II anti-CD20 antibodies include e.g., obinutuzumab (GA101; GAZYVA®), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1 .

Examples of type I anti-CD20 antibodies include e.g., rituximab, ofatumumab, veltuzumab, ocaratuzumab, ocrelizumab, PRO131921, ublituximab, HI47 IgG3 (ECACC, hybridoma), 2C6 IgG1 (as disclosed in WO 2005/103081), 2F2 IgG1 (as disclosed in WO 2004/035607 and WO 2005/103081) and 2H7 IgG1 (as disclosed in WO 2004/056312).

"CD3" refers to any native CD3 from any vertebrate source, including mammals such as primates (e.g., humans), non-human primates (e.g., cynomolgus monkeys) and rodents (e.g., mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no.

P07766 (version 144), or NCBI (www.ncbi.nlm.nih.gov/) RefSeq NP_000724.1. The amino acid sequence of cynomolgus [*Macaca fascicularis*] CD3ε is shown in NCBI GenBank no. BAB71849.1.

The terms "anti-CD20/anti-CD3 bispecific antibody" and "a bispecific antibody that binds to CD20 and CD3" can be used interchangeably and refer to a bispecific antibody that is capable of binding both CD20 and CD3 with sufficient affinity such that the antibody is useful as a diagnostic and/or therapeutic agent in targeting CD20 and/or CD3. In one embodiment, the extent of binding of an anti-CD20/anti-CD3 bispecific antibody to an unrelated, non-CD3 protein and/or non-CD20 protein is less than about 10% of the binding of the antibody to CD3 and/or CD20 as measured, e.g., by a radioimmunoassay (RIA). In certain embodiments, an anti-CD20/anti-CD3 bispecific antibody has a dissociation constant ($K_D$) of ≤1 M, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M) to CD20 and/or CD3. In certain embodiments, an anti-CD20/anti-CD3 bispecific antibody binds to an epitope of CD3 that is conserved among CD3 from different species and/or an epitope of CD20 that is conserved among CD20 from different species. One example of an anti-CD20/anti-CD3 bispecific antibody is glofitamab.

As used herein, the term "release of cytokines" or "cytokine release" is synonymous with "cytokine storm" or "cytokine release syndrome" (abbreviated as "CRS"), and refers to an increase in the levels of cytokines, particularly tumor necrosis factor alpha (TNF-α), interferon gamma (IFN-γ), interleukin-6 (IL-6), interleukin-10 (IL-10), interleukin-2 (IL-2) and/or interleukin-8 (IL-8), in the blood of a subject during or shortly after (e.g. within 1 day of) administration of a therapeutic agent, resulting in adverse symptoms. Cytokine release is a type of infusion-related reaction (IRR), which are common adverse drug reactions to therapeutic agent and timely related to administration of the therapeutic agent. IRRs typically occur during or shortly after an administration of the therapeutic agent, i.e., typically within 24 hours after infusion, predominantly at the first infusion. In some instances, e.g., after the administration of CAR-T cells, CRS can also occur only later, e.g., several days after administration upon expansion of the CAR-T cells. The incidence and severity typically decrease with subsequent infusions. Symptoms may range from symptomatic discomfort to fatal events, and may include fever, chills, dizziness, hypertension, hypotension, dyspnea, restlessness, sweating, flushing, skin rash, tachycardia, tachypnea, headache, tumor pain, nausea, vomiting and/or organ failure.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering, e.g., the binding characteristics of an Fc region, non-conservative amino acid substitutions, i.e., replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc region to glycine can be indicated as 329G, G329, $G_{329}$, P329G, or Pro329Gly.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art. A particular method for measuring affinity is Surface Plasmon Resonance (SPR).

As used herein, the term "antigen binding moiety" refers to a polypeptide molecule that specifically binds to an antigenic determinant. In one embodiment, an antigen binding moiety is able to direct the entity to which it is attached (e.g., a cytokine or a second antigen binding moiety) to a target site, for example to a specific type of tumor cell or tumor stroma bearing the antigenic determinant. Antigen binding moieties include antibodies and fragments thereof as further defined herein. Preferred antigen binding moieties include an antigen binding domain of an antibody, comprising an antibody heavy chain variable region and an antibody light chain variable region. In certain embodiments, the antigen binding moieties may include antibody constant regions as further defined herein and known in the art. Useful heavy chain constant regions include any of the five isotypes: α, δ, ε, γ, or μ. Useful light chain constant regions include any of the two isotypes: κ and λ.

By "specifically binds" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g., surface plasmon resonance technique (analyzed on a BIACORE® instrument) (Liljeblad et al., *Glyco J* 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 M, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e., complete abolishment of the interaction. Conversely, "increased binding" refers to an increase in binding affinity for the respective interaction.

As used herein, the term "antigen binding molecule" refers in its broadest sense to a molecule that specifically binds an antigenic determinant. Examples of antigen binding molecules are immunoglobulins and derivatives, e.g., fragments, thereof.

As used herein, the term "antigenic determinant" is synonymous with "antigen" and "epitope," and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, free in blood serum, and/or in the extracellular matrix (ECM). The proteins referred to as antigens herein (e.g., CD3) can be any native form the proteins from any vertebrate source, including mammals such as primates (e.g., humans) and rodents (e.g., mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g., splice variants or allelic variants. An exemplary human protein useful as antigen is CD3, particularly the epsilon subunit of CD3 (see UniProt no. P07766 (version 130), NCBI RefSeq no. NP_000724.1, for the human sequence; or UniProt no. Q95LI5 (version 49), NCBI GenBank no. BAB71849.1, for the cynomolgus [*Macaca fascicularis*] sequence). In certain embodiments the T cell activating bispecific antigen binding molecule of the invention binds to an epitope of CD3 or a target cell antigen that is conserved among the CD3 or target cell antigen from different species.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g., scFv), and multispecific antibodies formed from antibody fragments. The term "antibody fragment" as used herein also encompasses single-domain antibodies.

The term "immunoglobulin molecule" refers to a protein having the structure of a naturally occurring antibody. For example, immunoglobulins of the IgG class are heterotetrameric glycoproteins of about 150,000 Daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε (IgE), γ (IgG), or μ (IgM), some of which may be further divided into subclasses, e.g., $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., *Kuby Immunology*, $6^{th}$ ed., W.H. Freeman and Co., page 91 (2007). A single VH or VL domain may be sufficient to confer antigen binding specificity.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain.

Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991 (see also above). A "subunit" of an Fc domain as used herein refers to one of the two polypeptides forming the dimeric Fc domain, i.e., a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e., the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g., antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the term "effector cells" refers to a population of lymphocytes that display effector moiety receptors, e.g., cytokine receptors, and/or Fc receptors on their surface through which they bind an effector moiety, e.g., a cytokine, and/or an Fc region of an antibody and contribute to the destruction of target cells, e.g., tumor cells. Effector cells may for example mediate cytotoxic or phagocytic effects. Effector cells include, but are not limited to, effector T cells such as $CD8^+$ cytotoxic T cells, $CD4^+$ helper T cells, γδ T cells, NK cells, lymphokine-activated killer (LAK) cells and macrophages/monocytes.

As used herein, the terms "engineer, engineered, engineering," are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells.

Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g., a host cell that has been manipulated to express increased levels of one or more polypeptides having β(1,4)-N-acetylglucosaminyltransferase III (GnTIII) activity), a "host cell having increased ManII activity" (e.g., a host cell that has been manipulated to express increased levels of one or more polypeptides having α-mannosidase II (ManII) activity), or a "host cell having decreased α(1,6) fucosyltransferase activity" (e.g., a host cell that has been manipulated to express decreased levels of α(1,6) fucosyltransferase).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate proteins used for the present invention. In one embodiment, the host cell is engineered to allow the production of an antibody with modified oligosaccharides. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched $GlcNAcMan_5GlcNAc_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

By "antibody having increased/reduced antibody dependent cell-mediated cytotoxicity (ADCC)" is meant an antibody having increased/reduced ADCC as determined by any suitable method known to those of ordinary skill in the art. One accepted in vitro ADCC assay is as follows: 1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;
3) the assay is carried out according to following protocol:
i) the PBMCs are isolated using standard density centrifugation procedures and are suspended at $5\times10^6$ cells/ml in RPMI cell culture medium;
ii) the target cells are grown by standard tissue culture methods, harvested from the exponential growth phase with a viability higher than 90%, washed in RPMI cell culture medium, labeled with 100 micro-Curies of $^{51}Cr$, washed twice with cell culture medium, and resuspended in cell culture medium at a density of $10^5$ cells/ml;
iii) 100 microliters of the final target cell suspension above are transferred to each well of a 96-well microtiter plate;
iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above); vi) for the spontaneous release (SR) controls, 3 additional wells in the plate containing the labeled target cells, receive 50 microliters of RPMI cell culture medium instead of the antibody solution (point iv above);
vii) the 96-well microtiter plate is then centrifuged at 50×g for 1 minute and incubated for 1 hour at 4° C.;
viii) 50 microliters of the PBMC suspension (point i above) are added to each well to yield an effector:target cell ratio of 25:1 and the plates are placed in an incubator under 5% $CO_2$ atmosphere at 37° C. for 4 hours;
ix) the cell-free supernatant from each well is harvested and the experimentally released radioactivity (ER) is quantified using a gamma counter;
x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased/reduced ADCC" is defined as either an increase/reduction in the maximum percentage of specific lysis observed within the antibody concentration range tested above, and/or a reduction/increase in the concentration of antibody required to achieve one half of the maximum percentage of specific lysis observed within the antibody concentration range tested above. The increase/reduction in ADCC is relative to the ADCC, measured with the above assay, mediated by the same antibody, produced by the same type of host cells, using the same standard production, purification, formulation and storage methods, which are known to those skilled in the art, but that has not been engineered.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the terms "first", "second", "third" etc. with respect to antigen binding moieties or domains, are used for convenience of distinguishing when there is more than one of each type of moiety or domain. Use of these terms is not intended to confer a specific order or orientation unless explicitly so stated.

The terms "multispecific" and "bispecific" mean that the antigen binding molecule is able to specifically bind to at least two distinct antigenic determinants. Typically, a bispecific antigen binding molecule comprises two antigen binding sites, each of which is specific for a different antigenic determinant. In certain embodiments a bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e., one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3. In a particular embodiment the activating T cell antigen is CD3, particularly the epsilon subunit of CD3 (see UniProt no. P07766 (version 130), NCBI RefSeq no. NP_000724.1, for the human sequence; or UniProt no. Q95LI5 (version 49), NCBI GenBank no. BAB71849.1, for the cynomolgus [*Macaca fascicularis*] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating therapeutic agents used in the present invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma.

In a particular embodiment, the target cell antigen is CD20, particularly human CD20 (see UniProt no. P11836).

A "B-cell antigen" as used herein refers to an antigenic determinant presented on the surface of a B lymphocyte, particularly a malignant B lymphocyte (in that case the antigen also being referred to as "malignant B-cell antigen").

A "T-cell antigen" as used herein refers to an antigenic determinant presented on the surface of a T lymphocyte, particularly a cytotoxic T lymphocyte.

A "Fab molecule" refers to a protein consisting of the VH and CH1 domain of the heavy chain (the "Fab heavy chain") and the VL and CL domain of the light chain (the "Fab light chain") of an immunoglobulin.

By "chimeric antigen receptor" or "CAR" is meant a genetically engineered receptor protein comprising an antigen binding moiety, e.g., a single-chain variable fragment (scFv) of a targeting antibody, a transmembrane domain, an intracellular T-cell activating signaling domain (e.g., the CD3 zeta chain of the T-cell receptor) and optionally one or more intracellular co-stimulatory domains (e.g., of CD28, CD27, CD137 (4-1BB), Ox40). CARs mediate antigen recognition, T cell activation, and in the case of second-generation CARs—costimulation to augment T cell functionality and persistence. For a review see, e.g., Jackson et al., Nat Rev Clin Oncol (2016) 13, 370-383.

By "fused" is meant that the components (e.g., a Fab molecule and an Fc domain subunit) are linked by peptide bonds, either directly or via one or more peptide linkers.

An "effective amount" of an agent refers to the amount that is necessary to result in a physiological change in the cell or tissue to which it is administered.

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

By "therapeutic agent" is meant an active ingredient, e.g., of a pharmaceutical composition, that is administered to a subject in an attempt to alter the natural course of a disease in the subject being treated, and can be performed either for prophylaxis or during the course of clinical pathology. An "immunotherapeutic agent" refers to a therapeutic agent that is administered to a subject in an attempt to restore or enhance the subject's immune response, e.g., to a tumor.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

The term "package insert" or "instructions for use" is used to refer to instructions customarily included in commercial packages of therapeutic products that contain information about the indications, usage, dosage, administration, combination therapy, contraindications and/or warnings concerning the use of such therapeutic products.

The term "combination treatment" noted herein encompasses combined administration (where two or more therapeutic agents are included in the same or separate formulations), and separate administration, in which case, administration of an antibody as reported herein can occur prior to, simultaneously, and/or following, administration of the additional therapeutic agent or agents, preferably an antibody or antibodies.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CHi is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e., comprising a heavy chain composed of the heavy chain variable and constant domains (VH-CH1, in N- to C-terminal direction), and a light chain composed of the light chain variable and constant domains (VL-CL, in N- to C-terminal direction).

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term "nucleic acid molecule" refers to any one or more nucleic acid segments, e.g., DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g., ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The term “about” as used herein refers to the usual error range for the respective value readily known to the skilled person in this technical field. Reference to “about” a value or parameter herein includes (and describes) embodiments that are directed to that value or parameter per se.

By “B cell proliferative disorder” is meant a disease wherein the number of B cells in a patient is increased as compared to the number of B cells in a healthy subject, and particularly wherein the increase in the number of B cells is the cause or hallmark of the disease. A “CD20-positive B cell proliferative disorder” is a B cell proliferative disorder wherein B-cells, particularly malignant B-cells (in addition to normal B-cells), express CD20.

Exemplary B cell proliferation disorders include Non-Hodgkin’s lymphoma (NHL), diffuse large B-cell lymphoma (DLBCL; relapsed/refractory (R/R) DLBCL not otherwise specified (NOS), high grade B cell lymphoma (HGBCL), primary mediastinal large B-cell lymphoma (PMBCL), DLBCL arising from FL [transformed FL; trFL]; Richter’s transformation; follicular lymphoma (FL), including Grade 1-3b FL; mantle-cell lymphoma (MCL), marginal zone lymphoma (MZL), including splenic, nodal or extra-nodal MZL. In one embodiment the CD20-positive B cell proliferative disorder is a relapsed or refractory NHL (e.g., a relapsed or refractory DLBCL, a relapsed or refractory FL, or a relapsed or refractory MCL). “Previously untreated NHL” or “treatment naïve NHL” (e.g., previously untreated DLBCL or treatment naïve DLBCL) refers to previously untreated disease. In one embodiment the method of treatment described herein is a first line treatment. In one embodiment, the method of treatment is for subjects with histologically confirmed previously untreated DLBCL (international prognostics indicator (IPI) 2-5), that is expected to express CD20.

“Refractory disease” is defined as no complete remission to first line therapy. In one embodiment refractory disease defined as no response to or relapse within 6 months of prior therapy. In one embodiment refractory disease is characterized by one or more of the following: Progressive disease (PD) as best response to first line therapy, Stable disease (SD) as best response after at least 4 cycles of first line therapy (e.g., 4 cycles of rituximab, cyclophosphamide, doxorubicin hydrochloride (hydroxydaunorubicin), vincristine sulfate (Oncovin), and prednisone, also abbreviated as R-CHOP) or Partial response (PR) as best response after at least 6 cycles, and biopsy-proven residual disease or disease progression after the partial response. “Relapsed disease” is defined as complete remission to first line therapy. In one embodiment disease relapse is proven by biopsy. In one embodiment, patients have relapsed after or failed to respond to at least one prior systemic treatment regimen (including at least one prior regimen containing an anti CD20-directed therapy, e.g., rituximab or obinutuzumab). In one embodiment, patients have relapsed after or failed to respond to at least two prior systemic treatment regimens (including at least one prior regimen containing anthracycline, and at least one containing an anti CD20-directed therapy).

An “individual” or “subject” is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the individual or subject is a human.

As used herein, “treatment” (and grammatical variations thereof such as “treat” or “treating”) refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods of the invention are used to delay development of a disease or to slow the progression of a disease.

As used herein, “delaying progression” of a disorder or disease means to defer, hinder, slow, retard, stabilize, and/or postpone development of the disease or disorder (e.g., a CD20-positive B cell proliferative disorder, e.g., NHL, e.g., DLBCL). This delay can be of varying length of time, depending on the history of the disease and/or individual being treated. As is evident to one skilled in the art, a sufficient or significant delay can, in effect, encompass prevention, in that the individual does not develop the disease. For example, in a late-stage cancer, development of central nervous system (CNS) metastasis, may be delayed.

By “reduce” or “inhibit” is meant the ability to cause an overall decrease, for example, of 20%, 30%, 40%, 50%, 60%, 70%, 75%, 80%, 85%, 90%, 95%, or greater. For clarity the term also includes reduction to zero (or below the detection limit of the analytical method), i.e., complete abolishment or elimination. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the step-up dosing regimen of the invention relative to unchanging, preset dosing with the target dose of the anti-CD20/anti-CD3 bispecific antibody. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP). In other embodiments reduce or inhibit can refer to the symptoms of the CD20-positive B cell proliferative disorder being treated (e.g., an NHL (e.g., a DLBCL), an FL (e.g., a relapsed and/or refractory FL or a transformed FL), an MCL, a high-grade B cell lymphoma, or a PMLBCL), the presence or size of metastases, or the size of the primary tumor.

As used herein, “administering” is meant a method of giving a dosage of a compound (e.g., an anti-CD20/anti-CD3 bispecific antibody) or a composition (e.g., a pharmaceutical composition, e.g., a pharmaceutical composition including an anti-CD20/anti-CD3 bispecific antibody) to a subject. The compounds and/or compositions utilized in the methods described herein can be administered intravenously (e.g., by intravenous infusion).

A "fixed" or "flat" dose of a therapeutic agent (e.g., a bispecific antibody) herein refers to a dose that is administered to a patient without regard for the weight or body surface area (BSA) of the patient. The fixed or flat dose is therefore not provided as a mg/kg dose or a mg/$m^2$ dose, but rather as an absolute amount of the therapeutic agent (e.g., mg).

A "target dose" herein refers to the dose of the anti-CD20/anti-CD3 bispecific antibody that achieves therapeutic effect, i.e., achieves the desired clinical efficacy. For glofitamab a possible target dose is 16 mg or 30 mg. In a preferred embodiment, for glofitamab the target dose is 30 mg.

An "unchanging or preset dosing with target dose" and a "treatment regimen without a step-up dosing regimen" refers to a dosing schedule that uses the same dosage in the first and second dosing cycles and optionally also any subsequent treatment cycle, as opposed to step-up dosing, which uses lower dosages in the first few treatment cycles and only reaches the target dose in the second or in a later treatment cycle.

The terms "treatment cycle," "dosing cycle," or "cycle" (abbreviated: "C") as used herein mean a course of one or more doses of the anti-CD20/anti-CD3 bispecific antibody that is repeated on a regular schedule, optionally with periods of rest (no treatment) in between. In one aspect of the invention, the first treatment or dosing cycle comprises a first and a second dose of the anti-CD20/anti-CD3 bispecific antibody, followed by a period of rest. In one such embodiment, the first treatment or dosing cycle comprises a first dose of the anti-CD20/anti-CD3 bispecific antibody on day 1 of the first dosing cycle, and a second dose of the anti-CD20/anti-CD3 bispecific antibody on day 8 of the first dosing cycle, followed by 12 days of rest. In one embodiment the second and any subsequent dosing cycles each comprises one dose of the anti-CD20/anti-CD3 bispecific antibody given at day 1 of that dosing cycle, followed by 20 days of rest. In one embodiment, one treatment or dosing cycle comprises 21 days. The treatment or dosing cycle comprising one or more doses of the anti-CD20/anti-CD3 bispecific antibody may further comprise one or more dosages of one or more other therapeutic agents, such as e.g., an anti-CD20 antibody, in particular obinutuzumab. The treatment schedule according to the invention may comprise 2 or more treatment or dosing cycles, or 3, 4, 5, 6, 7, 8, 9, 10, 11, in particular 12 treatment or dosing cycles.

"Individual response" or "response" can be assessed using any endpoint indicating a benefit to the subject, including, without limitation, (1) inhibition, to some extent, of disease progression (e.g., progression of a CD20-positive B cell proliferative disorder, e. g., a non-Hodgkin's lymphoma (NHL)); including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e., reduction, slowing down or complete stopping) of metastasis; (5) relief, to some extent, of one or more symptoms associated with the CD20-positive B cell proliferative disorder, e.g., a B cell proliferative disorder; (6) increase or extend in the length of survival, including overall survival and progression-free survival; and/or (9) decreased mortality at a given point of time following treatment.

As used herein, "complete response" or "CR" refers to disappearance of all target lesions. In one embodiment, standard NHL response criteria are assessed for determining CR. (Lugano Criteria, Cheson et al. *J Clin Oncol.* 2014 Sep. 20; 32(27): 3059-3067.). CR can be determined by PET-CT ("complete metabolic response" or "CMR") or CT ("complete radiologic response"). In some embodiments, complete response (CR) can be used interchangeably with "complete metabolic response" or "CMR". The Lugano Criteria for assessing complete response vs partial response by PET-CT-based (complete metabolic response) and CT-based (complete radiologic response) are detailed below in Table 2.

TABLE 2

Lugano Response Criteria for Malignant Lymphoma (Cheson et al. 2014)

| Response and Site Complete | PET-CT-Based Response Complete metabolic response | CT-Based Response Complete radiologic response (all of the following) |
|---|---|---|
| Lymph nodes and extralymphatic sites | Score 1, 2, or 3 with or without a residual mass on Deauville 5-point scale It is recognized that in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic | Target nodes/nodal masses must regress to ≤1.5 cm in longest transverse diameter No extralymphatic sites of disease |

TABLE 2-continued

| Lugano Response Criteria for Malignant Lymphoma (Cheson et al. 2014) | | |
|---|---|---|
| Non-measured lesion | Not applicable | Absent |
| Organ enlargement | Not applicable | Regress to normal |
| New lesions | None | None |
| Bone marrow | No evidence of FDG-avid disease in marrow | Normal by morphology; if indeterminate, IHC negative |
| Partial | Partial metabolic response | Partial remission (all of the following) |
| Lymph nodes and extralymphatic sites | Score 4 or 5 with reduced uptake compared with baseline and residual mass(es) of any size<br>At interim, these findings suggest responding disease<br>At end of treatment, these findings indicate residual disease | ≥50% decrease in SPD of up to 6 target measurable nodes and extranodal sites<br>When a lesion is too small to measure on CT, assign 5 × 5 mm as the default value<br>When no longer visible, 0 × 0 mm<br>For a node >5 × 5 mm, but smaller than normal, use actual measurement for calculation |
| Non-measured lesion | Not applicable | Absent/normal, regressed, but no increase |
| Organ enlargement | Not applicable | Spleen must have regressed by >50% in length beyond normal |
| New lesions | None | Non |

"Duration of complete response" (DOCR) is defined as the time from the initial occurrence of a documented CR until documented disease progression or death due to any cause, whichever occurs first. In one embodiment, DOCR is assessed based on the Lugano Classification (Cheson et al. *J Clin Oncol.* 2014 Sep. 20; 32(27): 3059-3067.).

"Duration of objective response" (DOR) is defined as the first occurrence of a documented, objective response until the time of disease progression, relapse or death from any cause. In one embodiment, DOR is assessed based on the Lugano Classification (Cheson et al. *J Clin Oncol.* 2014 Sep. 20; 32(27): 3059-3067.).

"Progression-free survival" (PFS) is defined as the time from the first treatment with the anti-CD20/anti-CD3 bispecific antibody to the first occurrence of disease progression or death from any cause, whichever occurs first. In one embodiment, PFS is assessed based on the Lugano Classification (Cheson et al. *J Clin Oncol.* 2014 Sep. 20; 32(27): 3059-3067.).

"Overall survival" (OS) is defined as time from the first treatment with the anti-CD20/anti-CD3 bispecific antibody to the date of death from any cause.

"Time to first overall response" (TFOR) is defined as time from treatment start to first documented response. In one embodiment, TFOR is evaluated based on the Lugano Classification (Cheson et al. J Clin Oncol. 2014 Sep. 20; 32(27): 3059-3067.).

"Time to first complete response" (TFCR) defined as time from treatment start to first documented complete response. In one embodiment, TFCR is evaluated based on the Lugano Classification (Cheson et al. *J Clin Oncol.* 2014 Sep. 20; 32(27): 3059-3067.).

As used herein, "objective response rate" refers to the sum of patients with a complete response [CR], patients with a partial response [PR]) and patients with stable disease (SD) in a patient population. In one embodiment, objective response rate is evaluated based on the Lugano Classification (Cheson et al. *J Clin Oncol.* 2014 Sep. 20; 32(27): 3059-3067.).

The "overall response rate" (ORR) is defined as the sum of partial response (PR) rate and complete response (CR) rate. In one embodiment, overall response is evaluated based on the Lugano Classification (Cheson et al. *J Clin Oncol.* 2014 Sep. 20; 32(27): 3059-3067.).

A "high-risk subject" is a subject who has progression of disease within 24 months of frontline treatment or is refractory to multiple agent classes. In one embodiment, high-risk subjects include subjects who: (a) have relapsed after or are refractory to at least two prior therapies; (b) have relapsed after or are refractory to treatment with a phosphoinositide 3-kinase (PI3K) inhibitor; (c) experience progression of disease within 24 months of frontline treatment; and/or (d) have lesions, wherein the sum of the product of the lesion diameters is ≥3,000 mm$^2$.

III. Anti-CD20/Anti-CD3 Bispecific Antibodies

The present invention provides new dosages and combination therapies for anti-CD20/anti-CD3 bispecific antibodies. In one embodiment, the anti-CD20/antiCD3 bispecific antibody is a monoclonal antibody. In one embodiment, the anti-CD20/anti-CD3 bispecific antibody is a polyclonal antibody. In one embodiment the anti-CD20/anti-CD3 bispecific antibody is a human antibody. In one embodiment, the anti-CD20/anti-CD3 bispecific antibody is a humanized antibody. In one embodiment the anti-CD20/anti-CD3 bispecific antibody is a chimeric antibody. In one embodiment the anti-CD20/anti-CD3 bispecific antibody is a full-length antibody. In one embodiment the anti-CD20/anti-CD3 bispecific antibody is an IgG-class antibody, particularly an IgG1 subclass antibody. In one embodiment, the anti-CD20/anti-CD3 bispecific antibody is a recombinant antibody.

In certain embodiments, the anti-CD20/anti-CD3 bispecific antibody comprises an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacol-*

*ogy of Monoclonal Antibodies, vol.* 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. In one embodiment, the antibody fragment is a Fab fragment or a scFv fragment.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

In certain embodiments, the anti-CD20/anti-CD3 bispecific antibody is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, the anti-CD20/anti-CD3 bispecific antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, the anti-CD20/anti-CD3 bispecific antibody is a human antibody.

Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al, *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Binding domains comprised in the anti-CD20/anti-CD3 bispecific antibody may be isolated by screening combinatorial libraries for binding moieties with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al., *EMBO J,* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Techniques for making bispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The anti-CD20/anti-CD3 bispecific antibody herein also includes a "Dual Acting FAb" or "DAF" comprising an antigen binding site that binds to two different antigens (see, US 2008/0069820, for example).

"Crossmab" antibodies are also included herein (see e.g., WO2009080251, WO2009080252, WO2009080253, WO2009080254).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell. As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

In certain embodiments, the anti-CD20/anti-CD3 bispecific antibody may be further modified to contain additional nonproteinaceous moieties that are known in the art and readily available. The moieties suitable for derivatization of the anti-CD20/anti-CD3 bispecific antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The anti-CD20/anti-CD3 bispecific antibody may also be conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the anti-CD20/anti-CD3 bispecific antibody comprises an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16 :358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12 :1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, the anti-CD20/anti-CD3 bispecific antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the anti-CD20/anti-CD3 bispecific antibody is conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of the anti-CD20/anti-CD3 bispecific antibody and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of a radionucleotide to an antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

In one embodiment, the anti-CD20/anti-CD3 bispecific antibody is indicated for the treatment of cancer. In one embodiment, cancer is a B-cell proliferative disorder. In one embodiment, the cancer is a CD20-positive B-cell proliferative disorder. In one embodiment, the cancer is a non-Hodgkin's lymphoma (NHL). In one embodiment the NHL is a diffuse large B cell lymphoma (DLBCL), a high-grade B cell lymphoma (HGBCL), a DLBCL arising from FL [transformed FL; trFL] a primary mediastinal large B-cell lymphoma (PMBCL), or marginal zone lymphoma (MZL). MZL can be categorized as splenic, nodal and extra-nodal MZL. In one embodiment the DLBCL is a Richter's transformation. In one embodiment the NHL is a mantle cell lymphoma (MCL). In one embodiment the NHL is a Grade 1-3a Follicular Lymphoma (FL). In one embodiment the CD20-positive B cell proliferative disorder is a relapsed or refractory B cell proliferative disorder. In one embodiment the relapsed or refractory B cell proliferative disorder is relapsed or refractory NHL (e.g., a relapsed or refractory DLBCL, a relapsed or refractory FL, or a relapsed or refractory MCL). In one embodiment the anti-CD20/anti-CD3 bispecific antibody, e.g., glofitamab, is indicated for the treatment of relapsed or refractory diffuse large B cell lymphoma (DLBCL), DLBCL arising from follicular lymphoma, and high-grade B cell lymphoma (HGBCL), after two or more lines of systemic therapy.

In one embodiment the anti-CD20/anti-CD3 bispecific antibody, e.g., glofitamab, is indicated for the treatment of adult patients with relapsed or refractory large B-cell lymphoma after two or more lines of systemic therapy, including diffuse large B-cell lymphoma (DLBCL) not otherwise specified, DLBCL arising from follicular lymphoma, high-grade B-cell lymphoma (HGBCL), and primary mediastinal B-cell lymphoma (PMBCL).

In one embodiment the anti-CD20/anti-CD3 bispecific antibody, e.g., glofitamab, is indicated for the treatment of relapsed or refractory follicular lymphoma (FL), after two or more lines of systemic therapy.

In one embodiment the anti-CD20/anti-CD3 bispecific antibody, e.g., glofitamab, is indicated for the treatment of adult patients with relapsed or refractory follicular lymphoma (FL) after two or more lines of systemic therapy.

In one embodiment the anti-CD20/anti-CD3 bispecific antibody, e.g., glofitamab, is indicated for the treatment of relapsed or refractory mantle cell lymphoma (MCL), after two or more lines of systemic therapy.

In one embodiment the anti-CD20/anti-CD3 bispecific antibody, e.g., glofitamab, is indicated for the treatment of adult patients with relapsed or refractory mantle cell lymphoma (MCL) after two or more lines of systemic therapy.

In one embodiment the anti-CD20/anti-CD3 bispecific antibody, e.g., glofitamab, is indicated for the treatment of relapsed or refractory mantle cell lymphoma (MCL), after at least one line of systemic therapy that includes a Bruton tyrosine kinase (BTK) inhibitor.

In one embodiment the anti-CD20/anti-CD3 bispecific antibody, e.g., glofitamab, is indicated for the treatment of adult patients with relapsed or refractory mantle cell lymphoma (MCL) after at least one line of systemic therapy that includes a Bruton tyrosine kinase (BTK) inhibitor.

In one embodiment the anti-CD20/anti-CD3 bispecific antibody, e.g., glofitamab, is indicated for the treatment of previously untreated DLBCL, e.g., in combination with an anti-CD20 antibody, cyclophosphamide, doxorubicin and a corticosteroid. In one embodiment, the corticosteroid is prednisone and the anti-CD20 antibody is rituximab In one embodiment, the anti-CD20/anti-CD3 bispecific antibody specifically binds to CD3C.

In one embodiment, the anti-CD20/anti-CD3 bispecific antibody can compete for binding with antibody H2C (PCT publication no. WO2008/119567), antibody V9 (Rodrigues et al., *Int J Cancer Suppl* 7, 45-50 (1992) and U.S. Pat. No. 6,054,297), antibody FN18 (Nooij et al., *Eur J Immunol* 19, 981-984 (1986)), antibody SP34 (Pessano et al., *EMBO J* 4, 337-340 (1985)), antibody OKT3 (Kung et al., *Science* 206, 347-349 (1979)), antibody WT31 (Spits et al., *J Immunol* 135, 1922 (1985)), antibody UCHT1 (Burns et al., *J Immunol* 129, 1451-1457 (1982)), antibody 7D6 (Coulie et al., *Eur J Immunol* 21, 1703-1709 (1991)) or antibody Leu-4. In some embodiments, the anti-CD20/anti-CD3 bispecific antibody may also comprise an antigen binding moiety that specifically binds to CD3 as described in WO 2005/040220, WO 2005/118635, WO 2007/042261, WO 2008/119567, WO 2008/119565, WO 2012/162067, WO 2013/158856, WO 2013/188693, WO 2013/186613, WO 2014/110601, WO 2014/145806, WO 2014/191113, WO 2014/047231, WO 2015/095392, WO 2015/181098, WO 2015/001085, WO 2015/104346, WO 2015/172800, WO 2016/020444, or WO 2016/014974.

In some embodiments, the anti-CD20/anti-CD3 bispecific antibody may comprise an antibody or an antigen binding moiety from rituximab, obinutuzumab ocrelizumab, ofatumumab, ocaratuzumab, veltuzumab, and ublituximab.

In one embodiment, the anti-CD20/anti-CD3 bispecific antibody is XmAb® 13676. In one embodiment, the anti-CD20/anti-CD3 bispecific antibody is REGN1979. In one embodiment, the anti-CD20/anti-CD3 bispecific antibody is FBTA05 (Lymphomun). In a preferred embodiment, the anti-CD20/anti-CD3 bispecific antibody is glofitamab.

In some embodiments, the anti-CD20/anti-CD3 bispecific antibody may comprise a generic, biosimilar or non-comparable biologic version of an antibody, named herein.

In one embodiment, the anti-CD20/anti-CD3 bispecific antibody comprises at least one antigen binding domain that specifically binds to CD20, comprising a heavy chain variable region comprising:

(i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising:

(i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6.

In one embodiment, anti-CD20/anti-CD3 bispecific antibody comprises at least one antigen binding domain that specifically binds to CD20, comprising a heavy chain variable region sequence that is at least 80%, 85%, 90%, 95%, 96%, 97%, 98%, or 99% identical to of SEQ ID NO: 7 and a light chain variable region sequence that is at least 80%, 85%, 90%, 95%, 96%, 97%, 98%, or 99% identical to the sequence of SEQ ID NO: 8. In a further embodiment, the anti-CD20/anti-CD3 bispecific antibody comprises at least one antigen binding domain that specifically binds to CD20 comprising the heavy chain variable region sequence of SEQ ID NO: 7 and the light chain variable region sequence of SEQ ID NO: 8.

In one embodiment, the anti-CD20/anti-CD3 bispecific antibody comprises at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11;

and a light chain variable region comprising:

(i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

In one embodiment, anti-CD20/anti-CD3 bispecific antibody comprises at least one antigen binding domain that specifically binds to CD3, comprising a heavy chain variable region sequence that is at least 80%, 85%, 90%, 95%, 96%, 97%, 98%, or 99% identical to of SEQ ID NO: 15 and a light chain variable region sequence that is at least 80%, 85%, 90%, 95%, 96%, 97%, 98%, or 99% identical to the sequence of SEQ ID NO: 16. In a further embodiment, the anti-CD20/anti-CD3 bispecific antibody comprises at least one antigen binding domain that specifically binds to CD3 comprising the heavy chain variable region sequence of SEQ ID NO: and the light chain variable region sequence of SEQ ID NO: 16. In one embodiment, the anti-CD20/anti-CD3 bispecific antibody comprises a) at least one antigen binding domain that specifically binds to CD20 comprising a heavy chain variable region comprising (i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising (i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and b) at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11; and a light chain variable region comprising (i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and (ii) at least one antigen binding domain that specifically binds to CD3 comprising the heavy chain variable region sequence of SEQ ID NO: 15 and the light chain variable region sequence of SEQ ID NO: 16.

In one embodiment, the antigen binding domain that specifically binds to CD3 of the anti-CD20/anti-CD3 bispecific antibody is an antibody fragment, particularly a Fab molecule or a scFv molecule, more particularly a Fab molecule. In a particular embodiment, the antigen binding domain that specifically binds to CD3 of the anti-CD20/anti-CD3 bispecific antibody is a crossover Fab molecule wherein the variable domains or the constant domains of the Fab heavy and light chain are exchanged (i.e., replaced by each other).

In one embodiment, the anti-CD20/anti-CD3 bispecific antibody comprises at least one antigen binding domain that specifically binds to CD20, and one antigen binding domain that specifically binds to CD3. In one embodiment, the anti-CD20/anti-CD3 bispecific antibody comprises a first antigen binding domain that specifically binds to CD3, and a second and a third antigen binding domain that specifically bind to CD20. In one embodiment, the first antigen binding domain is a crossover Fab molecule, and the second and the third antigen binding domain are each a conventional Fab molecule. In one embodiment, the anti-CD20/anti-CD3 bispecific antibody further comprises an Fc domain. The anti-CD20/anti-CD3 bispecific antibody may comprise modifications in the Fc region and/or the antigen binding domains as described herein. In one embodiment, the anti-CD20/anti-CD3 bispecific antibody comprises an IgG1 Fc domain comprising one or more amino acid substitutions that reduce binding to an Fc receptor and/or effector function. In one embodiment the anti-CD20/anti-CD3 bispecific antibody comprises an IgG1 Fc domain comprising the amino acid substitutions L234A, L235A, and P329G (numbering according to Kabat EU index).

In one embodiment the anti-CD20/anti-CD3 bispecific antibody comprises (i) An antigen binding domain that specifically binds to CD3 which is fused at the C-terminus of the Fab heavy chain to the N-terminus of the first subunit of the Fc domain (ii) A first antigen binding domain that specifically binds to CD20 which is fused at the C-terminus of the Fab heavy chain to the N-terminus of the Fab heavy chain of the antigen binding domain that specifically binds to CD3, (iii) A second antigen binding domain that specifically binds to CD20 which is fused at the C-terminus of the Fab heavy chain to the N-terminus of the second subunit of the Fc domain.

In a particular embodiment, the anti-CD20/anti-CD3 bispecific antibody comprises a) a first Fab molecule which specifically binds to CD3, particularly CD3 epsilon; and wherein the variable domains VL and VH of the Fab light chain and the Fab heavy chain are replaced by each other;

b) a second Fab and a third Fab molecule which specifically bind to CD20, wherein in the constant domain CL of the second Fab and third Fab molecule the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 o of the second Fab and third Fab molecule the amino acid at position 147 is substituted by glutamic acid (E) (numbering according to Kabat EU index) and the amino acid at position 213 is substituted by glutamic acid (E) (numbering according to Kabat EU index); and c) a Fc domain composed of a first and a second subunit capable of stable association.

In one embodiment, the anti-CD20/anti-CD3 bispecific antibody comprises two antigen binding domains that specifically bind to CD20 and one antigen binding domain that specifically binds to CD3.

In one embodiment, the anti-CD20/anti-CD3 bispecific antibody is bivalent for CD20 and monovalent for CD3.

In one embodiment the first Fab molecule under a) is fused at the C-terminus of the Fab heavy chain to the N-terminus of one of the subunits of the Fc domain under c), the second Fab molecule under b) is fused at the C-terminus of the Fab heavy chain to the N-terminus of the heavy chain of the first Fab molecule under a), and the third Fab molecule under b) is fused at the C-terminus of the Fab heavy chain to the N-terminus of the other subunit of the Fc domain under c).

In one embodiment, the first Fab molecule under a) comprises a heavy chain variable region that is at least 95%, 96%, 97%, 98%, or 99% identical to the sequence of SEQ ID NO: 15, and a light chain variable region that is at least 95%, 96%, 97%, 98%, or 99% identical to the sequence of SEQ ID NO: 16.

In still a further embodiment, the first Fab molecule under a) comprises the heavy chain variable region sequence of SEQ ID NO: 15, and the light chain variable region sequence of SEQ ID NO: 16.

In one embodiment, the second Fab molecule and the third Fab molecule under b) each comprises a heavy chain variable region that is at least 95%, 96%, 97%, 98%, or 99% identical to the sequence of SEQ ID NO: 7, and a light chain variable region that is at least 95%, 96%, 97%, 98%, or 99% identical to the sequence of SEQ ID NO: 8.

In one embodiment, the second Fab molecule under and the third Fab molecule under b) each comprises the heavy chain variable region sequence of SEQ ID NO: 7, and the light chain variable region sequence of SEQ ID NO: 8.

In a particular embodiment, the anti-CD20/anti-CD3 bispecific antibody comprises a polypeptide that is at least 95%, 96%, 97%, 98%, or 99% identical to the sequence of SEQ ID NO: 17, a polypeptide that is at least 95%, 96%, 97%, 98%, or 99% identical to the sequence of SEQ ID NO: 18, a polypeptide that is at least 95%, 96%, 97%, 98%, or 99% identical to the sequence of SEQ ID NO: 19, and a polypeptide that is at least 95%, 96%, 97%, 98%, or 99% identical to the sequence of SEQ ID NO: 20. In a further particular embodiment, the anti-CD20/anti-CD3 bispecific antibody comprises a polypeptide sequence of SEQ ID NO:

17, a polypeptide sequence of SEQ ID NO: 18, a polypeptide sequence of SEQ ID NO: 19 and a polypeptide sequence of SEQ ID NO: 20. In a further particular embodiment, the anti-CD20/anti-CD3 bispecific antibody comprises one polypeptide chain comprising SEQ ID NO: 17, one polypeptide chain comprising SEQ ID NO: 18, one polypeptide chain comprising SEQ ID NO: 19, and two polypeptide chains comprising SEQ ID NO: 20.

Particular anti-CD20/anti-CD3 bispecific antibodies are described in PCT publication no. WO 2016/020309 and European patent application nos. EP15188093 and EP16169160 (each incorporated herein by reference in its entirety).

In one embodiment said anti-CD20/anti-CD3 bispecific antibody is glofitamab, as described below.

Antibody Formats

The components of the anti-CD20/anti-CD3 bispecific antibody can be fused to each other in a variety of configurations. Exemplary configurations are depicted in FIG. 1.

In particular embodiments, the antigen binding moieties comprised in the anti-CD20/anti-CD3 bispecific antibody are Fab molecules. In such embodiments, the first, second, third etc. antigen binding moiety may be referred to herein as first, second, third, etc. Fab molecule, respectively. Furthermore, in particular embodiments, the anti-CD20/anti-CD3 bispecific antibody comprises an Fc domain composed of a first and a second subunit capable of stable association.

In some embodiments, the first Fab molecule is fused at the C-terminus of the Fab heavy chain to the N-terminus of the first or the second subunit of the Fc domain.

Figures 1A, 1B, 1C, 1D, 1E, 1F:
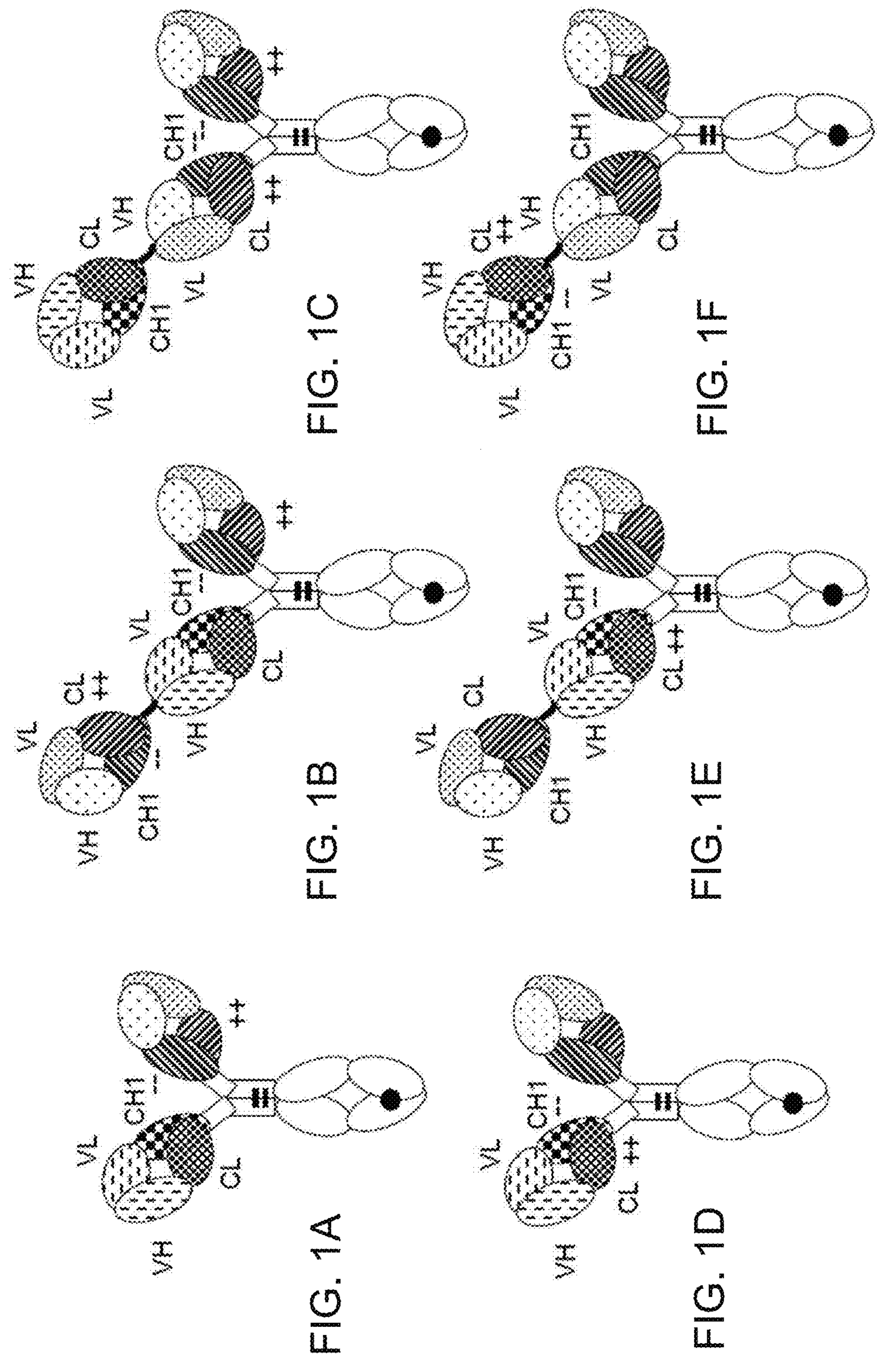
Figures 1G, 1H, 1I, 1J, 1K, 1L, 1M, 1N:
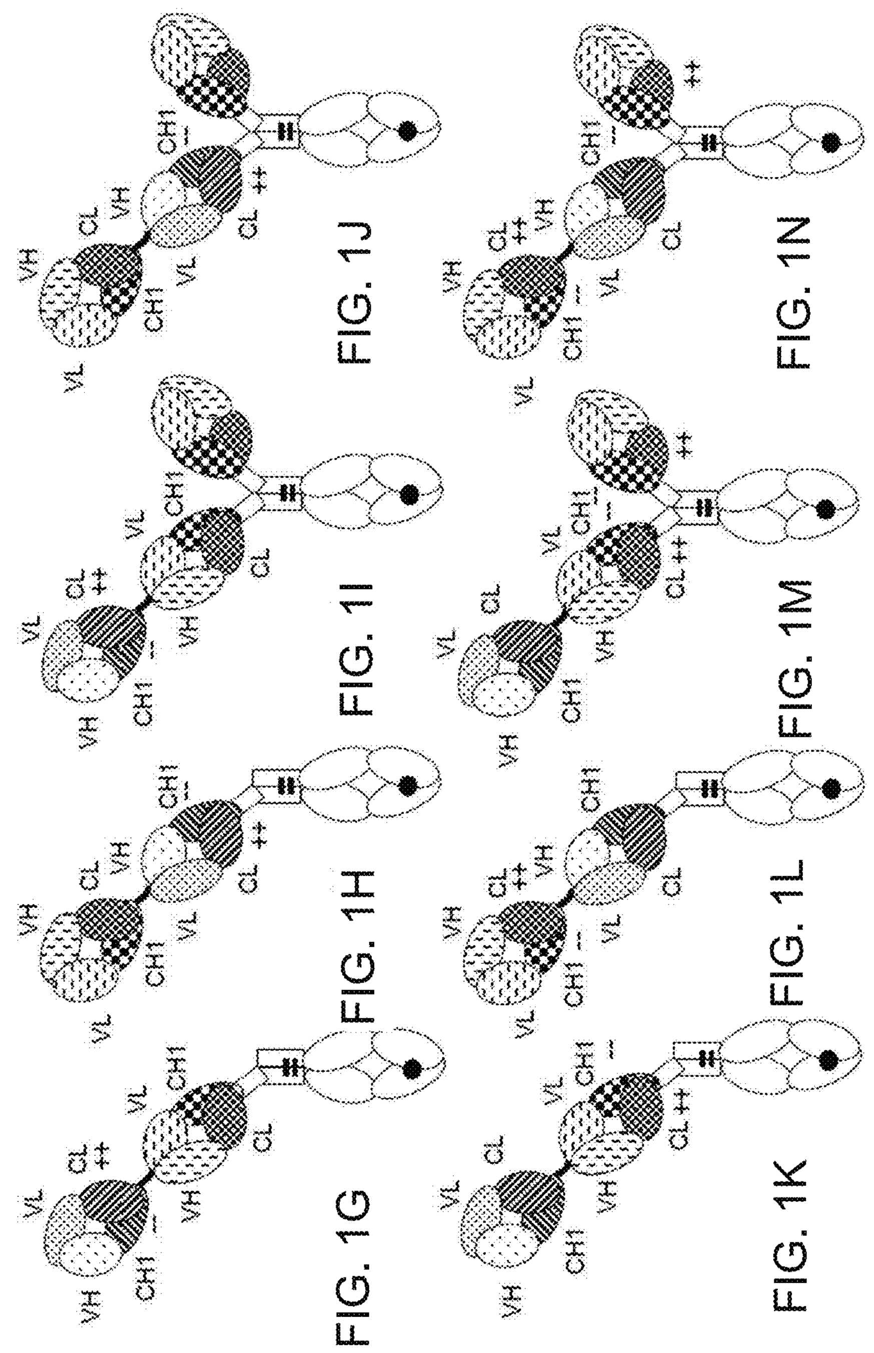

In one such embodiment, the second Fab molecule is fused at the C-terminus of the Fab heavy chain to the N-terminus of the Fab heavy chain of the first Fab molecule. In a specific such embodiment, the anti-CD20/anti-CD3 bispecific antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the first or the second subunit of the Fc domain and the second Fab molecule is fused at the C-terminus of the Fab heavy chain to the N-terminus of the Fab heavy chain of the first Fab molecule. Such a configuration is schematically depicted in FIG. 1G and FIG. 1K. Optionally, the Fab light chain of the first Fab molecule and the Fab light chain of the second Fab molecule may additionally be fused to each other.

In another embodiment, the second Fab molecule is fused at the C-terminus of the Fab heavy chain to the N-terminus of the first or second subunit of the Fc domain. In a specific such embodiment, the antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D. The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain.

In other embodiments, the second Fab molecule is fused at the C-terminus of the Fab heavy chain to the N-terminus of the first or second subunit of the Fc domain. In one such embodiment, the first Fab molecule is fused at the C-terminus of the Fab heavy chain to the N-terminus of the Fab heavy chain of the second Fab molecule. In a specific such embodiment, the antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1H and FIG. 1L. Optionally, the Fab light chain of the first Fab molecule and the Fab light chain of the second Fab molecule may additionally be fused to each other.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 21), $(SG_4)_n$ (SEQ ID NO: 22), or $G_4(SG_4)_n$ (SEQ ID NO: 23) peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3) (SEQ ID NOs: 27-58), in one embodiment x=4 and n=2 or 3, in a further embodiment x=4 and n=2. In one embodiment said peptide linker is $(G_4S)_2$ (SEQ ID NO: 24). A particularly suitable peptide linker for fusing the Fab light chains of the first and the second Fab molecule to each other is $(G_4S)_2$ (SEQ ID NO: 24). An exemplary peptide linker suitable for connecting the Fab heavy chains of the first and the second Fab fragments comprises the sequence (D)-$(G_4S)_2$ (SEQ ID NO: 25). Another suitable such linker comprises the sequence $(G_4S)_4$ (SEQ ID NO: 26). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

An antibody with a single antigen binding moiety (such as a Fab molecule) capable of specific binding to a target cell antigen (for example as shown in FIG. 1A, FIG. 1D, FIG. 1G, FIG. 1H, FIG. 1K, or FIG. 1L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have an antibody comprising two or more antigen binding moieties (such as Fab molecules) specific for a target cell antigen (see examples shown in FIG. 1B, FIG. 1C, FIG. 1E, FIG. 1F, FIG. 1I, FIG. 1J, FIG. 1M, or FIG. 1N), for example to optimize targeting to the target site or to allow crosslinking of target cell antigens.

Accordingly, in particular embodiments, the anti-CD20/anti-CD3 bispecific antibody comprises two anti-CD20 binding moieties, e.g., two Fab molecules targeting CD20. In one embodiment the two Fab molecules targeting CD20 are conventional Fab molecules. In one embodiment, the two Fab molecules targeting CD20 comprise the same heavy and light chain amino acid sequences and have the same arrangement of domains (i.e., conventional or crossover).

In alternative embodiments, the anti-CD20/anti-CD3 bispecific antibody comprises two anti-CD3 binding moieties, e.g., two Fab molecules targeting CD3. In one such embodiment, the two Fab molecules targeting CD3 are both crossover Fab molecules (a Fab molecule wherein the variable domains VH and VL or the constant domains CL and CH1 of the Fab heavy and light chains are exchanged/replaced by each other). In one such embodiment, the two Fab molecules targeting CD3 comprise the same heavy and light chain amino acid sequences and have the same arrangement of domains (i.e., conventional or crossover).

In one embodiment, the third Fab molecule is fused at the C-terminus of the Fab heavy chain to the N-terminus of the first or second subunit of the Fc domain.

In a particular embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1B and FIG. 1E (embodiments, wherein the third Fab molecule is a conventional Fab molecule and identical to the second Fab molecule), and FIG. 1I and FIG. 1M (embodiments, wherein the third Fab molecule is a crossover Fab molecule and preferably identical to the first Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In another embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1C and FIG. 1F (embodiments, wherein the third Fab molecule is a conventional Fab molecule and identical to the second Fab molecule) and in FIG. 1J and FIG. 1N (embodiments, wherein the third Fab molecule is a crossover Fab molecule and identical to the first Fab molecule). The first and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the antibody wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment, the immunoglobulin is an $IgG_1$ subclass immunoglobulin. In another embodiment the immunoglobulin is an $IgG_4$ subclass immunoglobulin. In a further particular embodiment, the immunoglobulin is a human immunoglobulin. In other embodiments the immunoglobulin is a chimeric immunoglobulin or a humanized immunoglobulin.

In some of the antibodies, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the antibodies.

In certain embodiments the antibody comprises a polypeptide wherein the Fab light chain variable region of the first Fab molecule shares a carboxy-terminal peptide bond with the Fab heavy chain constant region of the first Fab molecule (i.e., the first Fab molecule comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-CH2-CH3(-CH4)), and a polypeptide wherein the Fab heavy chain of the second Fab molecule shares a carboxy-terminal peptide bond with an Fc domain subunit ($VH_{(2)}$-$CH1_{(2)}$-CH2-CH3(-CH4)). In some embodiments the antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In certain embodiments the polypeptides are covalently linked, e.g., by a disulfide bond.

In certain embodiments the antibody comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-CH2-CH3(-CH4)), and a polypeptide wherein the Fab heavy chain of the second Fab molecule shares a carboxy-terminal peptide bond with an Fc domain subunit ($VH_{(2)}$-$CH1_{(2)}$-CH2-CH3(-CH4)). In some embodiments the antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In certain embodiments the polypeptides are covalently linked, e.g., by a disulfide bond.

In some embodiments, the antibody comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with an Fc domain subunit ($VL_{(1)}$-$CH1_{(1)}$-$VH_{(2)}$-$CH1_{(2)}$-CH2-CH3(-CH4)). In other embodiments, the antibody comprises a polypeptide wherein the Fab heavy chain of the second Fab molecule shares a carboxy-terminal peptide bond with the Fab light chain variable region of the first Fab molecule which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with an Fc domain subunit ($VH_{(2)}$-$CH1_{(2)}$-$VL_{(1)}$-$CH1_{(1)}$-CH2-CH3(-CH4)).

In some of these embodiments the antibody further comprises a crossover Fab light chain polypeptide of the first Fab molecule, wherein the Fab heavy chain variable region of the first Fab molecule shares a carboxy-terminal peptide bond with the Fab light chain constant region of the first Fab molecule ($VH_{(1)}$-$CL_{(1)}$), and the Fab light chain polypeptide of the second Fab molecule ($VL_{(2)}$-$CL_{(2)}$). In others of these embodiments the antibody further comprises a polypeptide wherein the Fab heavy chain variable region of the first Fab molecule shares a carboxy-terminal peptide bond with the Fab light chain constant region of the first Fab molecule which in turn shares a carboxy-terminal peptide bond with the Fab light chain polypeptide of the second Fab molecule ($VH_{(1)}$-$CL_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$), as appropriate.

The antibody according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain embodiments the polypeptides are covalently linked, e.g., by a disulfide bond.

In some embodiments, the antibody comprises a polypeptide wherein the Fab heavy chain variable region of the second Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with an Fc domain subunit ($VH_{(1)}$-$CL_{(1)}$-$VH_{(2)}$-$CH1_{(2)}$-CH2-CH3(-CH4)). In other embodiments, the antibody comprises a polypeptide wherein the Fab heavy chain of the second Fab molecule shares a carboxy-terminal peptide bond with the Fab heavy chain variable region of the first Fab molecule which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CH1_{(2)}$-$VH_{(1)}$-$CL_{(1)}$-CH2-CH3(-CH4)).

In some of these embodiments the antibody further comprises a crossover Fab light chain polypeptide of the first Fab molecule, wherein the Fab light chain variable region of the first Fab molecule shares a carboxy-terminal peptide bond with the Fab heavy chain constant region of the first Fab molecule ($VL_{(1)}$-$CH1_{(1)}$), and the Fab light chain polypeptide of the second Fab molecule ($VL_{(2)}$-$CL_{(2)}$). In others of these embodiments the antibody further comprises a polypeptide wherein the Fab light chain variable region of the first Fab molecule shares a carboxy-terminal peptide bond with the Fab heavy chain constant region of the first Fab molecule which in turn shares a carboxy-terminal peptide bond with the Fab light chain polypeptide of the second Fab molecule ($VL_{(1)}$-$CH1_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$), as appropriate.

The antibody according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain embodiments the polypeptides are covalently linked, e.g., by a disulfide bond.

In certain embodiments the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$-$CH1_{(1)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain embodiments the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) ($VH_{(3)}$-$CH1_{(3)}$-$VH_{(1)}$-$CH1_{(1)}$-$VH_{(2)}$-$CL_{(2)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule ($VL_{(2)}$-$CH1_{(2)}$-$VH_{(1)}$-$CH1_{(1)}$-$VH_{(3)}$-$CH1_{(3)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain variable region of the second Fab molecule shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule ($VH_{(2)}$-$CL_{(2)}$-$VH_{(1)}$-$CH1_{(1)}$-$VH_{(3)}$-$CH1_{(3)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$-$VL_{(3)}$-$CH1_{(3)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the antibody comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$-$VH_{(3)}$-$CL_{(3)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In certain embodiments the antibody comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(3)}$-$CH1_{(3)}$-$VL_{(2)}$-$CH1_{(2)}$-$VH_{(1)}$-$CH1_{(1)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the antibody comprises a polypeptide wherein the Fab heavy chain variable region of a third Fab molecule shares a carboxy-terminal peptide bond with the Fab light chain constant region of a third Fab molecule (i.e., the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(3)}$-$CL_{(3)}$-$VH_{(2)}$-$CL_{(2)}$-$VH_{(1)}$-$CH1_{(1)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

According to any of the above embodiments, components of the antibody (e.g., Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$ (SEQ ID NO: 21), $(SG_4)_n$ (SEQ ID NO: 22), or $G_4(SG_4)_n$ (SEQ ID NO: 23) peptide linkers, wherein n is generally an integer from 1 to 10, typically from 2 to 4.

Fc Domain

The anti-CD20/anti-CD3 bispecific antibody may comprise an Fc domain which consists of a pair of polypeptide chains comprising heavy chain domains of an antibody molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment, the Fc domain is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position 5228 (Kabat numbering), particularly the amino acid substitution S228P. This amino acid substitution reduces in vivo Fab arm exchange of $IgG_4$ antibodies (see Stubenrauch et al., *Drug Metabolism and Disposition* 38, 84-91 (2010)). In a further particular embodiment, the Fc domain is human.

(i) Fc Domain Modifications Promoting Heterodimerization

The anti-CD20/anti-CD3 bispecific antibody may comprise different components (e.g., antigen binding domains) fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of such antibodies in recombinant production, it will thus be advantageous to introduce in the Fc domain of the antibody a modification promoting the association of the desired polypeptides.

Accordingly, in particular embodiments the Fc domain comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

Several approaches for modifications in the CH3 domain of the Fc domain in order to enforce heterodimerization are well described e.g., in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with heavy-light chain modifications (e.g., variable or constant region exchange/replacement in Fab arms, or introduction of substitutions of charged amino acids with opposite charges in the CH1/CL interface) which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in a particular embodiment, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g., by site-specific mutagenesis, or by peptide synthesis.

In a specific embodiment, in the CH3 domain of the first subunit of the Fc domain (the "knob" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, *J Immunol Methods* 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A, and Y407V (numbering according to Kabat EU index).

In a particular embodiment the CD3 antigen binding moiety described herein is fused to the first subunit of the Fc domain (comprising the "knob" modification). Without wishing to be bound by theory, fusion of the CD3 antigen binding moiety to the knob-containing subunit of the Fc domain will (further) minimize the generation of bispecific antibodies comprising two CD3 antigen binding moieties (steric clash of two knob-containing polypeptides).

Other techniques of CH3-modification for enforcing the heterodimerization are contemplated as alternatives according to the invention and are described e.g., in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment is amino acid mutations R409D; K370E in one of the two CH3 domains (of the Fc domain) and amino acid mutations D399K; E357K in the other one of the CH3 domains of the Fc domain (numbering according to Kabat EU index).

In another embodiment the anti-CD20/anti-CD3 bispecific antibody comprises amino acid mutation T366W in the CH3 domain of the first subunit of the Fc domain and amino acid mutations T366S, L368A, and Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment the anti-CD20/anti-CD3 bispecific antibody comprises amino acid mutations S354C and T366W in the CH3 domain of the first subunit of the Fc domain and amino acid mutations Y349C, T366S, L368A, and Y407V in the CH3 domain of the second subunit of the Fc domain, or the antibody comprises amino acid mutations Y349C and T366W in the CH3 domain of the first subunit of the Fc domain and amino acid mutations S354C, T366S, L368A, and Y407V in the CH3 domains of the second subunit of the Fc domain and additionally amino acid mutations R409D; K370E in the CH3 domain of the first subunit of the Fc domain and amino acid mutations D399K;

E357K in the CH3 domain of the second subunit of the Fc domain (all numberings according to Kabat EU index).

In one embodiment the heterodimerization approach described in WO 2013/157953 is used alternatively. In one embodiment a first CH3 domain comprises amino acid mutation T366K and a second CH3 domain comprises amino acid mutation L351D (numberings according to Kabat EU index). In a further embodiment the first CH3 domain comprises further amino acid mutation L351K. In a further embodiment the second CH3 domain comprises further an amino acid mutation selected from Y349E, Y349D, and L368E (preferably L368E) (numberings according to Kabat EU index).

In one embodiment the heterodimerization approach described in WO 2012/058768 is used alternatively. In one embodiment a first CH3 domain comprises amino acid mutations L351Y and Y407A and a second CH3 domain comprises amino acid mutations T366A and K409F. In a further embodiment the second CH3 domain comprises a further amino acid mutation at position T411, D399, S400, F405, N390, or K392, e.g., selected from a) T411N, T411R, T411Q, T411K, T411D, T411E, or T411W; b) D399R, D399W, D399Y, or D399K; c) S400E, S400D, S400R, or S400K; d) F405I, F405M, F405T, F405S, F405V or F405W; e) N390R, N390K or N390D; and f) K392V, K392M, K392R, K392L, K392F, or K392E (numberings according to Kabat EU index). In a further embodiment a first CH3 domain comprises amino acid mutations L351Y and Y407A and a second CH3 domain comprises amino acid mutations T366V and K409F. In a further embodiment a first CH3 domain comprises amino acid mutation Y407A and a second CH3 domain comprises amino acid mutations T366A and K409F. In a further embodiment the second CH3 domain further comprises amino acid mutations K392E, T411E, D399R, and S400R (numberings according to Kabat EU index).

In one embodiment the heterodimerization approach described in WO 2011/143545 is used alternatively, e.g., with the amino acid modification at a position selected from the group consisting of 368 and 409 (numbering according to Kabat EU index).

In one embodiment the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment a first CH3 domain comprises amino acid mutation T366Y and a second CH3 domain comprises amino acid mutation Y407T (numberings according to Kabat EU index).

In one embodiment the anti-CD20/anti-CD3 bispecific antibody or its Fc domain is of $IgG_2$ subclass and the heterodimerization approach described in WO 2010/129304 is used.

In an alternative embodiment a modification promoting association of the first and the second subunit of the Fc domain comprises a modification mediating electrostatic steering effects, e.g., as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment a first CH3 domain comprises amino acid substitution of K392 or N392 with a negatively charged amino acid (e.g., glutamic acid (E), or aspartic acid (D), preferably K392D or N392D) and a second CH3 domain comprises amino acid substitution of D399, E356, D356, or E357 with a positively charged amino acid (e.g., lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g., glutamic acid (E), or aspartic acid (D), preferably K409D or R409D). In a further embodiment the first CH3 domain further or alternatively comprises amino acid substitution of K439 and/or K370 with a negatively charged amino acid (e.g., glutamic acid (E), or aspartic acid (D)) (all numberings according to Kabat EU index).

In yet a further embodiment the heterodimerization approach described in WO 2007/147901 is used alternatively. In one embodiment a first CH3 domain comprises amino acid mutations K253E, D282K, and K322D and a second CH3 domain comprises amino acid mutations D239K, E240K, and K292D (numberings according to Kabat EU index).

In still another embodiment the heterodimerization approach described in WO 2007/110205 can be used.

In one embodiment, the first subunit of the Fc domain comprises amino acid substitutions K392D and K409D, and the second subunit of the Fc domain comprises amino acid substitutions D356K and D399K (numbering according to Kabat EU index).

(ii) Fc Domain Modifications Reducing Fc Receptor Binding and/or Effector Function The Fc domain confers to an antibody, such as an anti-CD20/anti-CD3 bispecific antibody, favorable pharmacokinetic properties, including a long serum half-life which contributes to good accumulation in the target tissue and a favorable tissue-blood distribution ratio. At the same time it may, however, lead to undesirable targeting of the antibody to cells expressing Fc receptors rather than to the preferred antigen-bearing cells. Moreover, the co-activation of Fc receptor signaling pathways may lead to cytokine release which, in combination with other immunostimulatory properties the antibody may have and the long half-life of the antibody, results in excessive activation of cytokine receptors and severe side effects upon systemic administration.

Accordingly, in particular embodiments, the Fc domain of the anti-CD20/anti-CD3 bispecific antibody exhibits reduced binding affinity to an Fc receptor and/or reduced effector function, as compared to a native $IgG_1$ Fc domain. In one such embodiment the Fc domain (or the molecule, e.g. antibody, comprising said Fc domain) exhibits less than 50%, preferably less than 20%, more preferably less than 10% and most preferably less than 5% of the binding affinity to an Fc receptor, as compared to a native $IgG_1$ Fc domain (or a corresponding molecule comprising a native IgG1 Fc domain), and/or less than 50%, preferably less than 20%, more preferably less than 10% and most preferably less than 5% of the effector function, as compared to a native $IgG_1$ Fc domain (or a corresponding molecule comprising a native $IgG_1$ Fc domain). In one embodiment, the Fc domain (or the molecule, e.g., antibody, comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion.

In a particular embodiment the effector function is ADCC. In one embodiment the Fc domain exhibits substantially similar binding affinity to neonatal Fc receptor (FcRn), as compared to a native $IgG_1$ Fc domain domain. Substantially similar binding to FcRn is achieved when the Fc domain (or the molecule, e.g., antibody, comprising said Fc domain) exhibits greater than about 70%, particularly greater than about 80%, more particularly greater than about 90% of the binding affinity of a native $IgG_1$ Fc domain (or the corresponding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the molecule, e.g., antibody, comprising an engineered Fc domain exhibits less than 20%, particularly less than 10%, more particularly less than 5% of the binding affinity to an Fc receptor as compared to a corresponding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e., preservation of the binding affinity of the Fc domain to said receptor, is achieved when the Fc domain (or the molecule, e.g., antibody, comprising said Fc domain) exhibits greater than about 70% of the binding affinity of a non-engineered form of the Fc domain (or a corresponding molecule comprising said non-engineered form of the Fc domain) to FcRn. The Fc domain, or molecule (e.g., antibody) comprising said Fc domain, may exhibit greater than about 80% and even greater than about 90% of such affinity. In certain embodiments the Fc domain is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a corresponding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331, and P329 (numberings according to Kabat EU index). In a more specific embodiment, the Fc domain comprises an amino acid substitution at a position selected from the group of L234, L235, and P329 (numberings according to Kabat EU index). In some embodiments the Fc domain comprises the amino acid substitutions L234A and L235A (numberings according to Kabat EU index). In one such embodiment, the Fc domain is an $IgG_1$ Fc domain, particularly a human $IgG_1$ Fc domain. In one embodiment the Fc domain comprises an amino acid substitution at position P329. In a more specific embodiment, the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297, and P331 (numberings according to Kabat EU index). In a more specific embodiment, the further amino acid substitution is E233P, L234A, L235A, L235E, N297A, N297D, or P331S. In particular embodiments, the Fc domain comprises amino acid substitutions at positions P329, L234 and L235 (numberings according to Kabat EU index). In more particular embodiments the Fc domain comprises the amino acid mutations L234A, L235A, and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some embodiments the Fc domain is an $IgG_4$ Fc domain, particularly a human $IgG_4$ Fc domain. In one embodiment the $IgG_4$ Fc domain comprises amino acid substitutions at position S228, specifically the amino acid substitution S228P (numberings according to Kabat EU index). To further reduce its binding affinity to an Fc receptor and/or its effector function, in one embodiment the $IgG_4$ Fc domain comprises an amino acid substitution at position L235, specifically the amino acid substitution L235E (numberings according to Kabat EU index). In another embodiment, the $IgG_4$ Fc domain comprises an amino acid substitution at position P329, specifically the amino acid substitution P329G (numberings according to Kabat EU index). In a particular embodiment, the IgG4 Fc domain comprises amino acid substitutions at positions S228, L235, and P329, specifically amino acid substitutions S228P, L235E, and P329G (numberings according to Kabat EU index). Such $IgG_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A, and optionally P329G, or a human $IgG_4$ Fc domain comprising the amino acid substitutions S228P, L235E, and optionally P329G (numberings according to Kabat EU index).

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D) or glycine (N297G) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327, and 329 (U.S. Pat. No. 6,737,056) (numberings according to Kabat EU index). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIACORE® instrument (GE Healthcare), and Fc receptors such as may be obtained by recombinant expression. Alternatively, binding affinity of Fc domains or molecules comprising an Fc domain for Fc receptors may be evaluated using cell lines known to express particular Fc receptors, such as human NK cells expressing FcγIIIa receptor.

Effector function of an Fc domain, or a molecule (e.g., an antibody) comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. *Proc Natl Acad Sci USA* 83, 7059-7063 (1986) and Hellstrom et al., *Proc Natl Acad Sci USA* 82, 1499-1502 (1985); U.S. Pat. No. 5,821,337; Bruggemann et al., *J Exp Med* 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (PROMEGA®, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc Natl Acad Sci USA* 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or molecule (e.g., antibody) comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., *J Immunol Methods* 202, 163 (1996); Cragg et al., *Blood* 101, 1045-1052 (2003); and Cragg and Glennie, *Blood* 103, 2738-2743 (2004)).

Glofitamab

Figure 2:
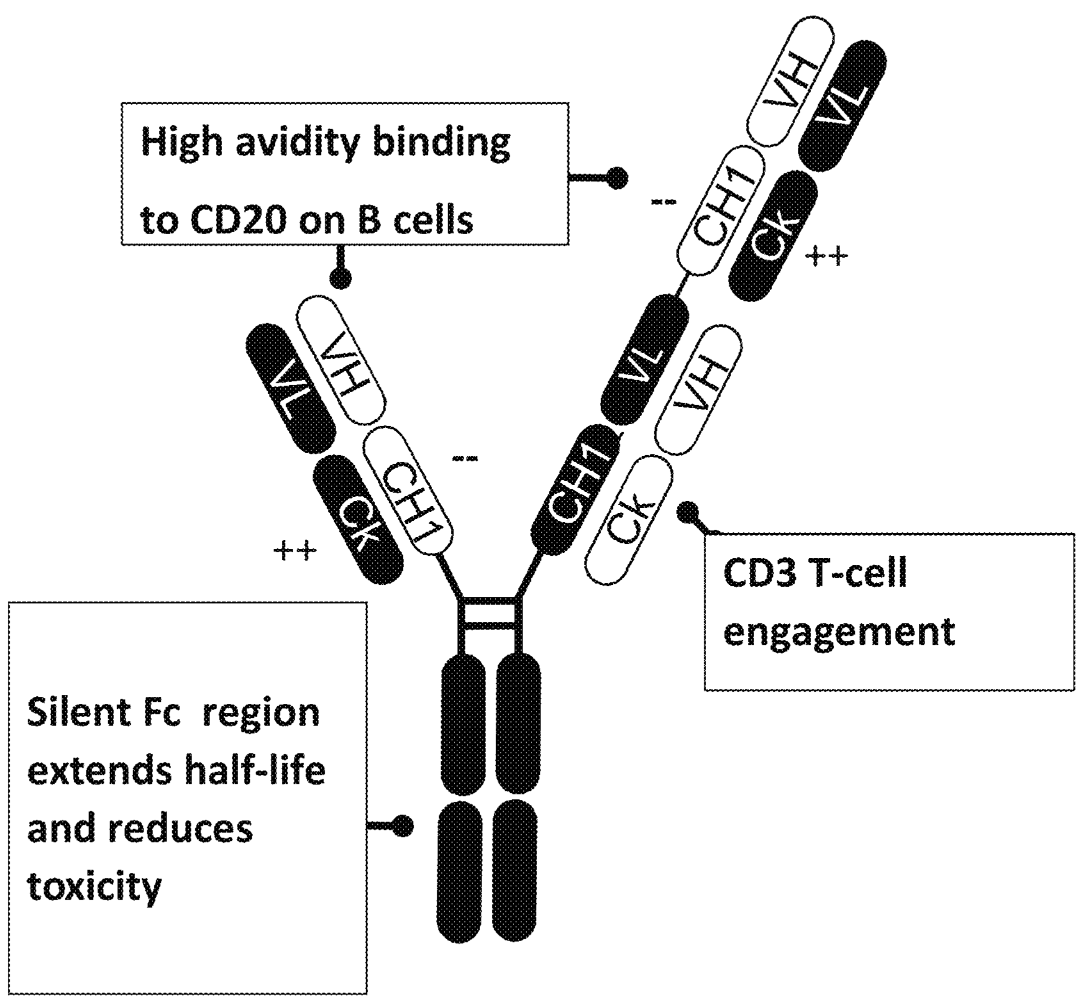
FIG. 2. Glofitamab structure.

In one embodiment the anti-CD20/anti-CD3 bispecific antibody useful in the methods provided herein is glofitamab. Glofitamab (WHO Drug Information (International Nonproprietary Names for Pharmaceutical Substances), Recommended INN: List 83, 2020, vol. 34, no. 1, p. 39; also known as CD20-TCB, RO7082859, or RG6026) is a novel T-cell-engaging bispecific full-length antibody with a 2:1 molecular configuration for bivalent binding to CD20 on B cells and monovalent binding to CD3, particularly the CD3 epsilon chain (CD3ε), on T cells. Its CD3-binding region is fused to one of the CD20-binding regions in a head-to-tail fashion via a flexible linker. This structure endows glofitamab with superior in vitro potency versus other CD20-CD3 bispecific antibodies with a 1:1 configuration, and leads to profound antitumor efficacy in preclinical DLBCL models. CD20 bivalency preserves this potency in the presence of competing anti-CD20 antibodies, providing the opportunity for pre- or co-treatment with these agents. Glofitamab comprises an engineered, heterodimeric Fc region with completely abolished binding to FcγRs and C1q. By simultaneously binding to human CD20-expressing tumor cells and to the CD3ε of the T-cell receptor (TCR) complex on T-cells, it induces tumor cell lysis, in addition to T-cell activation, proliferation and cytokine release. Lysis of B-cells mediated by glofitamab is CD20-specific and does not occur in the absence of CD20 expression or in the absence of simultaneous binding (cross-linking) of T-cells to CD20-expressing cells. In addition to killing, T-cells undergo activation due to CD3 cross-linking, as detected by an increase in T-cell activation markers (CD25 and CD69), cytokine release (IFNγ, TNFα, IL-2, IL-6, IL-10), cytotoxic granule release (Granzyme B) and T-cell proliferation. A schematic of the molecule structure of glofitamab is depicted in FIG. 2.

IV. Novel Dosing Schedules for Anti-CD20/Anti-CD3 Bispecific ANTIBODIES

The present invention relates to new dosing schedules for anti-CD20/anti-CD3 bispecific antibodies, particularly for glofitamab that result in acceptable safety and efficacy profiles, in particular with respect to cytokine release syndrome related side effects.

Bispecific antibody therapeutics involving T-cell activation have been associated with cytokine release syndrome (CRS). CRS is a potentially life-threatening symptom complex caused by the excessive release of cytokines by immune effector or target cells during an exaggerated and sustained immune response. CRS can be triggered by a variety of factors, including infection with virulent pathogens, or by medications that activate or enhance the immune response, resulting in a pronounced and sustained immune response.

Regardless of the inciting agent, severe or life-threatening CRS is a medical emergency. If unsuccessfully managed, it can result in significant disability or fatal outcome. Current clinical management focuses on treating the individual signs and symptoms, providing supportive care, and attempting to dampen down the inflammatory response using high-dose corticosteroids. However, this approach is not always successful, especially in the case of late intervention. Moreover, steroids may negatively impact T-cell function, which may diminish the clinical benefit of immune modulating therapies in the treatment of cancer.

CR5 Symptoms and Grading

CRS is graded according to the Modified Cytokine Release Syndrome Grading System established by Lee et al., *Blood,* 124: 188-195, 2014 or Lee et al., *Biol Blood Marrow Transplant,* 25(4): 625-638, 2019, as described in Table 3. In addition to diagnostic criteria, recommendations on management of CRS based on its severity, including early intervention with corticosteroids and/or anti-cytokine therapy, are provided and referenced in Tables 3 and 4.

TABLE 3

Cytokine release syndrome grading systems

| Grade | Modified Cytokine Release Syndrome Grading System | ASTCT Consensus Grading System |
|---|---|---|
| Grade 1 | Symptoms are not life threatening and require symptomatic treatment only (e.g. fever, nausea, fatigue, headache, myalgia, malaise) | Temperature ≥38° C. No hypotension No hypoxia |
| Grade 2 | Symptoms require and respond to moderate intervention Oxygen requirement <40%; or Hypotension responsive to fluids or low dose [a] of one vasopressor; or Grade 2 organ toxicity | Temperature ≥38° C.* with hypotension not requiring vasopressors and/or[†] hypoxia requiring low-flow nasal cannula[‡] or blow-by |
| Grade 3 | Symptoms require and respond to aggressive intervention Oxygen requirement ≥40%; or Hypotension requiring high dose [b] or multiple vasopressors; or Grade 3 organ toxicity or Grade 4 transaminitis | Temperature ≥38° C.* with hypotension requiring a vasopressor with or without vasopressin and/or[†] hypoxia requiring high-flow nasal cannula[‡], facemask, nonrebreather mask, or Venturi mask |
| Grade 4 | Life-threatening symptoms Requirement for ventilation support or Grade 4 organ toxicity (excluding transaminitis) | Temperature ≥38° C.* with hypotension requiring multiple vasopressors (excluding vasopressin) and/or[†] hypoxia requiring positive pressure (e.g., CPAP, BiPAP, intubation and mechanical ventilation) |
| Grade 5 | Death | Death |

Lee 2014 criteria: Lee et al., Blood, 124: 188-195, 2014.

ASTCT consensus grading: Lee et al., Biol Blood Marrow Transplant, 25(4): 625-638, 2019.

[a] Low-dose vasopressor: single vasopressor at doses below that shown in Table 3.

[b] High-dose vasopressor: as defined in Table 4.

*Fever is defined as temperature ≥38° C. not attributable to any other cause. In patients who have CRS then receive antipyretic or anticytokine therapy such as tocilizumab or steroids, fever is no longer required to grade subsequent CRS severity. In this case, CRS grading is driven by hypotension and/or hypoxia.

[†]CRS grade is determined by the more severe event: hypotension or hypoxia not attributable to any other cause. For example, a patient with temperature of 39.5° C., hypotension requiring 1 vasopressor, and hypoxia requiring low-flow nasal cannula is classified as Grade 3 CRS.

[‡]Low-fow nasal cannula is defined as oxygen delivered at ≤6 L/minute. Low flow also includes blow-by oxygen delivery, sometimes used in pediatrics. High-flow nasal cannula is defined as oxygen delivered at >6 l/minute.

TABLE 4

High-dose vasopressors
High-Dose Vasopressors (duration ≥3 hours)

| Pressor | Dose |
|---|---|
| Norepinephrine monotherapy | ≥20 μg/min |
| Dopamine monotherapy | ≥10 μg/kg/min |
| Phenylephrine monotherapy | ≥200 μg/min |
| Epinephrine monotherapy | ≥10 μg/min |
| If on vasopressin | Vasopressin + norepinephrine equivalent of ≥10 μg/min [a] |
| If on combination or vasopressors (not vasopressin) | Norepinephrine equivalent of ≥20 μg/min [a] |

min = minute;

VASST = Vasopressin and Septic Shock Trial.

[a] VASST vasopressor equivalent equation: norepinephrine equivalent dose = [norepinephrine (μg/min)] + [dopamine (μg/kg/min) ÷ 2] + [epinephrine (μg/min)] + [phenylephrine (μg/min) ÷ 10].

Mild to moderate presentations of CRS and/or infusion-related reaction (IRR) may include symptoms such as fever, headache, and myalgia, and may be treated symptomatically with analgesics, anti-pyretics, and antihistamines as indicated. Severe or life-threatening presentations of CRS and/or IRR, such as hypotension, tachycardia, dyspnea, or chest discomfort should be treated aggressively with supportive and resuscitative measures as indicated, including the use of high-dose corticosteroids, IV fluids, admission to intensive care unit, and other supportive measures. Severe CRS may be associated with other clinical sequelae such as disseminated intravascular coagulation, capillary leak syndrome, or macrophage activation syndrome (MAS). Standard of care for severe or life threatening CRS resulting from immune-based therapy has not been established; case reports and recommendations using anti-cytokine therapy such as tocilizumab have been published (Teachey et al., *Blood,* 121: 5154-5157, 2013; Lee et al., *Blood,* 124: 188-195, 2014; Maude et al., *New Engl J Med,* 371: 1507-1517, 2014).

In a Phase I/II multicenter, open-label, dose-escalation study designed to evaluate the efficacy, safety, tolerability, and PK pharmacokinetics of a novel T-cell-engaging bispecific full-length antibody (TCB), glofitamab, the maximum tolerated dose was determined with unchanging, preset dosing. Due to its specific structure as explained above, glofitamab is a very potent molecule which could potentially result in unwanted side effects, particularly cytokine release syndrome (CRS) related side effects.

Obinutuzumab [GAZYVA®] pretreatment was employed as CRS mitigation strategy in this study. Despite these strategies it was found that the target dose of 25 mg of glofitamab was not feasible due to unacceptable levels of severe side effects, particularly cytokine release syndrome (CRS) Grade 2 or higher. Therefore, there is a need to further find mechanisms to mitigate CRS risk for patients treated with glofitamab. The inventors of the present invention developed a statistical model to determine step-up-dosing schedules with the goal of decreasing the occurrence of any severe (i.e., Grade 3) CRS. The inventors of the present invention found that a specific step-up dosing regimen of glofitamab is a useful CRS mitigation strategy, allowing administration of a high glofitamab target dose of 30 mg, higher than the maximum tolerated dose, when using unchanging or preset dosing regimen and with a lower risk of CRS Grade 2 or higher. The new step-up dosing regimen is specifically tailored for anti-CD20/anti-CD3 bispecific antibodies, particularly for glofitamab. Clinical data of glofitamab provided in the Examples confirms an improved CRS profile. The novel step-up dosing regimens during the first dosing cycle (C1) further improve the clinical benefit/risk profile of glofitamab by reducing the occurrence and severity of first-cycle CRS. Thus, according to the invention, the dose of glofitamab is chosen such as to effectively reduce the risk of severe CRS in the subject while achieving the desired clinical efficacy.

In a first aspect the invention provides a method of treating a subject having a CD20-positive B cell proliferative disorder comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In one embodiment, the single dose of the second dosing cycle (C2D1) comprises 30 mg of the anti-CD20/anti-CD3 bispecific antibody. The inventors of the present invention found that a two-step increase of the dose in the first dosing cycle allows safe administration of the target dose in the second dosing cycle. In one embodiment, the first dose (C1D1) is administered on day 1 of the first dosing cycle and the second dose (C1D2) is administered on day 8 of the first dosing cycle. In one embodiment the single dose of the second dosing cycle (C2D1) is administered on day 1 of the second dosing cycle.

In one aspect the invention provides a method of treating a subject having a CD20-positive B cell proliferative disorder comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg and administered on day 1 of the first dosing cycle, and the C1D2 is 10 mg and administered on day 8 of the first dosing cycle; and (b) the second dosing cycle comprises a single dose (C2D1) of 30 mg of the anti-CD20/anti-CD3 bispecific antibody, which is administered on day 1 of the second dosing cycle.

In one embodiment the method comprises 1 to 10 additional dosing cycles (C3 to C12). In one such embodiment the 1 to 10 additional dosing cycles (C3 to C12) each comprises a single dose (C3D1 to C12D1) of either 16 or 30 mg of the anti-CD20/anti-CD3 bispecific antibody. In one embodiment the single dose of each of the additional dosing cycles (C3D1 to C12D1) comprises 30 mg of the anti-CD20/anti-CD3 bispecific antibody.

In one embodiment the single dose of the additional dosing cycles (C3D1 to C12D1) is administered on day 1 of the respective additional dosing cycle.

Thus in one aspect the invention provides a method of treating a subject having a CD20-positive B cell proliferative disorder comprising administering to the subject an anti-CD20/anti-CD3 bispecific antibody in a dosing regimen comprising 2 to 12 cycles, wherein:

(a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and
(b) the subsequent dosing cycles each comprises a single dose (C2D1 to C12D1) of either 16 or 30 mg of the anti-CD20/anti-CD3 bispecific antibody.

In one such embodiment the subsequent dosing cycles each comprises a single dose (C2D1 to C12D1) of 30 mg of the anti-CD20/anti-CD3 bispecific antibody.

Thus in one aspect the invention provides a method of treating a subject having a CD20-positive B cell proliferative disorder comprising administering to the subject an anti-CD20/anti-CD3 bispecific antibody in a dosing regimen comprising 2 to 12 cycles, wherein:

(a) the first dosing cycle comprises a first dose (C1D1) and a second dose (C1D2) of the anti-CD20/anti-CD3 bispecific antibody, wherein the C1D1 is 2.5 mg and is administered on day 1 of the first dosing cycle, and the C1D2 is 10 mg and is administered on day 8 of the first dosing cycle; and
(b) the subsequent dosing cycles each comprises a single dose (C2D1 to C12D1) of either 16 or 30 mg of the anti-CD20/anti-CD3 bispecific antibody, administered on day 1 of each subsequent dosing cycle.

In one such embodiment the subsequent dosing cycles each comprises a single dose (C2D1 to C12D1) of 30 mg of the anti-CD20/anti-CD3 bispecific antibody, administered on day 1 of each subsequent dosing cycle.

In one aspect the invention provides a method of treating a subject having a CD20-positive B cell proliferative disorder comprising administering to the subject glofitamab in a dosing regimen comprising at least a first dosing cycle and a second dosing cycle, wherein:

(a) the first dosing cycle comprises a first dose (C1D1) and a second dose (C1D2) of glofitamab, wherein the C1D1 is 2.5 mg, and the C1D2 is 10 mg; and
(b) the second dosing cycle comprises a single dose (C2D1) of either 16 or 30 mg of glofitamab.

In one embodiment, the single dose of the second dosing cycle (C2D1) comprises 30 mg of glofitamab. The inventors of the present invention found that a two-step increase of glofitamab dose in the first dosing cycle allows safe administration of the target dose in the second dosing cycle. In one embodiment, the first dose (C1D1) is administered on day 1 of the first dosing cycle and the second dose (C1D2) is administered on day 8 of the first dosing cycle. In one embodiment the single dose of the second dosing cycle (C2D1) is administered on day 1 of the second dosing cycle.

In one aspect the invention provides a method of treating a subject having a CD20-positive B cell proliferative disorder comprising administering to the subject glofitamab in a dosing regimen comprising at least a first dosing cycle and a second dosing cycle, wherein:

(a) the first dosing cycle comprises a first dose (C1D1) and a second dose (C1D2) of glofitamab, wherein the C1D1 is 2.5 mg and administered on day 1 of the first dosing cycle, and the C1D2 is 10 mg and administered on day 8 of the first dosing cycle; and
(b) the second dosing cycle comprises a single dose (C2D1) of 30 mg of glofitamab, which is administered on day 1 of the second dosing cycle.

In some embodiments, the dosing regimen comprises from six to 15 additional dosing cycles (e.g., from six to ten additional dosing cycles (e.g., six additional dosing cycles, seven additional dosing cycles, eight additional dosing cycles, nine additional dosing cycles, or ten additional dosing cycles) or from 11-15 additional dosing cycles (e.g., 11 additional dosing cycles, 12 additional dosing cycles, 13 additional dosing cycles, 14 additional dosing cycles, or 15 additional dosing cycles) beyond the second dosing cycle. In some embodiments, the additional dosing cycles are 21-day dosing cycles.

In one embodiment the method comprises 1 to 10 additional dosing cycles (C3 to C12). In one such embodiment the 1 to 10 additional dosing cycles (C3 to C12) each comprises a single dose (C3D1 to C12D1) of either 16 or 30 mg of glofitamab. In one embodiment the single dose of each of the additional dosing cycles (C3D1 to C12D1) comprises 30 mg of glofitamab.

In one embodiment the single dose of the additional dosing cycles (C3D1 to C12D1) is administered on day 1 of the respective additional dosing cycle.

Thus in one aspect the invention provides a method of treating a subject having a CD20-positive B cell proliferative disorder comprising administering to the subject glofitamab in a dosing regimen comprising 2 to 12 cycles, wherein:

(a) the first dosing cycle comprises a first dose (C1D1) and a second dose (C1D2) of glofitamab, wherein the C1D1 is 2.5 mg, and the C1D2 is 10 mg; and
(b) the subsequent dosing cycles each comprises a single dose (C2D1 to C12D1) of either 16 or 30 mg of glofitamab.

In one such embodiment the subsequent dosing cycles each comprises a single dose (C2D1 to C12D1) of 30 mg of glofitamab.

Thus in one aspect the invention provides a method of treating a subject having a CD20-positive B cell proliferative disorder comprising administering to the subject glofitamab in a dosing regimen comprising 2 to 12 cycles, wherein:

(a) the first dosing cycle comprises a first dose (C1D1) and a second dose (C1D2) of glofitamab, wherein the C1D1 is 2.5 mg and is administered on day 1 of the first dosing cycle, and the C1D2 is 10 mg and is administered on day 8 of the first dosing cycle; and
(b) the subsequent dosing cycles each comprises a single dose (C2D1 to C12D1) of either 16 or 30 mg of glofitamab, administered on day 1 of each subsequent dosing cycle.

In one such embodiment the subsequent dosing cycles each comprises a single dose (C2D1 to C12D1) of 30 mg of glofitamab, administered on day 1 of each subsequent dosing cycle.

In one embodiment the methods described above comprise 12 dosing cycles in total. In one embodiment one treatment cycle comprises 14 days or 21 days. In one embodiment one treatment cycle comprises 21 days.

In one embodiment the CD20-positive B cell proliferative disorder is a non-Hodgkin's lymphoma (NHL). In one embodiment the NHL is a diffuse large B cell lymphoma (DLBCL), a high grade B cell lymphoma (HGBCL), a DLBCL arising from FL [transformed FL; trFL] a primary mediastinal large B-cell lymphoma (PMBCL), or marginal zone lymphoma (MZL). MZL can be categorized as splenic, nodal and extra-nodal MZL. In one embodiment the DLBCL is a Richter's transformation. In one embodiment the NHL is a mantle cell lymphoma (MCL). In one embodiment the NHL is a Grade 1-3a Follicular Lymphoma (FL). In one embodiment the CD20-positive B cell proliferative disorder is a relapsed or refractory B cell proliferative disorder. In one embodiment the relapsed or refractory B cell proliferative disorder is relapsed or refractory NHL (e.g., a relapsed or refractory DLBCL, a relapsed or refractory FL, or a relapsed or refractory MCL). In one embodiment the NHL is indolent NHL (iNHL) or aggressive NHL (aNHL).

In one embodiment, patients have relapsed after or failed to respond to at least two prior systemic treatment regimens (including at least one prior regimen containing anthracycline, and at least one containing an anti CD20-directed therapy).

In one embodiment, patients with DLBCL have relapsed after or failed to respond to at least two prior systemic treatment regimens.

In one embodiment, patients with PMBCL and trFL have relapsed after or failed to respond to at least two prior systemic treatment regimens (including at least one prior regimen containing anthracycline, and at least one containing an anti CD20-directed therapy).

In one embodiment, patients with Grade 1-3a FL have relapsed after or failed to respond to at least two prior lines of systemic therapy and have received prior treatment with rituximab and alkylating agents In one embodiment, subjects with (CLL), Burkitt lymphoma, and lymphoplasmacytic lymphoma are excluded from the methods of treatment described above.

In one embodiment, the step-up dosing schedule of the anti-CD20/anti-CD3 bispecific antibody as provided herein effectively reduces cytokine release in the subject associated with the administration of the anti-CD20/anti-CD3 bispecific antibody, as compared to a corresponding treatment regimen without a step-up dosing schedule. In one embodiment, cytokine release is reduced at least 2-fold, at least 3-fold, at least 4-fold, at least 5-fold, at least 10-fold, at least 20-fold, at least 50-fold, or at least 100-fold as compared to a corresponding treatment regimen without a step-up dosing schedule. Cytokines can be detected by methods known in the art, such as e.g., ELISA, FACS or LUMINEX® assay.

Cytokines can be detected e.g., in a blood sample taken from the subject. In one embodiment, the cytokine concentration is the blood of the subject. In some embodiments, the cytokine is one or more cytokine(s) selected from the group consisting of tumor necrosis factor alpha (TNF-α), interferon gamma (IFN-γ), interleukin-6 (IL-6), interleukin-10 (IL-10), interleukin-2 (IL-2) and interleukin-8 (IL-8), particularly the group consisting of TNF-α, IFN-γ and IL-6. In some embodiments, the cytokine is TNF-α. In some embodiments, the cytokine is IFN-γ. In some embodiments, the cytokine is IL-6. In some embodiments, the cytokine is IL-10. In some embodiments, the cytokine is IL-2. In some embodiments, the cytokine is IL-8.

In some embodiments, the step-up dosing schedule of the anti-CD20/anti-CD3 bispecific antibody (e.g., glofitamab) as provided herein increases the safety of the anti-CD20/anti-CD3 bispecific antibody (e.g., glofitamab), as compared to a corresponding treatment regimen without a step-up dosing regimen (i.e., with a preset, unchanging dosing regimen) of the anti-CD20/anti-CD3 bispecific antibody (e.g., glofitamab). In some embodiments, the step-up dosing schedule of the anti-CD20/anti-CD3 bispecific antibody as provided herein reduces adverse events in the subject, as compared to a corresponding treatment regimen without a step-up dosing regimen of the anti-CD20/anti-CD3 bispecific antibody. In some embodiments, the treatment regimen reduces toxicity of the anti-CD20/anti-CD3 bispecific antibody, as compared to a corresponding treatment regimen without a step-up dosing regimen of the anti-CD20/anti-CD3 bispecific antibody.

In one embodiment the population of subjects exhibits cytokine release syndrome after administering the anti-CD20/anti-CD3 bispecific antibody, and wherein the rate of the cytokine release syndrome of a grade of 2 or greater is less than or equal to about 30%. In one embodiment the population of subjects exhibits cytokine release syndrome after administering the anti-CD20/anti-CD3 bispecific antibody, and wherein the rate of the cytokine release syndrome of a grade of 2 is less than or equal to about 12%. In one embodiment the rate of subjects exhibiting a cytokine release syndrome of a grade of 3 or greater is less than or equal to about 5%. In one embodiment the rate of subjects exhibiting a cytokine release syndrome of a grade of 3 or greater is less than or equal to about 3%. In one embodiment the rate of subjects exhibiting a cytokine release syndrome of a grade of 3 or greater is less than or equal to about 0%. In one embodiment the CRS grade is defined by the modified criteria of Lee et al. (Lee et al., *Blood,* 124: 188-195, 2014) and/or the ASTCT consensus grading (criteria of the American Society for Transplantation and Cellular Therapy, 2019; ASTCT; Lee et al., *Biol Blood Marrow Transplant,* 25(4): 625-638, 2019).

In one embodiment the step-up dosing schedule of the anti-CD20/anti-CD3 bispecific antibody as provided herein reduces the frequency of Grade 2 or higher CRS as compared to the Grade 2 or higher CRS rate of a patient population treated with a corresponding treatment regimen without a step-up dosing regimen of the anti-CD20/anti-CD3 bispecific antibody. In one embodiment the frequency of Grade 2 or higher CRS is about 45%, 50%, 55% or 60% lower as compared to the Grade 2 or higher CRS rate observed in a patient population treated with a corresponding treatment regimen without a step-up dosing regimen of the anti-CD20/anti-CD3 bispecific antibody. In one embodiment the CRS grade is defined by the modified criteria of Lee et al. (2014) and/or the ASTCT consensus grading (criteria of the American Society for Transplantation and Cellular Therapy, 2019; ASTCT).

In one embodiment the step-up dosing schedule of the anti-CD20/anti-CD3 bispecific antibody as provided herein results in an objective response rate of at least about 60% in the patient population. In one embodiment the step-up dosing schedule of the anti-CD20/anti-CD3 bispecific antibody as provided herein results in an objective response rate of at least about 70% in the patient population. In one embodiment the step-up dosing schedule of the anti-CD20/anti-CD3 bispecific antibody as provided herein results in a CRR of at least about 60% in a patient population.

In one embodiment the step-up dosing schedule of the anti-CD20/anti-CD3 bispecific antibody as provided herein results in an objective response rate of at least about 60% in a patient population with aggressive B-NHL (DLBCL, trFL, PMBCL, MCL, Richter's transformation). In one embodiment the step-up dosing schedule of the anti-CD20/anti-CD3 bispecific antibody as provided herein results in an objective response rate of at least about 70% in a patient population with aggressive B-NHL (DLBCL, trFL, PMBCL, MCL, Richter's transformation). In one embodiment the step-up dosing schedule of the anti-CD20/anti-CD3 bispecific antibody as provided herein results in an objective response rate of at least about 65% in a patient population with Grade 1-3A FL.

In one embodiment the step-up dosing schedule of the anti-CD20/anti-CD3 bispecific antibody as provided herein results in a complete response rate (CRR) of at least about 45% in a patient population with aggressive B-NHL (DLBCL, trFL, PMBCL, MCL, Richter's transformation). In one embodiment the step-up dosing schedule of the anti-CD20/anti-CD3 bispecific antibody as provided herein results in a CRR of at least about 50% in a patient population with Grade 1-3A FL.

In one embodiment CR occurs by cycle 3. In another embodiment complete response (CR) occurs at first or second response assessment (C3 or C6).

In one embodiment the step-up dosing schedule of the anti-CD20/anti-CD3 bispecific antibody as provided herein results in a DOR of at least about 5.5 months in patients with aggressive NHL (DLBCL, trFL, PMBCL, MCL, Richter's transformation).

In one embodiment the step-up dosing schedule of the anti-CD20/anti-CD3 bispecific antibody as provided herein results in progression free survival of at least 3 months. In one embodiment the step-up dosing schedule of the anti-CD20/anti-CD3 bispecific antibody as provided herein results in progression free survival of at least about 30% or about 34% at 6 months.

In one embodiment the step-up dosing schedule of the anti-CD20/anti-CD3 bispecific antibody as provided herein results in a DOR of at least about 10 months in patients with Grade 1-3A FL. In one embodiment the step-up dosing schedule of the anti-CD20/anti-CD3 bispecific antibody as provided herein results in progression free survival of at least about 11 months in patients with Grade 1-3A FL.

For certain indications, extended step-up dosing was found to result in a beneficial benefit-risk profile. In the extended step-up dosing regimen provided herein, an initial lower dose of glofitamab is administered on day 1 of dosing cycle 1 and day 8 of dosing cycle 1 followed by an intermediate dose in Cycle 2 and the first administration of the target treatment dose is in Cycle 3. Alternatively, an intermediate dose may also be administered in Cycle 3 and first target dose in Cycle 4. The smaller increase in glofitamab dose at each step-up can further improve the clinical benefit/risk of glofitamab by reducing the occurrence and severity of CRS in certain indications like Follicular Lymphoma.

In an embodiment of the invention, a method of treating a subject having diffuse large B cell lymphoma (DLBCL) is provided, comprising administering to the subject an anti-CD20/anti-CD3 bispecific antibody in a dosing regimen comprising at least a first dosing cycle and a second dosing cycle, wherein:

a) the first dosing cycle comprises a first dose (C1D1) and a second dose (C1D2) of the anti-CD20/anti-CD3 bispecific antibody, wherein the C1D1 is 2.5 mg, and the C1D2 is 10 mg of the anti-CD20/anti-CD3 bispecific antibody
b) the second dosing cycle comprises a single dose (C2D1) of 16 or 30 mg of the anti-CD20/anti-CD3 bispecific antibody.

In one embodiment, the single dose (C2D1) of the third dosing cycle comprises 30 mg of the anti-CD20/anti-CD3 bispecific antibody.

In one embodiment, the first dose (C1D1) is administered on day 1 of the first dosing cycle and the second dose (C1D2) is administered on day 8 of the first dosing cycle. In one embodiment, the single dose of the second dosing cycle (C2D1) is administered on day 1 of the second dosing cycle.

In one embodiment a method of treating a subject having diffuse large B cell lymphoma (DLBCL) is provided, comprising administering to the subject an anti-CD20/anti-CD3 bispecific antibody in a dosing regimen comprising at least a first dosing cycle and a second dosing cycle, wherein:

a) the first dosing cycle comprises a first dose (C1D1) and a second dose (C1D2) of the anti-CD20/anti-CD3 bispecific antibody, wherein the C1D1 is 2.5 mg and is administered on day 1 of the first dosing cycle, and the C1D2 is 10 mg and is administered on day 8 of the first dosing cycle; and b) the second dosing cycle comprises a single dose (C2D1) of 16 or 30 mg of the anti-CD20/anti-CD3 bispecific antibody administered on day 1 of the second dosing cycle.

In one embodiment the method of treating DLBCL comprises 1 to 10 additional dosing cycles (C3 to C12). In one embodiment, the 1 to 10 additional dosing cycles (C3 to C12) each comprises a single dose (C3D1 to C12D1) of either 16 or 30 mg of the anti-CD20/anti-CD3 bispecific antibody. In one embodiment, the single dose of each of the additional dosing cycles (C3D1 to C12D1) comprises 30 mg of the anti-CD20/anti-CD3 bispecific antibody. In one embodiment the single dose of the additional dosing cycles (C3D1 to C12D1) is administered on day 1 of the respective additional dosing cycle.

In an embodiment a method of treating a subject having diffuse large B cell lymphoma (DLBCL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody; and b) the subsequent dosing cycles each comprises a single dose (C2D1 to C12D1) of 16 or 30 mg of the anti-CD20/anti-CD3 bispecific antibody.

In one such embodiment the subsequent dosing cycles each comprises a single dose (C2D1 to C12D1) of 30 mg of the anti-CD20/anti-CD3 bispecific antibody.

In one embodiment a method of treating a subject having diffuse large B cell lymphoma (DLBCL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 2.5 mg and administered on day 1 of the first dosing cycle, and the C1D2 is 10 mg of the anti-CD20/anti-CD3 bispecific antibody and administered on day 8 of the first dosing cycle; and b) the subsequent dosing cycles each comprises a single dose (C2D1 to C12D1) of 16 or 30 mg of the anti-CD20/anti-CD3 bispecific antibody administered on day 1 of each subsequent dosing cycle.

In one such embodiment the subsequent dosing cycles each comprises a single dose (C2D1 to C12D1) of 30 mg of the anti-CD20/anti-CD3 bispecific antibody.

In one embodiment the method for treating DLBCL described above comprises 12 dosing cycles in total. In one embodiment, the DLBCL is a relapsed or refractory (R/R) DLBCL. In one embodiment the DLBCL arose from FL, is a transformed FL (trFL), or is a Richter's transformation. In one embodiment, patients with R/R DLBCL have relapsed after or failed to respond to at least two prior lines of systemic therapy.

In one embodiment one or more treatment cycles comprise 14 days or 21 days. In one embodiment one or more treatment cycles comprise 21 days.

In one embodiment, the anti-CD20/anti-CD3 bispecific antibody comprises a) at least one antigen binding domain that specifically binds to CD20 comprising
 a heavy chain variable region comprising
 (i) an HVR-H1 comprising the amino acid sequence of SEQ ID NO: 1;
 (ii) an HVR-H2 comprising the amino acid sequence of SEQ ID NO: 2; and
 (iii) an HVR-H3 comprising the amino acid sequence of SEQ ID NO:3;
 and a light chain variable region comprising
 (i) an HVR-L1 comprising the amino acid sequence of SEQ ID NO: 4;
 (ii) an HVR-L2 comprising the amino acid sequence of SEQ ID NO: 5; and
 (iii) an HVR-L3 comprising the amino acid sequence of SEQ ID NO: 6; and
b) at least one antigen binding domain that specifically binds to CD3 comprising
 a heavy chain variable region comprising:
 (i) an HVR-H1 comprising the amino acid sequence of SEQ ID NO: 9;
 (ii) an HVR-H2 comprising the amino acid sequence of SEQ ID NO: 10; and
 (iii) an HVR-H3 comprising the amino acid sequence of SEQ ID NO:11; and
 a light chain variable region comprising
 (i) an HVR-L1 comprising the amino acid sequence of SEQ ID NO: 12;
 (ii) an HVR-L2 comprising the amino acid sequence of SEQ ID NO: 13; and
 (iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and (ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In an embodiment of the invention, a method of treating a subject having diffuse large B cell lymphoma (DLBCL) is provided, comprising administering to the subject glofitamab in a dosing regimen comprising at least a first dosing cycle and a second dosing cycle wherein:

a) the first dosing cycle comprises a first dose (C1D1) and a second dose (C1D2) of glofitamab, wherein the C1D1 is 2.5 mg, and the C1D2 is 10 mg of glofitamab; and b) the second dosing cycle comprises a single dose (C2D1) of 16 or 30 mg of glofitamab.

In one embodiment, the single dose of the second dosing cycle (C2D1) comprises 30 mg of glofitamab.

In one embodiment, the first dose (C1D1) of glofitamab is administered on day 1 of the first dosing cycle and the second dose (C1D2) of glofitamab is administered on day 8 of the first dosing cycle. In one embodiment, the single dose of the second dosing cycle (C2D1) is administered on day 1 of the second dosing cycle.

In one embodiment a method of treating a subject having diffuse large B cell lymphoma (DLBCL) is provided, comprising administering to the subject glofitamab in a dosing regimen comprising at least a first dosing cycle and a second dosing cycle, wherein:

a) the first dosing cycle comprises a first dose (C1D1) and a second dose (C1D2) of glofitamab, wherein the C1D1 is 2.5 mg and is administered on day 1 of the first dosing cycle, and the C1D2 is 10 mg and is administered on day 8 of the first dosing cycle; and b) the second dosing cycle comprises a single dose (C2D1) of 16 or 30 mg of glofitamab administered on day 1 of the second dosing cycle.

In one embodiment, the method comprises 1 to 10 additional dosing cycles (C3 to C12). In one embodiment, the 1 to 10 additional dosing cycles (C3 to C12) each comprises a single dose (C3D1 to C12D1) of either 16 or 30 mg of glofitamab. In one embodiment, the single dose of each of the additional dosing cycles (C3D1 to C12D1) comprises 30 mg of glofitamab. In one embodiment, the single dose of the additional dosing cycles (C3D1 to C12D1) is administered on day 1 of the respective additional dosing cycle.

In one embodiment, a method of treating a subject having diffuse large B cell lymphoma (DLBCL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg, and the C1D2 is 10 mg of glofitamab and b) the subsequent dosing cycles each comprises a single dose (C2D1 to C12D1) of 16 or 30 mg of glofitamab.

In one such embodiment, the subsequent dosing cycles each comprises a single dose (C2D1 to C12D1) of 30 mg of glofitamab.

In one embodiment, a method of treating a subject having diffuse large B cell lymphoma (DLBCL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg and administered on day 1 of the first dosing cycle, and the C1D2 is 10 mg of glofitamab and administered on day 8 of the first dosing cycle; and b) the subsequent dosing cycles each comprises a single dose (C2D1 to C12D1) of 16 or 30 mg of glofitamab administered on day 1 of each subsequent dosing cycle.

In one such embodiment, the subsequent dosing cycles each comprises a single dose (C2D1 to C12D1) of 30 mg of glofitamab.

In an embodiment of the invention, a method of treating a subject having Follicular lymphoma (FL) is provided, comprising administering to the subject an anti-CD20/anti-CD3 bispecific antibody in a dosing regimen comprising at least a first dosing cycle and a second dosing cycle, wherein:

a) the first dosing cycle comprises a first dose (C1D1) and a second dose (C1D2) of the anti-CD20/anti-CD3 bispecific antibody, wherein the C1D1 is 2.5 mg, and the C1D2 is 10 mg of the anti-CD20/anti-CD3 bispecific antibody; and b) the second dosing cycle comprises a single dose (C2D1) of 16 or 30 mg of the anti-CD20/anti-CD3 bispecific antibody.

In one embodiment, the single dose (C2D1) of the third dosing cycle comprises 30 mg of the anti-CD20/anti-CD3 bispecific antibody.

In one embodiment, the first dose (C1D1) is administered on day 1 of the first dosing cycle and the second dose (C1D2) is administered on day 8 of the first dosing cycle. In one embodiment, the single dose of the second dosing cycle (C2D1) is administered on day 1 of the second dosing cycle.

In one embodiment a method of treating a subject having Follicular lymphoma (FL) is provided, comprising administering to the subject an anti-CD20/anti-CD3 bispecific antibody in a dosing regimen comprising at least a first dosing cycle and a second dosing cycle, wherein:

a) the first dosing cycle comprises a first dose (C1D1) and a second dose (C1D2) of the anti-CD20/anti-CD3 bispecific antibody, wherein the C1D1 is 2.5 mg and is administered on day 1 of the first dosing cycle, and the C1D2 is 10 mg and is administered on day 8 of the first dosing cycle; and b) the second dosing cycle comprises a single dose (C2D1) of 16 or 30 mg of the anti-CD20/anti-CD3 bispecific antibody administered on day 1 of the second dosing cycle.

In one embodiment the method of treating FL comprises 1 to 10 additional dosing cycles (C3 to C12). In one embodiment, the 1 to 10 additional dosing cycles (C3 to C12) each comprises a single dose (C3D1 to C12D1) of either 16 or 30 mg of the anti-CD20/anti-CD3 bispecific antibody. In one embodiment, the single dose of each of the additional dosing cycles (C3D1 to C12D1) comprises 30 mg of the anti-CD20/anti-CD3 bispecific antibody. In one embodiment the single dose of the additional dosing cycles (C3D1 to C12D1) is administered on day 1 of the respective additional dosing cycle.

In one embodiment a method of treating a subject having Follicular lymphoma (FL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody; and b) the subsequent dosing cycles each comprises a single dose (C2D1 to C12D1) of 16 or 30 mg of the anti-CD20/anti-CD3 bispecific antibody.

In one such embodiment the subsequent dosing cycles each comprises a single dose (C2D1 to C12D1) of 30 mg of the anti-CD20/anti-CD3 bispecific antibody.

In one embodiment a method of treating a subject having Follicular lymphoma (FL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 2.5 mg and administered on day 1 of the first dosing cycle, and the C1D2 is 10 mg of the anti-CD20/anti-CD3 bispecific antibody and administered on day 8 of the first dosing cycle; and b) the subsequent dosing cycles each comprises a single dose (C2D1 to C12D1) of 16 or 30 mg of the anti-CD20/anti-CD3 bispecific antibody administered on day 1 of each subsequent dosing cycle.

In one such embodiment the subsequent dosing cycles each comprises a single dose (C2D1 to C12D1) of 30 mg of the anti-CD20/anti-CD3 bispecific antibody.

In one embodiment the method for treating FL described above comprises 12 dosing cycles in total. In one embodiment, the FL is a relapsed or refractory (R/R) FL. In one embodiment the FL is Grade 1, 2, or 3a FL. In one embodiment, patients with Grade 1-3a FL have relapsed after or failed to respond to at least two prior lines of systemic therapy and have received prior treatment with rituximab and alkylating agents. In one embodiment, the subjects to be treated have FLIPI risk score ≥3.

In one embodiment, subjects with (CLL), Burkitt lymphoma, and lymphoplasmacytic lymphoma are excluded from the methods of treatment described above.

In one embodiment the FL is a transformed FL. In one embodiment, patients with trFL have relapsed after or failed to respond to at least two prior systemic treatment regimens (including at least one prior regimen containing anthracycline, and at least one containing an anti CD20-directed therapy). In one embodiment the subject is a high-risk subject who:

(a) has relapsed after or is refractory to at least two prior therapies;
(b) has relapsed after or is refractory to treatment with a phosphoinositide 3-kinase (PI3K) inhibitor;
(c) experiences progression of disease within 24 months of frontline treatment; and/or
(d) has lesions, wherein the sum of the product of the lesion diameters is ≥3,000 $mm^2$.

In one embodiment one or more treatment cycles comprise 14 days or 21 days. In one embodiment one or more treatment cycles comprise 21 days.

In one embodiment, the anti-CD20/anti-CD3 bispecific antibody comprises a) at least one antigen binding domain that specifically binds to CD20 comprising
a heavy chain variable region comprising
(i) an HVR-H1 comprising the amino acid sequence of SEQ ID NO: 1;
(ii) an HVR-H2 comprising the amino acid sequence of SEQ ID NO: 2; and
(iii) an HVR-H3 comprising the amino acid sequence of SEQ ID NO:3;
and a light chain variable region comprising
(i) an HVR-L1 comprising the amino acid sequence of SEQ ID NO: 4;
(ii) an HVR-L2 comprising the amino acid sequence of SEQ ID NO: 5; and
(iii) an HVR-L3 comprising the amino acid sequence of SEQ ID NO: 6; and
b) at least one antigen binding domain that specifically binds to CD3 comprising
a heavy chain variable region comprising:
(i) an HVR-H1 comprising the amino acid sequence of SEQ ID NO: 9;
(ii) an HVR-H2 comprising the amino acid sequence of SEQ ID NO: 10; and
(iii) an HVR-H3 comprising the amino acid sequence of SEQ ID NO:11; and
a light chain variable region comprising
(i) an HVR-L1 comprising the amino acid sequence of SEQ ID NO: 12;
(ii) an HVR-L2 comprising the amino acid sequence of SEQ ID NO: 13; and
(iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and
(ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In an embodiment of the invention, a method of treating a subject having Follicular lymphoma (FL) is provided, comprising administering to the subject glofitamab in a dosing regimen comprising at least a first dosing cycle and a second dosing cycle wherein:

a) the first dosing cycle comprises a first dose (C1D1) and a second dose (C1D2) of glofitamab, wherein the C1D1 is 2.5 mg, and the C1D2 is 10 mg of glofitamab; and
b) the second dosing cycle comprises a single dose (C2D1) of 16 or 30 mg of glofitamab.

In one embodiment, the single dose of the second dosing cycle (C2D1) comprises 30 mg of glofitamab.

In one embodiment, the first dose (C1D1) of glofitamab is administered on day 1 of the first dosing cycle and the second dose (C1D2) of glofitamab is administered on day 8 of the first dosing cycle. In one embodiment, the single dose of the second dosing cycle (C2D1) is administered on day 1 of the second dosing cycle.

In one embodiment a method of treating a subject having Follicular lymphoma (FL) is provided, comprising administering to the subject glofitamab in a dosing regimen comprising at least a first dosing cycle and a second dosing cycle, wherein:

a) the first dosing cycle comprises a first dose (C1D1) and a second dose (C1D2) of glofitamab, wherein the C1D1 is 2.5 mg and is administered on day 1 of the first dosing cycle, and the C1D2 is 10 mg and is administered on day 8 of the first dosing cycle; and
b) the second dosing cycle comprises a single dose (C2D1) of 16 or 30 mg of glofitamab administered on day 1 of the second dosing cycle.

In one embodiment, the method comprises 1 to 10 additional dosing cycles (C3 to C12). In one embodiment, the 1 to 10 additional dosing cycles (C3 to C12) each comprises a single dose (C3D1 to C12D1) of either 16 or 30 mg of glofitamab. In one embodiment, the single dose of each of the additional dosing cycles (C3D1 to C12D1) comprises 30 mg of glofitamab. In one embodiment, the single dose of the additional dosing cycles (C3D1 to C12D1) is administered on day 1 of the respective additional dosing cycle.

In one embodiment, a method of treating a subject having Follicular lymphoma (FL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg, and the C1D2 is 10 mg of glofitamab; and
b) the subsequent dosing cycles each comprises a single dose (C2D1 to C12D1) of 16 or 30 mg of glofitamab.

In one such embodiment, the subsequent dosing cycles each comprises a single dose (C2D1 to C12D1) of 30 mg of glofitamab.

In one embodiment, a method of treating a subject having Follicular lymphoma (FL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg and administered on day 1 of the first dosing cycle, dosing and the C1D2 is 10 mg of glofitamab and administered on day 8 of the first dosing cycle; and
b) the subsequent dosing cycles each comprises a single dose (C2D1 to C12D1) of 16 or 30 mg of glofitamab administered on day 1 of each subsequent dosing cycle.

In one such embodiment, the subsequent dosing cycles each comprises a single dose (C2D1 to C12D1) of 30 mg of glofitamab.

In another aspect of the invention, a method of treating a subject having Follicular lymphoma (FL) is provided, comprising administering to the subject an anti-CD20/anti-CD3 bispecific antibody in a dosing regimen comprising at least a first dosing cycle, a second dosing cycle and a third dosing cycle, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody,
b) the second dosing cycle comprises a single dose (C2D1) of 10 mg of the anti-CD20/anti-CD3 bispecific antibody, and
c) the third dosing cycle comprises a single dose (C3D1) of 16 or 30 mg of the anti-CD20/anti-CD3 bispecific antibody.

In one embodiment, the single dose of the third dosing cycle (C3D1) comprises 30 mg of the anti-CD20/anti-CD3 bispecific antibody.

In one embodiment, the first dose (C1D1) is administered on day 1 of the first dosing cycle and the second dose (C1D2) is administered on day 8 of the first dosing cycle. In one embodiment, the single dose of the second dosing cycle (C2D1) is administered on day 1 of the second dosing cycle. In one embodiment, the single dose of the third dosing cycle (C3D1) is administered on day 1 of the third dosing cycle.

In one embodiment a method of treating a subject having Follicular lymphoma (FL) is provided, comprising administering to the subject an anti-CD20/anti-CD3 bispecific antibody in a dosing regimen comprising at least a first dosing cycle, a second dosing cycle and a third dosing cycle, wherein:

a) the first dosing cycle comprises a first dose (C1D1) and a second dose (C1D2) of the anti-CD20/anti-CD3 bispecific antibody, wherein the C1D1 is 0.5 mg and is administered on day 1 of the first dosing cycle, and the C1D2 is 2.5 mg and is administered on day 8 of the first dosing cycle,
b) the second dosing cycle comprises a single dose (C2D1) of 10 mg of the anti-CD20/anti-CD3 bispecific antibody administered on day 1 of the second dosing cycle, and
c) the third dosing cycle comprises a single dose (C3D1) of 16 or 30 mg of the anti-CD20/anti-CD3 bispecific antibody administered on day 1 of the third dosing cycle.

In one embodiment the method of treating FL comprises 1 to 9 additional dosing cycles (C4 to C12). In one embodiment, the 1 to 9 additional dosing cycles (C4 to C12) each comprises a single dose (C4D1 to C12D1) of either 16 or 30 mg of the anti-CD20/anti-CD3 bispecific antibody. In one embodiment, the single dose of each of the additional dosing cycles (C4D1 to C12D1) comprises 30 mg of the anti-CD20/anti-CD3 bispecific antibody. In one embodiment the single dose of the additional dosing cycles (C4D1 to C12D1) is administered on day 1 of the respective additional dosing cycle.

In one embodiment a method of treating a subject having Follicular lymphoma (FL) is provided, comprising administering to the subject an anti-CD20/anti-CD3 bispecific antibody in a dosing regimen comprising three to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody,
b) the second dosing cycle comprises a single dose (C2D1) of 10 mg of the anti-CD20/anti-CD3 bispecific antibody, and
c) the subsequent dosing cycles each comprises a single dose (C3D1 to C12D1) of 16 or 30 mg of the anti-CD20/anti-CD3 bispecific antibody.

In one such embodiment the subsequent dosing cycles each comprises a single dose (C3D1 to C12D1) of 30 mg of the anti-CD20/anti-CD3 bispecific antibody.

In one embodiment a method of treating a subject having Follicular lymphoma (FL) is provided, comprising administering to the subject an anti-CD20/anti-CD3 bispecific antibody in a dosing regimen comprising three to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg and administered on day 1 of the first dosing cycle, and the C1D2 is 2.5 mg of the anti-CD20/anti-CD3 bispecific antibody and administered on day 8 of the first dosing cycle;
b) the second dosing cycle comprises a single dose (C2D1) of 10 mg of the anti-CD20/anti-CD3 bispecific antibody administered on day 1 of the second dosing cycle; and
c) the subsequent dosing cycles each comprises a single dose (C3D1 to C12D1) of 16 or 30 mg of the anti-CD20/anti-CD3 bispecific antibody administered on day 1 of each subsequent dosing cycle.

In one such embodiment the subsequent dosing cycles each comprises a single dose (C3D1 to C12D1) of 30 mg of the anti-CD20/anti-CD3 bispecific antibody.

In one embodiment the method for treating FL described above comprises 12 dosing cycles in total.

In one embodiment, the FL is a relapsed or refractory (R/R) FL. In one embodiment the FL is Grade 1, 2, or 3a FL. In one embodiment, patients with Grade 1-3a FL have relapsed after or failed to respond to at least two prior lines of systemic therapy and have received prior treatment with rituximab and alkylating agents. In one embodiment, the subjects to be treated have FLIPI risk score ≥3.

In one embodiment, subjects with (CLL), Burkitt lymphoma, and lymphoplasmacytic lymphoma are excluded from the methods of treatment described above.

In one embodiment the FL is a transformed FL. In one embodiment, patients with trFL have relapsed after or failed to respond to at least two prior systemic treatment regimens (including at least one prior regimen containing anthracycline, and at least one containing an anti CD20-directed therapy).

In one embodiment the subject is a high-risk subject who:

(a) has relapsed after or is refractory to at least two prior therapies;

(b) has relapsed after or is refractory to treatment with a phosphoinositide 3-kinase (PI3K) inhibitor;

(c) experiences progression of disease within 24 months of frontline treatment; and/or (d) has lesions, wherein the sum of the product of the lesion diameters is ≥3,000 $mm^2$.

In one embodiment one or more treatment cycles comprise 14 days or 21 days. In one embodiment one or more treatment cycles comprise 21 days.

In one embodiment, the anti-CD20/anti-CD3 bispecific antibody comprises a) at least one antigen binding domain that specifically binds to CD20 comprising a heavy chain variable region comprising (i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising (i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and b) at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11; and a light chain variable region comprising (i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and (ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In another aspect of the invention, a method of treating a subject having Follicular lymphoma (FL) is provided, comprising administering to the subject glofitamab in a dosing regimen comprising at least a first dosing cycle, a second dosing cycle and a third dosing cycle, wherein:

a) the first dosing cycle comprises a first dose (C1D1) and a second dose (C1D2) of glofitamab, wherein the C1D1 is 0.5 mg, and the C1D2 is 2.5 mg of glofitamab;

b) the second dosing cycle comprises a single dose (C2D1) of 10 mg of glofitamab; and c) the third dosing cycle comprises a single dose (C3D1) of 16 or 30 mg of glofitamab.

In one embodiment, the single dose of the third dosing cycle (C3D1) comprises 30 mg of glofitamab.

In one embodiment, the first dose (C1D1) of glofitamab is administered on day 1 of the first dosing cycle and the second dose (C1D2) of glofitamab is administered on day 8 of the first dosing cycle. In one embodiment, the single dose of the second dosing cycle (C2D1) is administered on day 1 of the second dosing cycle. In one embodiment, the single dose of the third dosing cycle (C3D1) is administered on day 1 of the third dosing cycle.

In one embodiment a method of treating a subject having Follicular lymphoma (FL) is provided, comprising administering to the subject glofitamab in a dosing regimen comprising at least a first dosing cycle, a second dosing cycle and a third dosing cycle, wherein:

a) the first dosing cycle comprises a first dose (C1D1) and a second dose (C1D2) of glofitamab, wherein the C1D1 is 0.5 mg and is administered on day 1 of the first dosing cycle, and the C1D2 is 2.5 mg and is administered on day 8 of the first dosing cycle, b) the second dosing cycle comprises a single dose (C2D1) of 10 mg of glofitamab administered on day 1 of the second dosing cycle, and c) the third dosing cycle comprises a single dose (C3D1) of 16 or 30 mg of glofitamab administered on day 1 of the third dosing cycle.

In one embodiment the method comprises 1 to 9 additional dosing cycles (C4 to C12). In one embodiment, the 1 to 9 additional dosing cycles (C4 to C12) each comprises a single dose (C4D1 to C12D1) of either 16 or 30 mg of glofitamab. In one embodiment, the single dose of each of the additional dosing cycles (C4D1 to C12D1) comprises 30 mg of glofitamab. In one embodiment the single dose of the additional dosing cycles (C4D1 to C12D1) is administered on day 1 of the respective additional dosing cycle.

In one embodiment a method of treating a subject having Follicular lymphoma (FL) is provided, comprising administering to the subject glofitamab in a dosing regimen comprising three to twelve dosing cycles, wherein:

a) the first dosing cycle comprises a first dose (C1D1) and a second dose (C1D2) of glofitamab, wherein the C1D1 is 0.5 mg, and the C1D2 is 2.5 mg of glofitamab, b) the second dosing cycle comprises a single dose (C2D1) of 10 mg of glofitamab, and c) the subsequent dosing cycles each comprises a single dose (C3D1 to C12D1) of 16 or 30 mg of glofitamab.

In one such embodiment the subsequent dosing cycles each comprises a single dose (C3D1 to C12D1) of 30 mg of glofitamab.

In one embodiment a method of treating a subject having Follicular lymphoma (FL) is provided, comprising administering to the subject glofitamab in a dosing regimen comprising three to twelve dosing cycles, wherein:

a) the first dosing cycle comprises a first dose (C1D1) and a second dose (C1D2) of glofitamab, wherein the C1D1 is 0.5 mg and administered on day 1 of the first dosing cycle, and the C1D2 is 2.5 mg of glofitamab and administered on day 8 of the first dosing cycle;

b) the second dosing cycle comprises a single dose (C2D1) of 10 mg of glofitamab administered on day 1 of the second dosing cycle; and c) the subsequent dosing cycles each comprises a single dose (C3D1 to C12D1) of 16 or 30 mg of glofitamab administered on day 1 of each subsequent dosing cycle.

In one such embodiment the subsequent dosing cycles each comprises a single dose (C3D1 to C12D1) of 30 mg of glofitamab.

In one embodiment the method for treating FL described above comprises 12 dosing cycles in total. In one embodiment, the FL is a relapsed or refractory (R/R) FL. In one embodiment the FL is Grade 1, 2, or 3a FL. In one embodiment, patients with Grade 1-3a FL have relapsed after or failed to respond to at least two prior lines of systemic therapy and have received prior treatment with rituximab and alkylating agents. In one embodiment, the subjects to be treated have FLIPI risk score ≥3.

In one embodiment the subject is a high-risk subject who:

(a) has relapsed after or is refractory to at least two prior therapies;

(b) has relapsed after or is refractory to treatment with a phosphoinositide 3-kinase (PI3K) inhibitor;

(c) experiences progression of disease within 24 months of frontline treatment; and/or (d) has lesions, wherein the sum of the product of the lesion diameters is ≥3,000 $mm^2$.

In one embodiment, subjects with (CLL), Burkitt lymphoma, and lymphoplasmacytic lymphoma are excluded from the methods of treatment described above.

In one embodiment the FL is a transformed FL. In one embodiment, patients with trFL have relapsed after or failed to respond to at least two prior systemic treatment regimens (including at least one prior regimen containing anthracycline, and at least one containing an anti CD20-directed therapy).

In one embodiment one or more treatment cycles comprise 14 days or 21 days. In one embodiment one or more treatment cycles comprise 21 days.

Mantle cell lymphoma (MCL) is a relatively rare and incurable B-cell lymphoma where areas of high unmet need include relapsed or refractory (r/r) patients previously treated with BTK inhibitors setting and previously untreated patients with high-risk pathologies. To date, relapsed patients are treated with rituximab based therapies or CAR-T therapy, and other targeted therapies have proven to be of limited use.

Post-BTKi MCL patients have a poor prognosis due to the aggressive nature of the disease and a lack of curative treatment options. The median overall survival is 6-12 months with an ORR of ~26% with available systemic therapies. Therefore, there is an urgent and currently unmet medical need for an improved method of treatment for MCL patients. Glofitamab monotherapy for MCL provides an off-the shelf, fixed duration therapy that compares favorably to systemic therapies such as rituximab based therapies and CAR-T therapy.

In an embodiment of the invention, a method of treating a subject having mantle cell lymphoma (MCL) is provided, comprising administering to the subject an anti-CD20/anti-CD3 bispecific antibody in a dosing regimen comprising at least a first dosing cycle and a second dosing cycle wherein:

a) the first dosing cycle comprises a first dose (C1D1) and a second dose (C1D2) of the anti-CD20/anti-CD3 bispecific antibody, wherein the C1D1 is 2.5 mg, and the C1D2 is 10 mg of the anti-CD20/anti-CD3 bispecific antibody; and b) the second dosing cycle comprises a single dose (C2D1) of 16 or 30 mg of the anti-CD20/anti-CD3 bispecific antibody.

In one embodiment, the single dose of the second dosing cycle (C2D1) comprises 30 mg of the anti-CD20/anti-CD3 bispecific antibody.

In one embodiment, the first dose (C1D1) of the anti-CD20/anti-CD3 bispecific antibody is administered on day 1 of the first dosing cycle and the second dose (C1D2) of the anti-CD20/anti-CD3 bispecific antibody is administered on day 8 of the first dosing cycle. In one embodiment, the single dose of the second dosing cycle (C2D1) is administered on day 1 of the second dosing cycle.

In one embodiment a method of treating a subject having mantle cell lymphoma (MCL) is provided, comprising administering to the subject the anti-CD20/anti-CD3 bispecific antibody in a dosing regimen comprising at least a first dosing cycle and a second dosing cycle, wherein:

a) the first dosing cycle comprises a first dose (C1D1) and a second dose (C1D2) of the anti-CD20/anti-CD3 bispecific antibody, wherein the C1D1 is 2.5 mg and is administered on day 1 of the first dosing cycle, and the C1D2 is 10 mg and is administered on day 8 of the first dosing cycle; and b) the second dosing cycle comprises a single dose (C2D1) of 16 or 30 mg of the anti-CD20/anti-CD3 bispecific antibody administered on day 1 of the second dosing cycle.

In one embodiment, the second dosing cycle of b) comprises a single dose (C2D1) of 30 mg of the anti-CD20/anti-CD3 bispecific antibody administered on day 1 of the second dosing cycle.

In one embodiment, the method comprises 1 to 10 additional dosing cycles (C3 to C12). In one embodiment, the 1 to 10 additional dosing cycles (C3 to C12) each comprises a single dose (C3D1 to C12D1) of either 16 or 30 mg of the anti-CD20/anti-CD3 bispecific antibody. In one embodiment, the single dose of each of the additional dosing cycles (C3D1 to C12D1) comprises 30 mg of the anti-CD20/anti-CD3 bispecific antibody. In one embodiment, the single dose of the additional dosing cycles (C3D1 to C12D1) is administered on day 1 of the respective additional dosing cycle.

In one embodiment, a method of treating a subject having mantle cell lymphoma (MCL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 2.5 mg, and the C1D2 is 10 mg of the anti-CD20/anti-CD3 bispecific antibody; and b) the subsequent dosing cycles each comprises a single dose (C2D1 to C12D1) of 16 or 30 mg of the anti-CD20/anti-CD3 bispecific antibody.

In one such embodiment, the subsequent dosing cycles each comprises a single dose (C2D1 to C12D1) of 30 mg of the anti-CD20/anti-CD3 bispecific antibody.

In one embodiment, a method of treating a subject having mantle cell lymphoma (MCL) is provided, comprising administering to the subject an anti-CD20/anti-CD3 bispecific antibody in a dosing regimen comprising two to twelve dosing cycles, wherein:

a) the first dosing cycle comprises a first dose (C1D1) and a second dose (C1D2) of the anti-CD20/anti-CD3 bispecific antibody, wherein the C1D1 is 2.5 mg and administered on day 1 of the first dosing cycle, and the C1D2 is 10 mg of the anti-CD20/anti-CD3 bispecific antibody and administered on day 8 of the first dosing cycle; and b) the subsequent dosing cycles each comprises a single dose (C2D1 to C12D1) of 16 or 30 mg of the anti-CD20/anti-CD3 bispecific antibody administered on day 1 of each subsequent dosing cycle.

In one such embodiment, the subsequent dosing cycles each comprises a single dose (C2D1 to C12D1) of 30 mg of the anti-CD20/anti-CD3 bispecific antibody.

In one embodiment, the method for treating MCL described above comprises 12 dosing cycles in total. In one embodiment, the method for treating MCL described above comprises 6, 7, 8, 9, or 10 dosing cycles in total. In one embodiment the MCL is a relapsed or refractory (R/R) MCL. In one embodiment, patients with R/R MCL have relapsed after or failed to respond to at least two prior lines of systemic therapy. In one embodiment, the subject has received at least one prior systemic treatment regimen comprising a Bruton tyrosine kinase inhibitor (BTKi). In one embodiment the BTKi comprises ibrutinib, acalabrutinib, or zanubrutinib.

In one embodiment one or more treatment cycles comprise 14 days or 21 days. In one embodiment one or more treatment cycles comprise 21 days.

In one embodiment, the anti-CD20/anti-CD3 bispecific antibody for the method of treating MCL comprises a) at least one antigen binding domain that specifically binds to CD20 comprising
a heavy chain variable region comprising
(i) an HVR-H1 comprising the amino acid sequence of SEQ ID NO: 1;
(ii) an HVR-H2 comprising the amino acid sequence of SEQ ID NO: 2; and
(iii) an HVR-H3 comprising the amino acid sequence of SEQ ID NO:3;
and a light chain variable region comprising
(i) an HVR-L1 comprising the amino acid sequence of SEQ ID NO: 4;
(ii) an HVR-L2 comprising the amino acid sequence of SEQ ID NO: 5; and
(iii) an HVR-L3 comprising the amino acid sequence of SEQ ID NO: 6; and b) at least one antigen binding domain that specifically binds to CD3 comprising
a heavy chain variable region comprising:
(i) an HVR-H1 comprising the amino acid sequence of SEQ ID NO: 9;
(ii) an HVR-H2 comprising the amino acid sequence of SEQ ID NO: 10; and
(iii) an HVR-H3 comprising the amino acid sequence of SEQ ID NO:11; and
a light chain variable region comprising
(i) an HVR-L1 comprising the amino acid sequence of SEQ ID NO: 12;
(ii) an HVR-L2 comprising the amino acid sequence of SEQ ID NO: 13; and
(iii) an HVR-L3 comprising the amino acid sequence of SEQ ID NO: 14.

In one embodiment, the anti-CD20/anti-CD3 bispecific antibody for the method of treating MCL comprises (i) at least one antigen binding domain that specifically binds to CD20 comprising the heavy chain variable region sequence of SEQ ID NO: 7 and the light chain variable region sequence of SEQ ID NO: 8, and (ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In an embodiment of the invention, a method of treating a subject having mantle cell lymphoma (MCL) is provided, comprising administering to the subject glofitamab in a dosing regimen comprising at least a first dosing cycle and a second dosing cycle wherein:

a) the first dosing cycle comprises a first dose (C1D1) and a second dose (C1D2) of glofitamab, wherein the C1D1 is 2.5 mg, and the C1D2 is 10 mg of glofitamab; and b) the second dosing cycle comprises a single dose (C2D1) of 16 or 30 mg of glofitamab.

In one embodiment, the single dose of the second dosing cycle (C2D1) comprises 30 mg of glofitamab.

In one embodiment, the first dose (C1D1) of glofitamab is administered on day 1 of the first dosing cycle and the second dose (C1D2) of glofitamab is administered on day 8 of the first dosing cycle. In one embodiment, the single dose of the second dosing cycle (C2D1) is administered on day 1 of the second dosing cycle.

In one embodiment a method of treating a subject having mantle cell lymphoma (MCL) is provided, comprising administering to the subject glofitamab in a dosing regimen comprising at least a first dosing cycle and a second dosing cycle, wherein:

a) the first dosing cycle comprises a first dose (C1D1) and a second dose (C1D2) of glofitamab, wherein the C1D1 is 2.5 mg and is administered on day 1 of the first dosing cycle, and the C1D2 is 10 mg and is administered on day 8 of the first dosing cycle; and b) the second dosing cycle comprises a single dose (C2D1) of 16 or 30 mg of glofitamab administered on day 1 of the second dosing cycle.

In one embodiment, the method comprises 1 to 10 additional dosing cycles (C3 to C12). In one embodiment, the 1 to 10 additional dosing cycles (C3 to C12) each comprises a single dose (C3D1 to C12D1) of either 16 or 30 mg of glofitamab. In one embodiment, the single dose of each of the additional dosing cycles (C3D1 to C12D1) comprises 30 mg of glofitamab. In one embodiment, the single dose of the additional dosing cycles (C3D1 to C12D1) is administered on day 1 of the respective additional dosing cycle.

In one embodiment, a method of treating a subject having mantle cell lymphoma (MCL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg, and the C1D2 is 10 mg of glofitamab; and b) the subsequent dosing cycles each comprises a single dose (C2D1 to C12D1) of 16 or 30 mg of glofitamab.

In one such embodiment, the subsequent dosing cycles each comprises a single dose (C2D1 to C12D1) of 30 mg of glofitamab.

In one embodiment, a method of treating a subject having mantle cell lymphoma (MCL) is provided, comprising administering to the subject glofitamab in a dosing regimen comprising two to twelve dosing cycles, wherein:

a) the first dosing cycle comprises a first dose (C1D1) and a second dose (C1D2) of glofitamab, wherein the C1D1 is 2.5 mg and administered on day 1 of the first dosing cycle, and the C1D2 is 10 mg of glofitamab and administered on day 8 of the first dosing cycle; and b) the subsequent dosing cycles each comprises a single dose (C2D1 to C12D1) of 16 or 30 mg of glofitamab administered on day 1 of each subsequent dosing cycle.

In one such embodiment, the subsequent dosing cycles each comprises a single dose (C2D1 to C12D1) of 30 mg of glofitamab.

In one embodiment, the method for treating MCL described above comprises 12 dosing cycles in total. In one embodiment, the method for treating MCL described above comprises 6, 7, 8, 9, or dosing cycles in total.

In one embodiment the MCL is a relapsed or refractory (R/R) MCL. In one embodiment, patients with R/R MCL have relapsed after or failed to respond to at least two prior lines of systemic therapy. In one embodiment, the subject has received at least one prior systemic treatment regimen comprising a Bruton tyrosine kinase inhibitor (BTKi). In one embodiment the BTKi comprises ibrutinib, acalabrutinib, or zanubrutinib.

In one embodiment one or more treatment cycles comprise 14 days or 21 days. In one embodiment one or more treatment cycles comprise 21 days.

In another aspect of the invention, a method of treating a subject having mantle cell lymphoma (MCL) is provided, comprising administering to the subject an anti-CD20/anti-CD3 bispecific antibody in a dosing regimen comprising at least a first dosing cycle, a second dosing cycle and a third dosing cycle, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody;

b) the second dosing cycle comprises a single dose (C2D1) of 10 mg of the anti-CD20/anti-CD3 bispecific antibody; and c) the third dosing cycle comprises a single dose (C3D1) of 16 or 30 mg of the anti-CD20/anti-CD3 bispecific antibody.

In one embodiment, the single dose of the third dosing cycle (C3D1) comprises 30 mg of the anti-CD20/anti-CD3 bispecific antibody.

In one embodiment, the first dose (C1D1) is administered on day 1 of the first dosing cycle and the second dose (C1D2) is administered on day 8 of the first dosing cycle. In one embodiment, the single dose of the second dosing cycle (C2D1) is administered on day 1 of the second dosing cycle. In one embodiment, the single dose of the third dosing cycle (C3D1) is administered on day 1 of the third dosing cycle.

In one embodiment a method of treating a subject having mantle cell lymphoma (MCL) is provided, comprising administering to the subject an anti-CD20/anti-CD3 bispecific antibody in a dosing regimen comprising at least a first dosing cycle, a second dosing cycle and a third dosing cycle, wherein:

a) the first dosing cycle comprises a first dose (C1D1) and a second dose (C1D2) of the anti-CD20/anti-CD3 bispecific antibody, wherein the C1D1 is 0.5 mg and is administered on day 1 of the first dosing cycle, and the C1D2 is 2.5 mg and is administered on day 8 of the first dosing cycle;

b) the second dosing cycle comprises a single dose (C2D1) of 10 mg of the anti-CD20/anti-CD3 bispecific antibody administered on day 1 of the second dosing cycle; and c) the third dosing cycle comprises a single dose (C3D1) of 16 or 30 mg of the anti-CD20/anti-CD3 bispecific antibody administered on day 1 of the third dosing cycle.

In one embodiment the method of treating MCL comprises 1 to 9 additional dosing cycles (C4 to C12). In one embodiment, the 1 to 9 additional dosing cycles (C4 to C12) each comprises a single dose (C4D1 to C12D1) of either 16 or 30 mg of the anti-CD20/anti-CD3 bispecific antibody. In one embodiment, the single dose of each of the additional dosing cycles (C4D1 to C12D1) comprises 30 mg of the anti-CD20/anti-CD3 bispecific antibody. In one embodiment the single dose of the additional dosing cycles (C4D1 to C12D1) is administered on day 1 of the respective additional dosing cycle.

In one embodiment a method of treating a subject having mantle cell lymphoma (MCL) is provided, comprising administering to the subject an anti-CD20/anti-CD3 bispecific antibody in a dosing regimen comprising three to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody;

b) the second dosing cycle comprises a single dose (C2D1) of 10 mg of the anti-CD20/anti-CD3 bispecific antibody; and c) the subsequent dosing cycles each comprises a single dose (C3D1 to C12D1) of 16 or 30 mg of the anti-CD20/anti-CD3 bispecific antibody.

In one such embodiment the subsequent dosing cycles each comprises a single dose (C3D1 to C12D1) of 30 mg of the anti-CD20/anti-CD3 bispecific antibody.

In one embodiment a method of treating a subject having mantle cell lymphoma (MCL) is provided, comprising administering to the subject an anti-CD20/anti-CD3 bispecific antibody in a dosing regimen comprising three to twelve dosing cycles, wherein:

a) the first dosing cycle comprises a first dose (C1D1) and a second dose (C1D2) of the anti-CD20/anti-CD3 bispecific antibody, wherein the C1D1 is 0.5 mg and administered on day 1 of the first dosing cycle, and the C1D2 is 2.5 mg of the anti-CD20/anti-CD3 bispecific antibody and administered on day 8 of the first dosing cycle;

b) the second dosing cycle comprises a single dose (C2D1) of 10 mg of the anti-CD20/anti-CD3 bispecific antibody administered on day 1 of the second dosing cycle; and c) the subsequent dosing cycles each comprises a single dose (C3D1 to C12D1) of 16 or 30 mg of the anti-CD20/anti-CD3 bispecific antibody administered on day 1 of each subsequent dosing cycle.

In one such embodiment the subsequent dosing cycles each comprises a single dose (C3D1 to C12D1) of 30 mg of the anti-CD20/anti-CD3 bispecific antibody.

In one embodiment, the method for treating MCL described above comprises 12 dosing cycles in total. In one embodiment the MCL is a relapsed or refractory (R/R) MCL. In one embodiment, patients with R/R MCL have relapsed after or failed to respond to at least two prior lines of systemic therapy. In one embodiment, the subject has received at least one prior systemic treatment regimen comprising a Bruton tyrosine kinase inhibitor (BTKi). In one embodiment the BTKi comprises ibrutinib, acalabrutinib, or zanubrutinib.

In one embodiment one or more treatment cycles comprise 14 days or 21 days. In one embodiment one or more treatment cycles comprise 21 days.

In one embodiment, the anti-CD20/anti-CD3 bispecific antibody comprises a) at least one antigen binding domain that specifically binds to CD20 comprising
  a heavy chain variable region comprising
(i) an HVR-H1 comprising the amino acid sequence of SEQ ID NO: 1;
(ii) an HVR-H2 comprising the amino acid sequence of SEQ ID NO: 2; and
(iii) an HVR-H3 comprising the amino acid sequence of SEQ ID NO:3;
  and a light chain variable region comprising
(i) an HVR-L1 comprising the amino acid sequence of SEQ ID NO: 4;
(ii) an HVR-L2 comprising the amino acid sequence of SEQ ID NO: 5; and
(iii) an HVR-L3 comprising the amino acid sequence of SEQ ID NO: 6; and
b) at least one antigen binding domain that specifically binds to CD3 comprising
  a heavy chain variable region comprising:
(i) an HVR-H1 comprising the amino acid sequence of SEQ ID NO: 9;
(ii) an HVR-H2 comprising the amino acid sequence of SEQ ID NO: 10; and
(iii) an HVR-H3 comprising the amino acid sequence of SEQ ID NO:11; and
  a light chain variable region comprising
(i) an HVR-L1 comprising the amino acid sequence of SEQ ID NO: 12;
(ii) an HVR-L2 comprising the amino acid sequence of SEQ ID NO: 13; and
(iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and
(ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In another aspect of the invention, a method of treating a subject having mantle cell lymphoma (MCL) is provided, comprising administering to the subject glofitamab in a dosing regimen comprising at least a first dosing cycle, a second dosing cycle and a third dosing cycle, wherein:

a) the first dosing cycle comprises a first dose (C1D1) and a second dose (C1D2) of glofitamab, wherein the C1D1 is 0.5 mg, and the C1D2 is 2.5 mg of glofitamab;
b) the second dosing cycle comprises a single dose (C2D1) of 10 mg of glofitamab; and
c) the third dosing cycle comprises a single dose (C3D1) of 16 or 30 mg of glofitamab.

In one embodiment, the single dose of the third dosing cycle (C3D1) comprises 30 mg of glofitamab.

In one embodiment, the first dose (C1D1) of glofitamab is administered on day 1 of the first dosing cycle and the second dose (C1D2) of glofitamab is administered on day 8 of the first dosing cycle. In one embodiment, the single dose of the second dosing cycle (C2D1) is administered on day 1 of the second dosing cycle. In one embodiment, the single dose of the third dosing cycle (C3D1) is administered on day 1 of the third dosing cycle.

In one embodiment a method of treating a subject having mantle cell lymphoma (MCL) is provided, comprising administering to the subject glofitamab in a dosing regimen comprising at least a first dosing cycle, a second dosing cycle, and a third dosing cycle, wherein:

a) the first dosing cycle comprises a first dose (C1D1) and a second dose (C1D2) of glofitamab, wherein the C1D1 is 0.5 mg and is administered on day 1 of the first dosing cycle, and the C1D2 is 2.5 mg and is administered on day 8 of the first dosing cycle;
b) the second dosing cycle comprises a single dose (C2D1) of 10 mg of glofitamab administered on day 1 of the second dosing cycle; and
c) the third dosing cycle comprises a single dose (C3D1) of 16 or 30 mg of glofitamab administered on day 1 of the third dosing cycle.

In one embodiment, the method comprises 1 to 9 additional dosing cycles (C4 to C12). In one embodiment, the 1 to 9 additional dosing cycles (C4 to C12) each comprises a single dose (C4D1 to C12D1) of either 16 or 30 mg of glofitamab. In one embodiment, the single dose of each of the additional dosing cycles (C4D1 to C12D1) comprises 30 mg of glofitamab. In one embodiment, the single dose of the additional dosing cycles (C4D1 to C12D1) is administered on day 1 of the respective additional dosing cycle.

In one embodiment, a method of treating a subject having mantle cell lymphoma (MCL) is provided, comprising administering to the subject glofitamab in a dosing regimen comprising three to twelve dosing cycles, wherein:

a) the first dosing cycle comprises a first dose (C1D1) and a second dose (C1D2) of glofitamab, wherein the C1D1 is 0.5 mg, and the C1D2 is 2.5 mg of glofitamab;
b) the second dosing cycle comprises a single dose (C2D1) of 10 mg of glofitamab; and
c) the subsequent dosing cycles each comprises a single dose (C3D1 to C12D1) of 16 or 30 mg of glofitamab.

In one such embodiment, the subsequent dosing cycles each comprises a single dose (C3D1 to C12D1) of 30 mg of glofitamab.

In one embodiment, a method of treating a subject having mantle cell lymphoma (MCL) is provided, comprising administering to the subject glofitamab in a dosing regimen comprising three to twelve dosing cycles, wherein:

a) the first dosing cycle comprises a first dose (C1D1) and a second dose (C1D2) of glofitamab, wherein the C1D1 is 0.5 mg and administered on day 1 of the first dosing cycle, and the C1D2 is 2.5 mg of glofitamab and administered on day 8 of the first dosing cycle;
b) the second dosing cycle comprises a single dose (C2D1) of 10 mg of glofitamab administered on day 1 of the second dosing cycle; and c) the subsequent dosing cycles each comprises a single dose (C3D1 to C12D1) of 16 or 30 mg of glofitamab administered on day 1 of each subsequent dosing cycle.

In one such embodiment, the subsequent dosing cycles each comprises a single dose (C3D1 to C12D1) of 30 mg of glofitamab.

In one embodiment, the method for treating MCL described above comprises 12 dosing cycles in total. In one embodiment the MCL is a relapsed or refractory (R/R) MCL. In one embodiment, patients with MCL have relapsed after or failed to respond to at least two prior lines of systemic therapy. In one embodiment, patients with MCL have relapsed after or failed to respond to at least one prior systemic treatment regimen that includes a Bruton tyrosine kinase (BTK) inhibitor (BTKi). In one embodiment the BTKi comprises ibrutinib, acalabrutinib, or zanubrutinib.

In one embodiment one or more treatment cycles comprise 14 days or 21 days. In one embodiment one or more treatment cycles comprise 21 days.

In one embodiment, the invention features a method of treating a subject with mantle cell lymphoma which has relapsed after or failed to respond to at least one prior systemic treatment regimen that includes a Bruton tyrosine kinase (BTK) inhibitor (BTKi), comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the Second Dosing Cycle Comprises a Single Dose (C2D1) of 30 mg of the Anti-CD20/Anti-CD3 Bispecific Antibody.

In one embodiment, the subject with mantle cell lymphoma has relapsed after or failed to respond to at least one prior systemic treatment regimen with a Bruton tyrosine kinase (BTK) inhibitor (BTKi).

In one embodiment the BTKi comprises ibrutinib, acalabrutinib, or zanubrutinib.

In one embodiment the first dose (C1D1) is administered on day 1 of the first dosing cycle and the second dose (C1D2) is administered on day 8 of the first dosing cycle.

In one embodiment the single dose of the second dosing cycle (C2D1) is administered on day 1 of the second dosing cycle.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 1 to 10 additional dosing cycles (C3 to C12). In one such embodiment the 1 to 10 additional dosing cycles (C3 to C12) each comprises a single dose (C3D1 to C12D1) of either 16 or 30 mg of the anti-CD20/anti-CD3 bispecific antibody. In one embodiment the single dose of each of the additional dosing cycles (C3D1 to C12D1) comprises 30 mg of the anti-CD20/anti-CD3 bispecific antibody. In one embodiment the single dose of the additional dosing cycles (C3D1 to C12D1) is administered on day 1 of the respective additional dosing cycle.

In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 12 dosing cycles in total. In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 6, 8, or 10 dosing cycles in total.

In one embodiment, one or more treatment cycles comprise 14 days or 21 days. In one embodiment, one or more treatment cycles comprise 21 days.

In one embodiment, the anti-CD20/anti-CD3 bispecific antibody comprises a) at least one antigen binding domain that specifically binds to CD20 comprising a heavy chain variable region comprising (i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising (i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and b) at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11; and a light chain variable region comprising (i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

In one embodiment, the anti-CD20/anti-CD3 bispecific antibody comprises (i) at least one antigen binding domain that specifically binds to CD20 comprising the heavy chain variable region sequence of SEQ ID NO: 7 and the light chain variable region sequence of SEQ ID NO: 8, and (ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In one embodiment, the invention features a method of treating a subject with mantle cell lymphoma which has relapsed after or failed to respond to at least one prior systemic treatment regimen that includes a Bruton tyrosine kinase (BTK) inhibitor (BTKi), comprising administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of 30 mg of glofitamab.

In one embodiment, the subject with mantle cell lymphoma has relapsed after or failed to respond to at least one prior systemic treatment regimen with a Bruton tyrosine kinase (BTK) inhibitor (BTKi). In one embodiment the BTKi comprises ibrutinib, acalabrutinib, or zanubrutinib.

In one embodiment the first dose (C1D1) is administered on day 1 of the first dosing cycle and the second dose (C1D2) is administered on day 8 of the first dosing cycle.

In one embodiment the single dose of the second dosing cycle (C2D1) is administered on day 1 of the second dosing cycle.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 1 to 10 additional dosing cycles (C3 to C12). In one such embodiment the 1 to 10 additional dosing cycles (C3 to C12) each comprises a single dose (C3D1 to C12D1) of either 16 or 30 mg of glofitamab. In one embodiment the single dose of each of the additional dosing cycles (C3D1 to C12D1) comprises 30 mg of glofitamab. In one embodiment the single dose of the additional dosing cycles (C3D1 to C12D1) is administered on day 1 of the respective additional dosing cycle.

In one embodiment the BTKi comprises ibrutinib, acalabrutinib, or zanubrutinib.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 12 dosing cycles in total. In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 6, 8, or 10 dosing cycles in total.

In one embodiment, one or more treatment cycles comprise 14 days or 21 days. In one embodiment, one or more treatment cycles comprise 21 days.

In one embodiment, the invention features a method of treating a subject with mantle cell lymphoma which has relapsed after or failed to respond to at least one prior systemic treatment regimen that includes a Bruton tyrosine kinase (BTK) inhibitor (BTKi), comprising administering to the subject an anti-CD20/anti-CD3 bispecific antibody in a dosing regimen comprising at least a first dosing cycle, a second dosing cycle, and a third dosing cycle, wherein: (a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg; (b) the second dosing cycle comprises a single dose (C2D1) of 10 mg of the anti-CD20/anti-CD3 bispecific antibody; and (c) the third dosing cycle comprises a single dose (C3D1) of 30 mg of the anti-CD20/anti-CD3 bispecific antibody.

In one embodiment, the subject with mantle cell lymphoma has relapsed after or failed to respond to at least one prior systemic treatment regimen with a Bruton tyrosine kinase (BTK) inhibitor (BTKi).

In one embodiment the BTKi comprises ibrutinib, acalabrutinib, or zanubrutinib.

In one embodiment the first dose (C1D1) is administered on day 1 of the first dosing cycle and the second dose (C1D2) is administered on day 8 of the first dosing cycle.

In one embodiment the single dose of the second dosing cycle (C2D1) is administered on day 1 of the second dosing cycle.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 1 to 9 additional dosing cycles (C4 to C12). In one such embodiment the 1 to 9 additional dosing cycles (C4 to C12) each comprises a single dose (C4D1 to C12D1) of 30 mg of the anti-CD20/anti-CD3 bispecific antibody. In one embodiment the single dose of each of the additional dosing cycles (C4D1 to C12D1) comprises 30 mg of the anti-CD20/anti-CD3 bispecific antibody. In one embodiment the single dose of the additional dosing cycles (C4D1 to C12D1) is administered on day 1 of the respective additional dosing cycle.

In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 12 dosing cycles in total. In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 6, 8, or 10 dosing cycles in total.

In one embodiment, one or more treatment cycles comprise 14 days or 21 days. In one embodiment, one treatment cycles comprise 21 days.

In one embodiment, the invention features a method of treating a subject with mantle cell lymphoma which has relapsed after or failed to respond to at least one prior systemic treatment regimen that includes a Bruton tyrosine kinase (BTK) inhibitor (BTKi), comprising administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 30 mg of glofitamab.

In one embodiment, the subject with mantle cell lymphoma has relapsed after or failed to respond to at least one prior systemic treatment regimen with a Bruton tyrosine kinase (BTK) inhibitor (BTKi).

In one embodiment the BTKi comprises ibrutinib, acalabrutinib, or zanubrutinib.

In one embodiment the first dose (C1D1) is administered on day 1 of the first dosing cycle and the second dose (C1D2) is administered on day 8 of the first dosing cycle.

In one embodiment the single dose of the second dosing cycle (C2D1) is administered on day 1 of the second dosing cycle.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 1 to 9 additional dosing cycles (C4 to C12). In one such embodiment the 1 to 9 additional dosing cycles (C4 to C12) each comprises a single dose (C4D1 to C12D1) of 30 mg of glofitamab. In one embodiment the single dose of each of the additional dosing cycles (C4D1 to C12D1) comprises 30 mg of glofitamab. In one embodiment the single dose of the additional dosing cycles (C4D1 to C12D1) is administered on day 1 of the respective additional dosing cycle.

In one embodiment the method of treating a subject having mantle cell lymphoma which has relapsed after or failed to respond to at least one prior systemic treatment regimen that includes a Bruton tyrosine kinase (BTK) inhibitor (BTKi) comprises 12 dosing cycles in total. In one embodiment the method of treating a subject having a mantle cell lymphoma which has relapsed after or failed to respond to at least one prior systemic treatment regimen that includes a Bruton tyrosine kinase (BTK) inhibitor (BTKi) comprises 6, 8, or 10 dosing cycles in total.

In one embodiment, one or more treatment cycles comprise 14 days or 21 days. In one embodiment, one or more treatment cycles comprise 21 days.

In one embodiment, the step-up dosing schedule of the anti-CD20/anti-CD3 bispecific antibody as provided herein reduces the frequency of Grade 3 or higher as compared to the Grade 3 or higher CRS rate of a patient population treated with a corresponding treatment regimen without a step-up dosing regimen of the anti-CD20/anti-CD3 bispecific antibody. In one embodiment, the frequency of Grade 3 or higher CRS is less than or about 30% (e.g., less than or about 25%, less than or about 20%, less than or about 15%, less than or about 10%, less than or about 5%, less than or about 4%, less than or about 3%, less than or about 2%, or less than or about 1%; e.g., about 10%, about 9%, about 8%, about 7%, about 6%, about 5%, about 4%, about 3%, about 2%, about 1%, or about 0%). In one embodiment, the rate of Grade 3 or higher CRS is less than about 30%. In one embodiment, the rate of Grade 3 or higher CRS is less than or about 5%. In one embodiment the CRS grade is defined by the modified criteria of Lee et al. (Lee et al., *Blood,* 124: 188-195, 2014) and/or the ASTCT consensus grading (criteria of the American Society for Transplantation and Cellular Therapy, 2019; ASTCT; Lee et al., *Biol Blood Marrow Transplant,* 25(4): 625-638, 2019).

In one embodiment, the step-up dosing schedule of the anti-CD20/anti-CD3 bispecific antibody as provided herein reduces the frequency of Grade 3 or higher as compared to the Grade 3 or higher CRS rate of a patient population with R/R FL treated with a corresponding treatment regimen without a step-up dosing regimen of the anti-CD20/anti-CD3 bispecific antibody. In one embodiment, the frequency of Grade 3 or higher CRS is less than or about 10% (e.g., less than or about 9%, less than or about 8%, less than or about 7%, less than or about 6%, less than or about 5%, less than or about 4%, less than or about 3%, less than or about 2%, or less than or about 1%; e.g., about 10%, about 9%, about 8%, about 7%, about 6%, about 5%, about 4%, about 3%, about 2%, about 1%, or about 0%). In one embodiment, the rate of Grade 3 or higher CRS is less than about 5%. In one embodiment, the rate of Grade 3 or higher CRS is less than or about 3%. In one embodiment, the rate of Grade 3 or higher CRS is about 0%. In one embodiment the CRS grade is defined by the modified criteria of Lee et al. (2014) and/or the ASTCT consensus grading (criteria of the American Society for Transplantation and Cellular Therapy, 2019; ASTCT).

In one embodiment, the step-up dosing schedule of the anti-CD20/anti-CD3 bispecific antibody as provided herein reduces the frequency of Grade 3 or higher as compared to the Grade 3 or higher CRS rate of a patient population with R/R MCL treated with a corresponding treatment regimen without a step-up dosing regimen of the anti-CD20/anti-CD3 bispecific antibody. In one embodiment, the frequency of Grade 3 or higher CRS is less than or about 10% (e.g., less than or about 9%, less than or about 8%, less than or about 7%, less than or about 6%, less than or about 5%, less than or about 4%, less than or about 3%, less than or about 2%, or less than or about 1%; e.g., about 10%, about 9%, about 8%, about 7%, about 6%, about 5%, about 4%, about 3%, about 2%, about 1%, or about 0%). In one embodiment, the rate of Grade 3 or higher CRS is less than about 5%. In one embodiment, the rate of Grade 3 or higher CRS is less than or about 3%. In one embodiment the CRS grade is defined by the modified criteria of Lee et al. (2014) and/or the ASTCT consensus grading (criteria of the American Society for Transplantation and Cellular Therapy, 2019; ASTCT).

In one embodiment, administration of the step-up dosing schedule of the anti-CD20/anti-CD3 bispecific antibody to a plurality of subjects as provided herein results in an overall response rate of at least about 45% (e.g., at least about 50%, at least about 55%, at least about 60%, at least about 65%, at least about 70%, at least about 75%, at least about 80%, at least about 80%, at least about 85%, at least about 90%, or more; e.g., between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 45% and 65%, between 65% and 85%, between 85% and 100%, between 55% and 75%, between 75% and 95%, or between 50% and 60%; e.g., about 45%, about 50%, about 51%, about 52%, about 53%, about 54%, about 55%, about 56%, about 57%, about 58%, about 59%, about 60%, about 65%, about 70%, about 75%, about 80%, about 85%, about 90%, about 95%, or more) in the patient population. In one embodiment, administration of the step-up dosing schedule of the anti-CD20/anti-CD3 bispecific antibody to a plurality of subjects as provided herein results in an overall response rate of at least about 45% in the patient population. In one embodiment, administration of the step-up dosing schedule of the anti-CD20/anti-CD3 bispecific antibody to a plurality of subjects as provided herein results in an overall response rate of at least about 55% in the patient population. In one embodiment administration of the step-up dosing schedule of the anti-CD20/anti-CD3 bispecific antibody to a plurality of subjects as provided herein results in an overall response rate of at least about 65% in the patient population.

In one embodiment, administration of the step-up dosing schedule of the anti-CD20/anti-CD3 bispecific antibody to a plurality of subjects as provided herein results in a complete response rate of at least about 30% (e.g., at least about 35%, at least about 40%, at least about 45%, at least about 50%, at least about 55%, at least about 60%, at least about 65%, at least about 70%, at least about 75%, at least about 80%, at least about 80%, at least about 85%, at least about 90%, or more; e.g., between 30% and 35%, between 35% and 40%, between 40% and 45%, between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 35% and 55%, between 55% and 75%, between 75% and 100%, between 45% and 65%, between 65% and 85%, or between 35% and 45%; e.g., about 30%, about 35%, about 36%, about 37%, about 38%, about 39%, about 40%, about 41%, about 42%, about 43%, about 44%, about 45%, about 50%, about 60%, about 65%, about 70%, about 75%, about 80%, about 85%, about 90%, about 95%, or more) in the patient population. In one embodiment, administration of the step-up dosing schedule of the anti-CD20/anti-CD3 bispecific antibody to a plurality of subjects as provided herein results in a complete response rate of at least about 30% in the patient population. In one embodiment, administration of the step-up dosing schedule of the anti-CD20/anti-CD3 bispecific antibody to a plurality of subjects as provided herein results in a complete response rate of at least about 40% in the patient population. In one embodiment administration of the step-up dosing schedule of the anti-CD20/anti-CD3 bispecific antibody to a plurality of subjects as provided herein results in a complete response rate of at least about 50% in the patient population.

In one embodiment, administration of the step-up dosing schedule of the anti-CD20/anti-CD3 bispecific antibody to a plurality of subjects as provided herein results in an overall response rate of at least about 70% (e.g., at least about 75%, at least about 80%, at least about 80%, at least about 85%, at least about 90%, or more; e.g., between 70% and 75%, between 75% and 80%, between 80% and 85%, between 85% and 90%, between 90% and 95%, between 95% and 100%, between 70% and 80%, between 80% and 90%, between 90% and 100%, or between 75% and 85%; e.g., about 70%, about 75%, about 76%, about 77%, about 78%, about 79%, about 80%, about 81%, about 82%, about 83%, about 84%, about 85%, about 90%, about 95%, or more) in the patient population with indolent NHL (iNHL). In one embodiment, administration of the step-up dosing schedule of the anti-CD20/anti-CD3 bispecific antibody to a plurality of subjects as provided herein results in an overall response rate of at least about 70% in the patient population with iNHL. In one embodiment, administration of the step-up dosing schedule of the anti-CD20/anti-CD3 bispecific antibody to a plurality of subjects as provided herein results in an overall response rate of at least about 80% in the patient population with iNHL. In one embodiment administration of the step-up dosing schedule of the anti-CD20/anti-CD3 bispecific antibody to a plurality of subjects as provided herein results in an overall response rate of at least about 90% in the patient population with iNHL.

In one embodiment, administration of the step-up dosing schedule of the anti-CD20/anti-CD3 bispecific antibody to a plurality of subjects as provided herein results in a complete response rate of at least about 60% (e.g., at least about 65%, at least about 70%, at least about 75%, at least about 80%, at least about 80%, at least about 85%, at least about 90%, or more; e.g., between 60% and 65%, between 65% and 70%, between 70% and 75%, between 75% and 80%, between 80% and 85%, between 85% and 90%, between 90% and 95%, between 95% and 100%, between 60% and 70%, between 70% and 80%, between 80% and 90%, between 90% and 100%, between 60% and 80%, or between 65% and 75%; e.g., about 60%, about 65%, about 66%, about 67%, about 68%, about 69%, about 70%, about 71%, about 72%, about 73%, about 74%, about 75%, about 80%, about 85%, about 90%, about 95%, or more) in the patient population with iNHL. In one embodiment, administration of the step-up dosing schedule of the anti-CD20/anti-CD3 bispecific antibody to a plurality of subjects as provided herein results in a complete response rate of at least about 60% in the patient population with iNHL. In one embodiment, administration of the step-up dosing schedule of the anti-CD20/anti-CD3 bispecific antibody to a plurality of subjects as provided herein results in a complete response rate of at least about 70% in the patient population with iNHL. In one embodiment administration of the step-up dosing schedule of the anti-CD20/anti-CD3 bispecific antibody to a plurality of subjects as provided herein results in a complete response rate of at least about 80% in the patient population with iNHL.

In one embodiment, administration of the step-up dosing schedule of the anti-CD20/anti-CD3 bispecific antibody to a plurality of subjects as provided herein results in an overall response rate of at least about 45% (e.g., at least about 50%, at least about 55%, at least about 60%, at least about 65%, at least about 70%, at least about 75%, at least about 80%, at least about 80%, at least about 85%, at least about 90%, or more; e.g., between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 45% and 65%, between 65% and 85%, between 85% and 100%, between 55% and 75%, between 75% and 95%, or between 50% and 60%; e.g., about 45%, about 50%, about 51%, about 52%, about 53%, about 54%, about 55%, about 56%, about 57%, about 58%, about 59%, about 60%, about 65%, about 70%, about 75%, about 80%, about 85%, about 90%, about 95%, or more) in the patient population with aNHL. In one embodiment, administration of the step-up dosing schedule of the anti-CD20/anti-CD3 bispecific antibody to a plurality of subjects as provided herein results in an overall response rate of at least about 45% in the patient population with aNHL. In one embodiment, administration of the step-up dosing schedule of the anti-CD20/anti-CD3 bispecific antibody to a plurality of subjects as provided herein results in an overall response rate of at least about 55% in the patient population with aNHL. In one embodiment administration of the step-up dosing schedule of the anti-CD20/anti-CD3 bispecific antibody to a plurality of subjects as provided herein results in an overall response rate of at least about 65% in the patient population with aNHL.

In one embodiment, administration of the step-up dosing schedule of the anti-CD20/anti-CD3 bispecific antibody to a plurality of subjects as provided herein results in a complete response rate of at least about 30% (e.g., at least about 35%, at least about 40%, at least about 45%, at least about 50%, at least about 55%, at least about 60%, at least about 65%, at least about 70%, at least about 75%, at least about 80%, at least about 80%, at least about 85%, at least about 90%, or more; e.g., between 30% and 35%, between 35% and 40%, between 40% and 45%, between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 35% and 55%, between 55% and 75%, between 75% and 100%, between 45% and 65%, between 65% and 85%, or between 35% and 45%; e.g., about 30%, about 35%, about 36%, about 37%, about 38%, about 39%, about 40%, about 41%, about 42%, about 43%, about 44%, about 45%, about 50%, about 60%, about 65%, about 70%, about 75%, about 80%, about 85%, about 90%, about 95%, or more) in the patient population with aNHL. In one embodiment, administration of the step-up dosing schedule of the anti-CD20/anti-CD3 bispecific antibody to a plurality of subjects as provided herein results in a complete response rate of at least about 30% in the patient population with aNHL. In one embodiment, administration of the step-up dosing schedule of the anti-CD20/anti-CD3 bispecific antibody to a plurality of subjects as provided herein results in a complete response rate of at least about 40% in the patient population with aNHL. In one embodiment administration of the step-up dosing schedule of the anti-CD20/anti-CD3 bispecific antibody to a plurality of subjects as provided herein results in a complete response rate of at least about 50% in the patient population with aNHL. In one embodiment administration of the step-up dosing schedule of the anti-CD20/anti-CD3 bispecific antibody to a plurality of subjects as provided herein results in a complete response rate of at least about 70% in the patient population with aNHL.

In one embodiment, the administration of step-up dosing schedule of the anti-CD20/anti-CD3 bispecific antibody to a plurality of subjects as provided herein results in a complete response rate of at least about 30% (e.g., at least about 35%, at least about 40%, at least about 45%, at least about 50%, at least about 55%, at least about 60%, at least about 65%, at least about 70%, at least about 75%, at least about 80%, at least about 80%, at least about 85%, at least about 90%, or more; e.g., between 30% and 35%, between 35% and 40%, between 40% and 45%, between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 35% and 55%, between 55% and 75%, between 75% and 100%, between 45% and 65%, between 65% and 85%, or between 35% and 45%; e.g., about 30%, about 35%, about 36%, about 37%, about 38%, about 39%, about 40%, about 41%, about 42%, about 43%, about 44%, about 45%, about 50%, about 60%, about 65%, about 70%, about 75%, about 80%, about 85%, about 90%, about 95%, or more) in the patient population. In one embodiment, administration of the step-up dosing schedule of the anti-CD20/anti-CD3 bispecific antibody to a plurality of subjects as provided herein results in a complete response rate of at least about 30% in the patient population. In one embodiment, administration of the step-up dosing schedule of the anti-CD20/anti-CD3 bispecific antibody to a plurality of subjects as provided herein results in a complete response rate of at least about 40% in the patient population. In one embodiment administration of the step-up dosing schedule of the anti-CD20/anti-CD3 bispecific antibody to a plurality of subjects as provided herein results in a complete response rate of at least about 50% in the patient population.

In one embodiment, administration of the step-up dosing schedule of the anti-CD20/anti-CD3 bispecific antibody to a plurality of subjects as provided herein results in an overall response rate of at least about 60% (e.g., at least about 65%, at least about 70%, at least about 75%, at least about 80%, at least about 80%, at least about 85%, at least about 90%, or more; e.g., between 60% and 65%, between 65% and 70%, between 70% and 75%, between 75% and 80%, between 80% and 85%, between 85% and 90%, between 90% and 95%, between 95% and 100%, between 60% and 70%, between 70% and 80%, between 80% and 90%, between 90% and 100%, between 60% and 80%, between 65% and 75%, between 85% and 95%, or between 75% and 85%; e.g., about 60%, about 65%, about 66%, about 67%, about 68%, about 69%, about 70%, about 71%, about 72%, about 73%, about 74%, about 75%, about 80%, about 85%, about 90%, about 95%, about 96%, about 87%, about 98%, about 99%, or more) in the patient population with relapsed or refractory (R/R) follicular lymphoma (FL). In one embodiment, administration of the step-up dosing schedule of the anti-CD20/anti-CD3 bispecific antibody to a plurality of subjects as provided herein results in an overall response rate of at least about 60% in the patient population with R/R FL. In one embodiment, administration of the step-up dosing schedule of the anti-CD20/anti-CD3 bispecific antibody to a plurality of subjects as provided herein results in an overall response rate of at least about 80% in the patient population with R/R FL. In one embodiment, administration of the step-up dosing schedule of the anti-CD20/anti-CD3 bispecific antibody to a plurality of subjects as provided herein results in an overall response rate of at least about 90% in the patient population with R/R FL. In one embodiment administration of the step-up dosing schedule of the anti-CD20/anti-CD3 bispecific antibody to a plurality of subjects as provided herein results in an overall response rate of at least about 95% in the patient population with R/R FL.

In one embodiment, administration of the step-up dosing schedule of the anti-CD20/anti-CD3 bispecific antibody to a plurality of subjects as provided herein results in a complete response rate of at least about 60% (e.g., at least about 65%, at least about 70%, at least about 75%, at least about 80%, at least about 80%, at least about 85%, at least about 90%, or more; e.g., between 60% and 65%, between 65% and 70%, between 70% and 75%, between 75% and 80%, between 80% and 85%, between 85% and 90%, between 90% and 95%, between 95% and 100%, between 60% and 70%, between 70% and 80%, between 80% and 90%, between 90% and 100%, between 60% and 80%, or between 65% and 75%; e.g., about 60%, about 65%, about 66%, about 67%, about 68%, about 69%, about 70%, about 71%, about 72%, about 73%, about 74%, about 75%, about 76%, about 77%, about 78%, about 79%, about 80%, about 85%, about 90%, about 95%, or more) in the patient population with R/R FL. In one embodiment, administration of the step-up dosing schedule of the anti-CD20/anti-CD3 bispecific antibody to a plurality of subjects as provided herein results in a complete response rate of at least about 60% in the patient population with R/R FL. In one embodiment, administration of the step-up dosing schedule of the anti-CD20/anti-CD3 bispecific antibody to a plurality of subjects as provided herein results in a complete response rate of at least about 70% in the patient population with R/R FL. In one embodiment administration of the step-up dosing schedule of the anti-CD20/anti-CD3 bispecific antibody to a plurality of subjects as provided herein results in a complete response rate of at least about 80% in the patient population with R/R FL.

In one embodiment, administration of the step-up dosing schedule of the anti-CD20/anti-CD3 bispecific antibody to a plurality of subjects as provided herein results in a complete response rate of at least about 40% (e.g., at least 45%, at least about 50%, at least about 55%, at least about 60%, at least about 65%, at least about 70%, at least about 75%, at least about 80%, at least about 80%, at least about 85%, at least about 90%, or more; e.g., between 40% and 45%, between 45% and 50%, between 50% and 55%, between 55% and 60%, between 60% and 65%, between 65% and 70%, between 70% and 75%, between 75% and 80%, between 80% and 85%, between 85% and 90%, between 90% and 95%, between 95% and 100%, between 40% and 60%, between 60% and 80%, between 80% and 100%, between 50% and 75%, between 75% and 100%, or between 45% and 55%; e.g., about 40%, about 45%, about 46%, about 47%, about 48%, about 49%, about 50%, about 51%, about 52%, about 53%, about 54%, about 55%, about 60%, about 65%, about 70%, about 75%, about 80%, about 85%, about 90%, about 95%, or more) in the high-risk patient population with R/R FL. In one embodiment, administration of the step-up dosing schedule of the anti-CD20/anti-CD3 bispecific antibody to a plurality of subjects as provided herein results in a complete response rate of at least about 40% in the high-risk patient population with R/R FL. In one embodiment, administration of the step-up dosing schedule of the anti-CD20/anti-CD3 bispecific antibody to a plurality of subjects as provided herein results in a complete response rate of at least about 50% in the high-risk patient population with R/R FL. In one embodiment administration of the step-up dosing schedule of the anti-CD20/anti-CD3 bispecific antibody to a plurality of subjects as provided herein results in a complete response rate of at least about 60% in the high-risk patient population with R/R FL.

In one embodiment, high-risk subjects comprise subjects who: (a) have relapsed after or are refractory to at least two prior therapies; (b) have relapsed after or are refractory to treatment with phosphoinositide 3-kinase (PI3K) inhibitor; (c) experience progression of disease within 24 months of frontline treatment; and/or (d) have lesions, wherein the sum of the product of the lesion diameters is ≥3,000 $mm^2$.

In one embodiment, administration of the step-up dosing schedule of the anti-CD20/anti-CD3 bispecific antibody to a plurality of subjects as provided herein results in an overall response rate of at least about 70% (e.g., at least about 75%, at least about 80%, at least about 80%, at least about 85%, at least about 90%, or more; e.g., between 70% and 75%, between 75% and 80%, between 80% and 85%, between 85% and 90%, between 90% and 95%, between 95% and 100%, between 70% and 80%, between 80% and 90%, between 90% and 100%, or between 75% and 85%; e.g., about 70%, about 75%, about 76%, about 77%, about 78%, about 79%, about 80%, about 81%, about 82%, about 83%, about 84%, about 85%, about 90%, about 95%, or more) in the patient population with relapsed or refractory (R/R) mantle cell lymphoma (MCL). In one embodiment, administration of the step-up dosing schedule of the anti-CD20/anti-CD3 bispecific antibody to a plurality of subjects as provided herein results in an overall response rate of at least about 70% in the patient population with R/R MCL. In one embodiment, administration of the step-up dosing schedule of the anti-CD20/anti-CD3 bispecific antibody to a plurality of subjects as provided herein results in an overall response rate of at least about 80% in the patient population with R/R MCL. In one embodiment administration of the step-up dosing schedule of the anti-CD20/anti-CD3 bispecific antibody to a plurality of subjects as provided herein results in an overall response rate of at least about 90% in the patient population with R/R MCL. In one embodiment, the subject has received at least one prior systemic treatment regimen comprising a Bruton tyrosine kinase inhibitor (BTKi). In one embodiment the BTKi comprises ibrutinib, acalabrutinib, or zanubrutinib.

In one embodiment, administration of the step-up dosing schedule of the anti-CD20/anti-CD3 bispecific antibody to a plurality of subjects as provided herein results in a complete response rate of at least about 55% (e.g., at least about 60%, at least about 65%, at least about 70%, at least about 75%, at least about 80%, at least about 80%, at least about 85%, at least about 90%, or more; e.g., between 55% and 60%, between 60% and 65%, between 65% and 70%, between 70% and 75%, between 75% and 80%, between 80% and 85%, between 85% and 90%, between 90% and 95%, between 95% and 100%, between 55% and 65%, between 65% and 75%, between 75% and 85%, between 85% and 95%, between 55% and 75%, between 75% and 95%, or between 60% and 70%; e.g., about 55%, about 60%, about 61%, about 62%, about 63%, about 64%, about 65%, about 66%, about 67%, about 68%, about 69%, about 70%, about 80%, about 85%, about 90%, about 95%, or more) in the patient population with R/R MCL. In one embodiment, administration of the step-up dosing schedule of the anti-CD20/anti-CD3 bispecific antibody to a plurality of subjects as provided herein results in a complete response rate of at least about 55% in the patient population with R/R MCL. In one embodiment, administration of the step-up dosing schedule of the anti-CD20/anti-CD3 bispecific antibody to a plurality of subjects as provided herein results in a complete response rate of at least about 65% in the patient population with R/R MCL. In one embodiment administration of the step-up dosing schedule of the anti-CD20/anti-CD3 bispecific antibody to a plurality of subjects as provided herein results in a complete response rate of at least about 75% in the patient population with R/R MCL. In one embodiment, the subject has received at least one prior systemic treatment regimen comprising a Bruton tyrosine kinase inhibitor (BTKi). In one embodiment the BTKi comprises ibrutinib, acalabrutinib, or zanubrutinib.

In one aspect, the invention features a method of treating a subject having relapsed or refractory non-Hodgkin's lymphoma (NHL), comprising administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment the initial treatment period is fixed at 12 cycles of glofitamab with two weekly (Q2W, i.e., treatment cycles with a duration of 14 days) or three weekly (Q3W, treatment cycles with a duration of 21 days) dosing in the monotherapy and combination therapy.

Known therapies for CD20-positive B cell proliferative disorders, e.g., NHL, are usually administered until progression of disease. The fixed treatment period as opposed to the treatment duration linked to disease progression has several advantages, e.g., patient convenience, less toxicity/side effects, cost and access considerations, and overall reduces the burden on social care infrastructure.

In one embodiment the initial treatment period is fixed at 12 cycles of glofitamab three weekly (Q3W, treatment cycles with a duration of 21 days) dosing in the monotherapy and combination therapy. In one embodiment the fixed treatment period of 12 cycles prevents the patients from becoming refractory in their CD20-positive B cell proliferative disorder. Thus in one embodiment, treatment is stopped after a total of 12 treatment cycles.

Re-treatment of glofitamab upon confirmed disease progression after completing an initial treatment period with glofitamab will be considered if progression is confirmed by radiographic imaging, as defined by the Lugano Criteria.

In one embodiment the patient is retreated with a method according to any of the embodiments described herein if a relapse occurs and/or if disease progresses. In one such embodiment progression is confirmed by radiographic imaging.

In one embodiment the anti-CD20/anti-CD3 bispecific antibody is administered intravenously. In one such embodiment the anti-CD20/anti-CD3 bispecific antibody is glofitamab. In one embodiment the subject is human. In one embodiment, the human is a high-risk subject.

V. Patient Population: Exclusion Criteria, Pretreatment

In one embodiment the methods provided herein are for treatment of subjects with a CD20-positive B cell proliferative disorders that have received prior systemic therapies. For example, the methods provided herein are for second- or third-line treatment of subjects suffering from CD20-positive NHL. In some embodiments, the subject has received a prior systemic therapy for the CD20-positive cell proliferative disorder. In some embodiments, the subject has received a first-line systemic therapy and a second-line systemic therapy for the CD20-positive B cell proliferative disorder. In some embodiments, the subject has exhibited progression of the CD20-positive B cell proliferative disorder within 24 months of the prior systemic therapy. In some embodiments, the prior systemic therapy comprises an anti-CD20 antibody. In some embodiments, the anti-CD20 antibody is rituximab. In some embodiments, the anti-CD20 antibody is obinutuzumab.

In some embodiments, the prior systemic therapy comprises a chemotherapeutic agent. In some embodiments, the chemotherapeutic agent is an alkylating agent. In some embodiments, the alkylating agent is bendamustine. In some embodiments, the chemotherapeutic agent is lenalidomide.

In some embodiments, the prior systemic therapy comprises an anti-CD20 antibody and a chemotherapeutic agent. In some embodiments, the prior systemic therapy comprises a radio-immunotherapy. In some embodiments, the radio-immunotherapy is ibritumomab tiuxetan. In some embodiments, the prior systemic therapy comprises a phosphoinositide 3-kinase (PI3K) inhibitor (PI3Ki). In some embodiments, the phosphoinositide 3-kinase inhibitor is idelalisib. In some embodiments, the prior systemic therapy comprises a CAR-T therapy. In some embodiments, the prior systemic therapy comprises an autologous stem-cell transplant. In some embodiments, the prior systemic therapy comprises cancer immunotherapy, e.g., systemic immunotherapeutic agents, including but not limited to radioimmunoconjugates, antibody-drug conjugates, immune/cytokines and monoclonal antibodies (e.g., anti-CTLA4, anti-PD1 and anti-PDL1).

In some embodiments, the prior systemic therapy or treatment regimen comprises Bruton tyrosine kinase (BTK) inhibitor (BTKi). In some embodiments, the BTKi is ibrutinib (IMBRUVICA®; CAS #: 936563-96-1), acalabrutinib (CALQUENCE®; CAS #: 1420477-60-6), or zanubrutinib (BRUKINSA®; CAS #: 1691249-45-2).

In one embodiment, patients have relapsed after or failed to respond to at least two prior systemic treatment regimens (including at least one prior regimen containing anthracycline, and at least one containing an anti CD20-directed therapy, e.g., an anti-CD20 antibody).

In one embodiment, patients with DLBCL have relapsed after or failed to respond to at least two prior lines of systemic therapy.

In one embodiment, patients with PMBCL and trFL have relapsed after or failed to respond to at least two prior systemic treatment regimens (including at least one prior regimen containing anthracycline, and at least one containing an anti CD20-directed therapy, e.g., an anti-CD20 antibody).

In one embodiment, patients with Grade 1-3a FL have relapsed after or failed to respond to at least two prior lines of systemic therapy and have received prior treatment with rituximab and alkylating agents.

In one embodiment, subjects with (CLL), Burkitt lymphoma, and lymphoplasmacytic lymphoma are excluded from the methods of treatment described above.

In one embodiment, patients have relapsed after, failed to respond to, or are refractory to at least one prior systemic treatment regimen comprising a Bruton tyrosine kinase (BTK) inhibitor (BTKi). In one embodiment, the subject has received at least one prior systemic treatment regimen comprising a BTKi. In one embodiment the BTKi comprises ibrutinib, acalabrutinib, or zanubrutinib.

In one embodiment patients treated with systemic immunotherapeutic agents, including but not limited to radioimmunoconjugates, antibody-drug conjugates, immune/cytokines and monoclonal antibodies (e.g., anti-CTLA4, anti-PD1 and anti-PDL1) within 4 weeks or five half-lives of the drug, whichever is shorter, before the first dose of the GAZYVA® pretreatment are excluded.

In one embodiment, patients treated with standard radiotherapy, any chemotherapeutic agent, or treatment with any other investigational anti-cancer agent, including CAR-T therapy (defined as treatment for which there is currently no regulatory authority approved indication) within 4 weeks prior to the first dose of the GAZYVA® pretreatment are excluded. In one embodiment the subject is human. In one embodiment, the human is a high-risk subject.

VI. Combination Therapies

In the present invention, the anti-CD20/anti-CD3 bispecific antibody of the methods provided herein can be used either alone or in combination with other agents in a therapy. For instance, the anti-CD20/anti-CD3 bispecific antibody may be co-administered with at least one additional therapeutic agent.

Such combination therapies noted above encompass combined administration (where two or more therapeutic agents are included in the same or separate formulations), and separate administration, in which case, administration of the anti-CD20/anti-CD3 bispecific antibody can occur prior to, simultaneously, and/or following, administration of an additional therapeutic agent or agents. In one embodiment, administration of the anti-CD20/anti-CD3 bispecific antibody and administration of an additional therapeutic agent occur within about one month, or within about one, two or three weeks, or within about one, two, three, four, five, or six days, of each other.

In the present invention, the anti-CD20/anti-CD3 bispecific antibody of the methods provided herein is administered in combination with an anti-CD20 antibody. In one embodiment the anti-CD20 antibody is selected from obinutuzumab or rituximab. In one embodiment obinutuzumab or rituximab is administered on the first day of the second dosing cycle (C2) and on the first day of any subsequent dosing cycle. In one embodiment obinutuzumab or rituximab is administered on the first day of the second dosing cycle (C2) and on the first day of the third (C3) to twelfth dosing cycle (C12). In one embodiment, combination therapy of the anti-CD20/antiCD3 bispecific antibody, e.g., glofitamab, with an anti-CD20 antibody, e.g., obinutuzumab, is used in a method of treating a subject having relapsed or refractory (R/R) diffuse large B cell lymphoma (DLBCL). In one embodiment obinutuzumab is administered at a dose of 1000 mg. In one embodiment, combination therapy of the anti-CD20/antiCD3 bispecific antibody, e.g., glofitamab, with an anti-CD20 antibody, e.g., obinutuzumab, is used in a method of treating a subject having relapsed or refractory (R/R) follicular lymphoma (FL). In one embodiment, combination therapy of the anti-CD20/anti-CD3 bispecific antibody, e.g., glofitamab, with an antiCD20 antibody, e.g., obinutuzumab, is used in a method of treating a subject having R/R mantle cell lymphoma (MCL), wherein the subject has received at least one prior systemic treatment regimen comprising a Bruton tyrosine kinase inhibitor (BTKi).

In one embodiment a method of treating a subject having a CD20-positive B cell proliferative disorder is provided, comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg and administered on day 1 of the first dosing cycle, and the C1D2 is 10 mg and administered on day 8 of the first dosing cycle; and (b) the second dosing cycle comprises a single dose (C2D1) of 30 mg of the anti-CD20/anti-CD3 bispecific antibody, which is administered on day 1 of the second dosing cycle and a single dose of (C2D1) of obinutuzumab or rituximab which is administered on day 1 of the second dosing cycle.

In additional embodiments the glofitamab step-up dosing is performed according to any of the embodiments described herein. In another embodiment, subjects foreseen for treatment with the methods provided herein are pretreated with an anti-CD20 antibody, as described above.

In one embodiment, the anti-CD20/anti-CD3 bispecific antibody is combined with rituximab, cyclophosphamide, doxorubicin, vincristine, and prednisone (R-CHOP). Before the studies disclosed herein (Examples 10 and 11), there was no or no sufficient data to support the tolerability of an anti-CD20/anti-CD3 bispecific antibody, e.g. glofitamab in combination with R-CHOP in patients with previously untreated DLBCL. One of the questions addressed by the clinical studies disclosed therein is to determine if standard of care R-CHOP therapy will not be compromised when administered in combination with glofitamab. Indeed, the preliminary data of the studies disclosed herein supports that addition of an anti-CD20/anti-CD3 bispecific antibody, e.g., glofitamab, to standard of care therapy R-CHOP does not affect the efficacy and safety of the standard of care. The addition of glofitamab to R-CHOP appears to have a positive benefit-risk profile in patients with treatment-naïve (i.e., previously untreated) DLBCL and only a single Grade 1 CRS event has occurred at the time of analysis of the data.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, corticosteroid, and anti-CD20/anti-CD3 bispecific antibody to a plurality of humans results in a complete response in at least about 60%, at least about 70% or at least about 80% of the humans in the plurality after treatment with the anti-CD20 antibody, cyclophosphamide, doxorubicin, corticosteroid, and anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, corticosteroid, and anti-CD20/anti-CD3 bispecific antibody to a plurality of humans results in an overall response in at least about 80%, at least about 85% or at least about 90% of the humans in the plurality after treatment with the anti-CD20 antibody, cyclophosphamide, doxorubicin, corticosteroid, and anti-CD20/anti-CD3 bispecific antibody.

In one embodiment, a method of treating a subject having a CD20-positive cell proliferative disorder is provided, comprising administering to the subject an anti-CD20 antibody, cyclophosphamide, doxorubicin, a corticosteroid, and an anti-CD20/anti-CD3 bispecific antibody, wherein administration of the anti-CD20 antibody, cyclophosphamide, doxorubicin, a corticosteroid, and the anti-CD20/anti-CD3 bispecific antibody does not result in Grade 2 or higher CRS. In one embodiment, the method of treating does not result in Grade 3 or 4 CRS. In one embodiment, administration of the anti-CD20 antibody, cyclophosphamide, doxorubicin, corticosteroid, and anti-CD20/anti-CD3 bispecific antibody to a plurality of humans does not result in any CRS events of any grade in at least about 80%, at least about 85%, at least about 90%, at least about 95% of the humans in the plurality after treatment with the anti-CD20 antibody, cyclophosphamide, doxorubicin, corticosteroid, and anti-CD20/anti-CD3 bispecific antibody. In one embodiment, administration of the anti-CD20 antibody, cyclophosphamide, doxorubicin, corticosteroid, and anti-CD20/anti-CD3 bispecific antibody to a plurality of humans does not result in any CRS events of Grade 2 or higher in at least about 80%, at least about 85%, at least about 90%, at least about 95% of the humans in the plurality after treatment with the anti-CD20 antibody, cyclophosphamide, doxorubicin, corticosteroid, and anti-CD20/anti-CD3 bispecific antibody.

In one embodiment, a method of treating a subject having a CD20-positive cell proliferative disorder is provided, wherein the method comprises a dosing regimen comprising at least a first dosing cycle, a second dosing cycle and a third dosing cycle, wherein:

(a) the first dosing cycle comprises a first dose (C1D1) of the anti-CD20 antibody, cyclophosphamide, doxorubicin and corticosteroid, and no dose of the anti-CD20/anti-CD3 bispecific antibody;
(b) the second dosing cycle comprises a second dose (C2D1) of the anti-CD20 antibody, cyclophosphamide, doxorubicin and corticosteroid, and a first dose (C2D1) and second dose (C2D2) of the anti-CD20/anti-CD3 bispecific antibody, wherein the C2D1 of the anti-CD20/anti-CD3 bispecific antibody is about 2.5 mg and the C1D2 of the anti-CD20/anti-CD3 bispecific antibody is about 10 mg; and
(c) the third dosing cycle comprises a third dose (C3D1) of the anti-CD20 antibody, cyclophosphamide, doxorubicin and corticosteroid, and a third dose (C3D1) of the anti-CD20/anti-CD3 bispecific antibody, wherein the C3D1 of the anti-CD20/anti-CD3 bispecific antibody is about 30 mg.

In one embodiment, the anti-CD20 antibody, cyclophosphamide, doxorubicin, and corticosteroid is administered on day 1 of each dosing cycle.

In one embodiment, the first dose (C2D1) of the anti-CD20/anti-CD3 bispecific antibody is administered on day 8 of the second dosing cycle and the second dose (C2D2) of the anti-CD20/anti-CD3 bispecific antibody is administered on day 15 of the second dosing cycle.

In one embodiment, the third dose of the of the anti-CD20/anti-CD3 bispecific antibody (C3D1) is administered on day 8 of the third dosing cycle.

In one embodiment, the method comprises 1 to 5 additional dosing cycles (C4 to C8).

In one embodiment, the additional dosing cycles (C4 to C8) each comprises a single dose of anti-CD20 antibody, cyclophosphamide, doxorubicin, corticosteroid, and a single dose (C4D1 to C8D1) of 30 mg of the anti-CD20/anti-CD3 bispecific antibody. In one embodiment, the single dose of the anti-CD20 antibody, cyclophosphamide, doxorubicin, and corticosteroid is administered on day 1 and the single dose of the anti-CD20/anti-CD3 bispecific antibody is administered on day 8 of the respective additional dosing cycle (C4 to C8).

In one embodiment, the corticosteroid is prednisone, prednisolone, or methylprednisolone. In one embodiment, the corticosteroid is prednisone, and the prednisone is administered orally at a dose of about 100 mg. In one embodiment, the corticosteroid is prednisolone, and the prednisolone is administered orally at a dose of about 100 mg. In one embodiment, the corticosteroid is methylprednisolone, and the methylprednisolone is administered intravenously at a dose of about 80 mg. In one embodiment, the corticosteroid is not hydrocortisone.

In one embodiment, the anti-CD20 antibody is rituximab. In one embodiment, rituximab is administered intravenously at a dose of about 375 mg/m$^2$. In one embodiment, the cyclophosphamide is administered intravenously at a dose of about 750 mg/m$^2$. In one embodiment, the doxorubicin is administered intravenously at a dose of about 50 mg/m$^2$.

In one embodiment, the corticosteroid is prednisone and the anti-CD20 antibody is rituximab.

In one embodiment, a method of treating a subject having a CD20-positive cell proliferative disorder is provided, comprising administering to the subject rituximab, cyclophosphamide, doxorubicin, vincristine, and prednisone (R-CHOP) and an anti-CD20/anti-CD3 bispecific antibody. This aspect of the invention in supported by the clinical data in Examples 10 and 11.

In one embodiment, a method of treating a subject having a CD20-positive cell proliferative disorder is provided, comprising administering to the subject rituximab, cyclophosphamide, doxorubicin, vincristine, and prednisone (R-CHOP) and an anti-CD20/anti-CD3 bispecific antibody, wherein administration of R-CHOP and the anti-CD20/anti-CD3 bispecific antibody to a plurality of humans results in a complete response in at least about 60%, at least about 70% or at least about 80% of the humans in the plurality after treatment with R-CHOP and the anti-CD20/anti-CD3 bispecific antibody.

In one embodiment, a method of treating a subject having a CD20-positive cell proliferative disorder is provided, comprising administering to the subject rituximab, cyclophosphamide, doxorubicin, vincristine, and prednisone (R-CHOP) and an anti-CD20/anti-CD3 bispecific antibody, wherein administration of R-CHOP and the anti-CD20/anti-CD3 bispecific antibody to a plurality of humans results in an overall response in at least about 80%, at least about 85% or at least about 90% of the humans in the plurality after treatment with R-CHOP and the anti-CD20/anti-CD3 bispecific antibody.

In one embodiment, administration of R-CHOP and the anti-CD20/anti-CD3 bispecific antibody to a plurality of humans does not result in Grade 2 or higher CRS. In one embodiment, a method of treating a subject having a CD20-positive cell proliferative disorder is provided, comprising administering to the subject R-CHOP and an anti-CD20/anti-CD3 bispecific antibody, wherein administration of R-CHOP and the anti-CD20/anti-CD3 bispecific antibody does not result in Grade 2 or higher CRS.

In one embodiment, the method of treating does not result in Grade 3 or 4 CRS. In one embodiment, administration of R-CHOP and the anti-CD20/anti-CD3 bispecific antibody to a plurality of humans does not result in any CRS events of any grade in at least about 80%, at least about 85%, at least about 90%, at least about 95% of the humans in the plurality after treatment with R-CHOP and the anti-CD20/anti-CD3 bispecific antibody. In one embodiment, administration of R-CHOP and the anti-CD20/anti-CD3 bispecific antibody to a plurality of humans does not result in any CRS events of Grade 2 or higher in at least about 80%, at least about 85%, at least about 90%, at least about 95% of the humans in the plurality after treatment with R-CHOP and the anti-CD20/anti-CD3 bispecific antibody.

In one embodiment, a method of treating a subject having a CD20-positive B cell proliferative disorder is provided, comprising administering to the subject rituximab, cyclophosphamide, doxorubicin, vincristine, and prednisone (R-CHOP) and an anti-CD20/anti-CD3 bispecific antibody in a dosing regimen comprising at least a first dosing cycle, a second dosing cycle and a third dosing cycle, wherein:

(a) the first dosing cycle comprises a first dose (C1D1) of the R-CHOP, and no dose of the anti-CD20/anti-CD3 bispecific antibody;

(b) the second dosing cycle comprises a second dose (C2D1) of the R-CHOP and a first dose (C2D1) and second dose (C2D2) of the anti-CD20/anti-CD3 bispecific antibody, wherein the C2D1 of the anti-CD20/anti-CD3 bispecific antibody is about 2.5 mg and the C2D2 of the anti-CD20/anti-CD3 bispecific antibody is about 10 mg; and (c) the third dosing cycle comprises a third dose (C3D1) of the R-CHOP and a third dose (C3D1) of the anti-CD20/anti-CD3 bispecific antibody, wherein the C3D1 of the anti-CD20/anti-CD3 bispecific antibody is about 30 mg.

In one embodiment, the R-CHOP is administered on day 1 of each dosing cycle.

In one embodiment, the first dose (C2D1) of the anti-CD20/anti-CD3 bispecific antibody is administered on day 8 of the second dosing cycle and the second dose (C2D2) of the anti-CD20/anti-CD3 bispecific antibody is administered on day 15 of the second dosing cycle.

In one embodiment, the third dose of the of the anti-CD20/anti-CD3 bispecific antibody (C3D1) is administered on day 8 of the third dosing cycle.

In one embodiment, the method comprises 1 to 5 additional dosing cycles (C4 to C8). In one such embodiment, the 1 to 5 additional dosing cycles (C4 to C8) each comprises a single dose of R-CHOP and a single dose (C4D1 to C8D1) of 30 mg of the anti-CD20/anti-CD3 bispecific antibody.

In one embodiment, the single dose of the R-CHOP is administered on day 1 and the single dose of the anti-CD20/anti-CD3 bispecific antibody is administered on day 8 of the respective additional dosing cycle (C4 to C8).

In one embodiment, the anti-CD20/anti-CD3 bispecific antibody comprises a) at least one antigen binding domain that specifically binds to CD20 comprising a heavy chain variable region comprising (i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising
(i) an HVR-L1 comprising the amino acid sequence of SEQ ID NO: 4;
(ii) an HVR-L2 comprising the amino acid sequence of SEQ ID NO: 5; and
(iii) an HVR-L3 comprising the amino acid sequence of SEQ ID NO: 6; and b) at least one antigen binding domain that specifically binds to CD3 comprising
a heavy chain variable region comprising:
(i) an HVR-H1 comprising the amino acid sequence of SEQ ID NO: 9;
(ii) an HVR-H2 comprising the amino acid sequence of SEQ ID NO: 10; and
(iii) an HVR-H3 comprising the amino acid sequence of SEQ ID NO:11; and
a light chain variable region comprising
(i) an HVR-L1 comprising the amino acid sequence of SEQ ID NO: 12;
(ii) an HVR-L2 comprising the amino acid sequence of SEQ ID NO: 13; and
(iii) an HVR-L3 comprising the amino acid sequence of SEQ ID NO: 14.

In one embodiment said anti-CD20/anti-CD3 bispecific antibody comprises
(i) at least one antigen binding domain that specifically binds to CD20 comprising the heavy chain variable region sequence of SEQ ID NO: 7 and the light chain variable region sequence of SEQ ID NO: 8, and
(ii) at least one antigen binding domain that specifically binds to CD3 comprising the heavy chain variable region sequence of SEQ ID NO: 15 and the light chain variable region sequence of SEQ ID NO: 16.

In one embodiment said anti-CD20/anti-CD3 bispecific antibody comprises two binding sites for CD20, and one binding site for CD3. In one such embodiment, the anti-CD20/anti-CD3 bispecific antibody comprises the HVRs as defined above. In one such embodiment, the anti-CD20/anti-CD3 bispecific antibody comprises the VL and VH sequences as defined above.

In one embodiment the anti-CD20/anti-CD3 bispecific antibody is glofitamab.

In one embodiment, a method of treating a subject having a CD20-positive cell proliferative disorder is provided, comprising administering to the subject rituximab, cyclophosphamide, doxorubicin, vincristine, and prednisone (R-CHOP) and glofitamab.

In one embodiment, a method of treating a subject having a CD20-positive cell proliferative disorder is provided, comprising administering to the subject rituximab, cyclophosphamide, doxorubicin, vincristine, and prednisone (R-CHOP) and glofitamab, wherein administration of R-CHOP and glofitamab to a plurality of humans results in a complete response in at least about 60%, at least about 70% or at least about 80% of the humans in the plurality after treatment with R-CHOP and glofitamab.

In one embodiment, a method of treating a subject having a CD20-positive cell proliferative disorder is provided, comprising administering to the subject rituximab, cyclophosphamide, doxorubicin, vincristine, and prednisone (R-CHOP) and glofitamab, wherein administration of R-CHOP and glofitamab to a plurality of humans results in an overall response in at least about 80%, at least about 85% or at least about 90% of the humans in the plurality after treatment with R-CHOP and glofitamab.

In one embodiment, administration of R-CHOP and glofitamab to a plurality of humans does not result in Grade 2 or higher CRS. In one embodiment, a method of treating a subject having a CD20-positive cell proliferative disorder is provided, comprising administering to the subject R-CHOP and glofitamab, wherein administration of R-CHOP and glofitamab does not result in Grade 2 or higher CRS.

In one embodiment, the method of treating does not result in Grade 3 or 4 CRS. In one embodiment, administration of R-CHOP and glofitamab to a plurality of humans does not result in any CRS events of any grade in at least about 80%, at least about 85%, at least about 90%, or at least about 95% of the humans in the plurality after treatment with R-CHOP and glofitamab.

In one embodiment, administration of R-CHOP and glofitamab to a plurality of humans does not result in any CRS events of Grade 2 or higher in at least about 80%, at least about 85%, at least about 90%, or at least about 95% of the humans in the plurality after treatment with R-CHOP and glofitamab.

In one embodiment, a method of treating a subject having a CD20-positive B cell proliferative disorder is provided, comprising administering to the subject rituximab, cyclophosphamide, doxorubicin, vincristine, and prednisone (R-CHOP) and glofitamab in a dosing regimen comprising at least a first dosing cycle, a second dosing cycle, and a third dosing cycle, wherein:
(a) the first dosing cycle comprises a first dose (C1D1) of the R-CHOP, and no dose of glofitamab;
(b) the second dosing cycle comprises a second dose (C2D1) of the R-CHOP and a first dose (C2D1) and second dose (C2D2) of glofitamab, wherein the C2D1 of glofitamab is about 2.5 mg and the C2D2 of glofitamab is about 10 mg; and
(c) the third dosing cycle comprises a third dose (C3D1) of the R-CHOP and a third dose (C3D1) of glofitamab, wherein the C3D1 of glofitamab is about 30 mg.

In one embodiment, the R-CHOP is administered on day 1 of each dosing cycle.

In one embodiment, the first dose (C2D1) of glofitamab is administered on day 8 of the second dosing cycle and the second dose (C2D2) of glofitamab is administered on day 15 of the second dosing cycle.

In one embodiment, the third dose of glofitamab (C3D1) is administered on day 8 of the third dosing cycle.

In one embodiment, the method comprises 1 to 5 additional dosing cycles (C4 to C8). In one such embodiment, the 1 to 5 additional dosing cycles (C4 to C8) each comprises a single dose of R-CHOP and a single dose (C4D1 to C8D1) of 30 mg of glofitamab.

In one embodiment, the single dose of the R-CHOP is administered on day 1 and the single dose of glofitamab is administered on day 8 of the respective additional dosing cycle (C4 to C8).

In one embodiment, rituximab is dosed at 375 mg/m$^2$ IV. In one embodiment, CHOP is administered with the following dosage: 750 mg/m$^2$ Cyclophosphamide; 50 mg/m$^2$ Doxorubicin; 1.4 mg/m$^2$ Vincristine; Prednisone 100 mg/day orally on Days 1-5. In one embodiment, prednisone on Day 1 may be administered IV, with the remaining doses on Days 2-5 to be administered orally.

In one embodiment, the method of treating a subject having a CD20-positive B cell proliferative disorder comprising administering to the subject rituximab, cyclophosphamide, doxorubicin, vincristine, and prednisone (R-CHOP) and glofitamab in a dosing regimen as described in any of the embodiments above does not comprise any administration of obinutuzumab. In one embodiment said method does not comprise pre-treatment with obinutuzumab as described in the section below.

In one embodiment, the method comprises 6 dosing cycles in total.

In one embodiment, one treatment cycle comprises 14 days or 21 days. In one embodiment, one treatment cycle comprises 21 days.

In one embodiment, the subject suffers from previously untreated (treatment-naïve) DLBCL. In one embodiment, the subject may not be adequately treated with standard-of-care therapy.

DLBCL patients can be defined by an international prognostics indicator (IPI), see e.g., Table 19. The IPI is a validated scoring system predictive of survival in de novo DLBCL (International NHL Prognostic 1993). The IPI score separates four prognostic groups based on the number of factors present (0, 1: low-risk group; 2: low intermediate-risk group; 3: high intermediate-risk group; and 4, 5: high-risk group). The IPI has been widely used and reproduced when various conventional, high-dose, and dose-dense regimens were analyzed, including R-CHOP (Ziepert et al. 2010). The methods provided herein are particularly suitable for patients without good prognostic factors, e.g., patients with IPI 2-5. In one embodiment, the subject to be treated has international prognostics indicator [IPI] 2-5. In one embodiment, the subject to be treated has an IPI of 4 or 5. In one embodiment, IPI is not age-dependent. In one embodiment the subject to be treated is of age 18 or older. In one embodiment, the subject to be treated is of age 60 or older and has an IPI of 4 or 5. In one embodiment, the subject to be treated is of age 18 to 59 and has an IPI of 2-5. In one embodiment, the subject suffers from previously untreated (treatment-naïve) DLBCL and has Eastern Cooperative Oncology Group performance status [ECOG PS] 0-3.

In one embodiment, the subject suffers from R/R NHL and has Eastern Cooperative Oncology Group performance status [ECOG PS] 0-2.

In one embodiment, the treatment additionally comprises maintenance treatment with the anti-CD20/anti-CD3 bispecific antibody, e.g., glofitamab. In one such embodiment, the anti-CD20/anti-CD3 bispecific antibody, e.g., glofitamab is administered every 2 months for <2 years. In one such embodiment the anti-CD20/anti-CD3 bispecific antibody, e.g., glofitamab, is administered with a dose of 30 mg.

In one embodiment, the CD20-positive B cell proliferative disorder is a non-Hodgkin's lymphoma (NHL). In one embodiment, the B cell proliferative disorder is previously untreated (treatment-naïve) DLBCL. In one embodiment, the subject to be treated has international prognostics indicator [IPI] 2-5.

In one embodiment, a method for treating diffuse large B-cell lymphoma (DLBCL) in a human in need thereof is provided, comprising administering to the human six 21-day cycles of treatment comprising:

(a) rituximab administered intravenously at a dose of about 375 mg/$m^2$ on day 1 of each 21-day cycle, (b) cyclophosphamide administered intravenously at a dose of about 750 mg/$m^2$ on day 1 of each 21-day cycle, (c) doxorubicin administered intravenously at a dose of about 50 mg/$m^2$ on day 1 of each 21-day cycle, (d) prednisone, administered orally at a dose of about 100 mg on each of days 1-5 of each 21-day cycle, and (e) glofitamab administered at a dose of 2.5 mg on day 8 and 10 mg on day 15 of the second 21-day cycle and at a dose of 30 mg on day 8 of each subsequent dosing cycle.

In one embodiment, rituximab in the first dosing cycle is replaced by obinutuzumab.

CRS Risk Mitigation Strategies

Pretreatment with an Anti-CD20 Antibody

In one aspect, the subjects foreseen for treatment with the methods provided herein are pretreated with an anti-CD20 antibody. In one embodiment the anti-CD20 antibody is rituximab or obinutuzumab. In a particular embodiment, the anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVARO®. This replaces all previous versions (e.g., Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In one embodiment, the anti-CD20 antibody is tositumomab.

Obinutuzumab is a humanized glyco-engineered type II anti-CD20 mAb that binds with high-affinity to the CD20 antigen, inducing antibody-dependent cellular cytotoxicity (ADCC) and antibody-dependent cellular phagocytosis (ADCP), low complement-dependent cytotoxicity (CDC) activity, and high direct cell death induction. Use of GAZYVA® pre-treatment (Gpt) can aid in the rapid depletion of B cells, both in the peripheral blood and in secondary lymphoid organs, such that the risk of highly relevant adverse events (AEs) from strong systemic T cell activation by T-cell activating therapeutic agents (e.g., CRS) is reduced, while supporting exposure levels of T-cell activating therapeutic agents that are high enough from the start of dosing to mediate tumor cell elimination. To date, the safety profile of obinutuzumab (including cytokine release) has been assessed and managed in hundreds of patients in ongoing obinutuzumab clinical trials. Finally, in addition to supporting the safety profile of T-cell activating therapeutic agents such as anti-CD20/anti-CD3 bispecific antibodies, particularly glofitamab, Gpt could also help prevent the formation of anti-drug antibodies (ADAs) to these unique molecules.

In a specific aspect the invention provides a method of treating a subject having a CD20-positive B cell proliferative disorder comprising (i) administering to the subject an anti-CD20 antibody before the first dose of the anti-CD20/anti-CD3 bispecific antibody; and (ii) administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In a further specific aspect, the invention provides a method of treating a subject having a CD20-positive B cell proliferative disorder comprising (i) administering to the subject obinutuzumab before the first dose of the anti-CD20/anti-CD3 bispecific antibody; and (ii) administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

In a further specific aspect, the invention provides a method of treating a subject having a CD20-positive B cell proliferative disorder comprising (i) administering to the subject obinutuzumab before the first dose of glofitamab; and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In a further specific aspect, the invention provides a method of treating a subject having a CD20-positive B cell proliferative disorder comprising:

(i) administering to the subject an anti-CD20 antibody before the first dose of the anti-CD20/anti-CD3 bispecific antibody, and (ii) administering to the subject the anti-CD20/anti-CD3 bispecific antibody in a dosing regimen comprising at least a first dosing cycle, a second dosing cycle, and a third dosing cycle, wherein: (a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg; (b) the second dosing cycle comprises a single dose (C2D1) of 10 mg of the anti-CD20/anti-CD3 bispecific antibody; and (c) the third dosing cycle comprises a single dose (C3D1) of 16 or 30 mg of the anti-CD20/anti-CD3 bispecific antibody.

In a further specific aspect, the invention provides a method of treating a subject having a CD20-positive B cell proliferative disorder comprising:

(i) administering to the subject obinutuzumab before the first dose of the anti-CD20/anti-CD3 bispecific antibody, and (ii) administering to the subject the anti-CD20/anti-CD3 bispecific antibody in a dosing regimen comprising at least a first dosing cycle, a second dosing cycle, and a third dosing cycle, wherein: (a) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg; (b) the second dosing cycle comprises a single dose (C2D1) of 10 mg of the anti-CD20/anti-CD3 bispecific antibody; and (c) the third dosing cycle comprises a single dose (C3D1) of 16 or 30 mg of the anti-CD20/anti-CD3 bispecific antibody.

In a further specific aspect, the invention provides a method of treating a subject having a CD20-positive B cell proliferative disorder comprising:

(i) administering to the subject obinutuzumab before the first dose of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment obinutuzumab or rituximab is administered 7 days before the first dose of the anti-CD20/anti-CD3 bispecific antibody (C1D1). In one embodiment obinutuzumab is administered at one dose of 1000 mg. In one embodiment obinutuzumab (GAZYVA®) pre-treatment is administered 7 days before the first dose of glofitamab (C1D1) in the monotherapy and combination therapy cohorts and step-up cohorts. In one such embodiment obinutuzumab is administered at one dose of 1000 mg. In one embodiment, pretreatment with obinutuzumab is used in the treatment of subjects with non-Hodgkin lymphoma (NHL; e.g., relapsed or refractory (R/R) NHL (e.g., R/R follicular lymphoma (FL) or R/R mantle cell lymphoma (MCL)), indolent NHL (iNHL), or aggressive NHL (aNHL)).

For specific histologies, a double pre-treatment with obinutuzumab (DGpt) prior to first dose of glofitamab is administered to the subject. Double pre-treatment can be achieved by either administration of two doses of obinutuzumab (Gpt) on the same day prior to the first dose of glofitamab. In one such aspect, two doses of obinutuzumab are administered 7 days before the first dose of glofitamab (e.g., 2 times 1000 mg obinutuzumab seven days before the first dose of glofitamab). In another aspect, two doses of Gpt are administered on different days prior to the first glofitamab dose. In one such embodiment, a first Gpt dose (1000 mg) is administered seven days before the first dose of glofitamab, and a second dose of Gpt (1000 mg) is administered one day before the first dose of glofitamab.

In one embodiment obinutuzumab or rituximab is administered 7 days before the first dose of the anti-CD20/anti-CD3 bispecific antibody (C1D1). In one embodiment the pretreatment comprises a second dose of obinutuzumab. The second dose of obinutuzumab prior to the first dose of glofitamab further reduces the occurrence and severity of CRS. DGpt may be administered prior to glofitamab monotherapy and also in glofitamab combination therapy.

In one such embodiment the first and second dose of obinutuzumab pretreatment is administered on the same day. Hence, in one embodiment obinutuzumab pretreatment is administered at one dose of 2000 mg. In one embodiment 2000 mg of obinutuzumab pretreatment is administered 7 days before the first dose of the anti-CD20/anti-CD3 bispecific antibody (C1D1).

In another embodiment the first and second dose of obinutuzumab pretreatment are administered on different days. In one such embodiment the first dose of obinutuzumab pretreatment is administered 7 days before the first dose (C1D1) of the anti-CD20/anti-CD3 bispecific antibody and the second dose of obinutuzumab pretreatment is administered one day before the first dose (C1D1) of the anti-CD20/anti-CD3 bispecific antibody. In one embodiment the first and second dose of obinutuzumab pretreatment is 1000 mg. In one embodiment, the obinutuzumab pretreatment comprising a single dose is used for treating a subject suffering from DLBCL. In one embodiment, the DLBCL is a R/R DLBCL. In one embodiment, the obinutuzumab pretreatment comprising a single dose is used for treating a subject suffering from FL. In one embodiment, the FL is a R/R FL. In one embodiment, the obinutuzumab pretreatment comprising a single dose is used for treating a subject suffering from MCL. In one embodiment, the MCL is a R/R MCL. In one embodiment said subject has received at least two prior systemic therapies. In one embodiment, the subject with MCL has received at least one prior systemic treatment regimen comprising a Bruton tyrosine kinase inhibitor (BTKi) (e.g., ibrutinib, acalabrutinib, or zanubrutinib).

In one embodiment the obinutuzumab pretreatment comprising a first and second dose are used in a method for treating a subject suffering from MCL. In one embodiment said subject has received at least two prior systemic therapies. In one embodiment, the subject has received at least one prior systemic treatment regimen comprising a Bruton tyrosine kinase inhibitor (BTKi) (e.g., ibrutinib, acalabrutinib, or zanubrutinib).

In a further specific aspect, the invention provides a method of treating a subject suffering from DLBCL comprising:

(i) administering to the subject a single dose of 1000 mg obinutuzumab before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg and (b) the second dosing cycle comprises a single dose (C2D1) of 16 or 30 mg of glofitamab.

In a further specific aspect, the invention provides a method of treating a subject suffering from DLBCL comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg and (b) the second dosing cycle comprises a single dose (C2D1) of 16 or 30 mg of glofitamab.

In a further specific aspect, the invention provides a method of treating a subject suffering from FL comprising:

(i) administering to the subject a single dose of 1000 mg obinutuzumab before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg and (b) the second dosing cycle comprises a single dose (C2D1) of 16 or 30 mg of glofitamab.

In a further specific aspect, the invention provides a method of treating a subject suffering from FL comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg and (b) the second dosing cycle comprises a single dose (C2D1) of 16 or 30 mg of glofitamab.

In a further specific aspect, the invention provides a method of treating a subject suffering from FL comprising:

(i) administering to the subject a single dose of 1000 mg obinutuzumab before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In a further specific aspect, the invention provides a method of treating a subject suffering from FL comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In a further specific aspect, the invention provides a method of treating a subject suffering from MCL comprising (i) administering to the subject two doses of 1000 mg obinutuzumab before the first dose of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In a further specific aspect, the invention provides a method of treating a subject suffering from MCL comprising (i) administering to the subject a dose of 2000 mg obinutuzumab 7 days before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In a further specific aspect, the invention provides a method of treating a subject suffering from MCL comprising (i) administering to the subject two doses of 1000 mg obinutuzumab before the first dose of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In a further specific aspect, the invention provides a method of treating a subject suffering from MCL comprising:

(i) administering to the subject a single dose of 1000 mg obinutuzumab before the first dose (C1D1) of glofitamab; and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In a further specific aspect, the invention provides a method of treating a subject suffering from MCL comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In a further specific aspect, the invention provides a method of treating a subject suffering from MCL comprising:

(i) administering to the subject a dose of 2000 mg obinutuzumab before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In a further specific aspect, the invention provides a method of treating a subject suffering from MCL comprising:

(i) administering to the subject a dose of 2000 mg obinutuzumab 7 days before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment, the invention features a method of treating a subject with mantle cell lymphoma which has relapsed after or failed to respond to at least one prior systemic treatment regimen that includes a Bruton tyrosine kinase (BTK) inhibitor (BTKi), comprising (i) administering to the subject two doses of 1000 mg obinutuzumab before the first dose of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment, the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), (i) administering to the subject a dose of 2000 mg obinutuzumab 7 days before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising (i) administering to the subject two doses of 1000 mg obinutuzumab before the first dose of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a single dose of 1000 mg obinutuzumab before the first dose (C1D1) of glofitamab; and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a dose of 2000 mg obinutuzumab before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a dose of 2000 mg obinutuzumab 7 days before the first dose (C1D1) of glofitamab, and (ii) administering to the subject glofitamab in a dosing regimen comprising at least a first dosing cycle, a second dosing cycle, and a third dosing cycle, wherein: (a) the first dosing cycle comprises a first dose (C1D1) and a second dose (C1D2) of glofitamab, wherein the C1D1 is 0.5 mg, and the C1D2 is 2.5 mg; (b) the second dosing cycle comprises a single dose (C2D1) of 10 mg of glofitamab; and (c) the third dosing cycle comprises a single dose (C3D1) of 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a single dose of 1000 mg obinutuzumab before the first dose (C1D1) of glofitamab; and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment the BTKi comprises ibrutinib, acalabrutinib, or zanubrutinib.

In a further specific aspect, the invention provides a method of treating a subject with mantle cell lymphoma which has relapsed after or failed to respond to at least one prior systemic treatment regimen that includes a Bruton tyrosine kinase (BTK) inhibitor (BTKi), comprising:

(i) administering to the subject a single dose of 1000 mg obinutuzumab 7 days before the first dose (C1D1) of glofitamab, and (ii) administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of either 16 or 30 mg of glofitamab.

In one embodiment, the BTKi comprises ibrutinib, acalabrutinib, or zanubrutinib.

In additional embodiments the glofitamab step-up dosing is performed according to any of the embodiments described, above.

Pretreatment or Management of CRS Related Symptoms with Tocilizumab

CRS is associated with high IL-6 levels (Panelli et al., *J Transl Med,* 2: 17, 2004; Lee et al., *Blood,* 124: 188-195, 2014; Doessegger and Banholzer, *Clin Transl Immunology,* 4: e39, 2015), and IL-6 correlates with the severity of CRS, with patients who experience severe or life-threatening CRS (NCI CTCAE Grades 4 or 5) having much higher IL-6 levels compared with their counterparts who do not experience CRS or experience milder CRS reactions (NCI CTCAE Grades 0-3) (Chen et al., J Immunol Methods, 434: 1-8, 2016).

Tocilizumab (ACTEMRA®/ROACTEMRA®) is a recombinant, humanized, anti-human monoclonal antibody directed against soluble and membrane-bound IL-6R, which inhibits IL-6 mediated signaling (see, e.g., WO 1992/019579, which is incorporated herein by reference in its entirety). Tocilizumab has been approved by the U.S. Food and Drug Administration for the treatment of severe or life-threatening CAR-T cell-induced CRS in adults and in pediatric patients 2 years of age and older. Initial clinical data (Locke et al., *Blood,* 130: 1547, 2017) suggests that tocilizumab prophylaxis may reduce the severity of CAR-T cell-induced CRS by blocking IL-6 receptors from signaling prior to cytokine release. Consequently, tocilizumab premedication may also reduce the frequency or lower the severity of CRS associated with bispecific antibody therapy. Other anti-IL-6R antibodies that could be used in combination with tocilizumab include sarilumab, vobarilizumab (ALX-0061), SA-237, and variants thereof.

In some aspects, an effective amount of tocilizumab is administered as a premedication, e.g., is administered to the subject prior to the administration of the anti-CD20/anti-CD3 bispecific antibody. Administration of tocilizumab as a premedication may reduce the frequency or severity of CRS. In some aspects, tocilizumab is administered as a premedication in Cycle 1, e.g., is administered prior to a first dose (C1D1), a second dose (C1D2), and/or a third dose (C1D3) of the anti-CD20/anti-CD3 bispecific antibody. In some aspects, tocilizumab is administered intravenously to the subject as a single dose of about 1 mg/kg to about 15 mg/kg, e.g., about 4 mg/kg to about 10 mg/kg, e.g., about 6 mg/kg to about 10 mg/kg, e.g., about 8 mg/kg. In some aspects, tocilizumab is administered intravenously to the subject as a single dose of about 8 mg/kg. Other anti-IL-6R antibodies that could be used in combination with tocilizumab include sarilumab, vobarilizumab (ALX-0061), SA-237, and variants thereof.

For example, in one aspect, the anti-CD20/anti-CD3 bispecific antibody is co-administered with tocilizumab (ACTEMRA®/ROACTEMRA®), wherein the subject is first administered with tocilizumab (ACTEMRA®/ROACTEMRA®) and then separately administered with the anti-CD20/anti-CD3 bispecific antibody (e.g., the subject is pre-treated with tocilizumab (ACTEMRA®/ROACTEMRA®)).

In another aspect, tocilizumab is administered to treat or alleviate symptoms associated with CRS in subjects treated with an anti-CD20/anti-CD3 bispecific antibody. If the subject has a Grade 2 or higher CRS event in the presence of extensive comorbidities following administration of the anti-CD20/anti-CD3 bispecific antibody, the method may further include administering to the subject a first dose of an IL-6R antagonist (e.g., an anti-IL-6R antibody, e.g., tocilizumab (ACTEMRA®/ROACTEMRA®)) to manage the Grade 2 or higher CRS event while suspending treatment with the anti-CD20/anti-CD3 bispecific antibody. In some instances, the first dose of tocilizumab is administered intravenously to the subject at a dose of about 8 mg/kg. Other anti-IL-6R antibodies that could be used in combination with tocilizumab include sarilumab, vobarilizumab (ALX-0061), SA-237, and variants thereof. In some instances, if the Grade 2 or higher CRS event resolves to a grade ≤1 CRS event within two weeks, the method further includes resuming treatment with the anti-CD20/anti-CD3 bispecific antibody at a reduced dose. In some instances, the reduced dose is 50% of the initial infusion rate of the previous cycle if the event occurred during or within 24 hours of the infusion. If, on the other hand, the Grade 2 or higher CRS event does not resolve or worsens to a grade ≥3 CRS event within 24 hours of treating the symptoms of the Grade 2 or higher CRS event, the method may further include administering to the subject one or more (e.g., one, two, three, four, or five or more) additional doses of an IL-6R antagonist (e.g., an anti-IL-6R antibody, e.g., tocilizumab) to manage the Grade 2 or Grade ≥3 CRS event. In some particular instances, the Grade 2 or higher CRS event does not resolve or worsens to a grade ≥3 CRS event within 24 hours of treating the symptoms of the Grade 2 or higher CRS event, and the method may further include administering to the subject one or more additional doses of tocilizumab to manage the Grade 2 or Grade ≥3 CRS event. In some instances, the one or more additional doses of tocilizumab is administered intravenously to the subject at a dose of about 1 mg/kg to about 15 mg/kg, e.g., about 4 mg/kg to about 10 mg/kg, e.g., about 6 mg/kg to about 10 mg/kg, e.g., about 8 mg/kg.

Other Pretreatments for CRS Risk Mitigation

In one embodiment, the treatment regimen provided herein further comprises administration of premedication prior to the administration of the anti-CD20/anti-CD3 bispecific antibody. In one embodiment the premedication comprises a corticosteroid (e.g., prednisolone, dexamethasone, or methylprednisolone), paracetamol/acetaminophen, and/or an anti-histamine (e.g., diphenhydramine). In one embodiment, the premedication is administered at least 60 minutes prior to the administration of the anti-CD20/anti-CD3 bispecific antibody. In one embodiment, the treatment regimen further comprises administration of premedication prior to the administration of glofitamab. In embodiment the premedication comprises a corticosteroid (e.g., prednisolone, dexamethasone, or methylprednisolone), an anti-pyretic (e.g., paracetamol/acetaminophen), and/or an anti-histamine (e.g., diphenhydramine). In one embodiment, the subject receives corticosteroid premedication prior to the anti-CD20/anti-CD3 bispecific antibody. It has been shown that premedication using dexamethasone reduced glofitamab-induced cytokine levels in mice pretreated with dexamethasone relative to methylprednisolone. Therefore, in one embodiment the corticosteroid is dexamethasone. In one embodiment, the premedication is administered at least 60 minutes prior to the administration of glofitamab. In one embodiment, the premedication is administered at least 60 minutes prior to each administration of glofitamab. In another embodiment pre-medication with corticosteroids is administered before the first dose (C1D1) and second dose (C1D2) of the first dosing cycle, before the first dose of the second (C2D1) and third (C3D1) dosing cycles and may be optional for subsequent dosing cycles where the target dose has been reached and tolerated for two doses for patients with no CRS in previous cycles.

In one embodiment, the premedication is administered at least 60 minutes prior to the administration of the pretreatment with the anti-CD20 antibody, particularly obinutuzumab. In one embodiment, corticosteroids are administered to manage any relevant adverse events arising after administration of the anti-CD20/anti-CD3 bispecific antibody, e.g., glofitamab.

VII. Administration of the Anti-CD20/Anti-CD3 Bispecific Antibody

The anti-CD20/anti-CD3 bispecific antibody can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. In one embodiment, the anti-CD20/anti-CD3 bispecific antibody is administered parenterally, particularly intravenously, e.g., by intravenous infusion. In one embodiment the infusion time for the anti-CD20/anti-CD3 bispecific antibody, particularly glofitamab, is at least 4 hours. In one embodiment the infusion time for the anti-CD20/anti-CD3 bispecific antibody may be reduced or extended. In one embodiment in the absence of infusion-related adverse events, the infusion time of glofitamab in subsequent dosing cycles is reduced to 2 hours±15 minutes. In one embodiment the infusion time is increased to up to 8 hours for subjects with high risk of experiencing CRS. In one embodiment, for patients who may be at an increased risk of CRS, patients who experience IRRs or CRS with their previous dose of glofitamab or who are at increased risk of recurrent IRR/CRS with subsequent doses, the time of infusion of glofitamab is extended to up to 8 hours.

In one embodiment the pretreatment of the anti-CD20 antibody is given with an infusion time of at least 4.75 hours.

The anti-CD20/anti-CD3 bispecific antibody would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

A further aspect of the present invention relates to the invention as described hereinbefore.

```
Sequences
Variable regions
CD3 VH
                                    (SEQ ID NO: 15)
EVQLLESGGG LVQPGGSLRL SCAASGFTFS

TYAMNWVRQA PGKGLEWVSR IRSKYNNYAT

YYADSVKGRF TISRDDSKNT LYLQMNSLRA

EDTAVYYCVR HGNFGNSYVS WFAYWGQGTL

VTVSSAS

CD3 VL
                                    (SEQ ID NO: 16)
QAVVTQE PSLTVSPGGT VTLTCGSSTG

AVTTSNYANW VQEKPGQAFR GLIGGTNKRA

PGTPARFSGS LLGGKAALTL SGAQPEDEAE

YYCALWYSNL WVFGGGTKLT VLSS

CD20 VH
                                     (SEQ ID NO: 7)
QVQLVQSGAE VKKPGSSVKV SCKASGYAFS

YSWINWVRQA PGQGLEWMGR IFPGDGDTDY

NGKFKGRVTI TADKSTSTAY MELSSLRSED

TAVYYCARNV FDGYWLVYWG QGTLVTVSS

CD20 VL
                                     (SEQ ID NO: 8)
DIVMTQTPLS LPVTPGEPAS ISCRSSKSLL

HSNGITYLYW YLQKPGQSPQ LLIYQMSNLV

SGVPDRFSGS GSGTDFTLKI SRVEAEDVGV

YYCAQNLELP YTFGGGTKVE IK

CD20 heavy chain CDRs Kabat:
HCDR1-Kabat:
                                     (SEQ ID NO: 1)
YSWIN

HCDR2-Kabat:
                                     (SEQ ID NO: 2)
RIFPGDGDTDYNGKFKG

HCDR3-Kabat:
                                     (SEQ ID NO: 3)
NVFDGYWLVY

CD20 light chain CDRs (Kabat):
LCDR1-Kabat:
                                     (SEQ ID NO: 4)
RSSKSLLHSNGITYLY

LCDR2-Kabat:
                                     (SEQ ID NO: 5)
QMSNLVS

LCDR3-Kabat:
                                     (SEQ ID NO: 6)
AQNLELPYT
```

-continued

```
CD3 heavy chain CDRs Kabat:
HCDR1-Kabat:
                                     (SEQ ID NO: 9)
TYAMN

HCDR2-Kabat:
                                    (SEQ ID NO: 10)
RIRSKYNNYATYYADSVKG

HCDR3-Kabat:
                                    (SEQ ID NO: 11)
HGNFGNSYVSWFAY

CD3 light chain CDRs (Kabat):
LCDR1-Kabat:
                                    (SEQ ID NO: 12)
GSSTGAVTTSNYAN

LCDR2-Kabat:
                                    (SEQ ID NO: 13)
GTNKRAP

LCDR3-Kabat:
                                    (SEQ ID NO: 14)
ALWYSNLWV

Full-length antibody
HC-knob
                                    (SEQ ID NO: 17)
QVQLVQSGAEVKKPGSSVKVSCKASGYAFSYSWIN

WVRQAPGQGLEWMGRIFPGDGDTDYNGKFKGRVTI

TADKSTSTAYMELSSLRSEDTAVYYCARNVFDGYW

LVYWGQGTLVTVSSASTKGPSVFPLAPSSKSTSGG

TAALGCLVEDYFPEPVTVSWNSGALTSGVHTFPAV

LQSSGLYSLSSVVTVPSSSLGTQTYICNVNHKPSN

TKVDEKVEPKSCDGGGGSGGGGSQAVVTQEPSLTV

SPGGTVTLTCGSSTGAVTTSNYANWVQEKPGQAFR

GLIGGTNKRAPGTPARFSGSLLGGKAALTLSGAQP

EDEAEYYCALWYSNLWVFGGGTKLTVLSSASTKGP

SVFPLAPSSKSTSGGTAALGCLVKDYFPEPVTVSW

NSGALTSGVHTFPAVLQSSGLYSLSSVVTVPSSSL

GTQTYICNVNHKPSNTKVDKKVEPKSCDKTHTCPP

CPAPEAAGGPSVFLFPPKPKDTLMISRTPEVTCVV

VDVSHEDPEVKFNWYVDGVEVHNAKTKPREEQYNS

TYRVVSVLTVLHQDWLNGKEYKCKVSNKALGAPIE

KTISKAKGQPREPQVYTLPPCRDELTKNQVSLWCL

VKGFYPSDIAVEWESNGQPENNYKTTPPVLDSDGS

FFLYSKLTVDKSRWQQGNVFSCSVMHEALHNHYTQ

KSLSLSP

HC-hole
                                    (SEQ ID NO: 18)
QVQLVQSGAEVKKPGSSVKVSCKASGYAFSYSWIN

WVRQAPGQGLEWMGRIFPGDGDTDYNGKFKGRVTI

TADKSTSTAYMELSSLRSEDTAVYYCARNVFDGYW

LVYWGQGTLVTVSSASTKGPSVFPLAPSSKSTSGG

TAALGCLVEDYFPEPVTVSWNSGALTSGVHTFPAV
```

-continued

```
LQSSGLYSLSSVVTVPSSSLGTQTYICNVNHKPSN

TKVDEKVEPKSCDKTHTCPPCPAPEAAGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALGAPIEKTISKAKGQPREPQV

CTLPPSRDELTKNQVSLSCAVKGFYPSDIAVEWES

NGQPENNYKTTPPVLDSDGSFFLVSKLTVDKSRWQ

QGNVFSCSVMHEALHNHYTQKSLSLSP

LC-CD3
                                (SEQ ID NO: 19)
EVQLLESGGGLVQPGGSLRLSCAASGFTFSTYAMN

WVRQAPGKGLEWVSRIRSKYNNYATYYADSVKGRF

TISRDDSKNTLYLQMNSLRAEDTAVYYCVRHGNFG

NSYVSWFAYWGQGTLVTVSSASVAAPSVFIFPPSD

EQLKSGTASVVCLLNNFYPREAKVQWKVDNALQSG

NSQESVTEQDSKDSTYSLSSTLTLSKADYEKHKVY

ACEVTHQGLSSPVTKSFNRGEC

LC-CD20
                                (SEQ ID NO: 20)
DIVMTQTPLSLPVTPGEPASISCRSSKSLLHSNGI

TYLYWYLQKPGQSPQLLIYQMSNLVSGVPDRFSGS

GSGTDFTLKISRVEAEDVGVYYCAQNLELPYTFGG

GTKVEIKRTVAAPSVFIFPPSDRKLKSGTASVVCL

LNNFYPREAKVQWKVDNALQSGNSQESVTEQDSKD

STYSLSSTLTLSKADYEKHKVYACEVTHQGLSSPV

TKSFNRGEC
```

EMBODIMENTS

In the following, some of the embodiments of the invention are listed.

1. An anti-CD20/anti-CD3 bispecific antibody for use in a method of treating a subject having a CD20-positive B cell proliferative disorder comprising administering to the subject the anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody.

2. The anti-CD20/anti-CD3 bispecific antibody for use in a method of treating a subject having a CD20-positive B cell proliferative disorder of embodiment 1, wherein the single dose of the second dosing cycle (C2D1) comprises 30 mg of the anti-CD20/anti-CD3 bispecific antibody.

3. The anti-CD20/anti-CD3 bispecific antibody for use in a method of treating a subject having a CD20-positive B cell proliferative disorder of embodiment 1 or 2, wherein the first dose (C1D1) is administered on day 1 of the first dosing cycle and the second dose (C1D2) is administered on day 8 of the first dosing cycle.

4. The anti-CD20/anti-CD3 bispecific antibody for use in a method of treating a subject having a CD20-positive B cell proliferative disorder of any one of embodiments 1 to 3, wherein the single dose of the second dosing cycle (C2D1) is administered on day 1 of the second dosing cycle.

5. The anti-CD20/anti-CD3 bispecific antibody for use in a method of treating a subject having a CD20-positive B cell proliferative disorder of any one of embodiments 1 to 4, comprising 1 to 10 additional dosing cycles (C3 to C12).

6. The anti-CD20/anti-CD3 bispecific antibody for use in a method of treating a subject having a CD20-positive B cell proliferative disorder of embodiment 5, wherein the 1 to 10 additional dosing cycles (C3 to C12) each comprises a single dose (C3D1 to C12D1) of either 16 or 30 mg of the anti-CD20/anti-CD3 bispecific antibody.

7. The anti-CD20/anti-CD3 bispecific antibody for use in a method of treating a subject having a CD20-positive B cell proliferative disorder of embodiment 5 or 6, wherein the single dose of each of the additional dosing cycles (C3D1 to C12D1) comprises 30 mg of the anti-CD20/anti-CD3 bispecific antibody.

8. The anti-CD20/anti-CD3 bispecific antibody for use in a method of treating a subject having a CD20-positive B cell proliferative disorder of any one of embodiments 5 to 7, wherein the single dose of the additional dosing cycles (C3D1 to C12D1) is administered on day 1 of the respective additional dosing cycle.

9. The anti-CD20/anti-CD3 bispecific antibody for use in a method of treating a subject having a CD20-positive B cell proliferative disorder of any one of embodiments 1 to 8, comprising 12 dosing cycles in total.

10. The anti-CD20/anti-CD3 bispecific antibody for use in a method of treating a subject having a CD20-positive B cell proliferative disorder of any one of embodiments 1 to 9, wherein one treatment cycle comprises 14 days or 21 days.

11. The anti-CD20/anti-CD3 bispecific antibody for use in a method of treating a subject having a CD20-positive B cell proliferative disorder of embodiment 10, wherein one treatment cycle comprises 21 days.

12. The anti-CD20/anti-CD3 bispecific antibody for use in a method of treating a subject having a CD20-positive B cell proliferative disorder of any one of embodiments 1 to 11, wherein the CD20-positive B cell proliferative disorder is a non-Hodgkin's lymphoma (NHL).

13. The anti-CD20/anti-CD3 bispecific antibody for use in a method of treating a subject having a CD20-positive B cell proliferative disorder of embodiment 12, wherein the B cell proliferative disorder is relapsed or refractory NHL.

14. The anti-CD20/anti-CD3 bispecific antibody for use in a method of treating a subject having a CD20-positive B cell proliferative disorder of embodiment 12 or 13, wherein the NHL is indolent NHL (iNHL) or aggressive NHL (aNHL).

15. The anti-CD20/anti-CD3 bispecific antibody for use in a method of treating a subject having a CD20-positive B cell proliferative disorder of embodiment 12 or 13, wherein the NHL is a diffuse large B cell lymphoma (DLBCL), high grade B cell lymphoma (HGBCL), primary mediastinal large B-cell lymphoma (PMBCL), or marginal zone lymphoma (MZL).

16. The anti-CD20/anti-CD3 bispecific antibody for use in a method of treating a subject having a CD20-positive B cell proliferative disorder of embodiment 15, wherein the DLBCL is a Richter's transformation.

17. The anti-CD20/anti-CD3 bispecific antibody for use in a method of treating a subject having a CD20-positive B cell proliferative disorder of embodiment 12 or 13, wherein the NHL is a mantle cell lymphoma (MCL).

18. The anti-CD20/anti-CD3 bispecific antibody for use in a method of treating a subject having a CD20-positive B cell proliferative disorder of embodiment 17, wherein the MCL is a relapsed or refractory (R/R) MCL.

19. The anti-CD20/anti-CD3 bispecific antibody for use in a method of treating a subject having a CD20-positive B cell proliferative disorder of embodiment 17 or 18, wherein the subject has received at least one prior systemic treatment regimen comprising a Bruton tyrosine kinase inhibitor (BTKi).

20. The anti-CD20/anti-CD3 bispecific antibody for use in a method of treating a subject having a CD20-positive B cell proliferative disorder of embodiment 19, wherein the BTKi comprises ibrutinib, acalabrutinib, or zanubrutinib.

21. The anti-CD20/anti-CD3 bispecific antibody for use in a method of treating a subject having a CD20-positive B cell proliferative disorder of embodiment 12 or 13, wherein the NHL is a follicular lymphoma (FL).

22. The anti-CD20/anti-CD3 bispecific antibody for use in a method of treating a subject having Follicular lymphoma (FL) according to embodiment 21, wherein the FL is Grade 1, 2, or 3a FL.

23. The anti-CD20/anti-CD3 bispecific antibody for use in a method of treating a subject having Follicular lymphoma (FL) according to embodiment 21 or 22, wherein the FL is a transformed FL.

24. The anti-CD20/anti-CD3 bispecific antibody for use in a method of treating a subject having Follicular lymphoma (FL) of any one of embodiments 21 to 23, wherein the FL is a relapsed or refractory (R/R) FL.

25. The anti-CD20/anti-CD3 bispecific antibody for use in a method of treating a subject having Follicular lymphoma (FL) of any one of embodiments 21 to 24, wherein the subject is a high risk subject who:

(a) has relapsed after or is refractory to at least two prior therapies;
(b) has relapsed after or is refractory to treatment with a phosphoinositide 3-kinase (PI3K) inhibitor;
(c) experiences progression of disease within 24 months of frontline treatment; and/or
(d) has lesions, wherein the sum of the product of the lesion diameters is ≥3,000 $mm^2$.

26. The anti-CD20/anti-CD3 bispecific antibody for use in a method of treating a CD20-positive B cell proliferative disorder of any one of embodiments 1 to 25 wherein the population of subjects having the CD20-positive B cell proliferative disorder exhibits cytokine release syndrome after administering the anti-CD20/anti-CD3 bispecific antibody, and wherein the rate of the cytokine release syndrome of a grade of 3 or greater (as defined by the American Society for Transplantation and Cellular Therapy, 2019; ASTCT) is less than or about 5%.

27. The anti-CD20/anti-CD3 bispecific antibody for use in a method of treating a CD20-positive B cell proliferative disorder of any one of embodiments 1 to 26, wherein administration of the anti-CD20/anti-CD3 bispecific antibody to a plurality of subjects results in a complete response rate of at least about 70%.

28. The anti-CD20/anti-CD3 bispecific antibody for use in a method of treating iNHL according to embodiment 14, wherein administration of the anti-CD20/anti-CD3 bispecific antibody to a plurality of subjects results in a complete response rate of at least about 70% in subjects suffering from iNHL.

29. The anti-CD20/anti-CD3 bispecific antibody for use in a method of treating aNHL according to embodiment 14, wherein administration of the anti-CD20/anti-CD3 bispecific antibody to a plurality of subjects results in a complete response rate of at least about 70% in subjects suffering from aNHL.

30. The anti-CD20/anti-CD3 bispecific antibody for use in a method of treating MCL of any one of embodiments 17 to 20, wherein administration of the anti-CD20/anti-CD3 bispecific antibody to a plurality of subjects results in an overall response rate of at least about 80%.

31. The anti-CD20/anti-CD3 bispecific antibody for use in a method of treating MCL of any one of embodiments 17 to 20, wherein administration of the anti-CD20/anti-CD3 bispecific antibody to a plurality of subjects results in a complete response rate of at least about 65%.

32. The anti-CD20/anti-CD3 bispecific antibody for use in a method of treating FL of any one of embodiments 21 to 24, wherein administration of the anti-CD20/anti-CD3 bispecific antibody to a plurality of subjects results in an overall response rate of at least about 80%.

33. The anti-CD20/anti-CD3 bispecific antibody for use in a method of treating FL of embodiment 25, wherein administration of the anti-CD20/anti-CD3 bispecific antibody to a plurality of subjects results in a complete metabolic response rate of at least about 40%.

34. An anti-CD20/anti-CD3 bispecific antibody for use in a method of treating a subject having Follicular lymphoma (FL), comprising administering to the subject the anti-CD20/anti-CD3 bispecific antibody in a dosing regimen comprising at least a first dosing cycle, a second dosing cycle and a third dosing cycle, wherein:

(i) the first dosing cycle comprises a first dose (C1D1) and a second dose (C1D2) of the anti-CD20/anti-CD3 bispecific antibody, wherein the C1D1 is 0.5 mg, and the C1D2 is 2.5 mg of the anti-CD20/anti-CD3 bispecific antibody
(ii) the second dosing cycle comprises a single dose (C2D1) of 10 mg of the anti-CD20/anti-CD3 bispecific antibody, and
(iii) the third dosing cycle comprises a single dose (C3D1) of 16 or 30 mg of the anti-CD20/anti-CD3 bispecific antibody.

35. The anti-CD20/anti-CD3 bispecific antibody for use in a method of treating a subject having Follicular lymphoma (FL) according to embodiment 34, wherein the single dose of the third dosing cycle (C3D1) comprises 30 mg of the anti-CD20/anti-CD3 bispecific antibody.

36. The anti-CD20/anti-CD3 bispecific antibody for use in a method of treating a subject having Follicular lymphoma (FL) according to embodiment 34 or 35, wherein the first dose (C1D1) is administered on day 1 of the first dosing cycle and the second dose (C1D2) is administered on day 8 of the first dosing cycle.

37. The anti-CD20/anti-CD3 bispecific antibody for use in a method of treating a subject having Follicular lymphoma (FL) of any one of embodiments 34 to 36, wherein the single dose of the second dosing cycle (C2D1) is administered on day 1 of the second dosing cycle.

38. The anti-CD20/anti-CD3 bispecific antibody for use in a method of treating a subject having Follicular lymphoma (FL) of any one of embodiments 34 to 37, wherein the single dose of the third dosing cycle (C3D1) is administered on day 1 of the third dosing cycle.

39. The anti-CD20/anti-CD3 bispecific antibody for use in a method of treating a subject having Follicular lymphoma (FL) of any one of embodiments 34 to 38, comprising 1 to 9 additional dosing cycles (C4 to C12).

40. The anti-CD20/anti-CD3 bispecific antibody for use in a method of treating a subject having Follicular lymphoma (FL) according to embodiment 39, wherein the 1 to 9 additional dosing cycles (C4 to C12) each comprises a single dose (C4D1 to C12D1) of either 16 or 30 mg of the anti-CD20/anti-CD3 bispecific antibody.

41. The anti-CD20/anti-CD3 bispecific antibody for use in a method of treating a subject having Follicular lymphoma (FL) according to embodiment 39 or 40, wherein the single dose of each of the additional dosing cycles (C4D1 to C12D1) comprises 30 mg of the anti-CD20/anti-CD3 bispecific antibody.

42. The anti-CD20/anti-CD3 bispecific antibody for use in a method of treating a subject having Follicular lymphoma (FL) of any one of embodiments 39 to 41, wherein the single dose of the additional dosing cycles (C4D1 to C12D1) is administered on day 1 of the respective additional dosing cycle.

43. The anti-CD20/anti-CD3 bispecific antibody for use in a method of treating a subject having Follicular lymphoma (FL) of any one of embodiments 34 to 42, comprising 12 dosing cycles in total.

44. The anti-CD20/anti-CD3 bispecific antibody for use in a method of treating a subject having Follicular lymphoma (FL) of any one of embodiments 34 to 43, wherein one treatment cycle comprises 14 days or 21 days.

45. The anti-CD20/anti-CD3 bispecific antibody for use in a method of treating a subject having Follicular lymphoma (FL) according to embodiment 44, wherein one treatment cycle comprises 21 days.

46. The anti-CD20/anti-CD3 bispecific antibody for use in a method of treating a subject having Follicular lymphoma (FL) of any one of embodiments 34 to 45, wherein the FL is Grade 1, 2, or 3a FL.

47. The anti-CD20/anti-CD3 bispecific antibody for use in a method of treating a subject having Follicular lymphoma (FL) of any one of embodiments 34 to 45, wherein the FL is a transformed FL.

48. The anti-CD20/anti-CD3 bispecific antibody for use in a method of treating a subject having Follicular lymphoma (FL) of any one of embodiments 34 to 45, wherein the FL is a relapsed or refractory (R/R) FL.

49. The anti-CD20/anti-CD3 bispecific antibody for use in a method of treating a subject having Follicular lymphoma (FL) according to embodiment 48, wherein the subject is a high risk subject who:

(a) has relapsed after or is refractory to at least two prior therapies;

(b) has relapsed after or is refractory to treatment with a phosphoinositide 3-kinase (PI3K) inhibitor;

(c) experiences progression of disease within 24 months of frontline treatment; and/or (d) has lesions, wherein the sum of the product of the lesion diameters is ≥3,000 $mm^2$.

50. An anti-CD20/anti-CD3 bispecific antibody for use in a method of treating a subject having Follicular lymphoma (FL) of any one of embodiments 34 to 49, wherein administration of the anti-CD20/anti-CD3 bispecific antibody to a plurality of subjects results in an overall response rate of at least about 80%.

51. The anti-CD20/anti-CD3 bispecific antibody for use in a method of treating a subject having R/R FL according to embodiment 49, wherein the subjects are high-risk subjects having R/R FL, and wherein administration of the anti-CD20/anti-CD3 bispecific antibody to a plurality of subjects results in a complete response rate of at least about 40%.

52. An anti-CD20/anti-CD3 bispecific antibody for use in a method of treating a subject having Follicular lymphoma (FL) of any one of embodiments 34 to 51, wherein the population of subjects having FL exhibits cytokine release syndrome after administering the anti-CD20/anti-CD3 bispecific antibody, and wherein the rate of the cytokine release syndrome of a grade of 3 or greater (as defined by the American Society for Transplantation and Cellular Therapy, 2019; ASTCT) is about 3%.

53. The anti-CD20/anti-CD3 bispecific antibody for use in a method of treating a subject of any one of the preceding embodiments, wherein the anti-CD20/anti-CD3 bispecific antibody is combined with administration of obinutuzumab or rituximab.

54. The anti-CD20/anti-CD3 bispecific antibody for use in a method of treating a subject of embodiment 53, wherein obinutuzumab or rituximab is administered 7 days before the first dose of the anti-CD20/anti-CD3 bispecific antibody (C1D1).

55. The anti-CD20/anti-CD3 bispecific antibody for use in a method of treating a subject of embodiment 54, wherein obinutuzumab is administered at a single dose of 1000 mg.

56. The anti-CD20/anti-CD3 bispecific antibody for use in a method of treating a subject of embodiment 54, wherein obinutuzumab is administered at a first and a second dose of each 1000 mg obinutuzumab.

57. The anti-CD20/anti-CD3 bispecific antibody for use in a method of treating a subject of embodiment 56, wherein the first and second dose of obinutuzumab are administered on the same day.

58. The anti-CD20/anti-CD3 bispecific antibody for use in a method of treating a subject of embodiment 56 or 57, wherein the subject suffers from MCL and has received at least two prior systemic therapies.

59. The anti-CD20/anti-CD3 bispecific antibody for use in a method of treating a subject of any one of embodiments 53 to 58, wherein obinutuzumab or rituximab is administered on the first day of the second dosing cycle (C2) and on the first day of any subsequent dosing cycle.

60. The anti-CD20/anti-CD3 bispecific antibody for use in a method of treating a subject of embodiment 59, wherein obinutuzumab or rituximab is administered on the first day of the second dosing cycle (C2) and on the first day of the third (C3) to twelfth dosing cycle (C12).

61. The anti-CD20/anti-CD3 bispecific antibody for use in a method of treating a subject of embodiment 59 or 60, wherein obinutuzumab is administered at a dose of 1000 mg.

62. The anti-CD20/anti-CD3 bispecific antibody for use in a method of treating a subject of any one of the preceding embodiments wherein the patient receives corticosteroid premedication prior to the anti-CD20/anti-CD3 bispecific antibody.

63. The anti-CD20/anti-CD3 bispecific antibody for use in a method of treating a subject of embodiment 62, wherein the corticosteroid premedication comprises prednisolone and methylprednisolone, and/or dexamethasone.

64. The anti-CD20/anti-CD3 bispecific antibody for use in a method of treating a subject of embodiment 62 or 63, wherein the corticosteroid premedication is given prior to the first dose (C1D1) of the anti-CD20/anti-CD3 bispecific antibody.

65. The anti-CD20/anti-CD3 bispecific antibody for use in a method of treating a subject of any one of embodiments 1 to 64, wherein treatment is stopped after a total of 12 treatment cycles.

66. The anti-CD20/anti-CD3 bispecific antibody for use in a method of treating a subject of embodiment 65, wherein the patient is retreated with a method of any one of embodiments 1 to 64 if a relapse occurs and/or if disease progresses.

67. An anti-CD20/anti-CD3 bispecific antibody for use in a method of treating a subject having a CD20-positive cell proliferative disorder comprising administering to the subject an anti-CD20 antibody, cyclophosphamide, doxorubicin, a corticosteroid, and the anti-CD20/anti-CD3 bispecific antibody.

68. The anti-CD20/anti-CD3 bispecific antibody for use in a method of treating a subject of embodiment 67, wherein administration of the anti-CD20 antibody, cyclophosphamide, doxorubicin, corticosteroid, and anti-CD20/anti-CD3 bispecific antibody to a plurality of humans results in a complete response in at least about 60%, at least about 70% or at least about 80% of the humans in the plurality after treatment with the anti-CD20 antibody, cyclophosphamide, doxorubicin, corticosteroid, and anti-CD20/anti-CD3 bispecific antibody.

69. The anti-CD20/anti-CD3 bispecific antibody for use in a method of treating a subject of embodiment 67 or 68, wherein administration of the anti-CD20 antibody, cyclophosphamide, doxorubicin, corticosteroid, and anti-CD20/anti-CD3 bispecific antibody to a plurality of humans results in an overall response in at least about 80%, at least about 85% or at least about 90% of the humans in the plurality after treatment with the anti-CD20 antibody, cyclophosphamide, doxorubicin, corticosteroid, and anti-CD20/anti-CD3 bispecific antibody.

70. The anti-CD20/anti-CD3 bispecific antibody for use in a method of treating a subject of any one of embodiments 67 to 69, wherein administration of the anti-CD20 antibody, cyclophosphamide, doxorubicin, corticosteroid, and anti-CD20/anti-CD3 bispecific antibody to the human does not result in Grade 2 or higher CRS.

71. The anti-CD20/anti-CD3 bispecific antibody for use in a method of treating a subject of any one of embodiments 67 to 70, wherein the method comprises a dosing regimen comprising at least a first dosing cycle, a second dosing cycle and a third dosing cycle, wherein:

(a) the first dosing cycle comprises a first dose (C1D1) of the anti-CD20 antibody, cyclophosphamide, doxorubicin and corticosteroid, and no dose of the anti-CD20/anti-CD3 bispecific antibody;

(b) the second dosing cycle comprises a second dose (C2D1) of the anti-CD20 antibody, cyclophosphamide, doxorubicin, and corticosteroid, and a first dose (C2D1) and second dose (C2D2) of the anti-CD20/anti-CD3 bispecific antibody, wherein the C2D1 of the anti-CD20/anti-CD3 bispecific antibody is about 2.5 mg and the C2D2 of the anti-CD20/anti-CD3 bispecific antibody is about 10 mg;

(c) the third dosing cycle comprises a third dose (C3D1) of the anti-CD20 antibody, cyclophosphamide, doxorubicin, and corticosteroid, and a third dose (C3D1) of the anti-CD20/anti-CD3 bispecific antibody, wherein the C3D1 of the anti-CD20/anti-CD3 bispecific antibody is about 30 mg.

72. The anti-CD20/anti-CD3 bispecific antibody for use in a method of treating a subject of embodiment 71, wherein the anti-CD20 antibody, cyclophosphamide, doxorubicin, and corticosteroid is administered on day 1 of each dosing cycle.

73. The anti-CD20/anti-CD3 bispecific antibody for use in a method of treating a subject of embodiment 71 or 72, wherein the first dose (C2D1) of the anti-CD20/anti-CD3 bispecific antibody is administered on day 8 of the second dosing cycle and the second dose (C2D2) of the anti-CD20/anti-CD3 bispecific antibody is administered on day 15 of the second dosing cycle.

74. The anti-CD20/anti-CD3 bispecific antibody for use in a method of treating a subject of any one of embodiments 71 to 73, wherein the third dose of the of the anti-CD20/anti-CD3 bispecific antibody (C3D1) is administered on day 8 of the third dosing cycle.

75. The anti-CD20/anti-CD3 bispecific antibody for use in a method of treating a subject of any one of embodiments 71 to 74, comprising 1 to 5 additional dosing cycles (C4 to C8).

76. The anti-CD20/anti-CD3 bispecific antibody for use in a method of treating a subject of embodiment 75, wherein the 1 to 5 additional dosing cycles (C4 to C8) each comprises a single dose of anti-CD20 antibody, cyclophosphamide, doxorubicin, corticosteroid, and a single dose (C4D1 to C8D1) of 30 mg of the anti-CD20/anti-CD3 bispecific antibody.

77. The anti-CD20/anti-CD3 bispecific antibody for use in a method of treating a subject of embodiment 75 or 76, wherein the single dose of the anti-CD20 antibody, cyclophosphamide, doxorubicin, and corticosteroid is administered on day 1 and the single dose (C4D1 to C8D1) of the anti-CD20/anti-CD3 bispecific antibody is administered on day 8 of the respective additional dosing cycle (C4 to C8).

78. The anti-CD20/anti-CD3 bispecific antibody for use in a method of treating a subject of any one of embodiments 67 to 77, wherein the corticosteroid is prednisone and the anti-CD20 antibody is rituximab.

79. The anti-CD20/anti-CD3 bispecific antibody for use in a method of treating a subject of embodiment 78, wherein the method comprises a dosing regimen comprising at least a first dosing cycle, a second dosing cycle and a third dosing cycle, wherein:

(a) the first dosing cycle comprises a first dose (C1D1) of rituximab, cyclophosphamide, doxorubicin, vincristine, and prednisone (R-CHOP), and no dose of the anti-CD20/anti-CD3 bispecific antibody;

(b) the second dosing cycle comprises a second dose (C2D1) of the R-CHOP and a first dose (C2D1) and second dose (C2D2) of the anti-CD20/anti-CD3 bispecific antibody, wherein the C2D1 of the anti-CD20/anti-CD3 bispecific antibody is about 2.5 mg and the C2D2 of the anti-CD20/anti-CD3 bispecific antibody is about 10 mg;

(c) the third dosing cycle comprises a third dose (C3D1) of the R-CHOP and a third dose (C3D1) of the anti-CD20/anti-CD3 bispecific antibody, wherein the C3D1 of the anti-CD20/anti-CD3 bispecific antibody is about 30 mg.

80. The anti-CD20/anti-CD3 bispecific antibody for use in a method of treating a subject of embodiment 79, wherein R-CHOP is administered on day 1 of each dosing cycle.

81. The anti-CD20/anti-CD3 bispecific antibody for use in a method of treating a subject of embodiment 79 or 80, wherein the first dose (C2D1) of the anti-CD20/anti-CD3 bispecific antibody is administered on day 8 of the second dosing cycle and the second dose (C2D2) of the anti-CD20/anti-CD3 bispecific antibody is administered on day 15 of the second dosing cycle.

82. The anti-CD20/anti-CD3 bispecific antibody for use in a method of treating a subject of any one of embodiments 79 to 81, wherein the third dose of the of the anti-CD20/anti-CD3 bispecific antibody (C3D1) is administered on day 8 of the third dosing cycle.

83. The anti-CD20/anti-CD3 bispecific antibody for use in a method of treating a subject of any one of embodiments 79 to 82, comprising 1 to 5 additional dosing cycles (C4 to C8).

84. The anti-CD20/anti-CD3 bispecific antibody for use in a method of treating a subject of embodiment 83, wherein the 1 to 5 additional dosing cycles (C4 to C8) each comprises a single dose of R-CHOP and a single dose (C4D1 to C8D1) of 30 mg of the anti-CD20/anti-CD3 bispecific antibody.

85. The anti-CD20/anti-CD3 bispecific antibody for use in a method of treating a subject of embodiment 84, wherein the single dose of the R-CHOP is administered on day 1 and the single dose (C4D1 to C8D1) of the anti-CD20/anti-CD3 bispecific antibody is administered on day 8 of the respective additional dosing cycle (C4 to C8).

86. The anti-CD20/anti-CD3 bispecific antibody for use in a method of treating a subject of any one of embodiments 79 to 85, wherein in the first dosing cycle rituximab is replaced by obinutuzumab.

87. The anti-CD20/anti-CD3 bispecific antibody for use in a method of treating a subject of any one of embodiments 71 to 86, comprising 6 dosing cycles in total.

88. The anti-CD20/anti-CD3 bispecific antibody for use in a method of treating a subject of any one of embodiments 71 to 87, wherein one treatment cycle comprises 14 days or 21 days.

89. The anti-CD20/anti-CD3 bispecific antibody for use in a method of treating a subject of embodiment 88, wherein one treatment cycle comprises 21 days.

90. The anti-CD20/anti-CD3 bispecific antibody for use in a method of treating a subject of any one of embodiments 67 to 89, wherein the CD20-positive B cell proliferative disorder is previously untreated DLBCL.

91. The anti-CD20/anti-CD3 bispecific antibody for use in a method of treating a subject of embodiment 90, wherein the subject to be treated has international prognostics indicator [IPI] 2-5

92. The anti-CD20/anti-CD3 bispecific antibody for use in a method of treating a subject of any one of embodiments 1 to 91, wherein the anti-CD20/anti-CD3 bispecific antibody is administered intravenously.

93. The anti-CD20/anti-CD3 bispecific antibody for use in a method of treating a subject of any one of embodiments 1 to 92, wherein the subject is human.

94. The anti-CD20/anti-CD3 bispecific antibody for use in a method of treating a subject of embodiment 93, wherein the human is a high-risk subject.

95. The anti-CD20/anti-CD3 bispecific antibody for use in a method of treating a subject of any one of embodiments 1 to 94, wherein the anti-CD20/anti-CD3 bispecific antibody comprises at least one antigen binding domain that specifically binds to CD20, comprising a heavy chain variable region comprising (i) an HVR-H1 comprising the amino acid sequence of SEQ ID NO: 1;

(ii) an HVR-H2 comprising the amino acid sequence of SEQ ID NO: 2;

(iii) an HVR-H3 comprising the amino acid sequence of SEQ ID NO:3;

and a light chain variable region comprising (i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6.

96. The anti-CD20/anti-CD3 bispecific antibody for use in a method of treating a subject of any one of embodiments 1 to 95, wherein the anti-CD20/anti-CD3 bispecific antibody comprises at least one antigen binding domain that specifically binds to CD20 comprising a VH domain comprising an amino acid sequence of SEQ ID NO: 7 and a VL domain comprising an amino acid sequence of SEQ ID NO: 8.

97. The anti-CD20/anti-CD3 bispecific antibody for use in a method of treating a subject of any one of embodiments 1 to 96, wherein anti-CD20/anti-CD3 bispecific antibody comprises at least one antigen binding domain that specifically binds to CD3 comprising a heavy chain variable region comprising:

(i) an HVR-H1 comprising the amino acid sequence of SEQ ID NO: 9;

(ii) an HVR-H2 comprising the amino acid sequence of SEQ ID NO: 10;

(iii) an HVR-H3 comprising the amino acid sequence of SEQ ID NO:11; and a light chain variable region comprising (i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14.

98. The anti-CD20/anti-CD3 bispecific antibody for use in a method of treating a subject of any one of embodiments 1 to 97, wherein the anti-CD20/anti-CD3 bispecific antibody comprises at least one antigen binding domain that specifically binds to CD3 comprising a VH domain comprising an amino acid sequence of SEQ ID NO: 15 and a VL domain comprising an amino acid sequence of SEQ ID NO: 16.

99. The anti-CD20/anti-CD3 bispecific antibody for use in a method of treating a subject of any one of embodiments 1 to 98, wherein the anti-CD20/anti-CD3 bispecific antibody comprises an antigen binding domain that specifically binds to CD3 and is a cross-Fab molecule wherein the variable domains or the constant domains of the Fab heavy and light chain are exchanged.

100. The anti-CD20/anti-CD3 bispecific antibody for use in a method of treating a subject of any one of embodiments 1 to 99, wherein the anti-CD20/anti-CD3 bispecific antibody comprises an IgG1 Fc domain comprising one or more amino acid substitutions that reduce binding to an Fc receptor and/or effector function.

101. The anti-CD20/anti-CD3 bispecific antibody for use in a method of treating a subject of any one of embodiments 1 to 100, wherein the anti-CD20/anti-CD3 bispecific antibody comprises an IgG1 Fc domain comprising the amino acid substitutions L234A, L235A, and P329G (numbering according to Kabat EU index).

102. The anti-CD20/anti-CD3 bispecific antibody for use in a method of treating a subject of any one of embodiments 1 to 101, wherein the anti-CD20/anti-CD3 bispecific antibody comprises at least one Fab molecule comprising an antigen binding domain that specifically binds to CD20, wherein in the constant domain CL of the Fab molecule the amino acid at position 124 is substituted by lysine (K) (numbering according to Kabat) and the amino acid at position 123 is substituted by arginine (R) or lysine (K) (numbering according to Kabat), and wherein in the constant domain CH1 of the Fab molecule the amino acid at position 147 is substituted by glutamic acid (E) (numbering according to Kabat EU index) and the amino acid at position 213 is substituted by glutamic acid (E) (numbering according to Kabat EU index).

103. The anti-CD20/anti-CD3 bispecific antibody for use in a method of treating a subject of any one of embodiments 1 to 102, wherein the anti-CD20/anti-CD3 bispecific antibody comprises two antigen binding domains that specifically bind to CD20 and one antigen binding domain that specifically binds to CD3.

104. The anti-CD20/anti-CD3 bispecific antibody for use in a method of treating a subject of any one of embodiments 1 to 103, wherein the anti-CD20/anti-CD3 bispecific antibody is bivalent for CD20 and monovalent for CD3.

105. The anti-CD20/anti-CD3 bispecific antibody for use in a method of treating a subject of any one of embodiments 1 to 104, wherein the anti-CD20/anti-CD3 bispecific antibody comprises (i) an antigen binding domain that specifically binds to CD3 which is fused at the C-terminus of the Fab heavy chain to the N-terminus of the first subunit of the Fc domain (ii) a first antigen binding domain that specifically binds to CD20 which is fused at the C-terminus of the Fab heavy chain to the N-terminus of the Fab heavy chain of the antigen binding domain that specifically binds to CD3, (iii) a second antigen binding domain that specifically binds to CD20 which is fused at the C-terminus of the Fab heavy chain to the N-terminus of the second subunit of the Fc domain.

106. The anti-CD20/anti-CD3 bispecific antibody for use in a method of treating a subject of any one of embodiments 1 to 105, wherein the anti-CD20/anti-CD3 bispecific antibody is glofitamab.

107. The invention as described hereinbefore.

EXAMPLES

The following are examples of methods and compositions of the invention. It is understood that various other embodiments may be practiced, given the general description provided above.

Example 1: A Dose Escalation Study of Glofitamab (R07082859) as a Single Agent and in Combination with Obinutuzumab, Administered after a Fixed, Single Pre-Treatment Dose of Obinutuzumab in Participants with Relapsed/Refractory B-Cell Non-Hodgkin's Lymphoma Objectives and Endpoints The primary objectives of this study are as follows:

To evaluate the safety, tolerability, and PK pharmacokinetics of glofitamab as single agent and in combination with obinutuzumab following obinutuzumab pretreatment (Gpt) in patients with relapsed/refractory CD20 positive B-cell Non-Hodgkin's Lymphoma (r/r NHL).

To determine the maximal tolerated dose (MTD) or optimal-biologic dose (OBD) and dose limiting toxicity (DLT) of glofitamab as single agent and in combination with obinutuzumab following Gpt in patients with r/r NHL.

To determine a recommended dose and schedule of glofitamab as a single agent and in combination with obinutuzumab following Gpt.

To evaluate the efficacy of glofitamab as single agent following Gpt in patients diagnosed with diffuse large B-cell lymphoma (DLBCL; r/r DLBCL not otherwise specified (NOS), high grade B-cell lymphoma [HGBCL], primary mediastinal B cell lymphoma [PMBCL], DLBCL arising from FL [transformed FL; trFL] and r/r FL) as measured by Independent Review Committee (IRC)-assessed complete response rate according to standard NHL response criteria.

The secondary objectives for this study are as follows:

To establish the safety, tolerability, and pharmacokinetics of Gpt

To make a preliminary assessment of the anti-tumor activity of glofitamab as a single agent and in combination with obinutuzumab following Gpt in patients with r/r NHL To assess the incidence of anti-drug antibodies (ADAs) to glofitamab To assess pharmacodynamic (PD) biomarkers, including but not limited to tumor tissue, B- and T-cell content and T-cell activation status in a subset of patients In Part III of the study, to assess disease-related symptoms, function, and health-related quality of life (HRQoL) according to the European Organization for Research and Treatment of Cancer Quality of Life Questionnaire Core 30 (EORTC QLQ-C30) and the Functional Assessment of Cancer Therapy Lymphoma (FACT-Lym) Lymphoma scale The exploratory objectives for this study are as follows:

To evaluate the relationship between glofitamab, as a single agent and in combination with obinutuzumab (following Gpt) exposure and PD biomarkers, including, but not limited to, soluble mediators, peripheral B- and T-cell number and T-cell activation status, as appropriate To make a preliminary assessment of tumor burden and/or biologic markers that might act as predictors of the safety or anti-tumor activity of glofitamab as single agent and in combination with obinutuzumab including, but not limited to minimal residual disease status (MRD), immune-modulatory phenotypic markers, and soluble mediators To assess the anti-tumor activity of re-treatment with glofitamab as single agent and in combination with obinutuzumab of patients who achieved an objective response (complete response [CR] or partial response [PR]) or stable disease (SD) and who subsequently show disease progression or relapse To make a preliminary assessment of the efficacy of tocilizumab in ameliorating the symptoms of severe cytokine release syndrome (CRS) following glofitamab treatment as single agent and in combination with obinutuzumab In Part III, to assess treatment-related symptoms using the Patient-Reported Outcome Common Terminology Criteria for Adverse Events (PRO-CTCAE).

In Part III DLBCL dexamethasone cohort, assess CRS incidence and severity after premedication using dexamethasone.

Study Design

This is a Phase I/II, multicenter, open-label, dose-escalation study designed to evaluate the efficacy, safety, tolerability, and PK pharmacokinetics of a novel TCB, glofitamab, administered by IV infusion as a single agent and in combination with obinutuzumab following pre-treatment with a fixed dose of obinutuzumab (Gpt). This entry into-human (EIH) study is divided in three parts (i.e., dose escalation [Parts I (applies to monotherapy only) and II] and dose expansion [Part III]), and will be conducted in patients with r/r NHL, including, but not limited to:

- For Parts I and II: Grade 1-3b FL; marginal zone lymphoma (MZL; splenic; nodal; extra-nodal); MCL; DLBCL; PMBCL; Richter's transformation; and/or trFL
- For Part III expansion cohorts:
  - DLBCL cohort (DLBCL NOS, HGBCL, PMBCL, trFL]): Patients with trFL are eligible, but they must be relapsed or refractory to standard treatments for trFL. Patients with Richter's transformation are not considered eligible for Part III.
  - FL cohort: Grade 1-3a FL Patients with CLL, Burkitt lymphoma, and lymphoplasmacytic lymphoma are excluded.

Patients will not be pre-screened for CD20 expression, but they must have been diagnosed with B cell malignancies that are expected to express CD20.

In Part I (applies to monotherapy only, Cohort A1) and in Part II (Cohort A2) glofitamab is administered as a single agent on a every 2 weeks (Q2W) dose schedule.

Patients who are deemed eligible to receive re-treatment with glofitamab may continue to receive glofitamab at the dosing schedule currently implemented for dose escalation or expansion and may receive the highest glofitamab dose cleared on Part II. This will be decided on a case by case basis, in collaboration with the Medical Monitor.

Patients who enter the trial under Protocol Versions 5 or above may receive glofitamab on a every 2 weeks (Q2W) (A2) dose schedule or receive glofitamab on a every 3 weeks (Q3W) dosing schedule, either as a monotherapy (Cohorts B2, D2, F2, B3, B4, D3, D4 and D5) or in combination with obinutuzumab, starting in Cycle 2 (Cohorts C2, E2, G2, C3, C4, E3, and E4).

Beginning with Protocol Version 8, the Part II dose escalation will explore step-up dosing regimens (Q3W) in which an initial lower dose of glofitamab, will be administered on day 1 of dosing cycle 1 followed by a higher dose administered on day 8 of dosing cycle 1 where the total dose administered in C1 will not exceed that previously cleared for safety (i.e., not to exceed the previously determined MTD for C1). The aim of this investigation will be to assess if step-up regimens during C1 can further improve the clinical benefit/risk profile of glofitamab by reducing the occurrence and severity of first-cycle CRS. In the step-up dose escalation cohorts (Part II), patients may be enrolled in parallel with patients being enrolled to receive glofitamab in the fixed dosing regimens in C1 in the expansion cohort (Part III).

Beginning with Protocol Version 9, the Part II dose escalation may explore an alternative stepup dosing schedule in selected dosing cohorts, (extended step-up dosing, FIG. 12) as part of the Step-up dosing in selected dosing cohorts to later cycles. In the extended step-up dosing, an initial lower dose of glofitamab will be administered on day lof dosing cycle 1 and day 8 of dosing cycle 1 followed by an intermediate dose in Cycle 2 and the first administration of the target treatment dose is in Cycle 3.

Alternatively, an intermediate dose may also be administered in Cycle 3 and first target dose in Cycle 4. The aim of this investigation will be to assess if a smaller increase in glofitamab dose at each step-up can further improve the clinical benefit/risk of glofitamab by reducing the occurrence and severity of CRS. The extended step-up may be tested in selected dosing cohorts in Part II in monotherapy cohorts and subsequently it may be tested in combination therapy cohorts.

Pre-treatment (Gpt) is administered 7 days before the first dose of glofitamab (C1D1) in the monotherapy and combination therapy cohorts and step-up cohorts.

Beginning with Protocol Version 9, a double pre-treatment with obinutuzumab (DGpt) prior to first dose of glofitamab may be tested in separate cohorts in Part II (e.g., in specific histologies).

Two dosing alternatives of DGpt may be tested, in separate dosing cohorts:

- Administration of two doses of Gpt 7 days before the first dose of glofitamab (2×1000 mg on C1D-7)
- Administration of two doses of obinutuzumab, first Gpt dose (1000 mg) on C1 Day −7 followed by a second dose of Gpt (1000 mg) on C1 Day −1

The aim of this investigation will be to assess if a second dose of obinutuzumab prior to the first dose of glofitamab can further help to reduce the occurrence and severity of CRS. DGpt may be tested in separate cohorts in Part II with monotherapy and subsequently in combination therapy. It may be investigated using fixed dosing, step-up dosing C1 and extended step-up dosing.

Patients in Part III dose-expansion cohorts may receive glofitamab on a Q2W or Q3W dosing schedule and using a fixed dose regimen or step-up dose regimen (C1 step-up or extended step-up) on Q3W dosing schedule, if supported by emerging data and/or recommended by the IMC. The Q2W and Q3W dosing schedules for cohorts in Part I, Part II, and Part III are provided.

Mandatory paired fresh baseline and on-treatment tumor biopsies will be requested from a subset of patients.

Starting from Protocol Version 9, the initial treatment period will be fixed at 12 cycles of glofitamab with Q2W or Q3W dosing in the monotherapy and combination therapy cohorts.

A schematic overview of the study is depicted in FIG. 3.

Re-treatment of glofitamab upon confirmed disease progression after completing an initial treatment period with glofitamab will be considered if progression is confirmed by radiographic imaging, as defined by the Lugano Criteria.

Hospitalization is not mandated for administration of Gpt (or DGpt), but safety measures will be implemented pre-infusion of each Gpt dose to diminish the risk of infusion-related reactions (IRRs).

To summarize, safety measures for each part of the study include but are not limited to:

- Hospitalization will initially be required for all patients until 24 hours following the completion of the first dose of glofitamab in the monotherapy and combination therapy cohorts (C1D1).
- For obinutuzumab and glofitamab administration, premedication with the following: fluids; anti-histamines; corticosteroids; analgesics; and anti-pyretic at each dose administered. Pre-medication with corticosteroids may be optional for subsequent dosing cycles where target dose has been reached and tolerated for two doses for patients with no CRS in previous cycles.

- Corticosteroids for relevant adverse events arising post-glofitamab administration, based upon investigator judgment
- 4.75 and 4-hour minimal infusion times of obinutuzumab and glofitamab, respectively
- See guidance on reducing the glofitamab infusion time, or increasing to 8 hours for patients with high risk of experiencing CRS
- Tumor lysis syndrome (TLS) prophylaxis for patients considered to be at risk
- A peripheral CD19+ B-cell check done within 1 working day of the first glofitamab infusion, and pre-infusion B-cell and T-cell subset analyses (CD3+, CD4+, CD8+). A peripheral blood smear and/or flow cytometry at screening to measure malignant and/or atypical cells.
- A platelet count check done prior to administration of the first dose of glofitamab to assess presence of obinutuzumab related thrombocytopenia
- Management of specific adverse events Dose Escalation An increment based escalation will be utilized in Part I (single patient cohorts) with dosing initiated at 5 μg (flat dose). Increments are 3-fold until a dose of 405 μg is reached, at which time the increment will change to 2-fold. Thus, the 5 μg starting dose is followed by doses of 15 μg, 45 μg, 135 μg, 405 μg and 810 μg. The study design switches to Part II (multiple patient cohorts) when either a flat dose of 810 μg is reached or a glofitamab-related Grade ≥2 adverse event (or DLT) occurs, whichever comes first. Incremental dose increases may be altered, based on emerging PK, PD and safety data, along with close monitoring of maintenance of B-cell depletion.

In addition to the option of changing incremental dose increases, the Sponsor may decide to switch from Part I to Part II in the absence of an observed glofitamab-related Grade ≥2 toxicity or prior to the dose level reaching 810 μg. The choice of 810 μg ensures that multiple-patient cohorts (Part II) will begin enrolling close to the start of the estimated therapeutic dose range of 1-10 mg.

In contrast, the mDA-CRM-EWOC model will guide the dose escalation of glofitamab in Part II to determine the MTD/MTDs. All dose-escalation decisions will be made based on recommendations of the IMC.

The dose-escalation cohorts (Parts I and II) are designed to ensure patient safety while minimizing the number of patients being exposed to sub-therapeutic doses of glofitamab. For this reason, single-patient dose-escalation cohorts will be used in Part I, followed by conversion to multiple patient dose-escalation cohorts (Part II), in order to define a tentative MTD or OBD. In addition, the Part II dose escalation will explore step-up-dosing regimens (Q3W) in which initial lower doses of glofitamab will be administered on day 1 of dosing cycle 1 followed by higher doses administered on day 8 of dosing cycle 1. In the step-up dose-escalation cohorts (Part II), patients may be enrolled in parallel with patients being enrolled to receive glofitamab in the fixed-dosing regimens in C1 (Part III).

Figure 4:
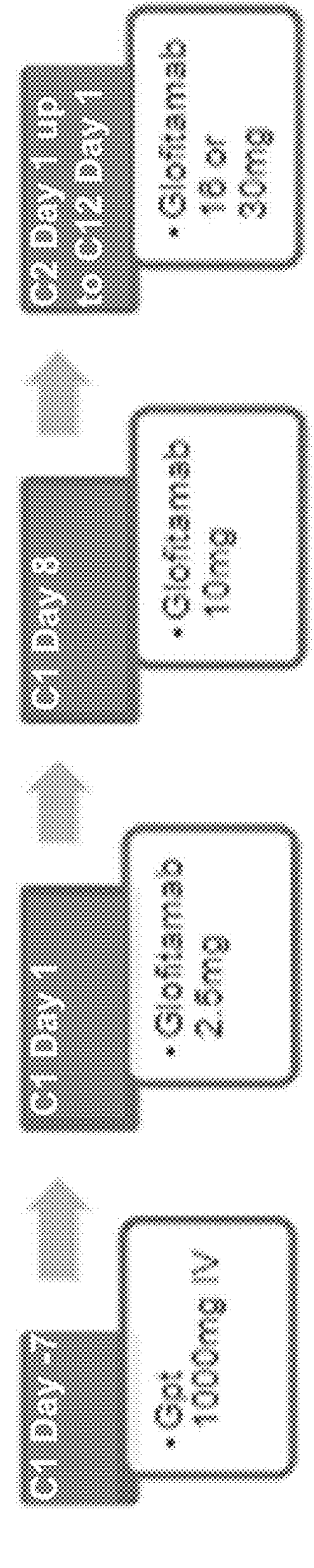
FIG. 4. Overview of Glofitamab Step-up dosing schedule. 1000 mg obinutuzumab (GAZYVA® pretreatment, Gpt) was administered 7 days prior to glofitamab administration. Glofitamab IV step up doses on cycle 1, day 1 (C1 Day 1) and day 8 (C1 Day 8) and at target dose from cycle 2, day 1 (C2 Day 1): 2.5, 10, 16 mg or 2.5, 10, 30 mg.

Part II dose escalation will explore step-up dosing regimens (Q3W) in which an initial lower glofitamab dose is administered on day 1 of dosing cycle 1 followed by a higher dose administered on day 8 of dosing cycle 1, where the total dose administered in Cycle 1 will not exceed that previously cleared for safety (i.e., will not exceed the determined MTD, see the Glofitamab Investigator's Brochure). The aim of this investigation will be to assess whether step-up regimens can further improve the clinical benefit/risk of glofitamab by reducing first dosing cycle CRS and severity. Patients may be enrolled in the step-up dose escalation cohorts in parallel with patients being enrolled to receive glofitamab in fixed dosing regimens in C1. Additional escalation from C2 may be explored, guided by the mDA-CRM-EWOC model. In the case of step-up dosing, hospitalizations at day 1 of dosing cycle 1 and day 1 of dosing cycle 2 if patient experienced CRS in C1 will be mandated until the IMC, review the requirements for mandatory hospitalizations. A schematic overview of the step-up dosing regimen is shown in FIG. 4.

Starting Dose for Combination Cohorts

Dose escalation in the combination cohorts will be conducted based on the glofitamab dose levels tested in the monotherapy escalation cohorts and the glofitamab starting dose may be initiated at least one dose level below the highest dose already cleared during monotherapy dose escalation. Depending on the safety data from combination cohorts, there is the potential that the combination escalation cohorts may yield a different MTD from that determined in the monotherapy escalation cohorts.

Criteria for Continuing Treatment During Possible Pseudo-progression

Based upon significant prior experience with immunotherapeutic agents administered to patients with solid tumors, it has been observed that an influx of immune responsive cells into a tumor may initially lead to an increase in tumor size. This phenomenon is known as "pseudoprogression" and it is important that pseudoprogression be differentiated from true tumor progression, especially for treatments designed to activate T-cells against tumor cells. Pseudoprogression has not been described with lymphoma immunotherapy; but, given the mechanism of action of T-cell bispecific agents like glofitamab, it is possible that this study agent may initially increase the risk of pseudoprogression. Given this risk, if the Study Investigator believes that a patient is deriving clinical benefit despite radiographic evidence of progressive disease, as defined by the response criteria used, that patient may continue study treatment, provided the following criteria are met:

- There is an absence of symptoms and signs (including worsening of laboratory values) indicating progression of disease.
- There is no decline in Eastern Cooperative Oncology Group (ECOG) performance status.
- There is an absence of tumor progression at critical anatomical sites including the central airway, the great vessels, and other organs or tissues where compromised function secondary to tumor progression would be expected to result acutely in severe and/or irreversible disability or death.

Patients continuing glofitamab therapy, despite apparent radiographic progression, will be encouraged to undergo a repeat tumor biopsy to assess whether increases in tumor volume are due to immune cell infiltration or neoplastic proliferation, provided that such a biopsy can be performed safely on a non-target lesion. If radiographic disease progression is confirmed at a subsequent tumor assessment, the patient will be ineligible to receive further glofitamab treatment.

Re-Treatment after Withdrawal Due to Progression/Pseudo-progression:

Patients withdrawn from study because of progression or pseudoprogression, who later achieve PR or CR without receiving any other therapy after last dose glofitamab will be allowed to enter the "follow-up till progression" and may be eligible for re-treatment provided they meet the re-treatment eligibility criteria.

Patients diagnosed with pseudoprogression who are allowed to continue the initial treatment course and who complete glofitamab treatment must also meet the re-treatment eligibility criteria in order to receive subsequent study treatment. Likewise, if radiographic disease progression is confirmed at a subsequent tumor assessment or at EOT, these patients will be ineligible to receive further glofitamab treatment.

Resuming glofitamab after prolonged treatment dose delays: In the event of a delayed response (CR or PR; [e.g., following pseudo progression that led to premature discontinuation/interruption of the study treatment]), re-treatment or resuming treatment (post treatment delay) may be allowed if investigator and Sponsor considers this in the best interest of the patient and if the "re-treatment eligibility criteria" are fulfilled. As a safety measure, Gpt should be re-initiated 7 days prior to resuming treatment with glofitamab and for patients enrolled into step-up dosing regimen, the step-up dosing of glofitamab is required with associated mandatory hospitalization for the first dosing cycle after the dose delay.

Inclusion Criteria

Patients must meet the following criteria for study entry:

1. Signed Informed Consent(s) Forms.

2. Patient must be willing and able to comply with protocol-mandated hospitalizations upon administration of glofitamab. Patient must also be willing to comply with all study-related procedures. In Part III, this includes completion of PROs.

3. Age ≥18 years.

4. Depending upon study part, a history or status of: 1) a histologically-confirmed hematological malignancy that is expected to express CD20; 2) relapse after or failure to respond to at least one prior treatment regimen; and 3) no available treatment options that are expected to prolong survival (e.g., standard chemotherapy or autologous stem cell transplant [ASCT]). Eligible R/R NHL patients include:

For Parts I and II: Grade 1-3b FL; MZL (splenic; nodal; extra-nodal); MCL; DLBCL; PMBCL; Richter's transformation; and trFL. The Sponsor retains the option to limit a dose escalation cohort to one or more specific histologies among the approved histologies in Part II.

For Part III expansion cohorts:

a) DLBCL cohort (DLBCL NOS, HGBCL,)

b) PMBCL and trFL. Patients must have relapsed after or failed to respond to at least two prior systemic treatment regimens (including at least one prior regimen containing anthracycline, and at least one containing an anti CD20-directed therapy). The Sponsor retains the option to limit the number of patients enrolled with trFL and PMBCL. Patients with Richter's transformation are not considered eligible for Part III.

For patients in the DLBCL cohort (DLBCL NOS, HGBCL, PMBCL or trFL) the pathology report for the initial histopathology diagnosis must be provided, if available. Patients with trFL must also provide the pathology report at the time of disease transformation, if available. The results of all tests conducted on the tissue at initial diagnosis, including but not limited to tests assessing cell of origin, BCL2 and MYC abnormalities, should be provided if done.

c) FL cohort: Grade 1-3a FL; patients must have relapsed after or failed to respond to at least two prior lines of systemic therapy and must have received prior treatment with rituximab and alkylating agents. The Sponsor retains the option to enroll a minimum number of patients who are refractory to both anti-CD20 directed therapy and an alkylating agent.

5. Measurable disease, defined as at least one bi-dimensionally measurable nodal lesion, defined as >1.5 cm in its longest dimension, or at least one bi-dimensionally measurable extranodal lesion, defined as >1.0 cm in its longest dimension 6. Able to provide a fresh biopsy from a safely accessible site, per investigator determination, providing the patient has more than one measurable target lesion 7. ECOG performance status of 0 or 1

8. Life expectancy (in the opinion of the investigator) of ≥12 weeks

9. Adverse events from prior anti-cancer therapy must have resolved to Grade ≤1

10. Adequate liver function: total bilirubin ≤1.5×ULN. Patients with documented history of Gilbert's Syndrome and in whom total bilirubin elevations are accompanied by elevated indirect bilirubin are eligible; AST/ALT ≤3×ULN.

11. Adequate hematological function: Neutrophil count of ≥$1.5\times10^9$ cells/l; platelet count of ≥75,000/μl (and platelet transfusion free within 14 days prior to administration of Gpt); Hemoglobin (Hb) ≥10.0 g/dl (6.2 mmol/l); transfusion free within 21 days prior to administration of Gpt.

12. Adequate renal function: serum creatinine ≤1.5 ULN or a creatinine clearance (CrCl) calculated by Cockroft-Gault formula of ≥50 ml/min for patients in whom, in the investigator's judgment, serum creatinine levels do not adequately reflect renal function.

13. Negative serum pregnancy test within 7 days prior to study treatment in women of childbearing potential. Women who are not of childbearing potential who are considered to be post-menopausal (≥12 months of non-therapy amenorrhea) or surgically sterile (absence of ovaries and/or uterus) are not required to have a pregnancy test.

14. Negative serologic or polymerase chain reaction (PCR) test results for acute or chronic HBV infection. (Note: Patients whose HBV infection status cannot be determined by serologic test results must be negative for HBV by PCR to be eligible for study participation).

15. Negative test results for HCV and HIV. Note: Patients who are positive for HCV antibody must be negative for HCV by PCR to be eligible for study participation.

16. Patients must agree to either remain completely abstinent or to use two effective contraceptive methods that result in a failure rate of <1% per year from screening until: (a) at least 3 months after pre-treatment with obinutuzumab or 2 months after the last dose of glofitamab, whichever is longer, if the patient is a male or (b) until at least 18 months after pre-treatment with obinutuzumab or 2 months after the last dose of glofitamab, whichever is longer, if patient is a female.

Exclusion Criteria

Patients who meet any of the following criteria will be excluded from study entry:

1. Inability to comply with protocol mandated hospitalizations and restrictions

2. Patients with CLL, Burkitt lymphoma, and lymphoplasmacytic lymphoma

3. Patients with a known or suspected history of HLH

4. Patients with acute bacterial, viral, or fungal infection at baseline, confirmed by a positive blood culture within 72 hours prior to Gpt infusion or by clinical judgment in the absence of a positive blood culture 5. Patients with known active infection, or reactivation of a latent infection, whether bacterial, viral (including, but not limited to, EBV, cytomegalovirus (CMV), hepatitis B, hepatitis C, and HIV), fungal, mycobacterial, or other pathogens (excluding fungal infections of nail beds) or any major episode of infection requiring hospitalization or treatment with IV antibiotics (for IV antibiotics this pertains to completion of last course of antibiotic treatment) within 4 weeks of dosing 6. Pregnant, breast-feeding, or intending to become pregnant during the study 7. Prior treatment with systemic immunotherapeutic agents, including but not limited to radioimmunoconjugates, antibody-drug conjugates, immune/cytokines and monoclonal antibodies (e.g., anti-CTLA4, anti-PD1 and anti-PDL1) within 4 weeks or five half-lives of the drug, whichever is shorter, before Gpt infusion on C1 Day −7

8. History of treatment-emergent immune-related adverse events associated with prior immunotherapeutic agents, as follows:

≥Grade 3 adverse events with the exception of Grade 3 endocrinopathy managed with replacement therapy Grade 1-2 adverse events that did not resolve to baseline after treatment discontinuation 9. Documented refractoriness to an obinutuzumab monotherapy containing regimen 10. Treatment with standard radiotherapy, any chemotherapeutic agent, or treatment with any other investigational anti-cancer agent, including CAR-T therapy (defined as treatment for which there is currently no regulatory authority approved indication) within 4 weeks prior to Gpt infusion 11. Prior solid organ transplantation 12. Prior allogeneic SCT 13. ASCT within 100 days prior to Gpt infusion 14. History of autoimmune disease, including but not limited to myocarditis, pneumonitis, myasthenia gravis, myositis, autoimmune hepatitis, systemic lupus erythematosus, rheumatoid arthritis, inflammatory bowel disease, vascular thrombosis associated with antiphospholipid syndrome, Wegener's granulomatosis, Sjögren's syndrome, Guillain-Barré syndrome, multiple sclerosis, vasculitis, or glomerulonephritis Patients with a remote history of, or well controlled, autoimmune disease may be eligible to enroll after discussion with and confirmation by the Medical Monitor Patients with a history of autoimmune-related hypothyroidism on a stable dose of thyroid replacement hormone may be eligible for this study.

Patients with a history of disease-related immune thrombocytopenic purpura or autoimmune hemolytic anemia may be eligible for this study.

Patients with a history of Type I Diabetes Mellitus who are well controlled (defined as a screening hemoglobin Alc <8% and no urinary ketoacidosis) are eligible.

Patients with eczema, psoriasis, lichen simplex chronicus, or vitiligo with dermatologic manifestations only (e.g., patients with psoriatic arthritis are excluded) are eligible for the study provided all of following conditions are met:

Rash must cover <10% of body surface area

Disease is well controlled at baseline and requires only low-potency topical corticosteroids No occurrence of acute exacerbations of the underlying condition requiring psoralen plus ultraviolet A radiation, methotrexate, retinoids, biologic agents, oral calcineurin inhibitors, or high potency oral corticosteroids within the previous 12 months 15. History of severe allergic or anaphylactic reactions to monoclonal antibody therapy (or recombinant antibody-related fusion proteins)

16. Patient with history of confirmed progressive multifocal leukoencephalopathy (PML)

17. Current or past history of CNS lymphoma

18. Current or past history of CNS disease, such as stroke, epilepsy, CNS vasculitis, or neurodegenerative disease Note: Patients with a history of stroke who have not experienced a stroke or transient ischemic attack in the past 2 years and have no residual neurologic deficits, as judged by the investigator, are allowed 19. Evidence of significant, uncontrolled concomitant diseases that could affect compliance with the protocol or interpretation of results, including diabetes mellitus, history of relevant pulmonary disorders (bronchospasm, obstructive pulmonary disease), and known autoimmune diseases 20. Major surgery or significant traumatic injury <28 days prior to the Gpt infusion (excluding biopsies) or anticipation of the need for major surgery during study treatment 21. Patients with another invasive malignancy in the last 2 years (with the exception of basal cell carcinoma and tumors deemed by the investigator to be of low likelihood for recurrence)

22. Significant cardiovascular disease such as New York Heart Association Class III or IV cardiac disease, myocardial infarction within the last 6 months, unstable arrhythmias, or unstable angina)

23. Administration of a live, attenuated vaccine within 4 weeks before Gpt infusion or anticipation that such a live attenuated vaccine will be required during the study. (Note: Influenza vaccination should be given during influenza season only). Patients must not receive live, attenuated influenza vaccine (e.g., Flumist®) at any time during the study treatment period.

24. Received systemic immunosuppressive medications (including but not limited to cyclophosphamide, azathioprine, methotrexate, thalidomide, and anti-tumor necrosis factor agents) within 2 weeks prior to Gpt infusion. Treatment with corticosteroid ≤25 mg/day prednisone or equivalent is allowed. Inhaled and topical steroids are permitted.

25. History of illicit drug or alcohol abuse within 12 months prior to screening, in the Investigator's judgment.

26. Any other diseases, metabolic dysfunction, physical examination finding, or clinical laboratory finding giving reasonable suspicion of a disease or condition that would contraindicate the use of an investigational drug.

27. In Part III DLBCL dexamethasone cohort, patients with a history of hypersensitivity to dexamethasone or systemic corticosteroids will be excluded.

Length of Study

The full treatment period for this study is 12 cycles (Q2W and Q3W dosing) of glofitamab exposure, or until unacceptable toxicity or disease progression.

Safety Outcome Measures

All patients who participate in this study will be clinically evaluated at screening and on a regular basis during the course of the study. The safety monitoring plan will include routinely-monitored parameters (e.g., heart rate, diastolic and systolic blood pressure [BP], electrocardiogram), laboratory analysis (e.g., hematology, biochemistry, urinalysis) and regular collection and review of adverse events. In addition, specific activities and parameters related to the mechanism of action of obinutuzumab and glofitamab will also be carefully monitored, and the study will be conducted in association with the IMC, as well as in consultation with all study investigators.

In summary, the safety/tolerability outcome measures for this study are as follows:

Parts I and II:

Incidence and nature of dose-limiting toxicities (DLTs)

Parts I-III:

Incidence, nature and severity of all adverse events

Incidence of ADA formation and events related to immune complex deposition and activation Incidence of cytokine release related events (CRS and IRRs)

Changes in VS and clinical laboratory values: hematology; biochemistry; urinalysis; coagulation parameters; and physical examination, including ECOG status and VS Triplicate 12-lead ECGs Efficacy Outcome Measures The efficacy outcome measures to be evaluated in this study are as follows:

Independent review committee (IRC)-assessed complete response (CR) rate according to Lugano Classification Investigator assessed complete response (CR) rate according to Lugano Classification IRC-assessed complete response (CR) rate according to standard NHL response criteria Overall response (OR) rate, defined as partial response (PR) or complete response (CR), as assessed by IRC and investigator according to Lugano Classification and by IRC Duration of complete response (DOCR), defined as the time from the initial occurrence of a documented CR until documented disease progression or death due to any cause, whichever occurs first. This will be evaluated using IRC and investigator assessment based on the Lugano Classification Duration of objective response (DOR), defined as the first occurrence of a documented, objective response until the time of disease progression, relapse or death from any cause. This will be evaluated using IRC and investigator assessment based on the Lugano Classification Progression-free survival (PFS), defined as the time from the first study treatment to the first occurrence of disease progression or death from any cause, whichever occurs first. This will be evaluated using IRC and investigator assessment based on the Lugano Classification Overall survival (OS), defined as time from the first study treatment to the date of death from any cause Time to first overall response (TFOR), defined as time from treatment start to first documented response. This will be evaluated using IRC and investigator assessment based on the Lugano Classification Time to first complete response (TFCR) defined as time from treatment start to first documented complete response. This will be evaluated using IRC and investigator assessment based on the Lugano Classification Investigational Medicinal Products Glofitamab and Obinutuzumab Obinutuzumab and glofitamab must be administered in a clinic or hospital equipped for systemic (IV) cancer treatment. Flat dosing, independent of body weight, will be used for obinutuzumab and glofitamab.

Glofitamab: The dose of glofitamab for each patient will depend on their dose level assignment. Glofitamab will be administered on study day 1 of each 14-day cycle (i.e., Q2W) or Day 1 of each 21-day cycle (i.e., Q3W).

Obinutuzumab: Flat dosing, independent of body weight, will be used for obinutuzumab (1000 mg for each patient). Obinutuzumab dose may be split over 2 days if needed for management of infusion-related reactions (IRRs).

Glofitamab should be administered to patients by IV infusion using a dedicated infusion line and a catheter for the administration. For obinutuzumab combination treatment, obinutuzumab will be administered first, followed by glofitamab, with glofitamab infusion to begin at least 60 minutes after the completion of the obinutuzumab infusion, provided that patients have recovered from any acute toxicity mediated by the preceding administration. If not, glofitamab may be administered on the following day. Obinutuzumab dose may be split over 2 days if needed for management of infusion related reactions.

First administration of glofitamab (C1D1) will be administered over 4 hours±15 minutes. For patients who develop CRS with an onset of associated signs/symptoms during glofitamab infusion, the infusion must be discontinued immediately with no further re-starts of the infusion for this administration, unless limited to Grade 1 CRS. In the absence of infusion-related adverse events, the infusion time of glofitamab in subsequent dosing cycles may be reduced to 2 hours±15 minutes, at the discretion of the investigator. For patients who may be at an increased risk of CRS, patients who experience IRRs or CRS with their previous dose of glofitamab or who are at increased risk of recurrent IRR/CRS with subsequent doses, the time of infusion may be extended to up to 8 hours. Patients who undergo intra-patient dose escalation in Part I should also receive the next higher dose of glofitamab over a minimum of 4 hours. Patients in step-up dosing cohorts should also receive C1D2 and C2D1 doses over a minimum of 4 hours.

Tocilizumab

Tocilizumab should be administered when necessary for the management of CRS during or after any infusion of glofitamab. Tocilizumab infusion will follow the methods described in SmPC, USPI, or other similar local prescribing documents. Tocilizumab is approved by the FDA and EMA for the treatment of Cytokine Release Syndrome (CRS) induced by chimeric antigen receptor (CAR) T-cell in adults and pediatric patients 2 years of age and older (Tocilizumab IB).

Obinutuzumab Pre-Treatment

Obinutuzumab pre-treatment (i.e., GAZYVA®/GAZYVARO® pre-treatment [Gpt]) in this trial) is a safety measure used to deplete B-cells both in the peripheral blood and in the secondary lymphoid organs, thereby strongly reducing the risk of sudden cytokine release associated with the first glofitamab administration (Glofitamab Investigator's Brochure).

In this study, all cohorts (monotherapy or combination) are receiving obinutuzumab pre-treatment prior to starting glofitamab administration. Double pre-treatment with obinutuzumab (DGpt) prior to the first dose of glofitamab may be tested in separate cohorts in Part II as an additional mitigation of CRS.

Two dosing alternatives of DGpt may be tested, in separate dosing cohorts:

Administration of two doses of Gpt 7 days before the first dose of glofitamab (2×1000 mg on C1D-7)

Administration of two doses of obinutuzumab, first Gpt dose (1000 mg) on C1 Day −7 followed by a second dose of Gpt (1000 mg) on C1 Day −1

The aim of this investigation will be to assess if a second dose of obinutuzumab prior to the first dose of glofitamab can further help to reduce the occurrence and severity of CRS. DGpt may be tested in separate cohorts in Part II with monotherapy and subsequently in combination therapy. It may be investigated using fixed dosing, step-up dosing Cycle 1 and extended step-up dosing. Patients in Part III dose-expansion cohorts may receive glofitamab on a Q2W or Q3W dosing schedule and using a fixed dose regimen or step-up dose regimen (Cycle 1 step-up or extended step-up) on Q3W dosing schedule, if supported by emerging data and/or recommended by the IMC.

Rationale for Step-Up Dosing (Monotherapy or Combination Cohorts)

CRS is the main dose-limiting toxicity for glofitamab. The preliminary clinical safety results from Part I and Part II of this study revealed that escalating doses of glofitamab as a single agent and in combination with obinutuzumab were associated with acceptable tolerability up to 16 mg Q3W. Further, dose escalation was limited at the highest investigated dose, 25 mg Q3W, which was associated with increasing frequency of C1 CRS events. Clinical characterization of onset, incidence, severity, and duration of CRS revealed a transient, dose-dependent profile with onset and duration mainly limited to initial dosing of glofitamab and mainly confined within the initial 24 hours after the end of infusion. Thus, the CRS events are generally confined to C1 for the vast majority of patients.

Gpt has been shown to effectively deplete peripheral B-cells with the aim to reduce the risk of CRS following glofitamab. The proof-of-concept is based on completed nonclinical experiments conducted in vitro and in vivo in multiple species (Bacac M, Colombetti S, Herter S, et al. CD20-TCB with obinutuzumab pretreatment as next-generation treatment of hematologic malignancies. *Clinical Cancer Research.* 2018 Oct. 1; 24(19):4785-97). Investigation of step-up dosing as an additional safety measure for CRS mitigation will be introduced into Part II of the study in order to explore options to further optimize the benefit-risk profile of glofitamab. Based on the clinical characterization of the CRS time-course data showing that CRS events have occurred primarily following the initial glofitamab dose, use of step-up dosing regimens could mitigate first dose associated CRS.

For step-up dosing, step doses of glofitamab will be administered on day 1 of dosing cycle 1 and day 8 of dosing cycle 1, and the total dose administered in C1 will not exceed that previously cleared for safety (i.e., will not exceed the determined MTD, see the Glofitamab Investigator's Brochure). Higher doses may be explored from C2 or later cycles guided by the mDA-CRM-EWOC model. Step-up dosing will initially require hospitalization at day 1 of dosing cycle 1 (C1D1 dose), day 8 of dosing cycle 1 (C1D2 dose), and day 1 of dosing cycle 2 (C2D1 dose). The IMC will review hospitalization requirement based on emerging safety data. A schematic overview of the step-up dosing regimen is shown in FIG. 4.

The Part II dose escalation may explore an alternative step-up dosing schedule (extended step-up dosing, see FIG. 12) in selected dosing cohorts. In the extended step-up dosing, an initial lower dose of glofitamab will be administered on day 1 of dosing cycle 1 and day 8 of dosing cycle 1 followed by an intermediate dose in Cycle 2 and the first administration of the target treatment dose is in Cycle 3. Alternatively, an intermediate dose may also be administered in Cycle 3 and first target dose in Cycle 4. The aim of this investigation will be to assess if a smaller increase in glofitamab dose at each step-up can further improve the clinical benefit/risk of glofitamab by reducing the occurrence and severity of CRS.

Premedication with Dexamethasone

CRS is the main dose-limiting toxicity for glofitamab. The inclusion of dexamethasone as premedication is based on data from nonclinical studies in cell line xenograft models in humanized immunocompromised mice, where preliminary evidence suggests reduced glofitamab-induced cytokine levels in mice pretreated with dexamethasone relative to methylprednisolone. In these studies, neither dexamethasone nor methylprednisolone impaired glofitamab's ability to reduce tumor volume. Hence, dexamethasone will be included as an option for steroid premedication for all patients. In addition, a R/R DLBCL expansion cohort in Part III will require patients to receive premedication with dexamethasone and will investigate (exploratory objective) if this can further help to reduce the occurrence and severity of CRS.

Premedication Regimens to Reduce Infusion-Related Reactions (Including CRS) to Obinutuzumab and Glofitamab Since some patients may develop hypersensitivity or other infusion-related reactions to obinutuzumab or glofitamab, premedication with oral acetaminophen/paracetamol (500-1000 mg) and an anti-histamine, such as diphenhydramine (50-100 mg), must be administered at least 30 minutes prior to the start of each study medication infusion (unless contraindicated). Pre-medication with corticosteroids (80 mg IV methylprednisolone or equivalent dose of prednisone [100 mg] or prednisolone [100 mg] or 20 mg IV dexamethasone) should be administered at least 60 minutes prior to the administration of obinutuzumab and glofitamab. Corticosteroid premedication will be optional at later cycles based on investigator's assessment for patients who have tolerated the step-up doses and two target doses of glofitamab without experiencing any grade CRS. However, if the patient experiences CRS, premedication with steroids is required to be administered for the subsequent doses until no additional CRS events are observed. Changes from this corticosteroid regimen need to be medically justified. Hydrocortisone should not be used (see Table 5).

In the dexamethasone DLBCL expansion cohort (D5, FIG. 3), premedication with 20 mg IV dexamethasone prior to glofitamab infusion will be mandated for all patients, other choice of corticosteroids will not be acceptable. In addition, the Sponsor retains the option to mandate a selected corticosteroid (of the ones listed above) as premedication in a specific dose escalation cohort, expansion cohort or sub-cohort.

In the obinutuzumab combination cohort, premedication must be administered prior to the start of obinutuzumab infusion and should only be repeated if obinutuzumab and glofitamab are administered over 2 days.

TABLE 5

Overview of Pre-medications before Gpt, Obinutuzumab and Glofitamab Infusions

| Timepoint | Patients Requiring Pre-Medication | Pre-Medication | Administration |
|---|---|---|---|
| Gpt [a] Cycle 1 Day-7 And/or Cycle 1 Day-1 | All Patients | IV glucocorticoids [b] | At least 60 min prior to obinutuzumab infusion |
| | | Oral or IV analgesic Oral or IV antihistamine [c] | At least 30 min prior to obinutuzumab infusion |
| | Patients at risk of TLS (e.g., because of bulky disease or renal impairment (creatinine clearance <70 ml/min) | Allopurinol or suitable alternative, such as rasburicase, along with adequate hydration | |
| Obinutuzumab in combination with glofitamab [a, d] | All patients | IV glucocorticoids [b] | At least 60 min prior to obinutuzumab infusion |
| | | Oral or IV analgesic Oral or IV antihistamine [c] | At least 30 min prior to obinutuzumab infusion |
| Starting on Cycle 2 Day 1; Q3W | Patients at risk of TLS (e.g., because of bulky disease or renal impairment (creatinine clearance <70 ml/min) | Allopurinol or suitable alternative, such as rasburicase, along with adequate hydration | |
| Glofitamab [d] | All Patients | IV glucocorticoids [b] | At least 60 min prior to obinutuzumab infusion |
| Cycle 1 onward; All doses | | Oral or IV analgesic Oral or IV antihistamine [c] | At least 30 min prior to obinutuzumab infusion |
| | Patients at risk of TLS (e.g., because of bulky disease or renal impairment (creatinine clearance <70 ml/min) | Allopurinol or suitable alternative, such as rasburicase, along with adequate hydration | |

Footnotes for table 5

CRS: cytokine release syndrome;

Gpt: obinutuzumab pre-treatment;

IV: intravenous;

min: minutes;

Q3W: every 3 weeks;

TLS: tumor lysis syndrome.

[a] Closely monitor patients during the entire infusion. Infusion reactions within 24 hours of receiving obinutuzumab have occurred.

[b] 80 mg IV methylprednisolone or equivalent dose of IV prednisone (100 mg) or 20 mg IV dexamethasone; hydrocortisone should not be used as it has not been effective in reducing the rate of infusion reactions. In dexamethasone DLBCL expansion cohort, 20 mg IV dexamethasone should be used.

[c] e.g., 50- 100 mg diphenhydramine (unless contraindicated).

[d] All glofitamab doses will be administered to well-hydrated patients.

[e] Optional at later cycles based on investigator's assessment for patients that have tolerated two target doses of glofitamab without experiencing CRS.

Grading Scale for Cytokine Release Syndrome

In this study, grading and treatment of the adverse event of CRS arising from glofitamab treatment will be based on published criteria of Lee et al. (Lee et al., *Blood,* 124: 188-195, 2014) and are described in Table 6.

The American Society for Transplantation and Cellular Therapy (ASTCT) consensus grading for CRS is currently considered the most clinical relevant grading scale for CRS (Lee et al., *Biol Blood Marrow Transplant,* 25(4): 625-638, 2019). Although the protocol specified CRS grading system for Study NP3a179 is per Lee et al. 2014, the study electronic case report form (eCRF) collects details on the supportive management of hypoxia and hypotension which allows a programmatical derivation of the ASTCT grade for CRS events.

TABLE 6

Recommendations for Cytokine Release Syndrome Management for Glofitamab (Event Onset after the End of Infusion)

| Event[a] | Initial Management Recommendation[b] | Action to Be Taken with Glofitamab at Next Dose |
|---|---|---|
| Grade 1 | Treat symptomatically as indicated, including antihistamines, antipyretics, and/or analgesics as needed | Continue treatment with glofitamab, consider reduced rate of infusion |
| Fever, constitutional symptoms | Treat fever and neutropenia if present Monitor fluid balance; administer IV fluids as clinically indicated For prolonged CRS (>2 days) in patients with significant symptoms or comorbidities (per investigator discretion [e.g., impaired | Hospitalize for next dose if prolonged CRS |

TABLE 6-continued

Recommendations for Cytokine Release Syndrome Management for Glofitamab (Event Onset after the End of Infusion)

| Event[a] | Initial Management Recommendation[b] | Action to Be Taken with Glofitamab at Next Dose |
|---|---|---|
| | cardiovascular function, reduced pulmonary reserve]), consider IV corticosteroids[d] and tocilizumab[e] | |
| Grade 2<br>Hypotension: Responds to fluids or a single low dose vasopressor[c] | No or minimal comorbidities<br>Follow all Grade 1 recommendations<br>Monitor cardiac and other organ function closely<br>Hemodynamic support as indicated<br>Oxygen for hypoxia<br>Admit to ICU as appropriate | May receive the next dose of glofitamab if symptoms resolve to Grade ≤1 for 3 consecutive days with approval of Medical Monitor |
| Hypoxia: requires <40% $FiO_2$ to maintain adequate hemoglobin oxygen saturation | Administer tocilizumab IV[e]<br>Administer IV corticosteroids[d]<br>If no improvement within 24 hours:<br>a) Notify Medical Monitor<br>b) Initiate work-up and assess for signs and symptoms of HLH | Consider extending infusion time (slower infusion rate) for subsequent doses |
| Organ toxicity: Assessed as Grade 2 | Manage per Grade 3 if no improvement within 8-12 hours after starting tocilizumab<br>Extensive comorbidities<br>Follow Grade 3 management guidelines | Hospitalize for next dose |
| Grade 3<br>Hypotension: Requires multiple pressors or high dose vasopressor[c] | Strongly consider cardiopulmonary and organ function monitoring in Intensive Care Unit<br>Closely monitor and maintain fluid balance; administer IV fluids as clinically indicated | Patient may receive the next dose of glofitamab if symptoms resolve to Grade 1 or better for 3 consecutive days with approval of Medical Monitor |
| Hypoxia: requires ≥40% $FiO_2$ to maintain adequate hemoglobin oxygen saturation | Oxygen for hypoxia<br>Vasopressor support for hypotension at high and repeated doses if required<br>Other supportive care as clinically indicated (e.g., fever and neutropenia, infection) | The dose of glofitamab for the subsequent administration must be discussed with the Medical Monitor |
| Organ toxicity: Assessed as Grade 3 (Grade 4 transaminitis) | Administer Tocilizumab as per Grade 2, If maximum dose not reached within a 24-hour period<br>Administer IV corticosteroids[d] in addition to antihistamines, antipyretics and/or analgesics<br>Initiate work-up and assess for signs And symptoms of HLH | Consider extending infusion time (slower infusion rate) for subsequent doses<br>Hospitalize for next dose<br>If Grade 3 CRS recurs with subsequent doses, consider permanent discontinuation of glofitamab |
| Grade 4<br>Hypoxia: Mechanical ventilation required<br>Organ toxicity: Grade 4 (excluding transaminitis) | ICU admission, follow all Grade 3 guidelines<br>For patients refractory to tocilizumab, consider siltuximab, anakinra, dasatinib and emapalumab, based on discretion of the investigator; management should be discussed with the Medical Monitor[f] | Permanently discontinue glofitamab [g] |

Footnotes for Table 6:

HLH: Hemophagocytic lymphohistiocytosis;

IV: intravenous

[a]Refer to the NCI-CTCAE, v4.03 scale for the grading of symptoms.

[b]Guidance for CRS management is based on Lee et al. 2014 (Lee DW, Gardner R, Porter DL, et al. Current concepts in the diagnosis and management of cytokine release syndrome. Blood 2014; 124(2):188-95.) and Thompson et al. 2019 (Thompson JA, Schneider BJ, Brahmer J, Andrews S, Armand P, Bhatia S, Budde LE, Costa L, Davies M, Dunnington D, Ernstoff MS. Management of Immunotherapy-Related Toxicities, Version 1.2019, NCCN Clinical Practice Guidelines in Oncology. J Natl Compr Cancer Netw. 2019;17(3)).

[c]Vasopressor use is defined as low dose if:

Norepinephrine monotherapy <20 μg/min; or

Dopamine monotherapy <10 μg/min; or

Phenylephrine monotherapy <200 μg/min; or

Epinephrine monotherapy <10 μg/min; or

Vasopressin + Norepinephrine equivalent <10 μg/min; or

On a combination of vasopressors, Norepinephrine equivalent of <20 μg/min

Equivalent equation: norepinephrine equivalent dose = [norepinephrine (μg/min)] + [dopamine (μg/kg/min)] + [phenylephrine (μg/min) ÷ 10].

High dose vasopressor use is defined as all doses required for ≥3 hours:

Norepinephrine monotherapy ≥20 μg/min; or

Dopamine monotherapy ≥10 μg/min; or

Phenylephrine monotherapy ≥200 μg/min; or

Epinephrine monotherapy ≥10 μg/min; or

Vasopressin + Norepinephrine equivalent >10 μg/min; or

On a combination of vasopressors, Norepinephrine equivalent of ≥20 μg/min

Equivalent equation: norepinephrine equivalent dose = [norepinephrine (μg/min)] + [dopamine (μg/kg/min)] + [phenylephrine (μg/min) ÷ 10].

TABLE 6-continued

| Recommendations for Cytokine Release Syndrome Management for Glofitamab (Event Onset after the End of Infusion) | | |
|---|---|---|
| Event[a] | Initial Management Recommendation[b] | Action to Be Taken with Glofitamab at Next Dose |

[d]IV corticosteroids (e.g., methylprednisolone 2 mg/kg/day or dexamethasone 10 mg).

[e]Tocilizumab IV (8 mg/kg for patients at or above 30-kg weight; 12 mg/kg for patients less than 30-kg weight, not to exceed 800 mg/dose).

[f]Reference: Riegler et al. 2019 (Riegler LL, Jones GP, Lee DW. Current approaches in the grading and management of cytokine release syndrome after chimeric antigen receptor T-cell therapy. Ther Clin Risk Manag. 2019; 15:323.); Wu et al. 2019 (Wu BX, Song NJ, Riesenberg BP, et al. Development of molecular and pharmacological switches for chimeric antigen receptor T cells. Experimental Hematology & Oncology. 2019 8:27.).

[g] Resumption of glofitamab may be considered in patients who are deriving benefit and have fully recovered from the adverse event. Patients can be re-challenged with glofitamab only after approval has been documented by both the investigator (or an appropriate delegate) and the Medical Monitor.

Example 2: Glofitamab, a Novel, Bivalent CD20 Targeting T-Cell Engaging Bispecific Antibody, Induces Durable Complete Remissions in Relapsed/Refractory B-Cell Non-Hodgkin Lymphoma: A Phase I Trial Study NP30179 (ClinicalTrials.gov identifier: NCT03075696) is a first-in-human, phase I study, investigating the clinical activity of single-agent glofitamab after single-dose GAZYVA® (obinutuzumab; Genentech/Roche) pretreatment (Gpt) and glofitamab with ongoing, co-administered obinutuzumab. Here, we present data for glofitamab monotherapy with single-dose Gpt.

Methods

Patients

The trial included patients aged ≥18 years with histologically confirmed B-NHL expected to express CD20; who had ≥1 prior lymphoma treatment, with no available life-extending treatment options; and ≥1 measurable target lesion >1.5 cm. Key exclusion criteria were a history of central nervous system (CNS) lymphoma or other CNS pathology; anticancer therapy within 4 weeks or five half-lives of the drug prior to Gpt; ASCT within 100 days prior to Gpt; or prior allogeneic stem cell transplantation.

Study Design

NP30179 is a phase I, multicenter, open-label, dose-escalation and dose-expansion study comprising three parts. Herein, we describe Part 1 (single-patient dose escalation) and Part 2 (multiple-patient dose-escalation; FIG. 3); Part 3 (dose expansion) is ongoing.

Seven days before the first dose of glofitamab, all patients received 1,000 mg Gpt intravenously, in order to deplete peripheral and tissue-based B-cells and hereby mitigate serious CRS.

Obinutuzumab was chosen as pre-treatment due to its deeper clearance of peripheral and tissue-based B-cells as compared to rituximab. Glofitamab was given as an initial 4-hour intravenous (IV) infusion, and infusion time was reduced to 2 hours once a prior infusion had occurred without complications. Dose escalation was guided by a Bayesian-modified continuous reassessment method with overdose control based on emerging toxicity data. In Part 1, which included only three patients in single-patient cohorts, glofitamab was administered at doses of 0.005-0.045 mg. Part 2 dose escalation started at 0.015 mg. Glofitamab was administered on day 1 and 8 of cycle 1, then on day 1 of each 14-day cycle for up to 12 cycles. Based on early pharmacokinetic (PK) data confirming a clinical half-life of glofitamab in-line with IgG antibodies, dosing at cycle 1 day 8 was omitted at doses ≥0.3 mg, and a 21-day cycle was adopted from cycle 2 at doses of ≥10 mg, for up to 12 cycles. All patients were hospitalized for 48 hours following the first administration of glofitamab for monitoring of treatment-emergent toxicities.

The primary study endpoints were safety/tolerability, pharmacokinetics, maximum tolerated dose (MTD) and dose-limiting toxicities. Secondary endpoints included CR and overall response rates (ORR) by Lugano classification, duration of response (DOR), duration of complete response (DOCR), PFS, pharmacodynamic (PD) biomarkers, and incidence of anti-drug antibodies.

All measurable disease was documented by fluorodeoxyglucose-positron emission tomography and computerized tomography. Tumor evaluations were conducted at baseline, after 2 and 5 cycles, at the end of treatment, and every 3 months until disease progression. Adverse events (AEs) were evaluated according to the National Cancer Institute-Common Terminology Criteria for Adverse Events (CTCAE), version 4.03.17 Investigators managed CRS according to local practices. On-site availability of tocilizumab was a requirement. As consensus criteria for ICANS were not available at the time of study initiation, ICANS were analyzed using a Standardized MedDRA Query of ‘Non-infectious Encephalitis’ plus the CTCAE term of ‘headache’.

All enrolled patients provided written informed consent. The study was approved by each center's ethics committee or institutional review board and conducted in conformance with the Declaration of Helsinki, International Conference on Harmonisation Guidelines for Good Clinical Practice, and appropriate laws and regulations.

Statistical Analysis

The planned sample size was based on dose-escalation stopping criteria and approximated using computational simulation across different scenarios; 160 patients were estimated to reach the MTD. A minimum of three patients per cohort were required for dose escalation; however, the size of individual cohorts was designed to be flexible and increased with dose to further establish the efficacy and safety of glofitamab at clinically effective doses, and to determine the MTD for the first administration.

Analyses included all patients who received Gpt or glofitamab, and were conducted by dose group and pooled for selected analysis. Patients who did not complete any response assessments were considered as non-responders and censored at day 1 for time-to-event endpoints; if disease progression or death was reported then patients were considered an event at this time. 95% confidence intervals (CI), calculated using the Clopper-Pearson method, are provided for response rates. DOR (time from first response to disease progression or death), DOCR (time from first complete response to disease progression or death), and PFS (time from Gpt to disease progression or death), were analyzed by Kaplan-Meier estimation; patients without disease progression or death were censored at the time of the last response assessment. Time to CR was analyzed using cumulative incidence, with disease progression or death considered a competing risk. Pre-planned subgroup analyses included number and type of prior therapy, time since last prior therapy, refractory status, tumor burden, and International Prognostic Index.2 Refractory status was defined as no response to, or relapse within 6 months of prior therapy.

Data were analyzed using SAS version 9.4. The clinical cutoff date was Aug. 3, 2020.

Results

Patients

Three patients were enrolled into single-patient (Part 1) cohorts and dosed at 0.005 mg, 0.015 mg and 0.045 mg; no responses were observed. All 3 patients experienced at least one serious adverse event (SAE), including one Grade 4 neutropenia and one Grade 1 viral infection considered related to glofitamab. No AEs led to treatment withdrawal; all patients withdrew from treatment due to progressive disease.

Part two of the trial had multiple-patient dose-escalation cohorts and was triggered following an episode of Grade 2 neutropenia in Part 1. The first dose level was 0.015 mg and a total of 171 patients with R/R B-NHL were enrolled into this part of the trial. The median (range) duration of follow-up of these patients was 13.5 (0-30.4) months. Significant clinical activity was observed at doses starting from 0.6 mg, and subsequent cohorts were increased in size to provide additional clinical efficacy and safety data. At a day-one dose of 25 mg, CRS was reported in all patients, including one Grade 3 and one Grade 4 event, and this was considered the maximum tolerated day-one dose during Cycle 1. Based on clinical safety data and PK/PD modelling, two step-up dosing (SUD) cohorts were subsequently tested with weekly dosing of 2.5 mg (C1D1 on day 1 of dosing cycle 1), 10 mg (C1D2 on day 8 of dosing cycle 1) and 16 mg or 30 mg (C1D3 on day 15 of dosing cycle 1). Full details can be found in FIG. 7, FIG. 8, and FIG. 9.

Patients in Part 2 had a median age of 64 (range: 22-85) years, with 62.0% (106/171) patients aged >60 years, and 48.8% (83/171) had an Eastern Cooperative Oncology Group performance status of 1-2 (FIG. 7). Most patients had aggressive NHL (n=127; 74.3%); 73 (42.7%) had DLBCL, 29 (17.0%) had DLBCL arising from FL (transformed FL [trFL]), and 10 (5.8%) had Richter's transformation from chronic lymphocytic leukemia. Patients had a median number of 3 (range: 1-13) prior lines of therapy; 144 patients (84.2%) were refractory to previous anti-CD20 treatment, and 155 (90.6%) were refractory to any prior therapy (FIG. 7). Eleven patients (6.4%) received only one prior therapy. Forty patients (23.4%) had undergone autologous stem cell transplantation (ASCT) and 5 (2.9%) received CAR-T therapy. Median (range) time since last prior therapy and last prior anti-CD20 regimen were 2.4 (0.6-128.8) and 5.8 (0.6-146.7) months, respectively.

Safety

AEs were reported in 168/171 patients (98.2%) (FIG. 8); 143 patients (83.6%) had at least one AE that was considered glofitamab-related. The most common AE was CRS (FIG. 8), occurring in 86/171 patients (50.3%; Grade 1, 21.6%; Grade 2, 25.1%; Grade 3, 2.3% and Grade 4, 1.2%). 18 The most frequently (≥10%) associated symptoms of CRS were pyrexia (n=79; 46.2%), hypotension (n=42; 24.6%), tachycardia (n=27; 15.8%), and chills (n=21; 12.3%). Symptoms of immune effector cell-associated neurotoxicity syndrome (ICANS) during CRS were uncommon: confusional state in 6 patients (3.5%; Grade 1-2, n=4 [2.3%]; Grade 3, n=2 [1.2%]), headache in 8 (4.7%; Grade 3, n=1), aphasia in 1 (0.6%, Grade 3), and depressed level of consciousness in one patient (0.6%, Grade 2); all resolved within 3 to 72 hours. No seizures and no increased intracranial pressure were reported. Median time to onset and duration of the first CRS events relative to the last prior glofitamab dose were 10.8 hours (range: 3.0-47) and 2.2 days (range: 0.0-31.0), respectively. Incidence and severity of CRS increased with dose but declined considerably after the first administration: 21/160 patients (13.1%) experienced CRS at cycle 2, and 8/132 (6.1%) experienced CRS at cycle 3 or later (one Grade 3, all others Grade 1-2) (FIG. 11).

At fixed doses of 10-25 mg (without step-up), CRS occurred in 33/46 (71.7%) patients (Grade 2, 43.5%; Grade 3 and 4, 2.2% each; managed by tocilizumab, steroids or both in 10.9%, 21.7% and 13.0%, respectively); in step-up dosing cohorts in 33/52 (63.5%) patients (Grade 2, 26.9%; Grade 3 [after 2.5 mg] and 4 [after 30 mg], 1.9% each; managed by tocilizumab, steroids or both in 9.6%, 11.5% and 7.7%, respectively); and in 25/35 (71.4%) patients (Grade 2, 22.9%; Grade 3 and 4, 2.9% each; managed by tocilizumab, steroids or both in 11.4%, 11.4% and 8.6%, respectively) at the selected recommended phase II dose (RP2D) of 2.5/10/30 mg. See FIG. 6.

CTCAE-defined neurological AEs were observed in 74 patients (43.3%), with ICANS-like events in 31 patients (18.1%); the most common event was headache (n=22; 12.9%). Two Grade 3 events occurred in one patient (facial paralysis and dysphagia), both were related to local effects of underlying disease and neither considered glofitamab-related.

Figure 5:
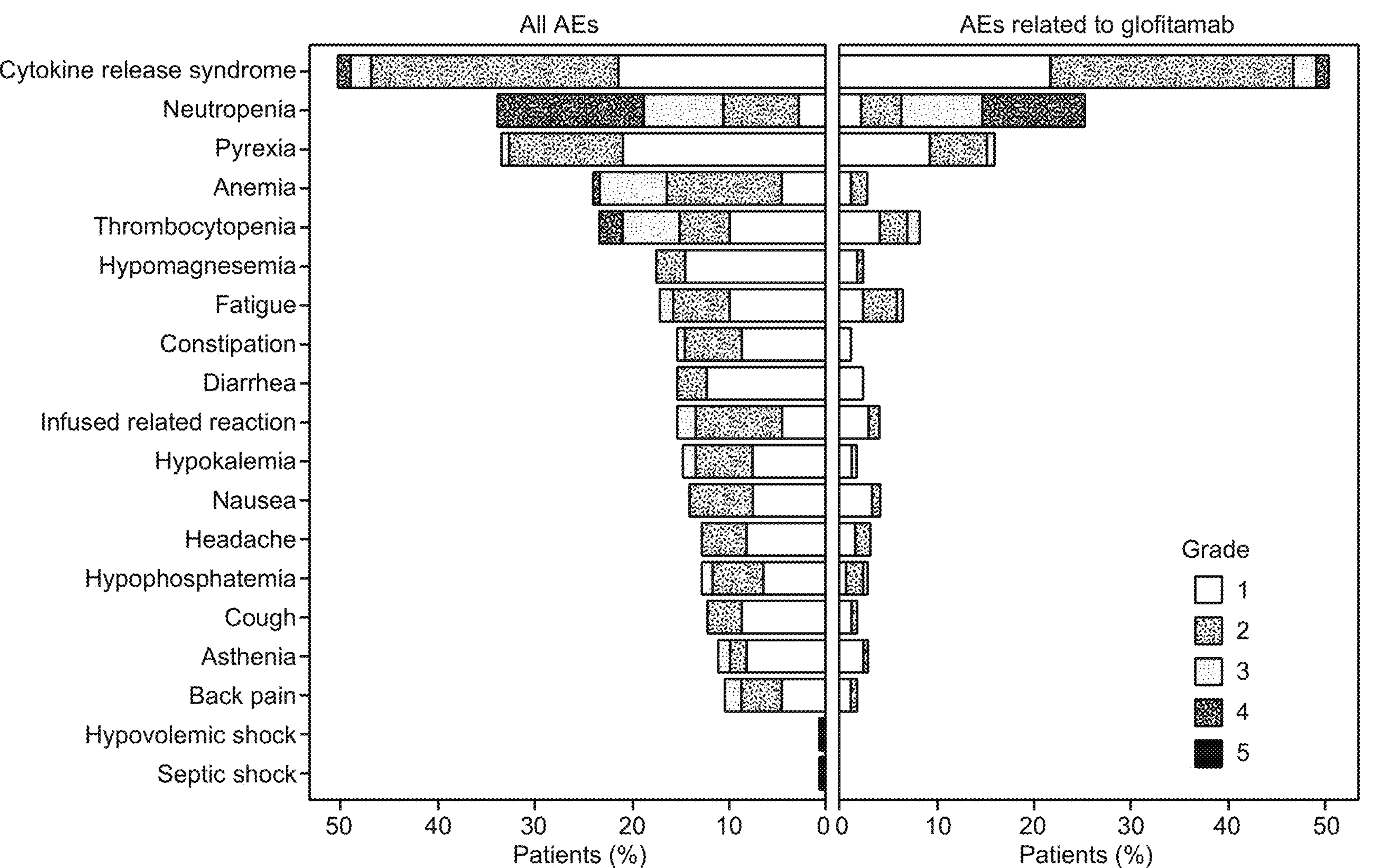
FIG. 5. Adverse events with an incidence of ≥10% or an NCI-CTCAE grade of 5.

SAEs were reported in 100 patients (58.5%) and were considered glofitamab-related in 77 patients (45.0%); in 71/167 cases (42.5%), they occurred during cycle 1. SAEs in 61 patients (127 events) were due to CRS. Grade 5 (fatal) AEs occurred in one patient at 25 mg (hypovolemic shock due to gastrointestinal hemorrhage after CRS recovery) and in one patient at 0.015 mg (septic shock without prior CRS); both were considered by the investigator to be unrelated to glofitamab (FIG. 5).

Grade ≥3 neutropenia, anemia, and thrombocytopenia occurred in 43 (25.1%), 13 (7.6%), and 14 patients (8.2%), respectively (FIG. 8). Among the 43 patients with Grade ≥3 neutropenia, neutropenia was considered glofitamab-related in 34 patients. Granulocyte colony-stimulating factor support was given to 37 patients (21.6%), and platelet and red blood transfusions to four (2.3%) and nine (5.3%) patients, respectively. Median times to onset and duration of first all-Grade events were 21.5 and 7.9 days (neutropenia), 6.0 and 7.1 days (anemia), 10.4 and 12.8 days (thrombocytopenia), respectively. Febrile neutropenia occurred in 5 patients (2.9%). Infections were observed in 88 patients (51.5%); 30 (17.5%) had Grade ≥3 events, the most common being pneumonia (n=5). Five patients (2.9%) discontinued treatment due to AEs; one acute myocardial infarction (at 0.22 mg), one Grade 3 cytomegalovirus chorioretinitis (at 1 mg), one fatal event of hypovolemic shock (at 25 mg), one Grade 4 neutropenia (at 2.5/10/30 mg), and one patient with Grade 3 sepsis and Grade 4 colitis (at 2.5/10/30 mg).

Efficacy

Clinical activity was observed at all doses, increasing substantially with dose escalation.

Among patients with aggressive B-NHL (DLBCL, trFL, PMBCL, MCL, Richter's transformation), ORR and CRR were 48.0% (61/127) and 33.1% (42/127) respectively, including 41.1% (30/73) and 28.8% (21/73), respectively, in patients with DLBCL, and 55.2% (16/29) and 34.5% (10/

29), respectively, in patients with trFL (FIG. 9). At doses ≥10 mg, ORR and CRR among patients with aggressive B-NHL were 60.9% (42/69) and 49.3% (34/69), respectively, including 55.3% (21/38) and 42.1% (16/38), respectively, for DLBCL, and 64.3% (9/14, all CRs) for trFL (FIG. 9). At the RP2D, ORR and CR were 71.4% (10/14) and 64.3% (9/14), respectively in patients with aggressive B-NHL (FIG. 9).

Of 44 patients with Grade 1-3A FL, 21 (47.7%) achieved CR. At doses ≥10 mg, ORR and CR rates were 69.0% (20/29) and 58.6% (17/29), respectively, and at the RP2D 61.9% (13/21) and 52.4% (11/21), respectively.

Time to CR was short, with the majority occurring by cycle 3. Responses were observed across patient subgroups, including high-risk populations with ≥4 prior regimens and refractory disease.

In patients with aggressive NHL, median DOR was 5.5 months (95% CI, 4.4—Not Estimable [NE]; range: 0.8-28.8 months) and median DOCR was not reached (range: 0.0-27.4 months), with 48.6% (any response) and 72.8% (CR) of patients still responding at 12 months. Median PFS was 2.9 (95% CI, 2.1-3.9) months, with an estimated PFS of 34.8% at 6 months and a plateau of approximately 24% from 8 months onwards (to a maximum follow-up of 30 months). In patients with Grade 1-3A FL, median PFS was 11.8 months (95% CI, 6.3-24.2). Of the 31 responders, median DOR was 10.8 months (95% CI, 3.8-NE). Median DOCR was not reached and 19/21 (90.5%) patients remain in CR up to 22.9 months.

Pharmacokinetics

Following IV infusion, glofitamab serum concentrations peak at the end of the infusion and decline in a biphasic manner thereafter. Glofitamab appears to be eliminated with an apparent half-life of 6 to 11 days, and demonstrated dose-linear pharmacokinetics across the 0.005 to 25 mg range. There was no evidence of either substantial accumulation or time-dependence upon multiple dosing across treatment cycles. Overall, glofitamab pharmacokinetics showed moderate between-patient variability. Median (range) obinutuzumab serum concentration at baseline (before first glofitamab administration) was 249 (98.4-858) μg/ml. Anti-glofitamab antibodies were not detected in any patient.

Pharmacodynamics

Biomarker data were obtained from 122 patients dosed with glofitamab 0.005 mg to 25 mg. Glofitamab infusion resulted in a rapid and transient reduction in T cells in the peripheral circulation in all patients, with the nadir recorded 6 hours after the infusion. This T-cell redistribution was associated with dose level and receptor occupancy. Following administration of glofitamab ≥0.6 mg, responding patients showed long-term T-cell activation up to cycle 5. This was demonstrated by two-to-fourfold elevation of T-cell activation markers, such as Ki67, HLA-DR, PD-1, and Tim3. In line with the clinical activity, this was not observed at doses below 0.6 mg.

Discussion

This study demonstrated that the novel bispecific CD20 antibody T-cell engager glofitamab offers significant antitumor activity in patients with heavily pretreated B-NHL refractory to prior therapy (90.6%).

CRS was manageable with moderate (25%) use of steroids or tocilizumab. CRS events fully resolved in all but five patients with no treatment withdrawals due to CRS. Time to onset of CRS was predictable and mostly confined to the first administration; only 13.1% and 6.1% of patients experienced CRS at Cycles 2 or at Cycle 3 or later, respectively. Factors associated with severe CRS included high disease burden (Ann Arbor stage) and bone marrow infiltration (data not shown). Use of Gpt to mitigate the risk of CRS allowed escalation of glofitamab to clinically active doses. While overall CRS rates were similar between the highest fixed-dosing cohorts and the step-up dosing cohorts, step-up dosing reduced the frequency of Grade 2 or higher CRS and was therefore selected as RP2D (Grade ≥2; 47.8% in the ≥10 mg fixed-dosing versus 28.6% in the 2.5/10/30 mg step-up dosing cohort).

ICANS-like neurological AEs were observed; these were mostly headache, mild and self-limiting and considered qualitatively different to those seen with anti-CD19 CAR-T therapies and bispecifics where neurological toxicity is dose limiting. Treatment-emergent cytopenias did not lead to increased rates of serious infections or the need for transfusion. No unexpected safety signals were observed; the discontinuation rate of 2.9% due to AEs suggests a favorable benefit-risk profile.

High response rates were observed. At doses ≥10 mg, CR rates were 49.3% in patients with aggressive B-NHL, and 42.1% and 64.3% in patients with DLBCL and trFL, respectively. CRs were achieved rapidly in patients with high tumor burden, bulky disease, and refractoriness to multiple therapies including ASCT. Duration of benefit assessment was impaired by limited follow-up, but 34/42 (81.0%) CRs in patients with aggressive histologies are ongoing with follow-up up to 27.4 months. In addition, SUD maintained the high ORR and CR rates observed in the cohorts receiving fixed dosing.

Pharmacokinetic results indicate that the half-life of glofitamab is in the range of 7 days, enabling convenient dosing (every 3 weeks). As both obinutuzumab and glofitamab bind to the same CD20 epitope, the observed concentration profiles, alongside biomarker and clinical data, support potent glofitamab activity despite CD20 receptor competition. The preservation of clinical activity in the presence of residual or in combination with another anti-CD20 monoclonal antibody represents a unique benefit of glofitamab. The high potency of glofitamab is further supported by population pharmacokinetic and exposure-response analyses, confirming efficacy at CD20 receptor occupancies by Cycle 3 of <1%, 20 which is achievable at the dose levels evaluated in this study. Based on these analyses, SUD was introduced to decrease incidence and severity of CRS in the first dosing cycle. A weekly dosing schedule of 2.5 mg (day 1), 10 mg (day 8), 30 mg (day 15) followed by 30 mg at subsequent dosing cycles in a three-weekly regimen was considered safe, demonstrated clinical activity in the range of the highest non-fractionated dose levels, and was taken forward as RP2D.

Glofitamab is an available and accessible 'off-the-shelf' T-cell engaging therapy. These properties contrast with those of current CAR-T cell therapies, which require manufacturing, may require bridging therapy and may not be feasible in patients with rapidly progressive disease. So far, the clinical activity of glofitamab appears to exceed that of blinatumomab and to be in the range of registered CAR-T therapies with possibly a more favorable safety profile. The observation of rapidly achieved CRs lasting more than 18 months across a range of doses suggests that glofitamab is highly active in a difficult-to-treat patient group with few clinical treatment options.

In conclusion, this novel T-cell-engaging bispecific antibody has shown high levels of single-agent activity in R/R B-NHL. Glofitamab has demonstrated frequent, durable CRs, a manageable tolerability profile, and allows off-the-shelf treatment for refractory B-NHL patients in need of timely therapy.

Example 3—Model for Decreasing CRS

Introduction: Glofitamab (RG6026; R07082859; CD20-TCB) is a novel '2:1' format T-cell-engaging bispecific antibody that has two CD20 binding domains and one CD3 binding domain, enabling increased tumor antigen avidity, rapid T-cell activation, and enhanced tumor cell killing in B-cell malignancies. Clinical data from NP30179 demonstrated that fixed dosing of glofitamab (0.6-25 mg) induced high and durable complete responses with a manageable safety profile in heavily pre-treated R/R NHL patients (pts; Dickinson, et al. EHA 2020). Obinutuzumab pretreatment (Gpt) 7 days prior to first administration of glofitamab was shown to be effective in mitigating the risk of cytokine release syndrome (CRS), allowing for rapid escalation of glofitamab to clinically active doses (Dickinson, et al. EHA 2020). We previously investigated population pharmacokinetics (popPK) and exposure-response (ER) relationships for glofitamab in NP30179; NCT03075696 (Djebli N, et al. Blood 2019), where modelling indicated step-up dosing would further mitigate CRS while maximizing efficacy. The present analysis is an update of previous models, including confirmatory data from the first step-up dosing (SUD) pts.

Methods: Pts with indolent (i) or aggressive (a) R/R NHL received glofitamab fixed dosing (0.005-25 mg every 2 or 3 weeks) or SUD (n=31, 2.5/10/16 and 2.5/10/30 mg) following single Gpt 1000 mg on Cycle (C) 1 Day −7 to mitigate CRS. Serial and sparse glofitamab, and sparse G PK data were used to develop a popPK model in NONMEM® software (v7.4). The cut-off date of Apr. 17, 2020, enabled inclusion of 16 (2.5/10/16 mg) and 15 (2.5/10/30 mg) SUD pts. Physiologically relevant covariates were investigated for their potential influence on glofitamab PK variability. Using the established G popPK model (Gibiansky, et al. CPT Pharmacometrics Syst Pharmacol 2014), G concentration-time profiles were constructed to estimate glofitamab receptor occupancy (RO %) in the presence of G competing for CD20 receptors over time. The relationship between glofitamab AvgRO % over the first 24 hours and CRS, with a focus on Grade (Gr) ≥2 CRS (defined by ASTCT criteria [Lee et al., *Biol Blood Marrow Transplant,* 25(4): 625-638, 2019]) was investigated in iNHL and aNHL pts combined. ER relationships between glofitamab time-averaged RO % (AvgRO %) up to C3 Day 1, which is when the first response assessment was taken, and complete response rate (CRR) were characterized in aNHL pts who reached C3 Day 1.

Results: PopPK were analyzed in 230 iNHL and aNHL pts with ≥1 PK sample (fixed and SUD). ER relationships were analyzed in 95 aNHL pts with PK/efficacy data at C3D1, and in 204 iNHL and aNHL pts with PK/safety data. Glofitamab PK were best described using a two-compartment PK model with linear clearance and were comparable in pts with iNHL and aNHL. The effect of bodyweight on volumes and clearances was retained. Positive ER relationships were observed between AvgRO % over the first 24 hours and Gr ≥2 CRS in both iNHL and aNHL pts (p=0.002), and between AvgRO % up to C3D1 and efficacy in aNHL pts (p=0.008). Based on previous ER analyses (Djebli, et al. Blood 2019) of data from pts receiving fixed dosing, a SUD regimen (2.5/10/30 mg Q3W) was selected to optimize the benefit/risk profile by beginning treatment at a dose to have CRS at manageable levels whilst allowing escalation to a higher dose associated with better clinical response. Updated ER analysis from fixed (n=199) and SUD (n=31) pts predicts an AvgRO % in the first 24 hours of 0.16% (0.10-0.29%), corresponding to a predicted Gr≥2 CRS rate of 23.3% (20.8-26.8%) in iNHL and aNHL pts, and an AvgRO % to C3D1 of 0.75% (0.49-1.98%) corresponding to an anticipated CRR at Cycle 3 of 46.1% (42.7-53.8%) in aNHL pts. In comparison, clinical data from aNHL and iNHL pts receiving 2.5/10/16 and 2.5/10/30 mg SUD (Hutchings, et al. ASH 2020) demonstrated a Gr≥2 CRS rate of 21.6% following the 2.5 mg glofitamab dose (n=37), and a complete metabolic response rate of 40.6% (n=32).

Conclusions: Glofitamab PopPK and ER relationships for efficacy/safety were updated, including data from SUD pts. These models and emerging SUD clinical data confirm that in NHL pts, the SUD regimen allowed glofitamab escalation up to 30 mg to maximize efficacy while minimizing the risk of increased CRS at the first administration. These models are being developed further to support optimal biological-dose selection of glofitamab, both as monotherapy and in combination with other agents.

Example 4—Glofitamab Step-Up Dosing Induces High Response Rates in Patients with Hard-to-Treat Refractory or Relapsed Non-Hodgkin Lymphoma Introduction: Glofitamab (RG6026) is a novel T-cell-engaging, bispecific, full-length antibody with a 2:1 molecular configuration that facilitates bivalent binding to CD20 on B-cells, and monovalent binding to CD3 on T-cells. Preclinically, glofitamab had superior potency compared with other tested bispecifics with 1:1 formats (Bacac, et al. *Clin Cancer Res* 2018). NP30179 (NCT03075696) is an ongoing multicenter, Phase I/Ib, dose-escalation and dose-expansion trial evaluating the safety, tolerability, pharmacokinetics, biomarker responses, and efficacy of glofitamab in patients (pts) with relapsed or refractory (R/R) non-Hodgkin lymphoma (NHL). Clinical data from NP30179 demonstrated that fixed dosing of glofitamab (0.6-25 mg) induced high and durable complete responses with a manageable safety profile in pts with heavily pre-treated R/R NHL (Dickinson, et al. EHA 2020). Obinutuzumab pretreatment (Gpt) was shown to be effective in mitigating the risk of cytokine release syndrome (CRS), allowing for rapid escalation of glofitamab to clinically active doses (Dickinson, et al. EHA 2020). Step-up dosing of glofitamab was used in addition to Gpt to further reduce the risk of CRS. This is the first presentation of clinical data of glofitamab step-up dosing with Gpt in pts with R/R NHL.

Methods: Pts received 1000 mg obinutuzumab 7 days prior to first glofitamab administration. Glofitamab was given intravenously with step-up dosing on Cycle (C) 1 Day 1 and 8 and then at the target dose from C2D1, every 3 weeks for up to 12 cycles (2.5/10/16 mg or 2.5/10/30 mg). Response rates reported are based on the Lugano criteria (Cheson, et al. *J Clin Oncol* 2014).

Results: As of Apr. 17, 2020, 38 pts received step-up doses of glofitamab; 17 pts received 2.5/10/16 mg, and 21 pts received 2.5/10/30 mg. Twenty-eight pts (73.7%) had aggressive NHL (aNHL) histologies and ten pts had indolent NHL (iNHL). The median age was 68 years (range 52-85) and median number of prior lines of therapy was 3 (range 1-12). Twenty-seven (71.1%) pts were refractory to their last therapy, and 28 (73.7%) pts were refractory to prior CD20 therapy.

After a median follow-up of 2.8 months, across all efficacy-evaluable pts (n=32) the overall response rate (ORR) and complete metabolic response (CMR) rate was 62.5% and 40.6%, respectively. For pts with aNHL (n=24), the ORR was 50.0% with CMR rates of 29.2%. As of the data cut-off date, 17 pts with aNHL (70.8%) had reached the first response assessment only (C3) and remain on treatment; four pts (16.7%) had reached the second response assessment (C6). For pts with iNHL (n=8), the ORR was 100.0% with 75.0% of pts achieving CMR.

Across the safety-evaluable population (n=38), the most common AEs were CRS (57.9%), pyrexia (31.6%), neutropenia, thrombocytopenia and hypophosphatemia (28.9% each). No AEs led to treatment discontinuation. Of 22 patients who experienced CRS events, the CRS events only occurred in C1 and C2; 15 had CRS after the 2.5 mg dose, 12 after the 10 mg dose, and 5 during C2 (16 or 30 mg dose; FIG. 11). Eight pts (21.1%) and 13 pts (34.2%) experienced Grade (Gr) 1 and 2 CRS, respectively; none experienced Gr 3 CRS. One pt (2.6%) experienced Gr 4 CRS after the 30 mg dose. No CRS events occurred after C2. Tocilizumab was used to manage CRS in six (15.8%) pts: n=2 for 2.5/10/16 mg and n=4 for 2.5/10/30 mg cohorts. CRS events were manageable and resolved for 21 pts (95.4%) at data cut-off. No Gr ≥3 neurologic adverse events were reported.

- CRS events were confined to C1 and C2.
- Median time to CRS from the first glofitamab dose was 14.23 hrs with median duration of 28.7 hrs
- One patient with FL experienced a Grade 3 CRS after 2.5 mg dose (achieved CR; on treatment) and one patient with MCL experienced Grade 4 CRS after the 30 mg dose (experienced PD)
- Tocilizumab was used to manage CRS in 8 (15.4%) patients Consistent with prior biomarker data from fixed-dose regimens, glofitamab administered with step-up dosing induced a transient T-cell redistribution.

Conclusions: Step-up dosing of glofitamab allowed escalation up to 30 mg to maximize efficacy, while minimizing the risk of increased CRS. High ORR and CMR rates were observed in pts with NHL who had failed several lines of treatment. Toxicity was manageable with the main safety signal being low-grade CRS observed in early cycles.

Thus, step-up dosing of glofitamab is a useful CRS mitigation strategy in addition to obinutuzumab [GAZYVA®] pretreatment, allowing administration of a high glofitamab target dose of 30 mg, higher than the maximum tolerated dose, when using fixed-dose regimen and with a lower risk of CRS Grade 2 or higher.

FIG. 10 shows that a high response to glofitamab was maintained with step up dosing. The newly introduced step-up dosing schedule with glofitamab shows strong clinical activity with high CR rates. Table 7 below provides updated response rates of the same cohort (SUD) as depicted in FIG. 10, now including 8 missing responses and additional patients which had their C6 or later response assessment. The new data indicate higher response rates with the SUD regimen compared to the set dosing as depicted in FIG. 10.

TABLE 7

Updated response rates for SUD cohort in study NP30179

| | SUD iNHL (FL1-3A) 2.5/10/30 mg N = 21 | SUD aNHL 2.5/10/30 mg N = 14 |
|---|---|---|
| ORR | 16 (76.2%) | 11 (78.6%) |
| CMR | 15 (71.4%) | 10 (71.4%) |
| PMR | 1 (4.8%) | 1 (7.1%) |
| NMD | 1 (4.8%) | 1 (7.1%) |
| PMD | 3 (14.3%) | 1 (7.1%) |
| Missing | 1 (4.8%) | 1 (7.1%) |

FIG. 11 shows CRS severity of unchanging, set dosing versus step up dosing. Step up dosing allows administration of a high target dose of glofitamab. While the overall CRS rates were similar between the fixed dosing and step-up dosing cohorts, step up dosing reduced the frequency of high-grade CRS (Grade 2; 36.3% in the 10 mg fixed dosing versus 30.7% in the step-up dosing cohort).

Example 5—Glofitamab Monotherapy Provides Durable Responses after Fixed-Length Dosing in Relapsed/Refractory (R/R) Non-Hodgkin Lymphoma (NHL) Patients (Pts)

Here, we present updated data from the glofitamab monotherapy fixed-dosing and SUD cohorts of study NP30179 in pts with R/R NHL. Step-up dosing (SUD) of glofitamab, in addition to Gpt, allowed dose escalation up to 30 mg to maximize efficacy, while mitigating cytokine release syndrome (CRS).

Methods: Pts received 1000 mg obinutuzumab seven days prior to first glofitamab administration. Glofitamab was given intravenously at a fixed dose (0.6-25 mg) every two weeks (q2w) or every three weeks (q3w) or with SUD (2.5/10/16 mg or 2.5/10/30 mg) on Cycle (C) 1 Day 1 and 8, and then at the target dose from C2 Day 1 q3w, for up to 12 cycles. Response rates reported are based on Lugano criteria (Cheson et al. *J Clin Oncol.* 2014, 32(27): 3059-3067).

Results: As of May 18, 2021, 216 pts were enrolled into the previously specified cohorts. The median age was 64.0 (range, 22-86) years, 63.0% were male, and the median number of prior therapies was three (range, 1-12). A total of 146 (67.6%) pts had aggressive NHL (aNHL), and 70 (32.4%) had indolent NHL (iNHL). Of the pts with aNHL, 77 pts had DLBCL, 26 had mantle cell lymphoma, 22 had transformed follicular lymphoma (FL), and 8 pts had Richter's transformation. All pts with iNHL had Grade 1-3A FL. Response rates are reported across all doses investigated (Tables 8 A and B). In efficacy-evaluable pts with aNHL (n=138), the overall response rate (ORR) was 57.2% and the CR rate was 43.5%. At the clinical cut-off date (CCOD), the median duration of follow-up was 13.3 (range, 0-32) months. The median duration of CR had not yet been reached (95% confidence interval [CI], 12.1—not estimable [NE], n=60) (FIG. 13); 71.7% of pts with a CR (43/60) were still in CR at the time of analysis. The median DoR (CR plus partial response) had not yet been reached (95% CI, 6.0-NE; responders, n=79). In pts with iNHL (n=70), the ORR was 81.4% and CR rate was 70.0%. At the CCOD, median follow-up was 6.7 (range, 0-24) months. The median duration of CR had not yet been reached (95% CI, 10.5-NE, n=49) (FIG. 13); 81.6% of pts with a CR (40/49) were still in CR at the time of the analysis. The median DoR was 13.5 months (95% CI, 8.60-NE; responders, n=57). The overall safety profile of glofitamab was consistent with its mechanism of action. A total of 127/216 pts (58.8%) experienced a serious adverse event (AE). CRS was the most prevalent AE, occurring in 136/216 pts (63.0%), which included: Grade (Gr) 1-2, 126 (58.3%) pts; Gr 3, eight (3.7%) pts; Gr 4, two pts (0.9%); the majority of CRS events were mild. Four pts (1.9%) experienced a glofitamab-related AE that led to withdrawal of the study drug. Seventy-five (34.7%) pts experienced a neurological AE; the majority of events were Gr 1 (44/216; 20.4%) or Gr 2 (30/216; 13.9%). One pt experienced a Gr 3 neurological AE (facial paralysis), which was considered unrelated to glofitamab treatment.

Conclusions: The current dataset on duration of response is the largest presented to date for a CD20-CD3 bispecific antibody. Glofitamab, with a fixed treatment duration and 'off-the-shelf' accessibility, has demonstrated high levels of monotherapy activity in heavily pretreated pts with R/R NHL, who have received two or more lines of systemic therapy. Glofitamab has shown promising response rates and durable responses across a range of different doses for both aNHL and iNHL. Duration of responses in pts with aNHL were in the range of those observed in pts with refractory aNHL from an early CAR-T data set (Neelapu, et al. *N. Engl. J. Med.* 2017, 377: 2531-2544).

TABLE 8A

Summary of clinical efficacy (efficacy-evaluable population)

| | aNHL (n = 138) | iNHL (n = 70) |
|---|---|---|
| Overall response rate, | | |
| N (%) | 79 (57.2) | 57 (81.4) |
| 95% Confidence Interval | [48.6, 65.6] | [70.3, 89.7] |
| Complete response | | |
| N (%) | 60 (43.5) | 49 (70.0) |
| 95% Confidence Interval | [35.1, 52.2] | [57.9, 80.4] |
| Partial response | | |
| N (%) | 19 (13.8) | 8 (11.4) |
| 95% Confidence Interval | [8.5, 20.7] | [5.1, 21.3] |

TABLE 8B

Summary of clinical efficacy (efficacy-evaluable population), updated data

| | aNHL, all doses (n = 175) | aNHL, RP2D 2.5/10/30 mg (n = 14) | iNHL, all doses (n = 75) |
|---|---|---|---|
| Overall response rate, n (%) | 94 (53.7) | 11 (78.6) | 61 (81.3) |
| [95% CI] | [46.0, 61.3] | [42.9, 95.3] | [70.7, 89.4] |
| Complete response rate, n (%) | 69 (39.4) | 10 (71.4) | 52 (69.3) |
| [95% CI] | [32.1, 47.1] | [41.9, 91.6] | [57.6, 79.5] |
| Partial response rate, n (%) | 25 (14.3) | 1 (7.1) | 9 (12.0) |
| [95% CI] | [9.5, 20.4] | [0.2, 33.9] | [5.6, 21.6] |

Example 6—Treatment of Mantle Cell Lymphoma (MCL) and GAZYVA® Double-Pretreatment (DGpt)

The aim of this investigation was to assess if an increased dose of obinutuzumab prior to the first dose of glofitamab can further help to reduce the occurrence and severity of CRS. DGpt was tested in separate cohorts with Glofitamab monotherapy. Table 9 shows the MCL patients treated with Glofitamab in study NP30179. One cohort received a fixed dose regimen of glofitamab with a single dose GAZYVA® pretreatment (1000 mg on C1 Day −7), the second cohort received a step-up dosing regimen of glofitamab with a single dose GAZYVA® pretreatment (1000 mg on C1 Day −7) and a third cohort received a step-up dosing regimen of glofitamab with a double pre-treatment with obinutuzumab (DGpt) prior to first dose of glofitamab, i.e., two doses of Gpt were administered 7 days before the first dose of glofitamab (2 ×1000 mg on C1 Day −7). In this cohort, glofitamab was given at 2.5/10/30 mg on day 1 of dosing cycle 1, day 8 of dosing cycle 1, and day 1 of dosing cycle 2.

TABLE 9

MCL patients treated with Glofitamab in study NP30179. SUD = Step-up dosing, DGpt = Double GAZYVA ® pretreatment (2000 mg on D-7)

| Fixed dosing | | SUD (2.5/10/16 or 2.5/10/30 mg) | | DGpt + 2.5/10/30 mg | |
|---|---|---|---|---|---|
| Dose/regimen | N | Dose/regimen | N | Dose/regimen | N |
| 0.6 mg | 1 | 2.5/10/16 mg | 2 | 2.5/10/30 mg | 11 |
| 16 mg (G-combo) | 1 | 2.5/10/30 mg | 3 | | |
| 25 mg | 1 | 2.5/10/30 mg (G-combo) | 1 | | |
| TOTAL | 3 | TOTAL | 6 | TOTAL | 11 |

Tables 10, 11A, and 11B summarize CRS frequency and severity in MCL patients in study NP30179 and Table 12 summarizes response rates in MCL patients treated with Glofitamab monotherapy and GAZYVA® pretreatment (Gpt) at 1000 mg or "double" GAZYVA® (DGpt) pretreatment at 2000 mg on Day −7.

TABLE 10

CRS frequency and severity in MCL patients in study NP30179 SUD = Step-up dosing, DGpt = Double GAZYVA ® pretreatment (2000 mg on D-7)

| ASTCT | Fixed dosing and SUD (n = 9) | DGpt + 2.5/10/30 mg (n = 11) |
|---|---|---|
| Any grade CRS | 7 (78%) | 3 (27.3%) |
| Grade 1 | 5 (55%) | 2 (18.2%) |
| Grade 2 | 1 (11%) | 1 (9.0%) |
| Grade 3 | 0 | 0 |
| Grade 4 | 1 (11%) | 0 |

TABLE 11

CRS frequency and severity per dose in MCL patients
A: SUD (2.5/10/16 or 2.5/10/30 mg) Monotherapy

| ASTCT | 1st dose 2.5 mg (n = 6) | 2nd dose 10 mg (n = 6) | 3rd dose 16 mg (n = 2) | 3rd dose 30 mg (n = 4) |
|---|---|---|---|---|
| Any Grade | 50% (3/6) | 33% (2/6) | 0 | 50% (2/4) |
| Grade 1 CRS | 33% (2/6) | 33% (2/6) | 0 | 25% (1/4) |
| Grade 2 CRS | 17% (1/6) | 0 | 0 | 0 |
| Grade 3 CRS | 0 | 0 | 0 | 0 |
| Grade 4 CRS | 0 | 0 | 0 | 25% (1/4) |

TABLE 11

CRS frequency and severity per dose in MCL patients
B: DGpt + 2.5/10/30 mg Monotherapy

| ASTCT | 1st dose 2.5 mg (n = 11) | 2nd dose 10 mg (n = 11) | 3rd dose 30 mg (n = 8) |
|---|---|---|---|
| Any Grade | 27.3% (3/11) | 0 | 0 |
| Grade 1 CRS | 18.2% (2/11) | 0 | 0 |
| Grade 2 CRS | 9.1% (1/11) | 0 | 0 |
| Grade 3 CRS | 0 | 0 | 0 |
| Grade 4 CRS | 0 | 0 | 0 |

TABLE 12

Response rates in MCL patients with Glofitamab monotherapy

| | Fixed dosing, n = 2 (0.6 mg*, 25 mg) | SUD , n = 6 (2.5/10/16 mg n = 2, 2.5/10/30 mg n = 3) | DGpt + 2.5/10/30 mg n = 1 | All treatments n = 9 |
|---|---|---|---|---|
| ORR | 100% (2/2) | 83% (5/6) | 100% (1/1) | 89% (8/9) |
| CR | 100% (2/2) | 83% (5/6) | 100% (1/1) | 89% (8/9) |

Example 7—Glofitamab Step-Up Dosing (SUD) Induces High Response Rates in Patients (Pts) with Hard-to-Treat Relapsed or Refractory (R/R) Mantle Cell Lymphoma (MCL)

MCL is an aggressive subtype of non-Hodgkin lymphoma (NHL) and pts with progressive disease following Bruton's tyrosine kinase inhibitor (BTKi) therapy have a poor prognosis (Martin et al. *Blood.* 2016, 127(12): 1559-1563). Here, we report preliminary efficacy and safety data from the NP30179 Phase I/II trial in pts with R/R MCL who received a single (1000 mg) or double (2000 mg) dose of Gpt (DGpT) prior to glofitamab monotherapy.

Methods: All pts received Gpt 7 days prior to the first glofitamab dose. Intravenous glofitamab SUD was administered on Days 1 and 8 of Cycle (C) 1, then at the target dose from C2 Day 1 (from C3 Day 1 for extended SUD, n=1), every 3 weeks for up to 12 cycles (0.5/2.5/10/30 mg, 2.5/10/16 mg or 2.5/10/30 mg after 1000 mg of Gpt, or 2.5/10/30 mg after 2000 mg of Gpt). Pts in the fixed dosing cohort received a fixed dose of glofitamab (0.6 mg, 16 mg or 25 mg) after 1000 mg of Gpt from C1 for up to 12 cycles. Response rates are based on the Lugano criteria (Cheson et al. *J Clin Oncol.* 2014, 32(27): 3059-3067).

Results: As of 18 May 2021, 29 pts with MCL had received glofitamab: fixed dosing (n=3); SUD after 1000 mg of Gpt (n=7) or after 2000 mg of DGpt (n=19). Median age was 69 years (range, 41-84), 69% of pts were male, 41.4% had an ECOG performance status of 1, 83% had Ann Arbor Stage III-IV and 62.1% had a MCL international prognostic index score ≥6 at study entry. Most pts (69%; n=20) had received ≥3 prior lines of therapy, with 69% (n=20) previously treated with BTKi therapy and 14% (n=4) with lenalidomide. Median prior lines of therapy was 3. Most pts were refractory to their first prior therapy (51.7%; n=15) and more were refractory to their last prior therapy (69.0%; n=20). Median time since last therapy was 1.7 months (range, 0.1-107.5).

In efficacy-evaluable pts (n=21), the overall response rate (ORR) was 81.0% (n=17) and complete metabolic response rate (CMR) was 66.7% (n=14; Table 13). No pts had progressive metabolic disease as their best overall response. When stratified by pts who had received prior BTKi therapy, similar response rates were observed (ORR, 82.4%; CMR, 64.7%; Table 14). Median duration of CR follow-up was 2.4 months; 85.7% (12/14) of pts who achieved a CR remained in remission at the data cut-off (median duration of response and median duration of CR were not reached).

In safety-evaluable pts (n=29), the most common adverse events (AEs) were CRS (58.6%) and infusion-related reactions (24.1%). All CRS events were Gr 1-2 (by ASTCT criteria), except for one Gr 4 CRS (pt died due to cardiopulmonary insufficiency as a result of rapid disease progression; at time of death CRS was persisting) in the 1000 mg Gpt+SUD cohort (3.4%).

CRS rates were lower in the 2000 mg DGpt+SUD cohort (47.4%) vs the 1000 mg Gpt+SUD (71.4%) and 1000 mg Gpt+fixed dosing (100%) cohorts. Overall, median time to first CRS event and duration of CRS event were 16.8 hrs and 38.8 hrs, respectively. All CRS events were manageable and most resolved at data cut-off. Neurologic AEs, by Nervous System and Psychiatric Disorder SOCs, were observed in 6 pts (20.7%, all Gr 1 [n=5] or 2 [n=1]). No pts discontinued treatment due to AEs. Three deaths were reported and considered unrelated to study treatment: progressive disease (n=2); cardiac arrest (n=1).

Conclusions: Glofitamab SUD as monotherapy following Gpt induced high response rates in pts with MCL, most of whom had failed prior BTKi therapy. CRS rates were manageable and mostly low grade. No treatment discontinuations due to AEs were observed.

TABLE 13

Response rates stratified according to glofitamab regimen in pts with MCL

| % (95% CI) | Fixed dosing (n = 3) | SUD (n = 7) | SUD + DGpT (n = 11) | All pts (N = 21) |
|---|---|---|---|---|
| ORR | 66.7 (9.4-99.2) | 71.4 (29.0-96.3) | 90.9 (58.7-99.8) | 81.0 (58.1-94.6) |
| CMR | 66.7 (9.4-99.2) | 71.4 (29.0-96.3) | 63.6 (30.8-89.1) | 66.7 (43.0-85.4) |
| PMR | 0 | 0 | 27.3 (6.0-61.0) | 14.3 (3.1-36.3) |

TABLE 14

| Response rates stratified according to prior BTKi therapy in pts with MCL receiving glofitamab | | | |
|---|---|---|---|
| % | Prior BTKi therapy | | |
| (95% CI) | Yes (n = 17) | No (n = 4) | All pts (N = 21) |
| ORR | 82.4 (56.6-96.2) | 75.0 (19.4-99.4) | 81.0 (58.1-94.6) |
| CMR | 64.7 (38.3-85.8) | 75.0 (19.4-99.4) | 66.7 (43.0-85.4) |
| PMR | 17.6 (3.80-43.4) | 0 | 14.3 (3.1-36.3) |

Example 8—Extended Step-Up Dosing in Follicular Lymphoma Grade 1-3A Patients

In the extended step-up (eSUD) dosing for Follicular Lymphoma Grade 1-3A (FL1-3A) patients, an initial lower dose of glofitamab (0.5 mg) was administered on day 1 of dosing cycle 1, 2.5 mg of glofitamab was administered on day 8 of dosing cycle 1, followed by an intermediate dose of 10 mg in Cycle 2 (day 1 of dosing cycle 2) and the first administration of the target treatment dose (30 mg) is in Cycle 3 (day 1 of dosing cycle 3). Data were compared to a FL1-3A patient cohort which received glofitamab monotherapy in step-up dosing (SUD) with 2.5 mg at day 1 of dosing cycle 1, 10 mg at day 8 of dosing cycle 1 and 16 or 30 mg at day 1 of dosing cycle 2 and with a FL1-3A patient cohort which received glofitamab step-up dosing (SUD) with 2.5 mg at day 1 of dosing cycle 1, 10 mg at day 8 of dosing cycle 1 and 30 mg at day 1 of dosing cycle 2 in combination with 1000 mg GAZYVA® as of day 1 of dosing cycle 2 ("G-Combo", see FIG. 12). All cohorts received GAZYVA® pretreatment of 1000 mg GAZYVA® 7 days before the start of the first dosing cycle. FIG. 12 depicts an overview of SUD, G-combo and e-SUD regimens in FL1-3A patients. Table 15 summarizes CRS frequency and severity in FL1-3A patients treated with glofitamab monotherapy SUD, glofitamab SUD combined with GAZYVA® and glofitamab monotherapy eSUD. Table 16 summarizes response rates in FL1-3A patients which received 30 mg of glofitamab as target dose.

TABLE 15

| CRS frequency and severity in FL 1-3A patients | | | |
|---|---|---|---|
| ASTCT Grading | SUD (2.5/10/16 & 2.5/10/30 mg) N = 24 | SUD G-Combo (2.5/10/30 mg) N = 19 | eSUD (0.5/2.5/ 10/30 mg) N = 20 |
| Any grade CRS | 19 (79.2%) | 15 (78.9%) | 11 (55%) |
| Grade 1 | 15 (62.5%) | 10 (66.7%) | 7 (35%) |
| Grade 2 | 3 (12.5%) | 5 (33.3%) | 4 (20%) |
| Grade 3 | 1 (4.2%) | — | — |

TABLE 16

| Response rates in FL1-3A patients which received 30 mg of glofitamab as target dose. | | | | |
|---|---|---|---|---|
| | SUD 2.5/10/30 mg N = 21 | SUD G-Combo 2.5/10/30 mg N = 19 | eSUD 0.5/2.5/10/30 mg N = 19 | All FL pts with target dose 30 mg N = 59 |
| ORR | 16 (76.2%) | 19 (100%) | 17 (89.5%) | 52 (88.1%) |

Example 9—Glofitamab as Monotherapy and in Combination with Obinutuzumab Induces High Complete Response Rates in Patients (Pts) with Multiple Relapsed or Refractory (R/R) Follicular Lymphoma (FL)

FL is an indolent, yet incurable disease characterized by recurrent relapses. Pts with R/R FL have a poor prognosis and limited treatment options, particularly those who have progression of disease within 24 months of frontline treatment (POD24) or are refractory to multiple agent classes.

We present updated data from pts with R/R FL treated with glofitamab monotherapy (mono) or in combination with obinutuzumab (combo) SUD cohorts.

Methods: Obinutuzumab (1000 mg) was given to pts 7 days pre-glofitamab initial dose. For the mono cohorts, intravenous glofitamab SUD was given on Days 1 and 8 of Cycle (C) 1; then at target dose on C2, or as extended SUD on day 1 of dosing cycle 1, day 8 of dosing cycle 1, day 1 of dosing cycle 2 and target dose on day 1 of dosing cycle 3. For the combo cohorts, glofitamab SUD was given on days 1 and 8 of C1; then at target dose on day 1 of C2 and obinutuzumab 1000 mg was introduced on day 1 of dosing cycle 2. Glofitamab and obinutuzumab were continued every 21 days, for up to 12 cycles. Response rates were based on the Lugano criteria (Cheson et al. *J Clin Oncol.* 2014, 32(27): 3059-3067).

Results: As of May 18, 2021, 53 pts received glofitamab mono SUD (2.5/10/16 mg, n=3; 2.5/10/30 mg, n=21; 0.5/2.5/10/30 mg, n=29), and 19 pts received glofitamab combo SUD (2.5/10/30 mg). All pts had FL Grade 1-3A (FLIPI I risk score ≥3: mono, 28 [53%] pts; combo, 11 [58%] pts). Median age was 64 years (range 33-83) in mono cohorts and 61 years (range 41-78) in combo cohorts; median number of prior therapies was 3 (range 1-12) and 2 (range 1-5), respectively. Twenty-eight (53%) pts in the mono cohorts and 8 (42%) pts in the combo cohorts were refractory to last therapy; 16 (30%) and 7 (37%), respectively, were refractory to prior CD20 and alkylating therapy.

In the mono cohorts, overall response rate (ORR) was 81% (n=43) and complete metabolic response rate (CMR) was 70% (n=37), with CMR highest in the 0.5/2.5/10/30 mg cohorts (72% [n=21]; 2.5/10/16 mg [n=2] and 2.5/10/30 mg [n=14] cohorts both 67%). In the combo cohorts, ORR and CMR were 100% and 73.7%, respectively. In the mono cohorts, 87% (32/37) of pts achieving CMR remained in remission at the data cut-off. With a median follow up of 2.5 months, there are currently insufficient follow-up data to fully assess median duration of CMR. In the combo cohorts, 71% (10/14) of pts achieving CMR remained in remission at the data cut-off (median duration of CMR follow up: 4.2 mo; median duration of CMR: not reached). CMR rates observed in high risk pts, including those with double refractory disease were: (mono 8/16 [50%]; combo 3/7 [43%]), POD24 (mono 11/19 [58%], combo (7/10 [70%]), phosphoinositide 3-kinase inhibitor (PI3Ki) refractory (mono 3/7 [43%], combo (1/2 [50%]) and in those who had sum of the product of the diameters ≥3000 mm$^2$ (mono 15/24 [63%], combo 3/7 [43%]).

The most common adverse events (AEs) were CRS (66%), infusion-related reactions and pyrexia (both 28%), and neutropenia (26%) with mono, and CRS (79%), neutropenia (58%), anemia (37%) and thrombocytopenia (32%) with combo. Of mono-treated pts with CRS, 3 (100%) were in the 2.5/10/16 mg cohorts, 16 (76%) in the 2.5/10/30 mg cohorts and 16 (55%) in the 0.5/2.5/10/30 mg cohorts. CRS events (ASTCT; Lee et al., *Biol Blood Marrow Transplant,*

25(4): 625-638, 2019) were mostly Grade (Gr) 1 and 2. In the mono 2.5/10/16 mg cohorts 1 pt had Gr 3 CRS. With combo 52.6% and 26.3% pts had Gr 1 and 2 CRS, respectively. There were no Gr3 CRS events in the combo cohorts and no Gr 4/5 CRS events with either regimen. All CRS events were manageable and resolved at data cut-off. Neurologic AEs (Preferred Terms in system organ class [SOC] Nervous System Disorders and SOC Psychiatric Disorders) were seen in 26 pts (16 mono, 10 combo; 36%); all Gr 1 (n=17) or 2 (n=9). CMR rates for the different high-risk groups are summarized in Table 17.

TABLE 17

CMR rates with glofitamab as monotherapy or in combination with obinutuzumab by high-risk subgroup

| | CMR rate | |
|---|---|---|
| Patients n (%) | Glofitamab monotherapy (n = 53) | Glofitamab in combination with obinutuzumab (n = 19) |
| Double-refractory* | 8/16 (50%) | 3/7 (43%) |
| POD24 | 11/19 (58%) | 7/10 (70%) |
| P13 Ki-refractory | 3/7 (43%) | 1/2 (50%) |
| SPD ≥3000 mm$^2$ | 15/24 (63%) | 3/7 (43%) |

*Pts refractory to anti-CD20 antibodies and alkylating agents

CMR, complete metabolic response; PI3Ki, phosphoinositide 3-kinase inhibitor; POD24, progression of disease within 24 months of frontline treatment; SPD, sum of the product of the diameters Conclusions: Glofitamab SUD administered as monotherapy (mono) or combination therapy (combo) achieved high response rates in pts with heavily pretreated R/R FL, including high-risk subgroups. Response rates were comparable to those reported for CAR-T in R/R FL. The safety profile of glofitamab as mono or combo was manageable; CRS events were mostly low grade and occurred mainly in C1 and C2.

Example 10—Glofitamab Plus R-CHOP Induces High Response Rates with Minimal Cytokine Release Syndrome (CRS) in Patients with Relapsed/Refractory (R/R) Non-Hodgkin Lymphoma (NHL) and Previously Untreated (1 L) Diffuse Large B-Cell Lymphoma (DLBCL): Preliminary Results From a Dose-Escalation and Safety Run-in Phase Ib Study Background: Over a third of patients with 1 L DLBCL do not respond to, or relapse after, rituximab, cyclophosphamide, doxorubicin, vincristine, and prednisone (R-CHOP; [Sarkozy and Sehn. Ann Lymphoma 2019]). Despite recent advances, patients with R/R NHL have limited curative options. Glofitamab is a novel, T-cell-engaging bispecific antibody with a 2:1 molecular configuration that allows bivalent binding to CD20 on B cells and monovalent binding to CD3 on T cells. Unlike other CD20×CD3 bispecific antibodies, this format uniquely enables combination with anti-CD20 antibodies, including rituximab. Glofitamab monotherapy induces high response rates in R/R B-cell NHL (Hutchings et al. J Clin Oncol 2021). In this example, results of the ongoing NP40126 study (NCT03467373) are presented, designed to assess the feasibility and safety of glofitamab+R-CHOP in R/R NHL (dose-escalation phase) and 1 L DLBCL (safety run-in phase). FIG. 14, FIG. 15, and FIG. 16 show a schematic overview of the study arms.

Methods: R/R NHL dose-escalation: Patients (Eastern Cooperative Oncology Group performance status [ECOG PS]0-2) received increasing glofitamab doses in separate cohorts (70 μg, 1800 μg, 10 mg and 30 mg) plus standard R-CHOP for 6-8 cycles (each 21-day). To mitigate CRS risk, R- or obinutuzumab (G)-CHOP was given in Cycle (C)1, with the aim of tumor debulking. Glofitamab was given from C2 onwards. For 70 μg and 1800 μg cohorts, fixed-dose glofitamab was given on C2 Day 8 and onwards. For 10 mg and 30 mg cohorts, step-up dosing was used to further mitigate CRS risk (2.5 mg Cycle 2 Day 8, 10 mg Cycle 2 Day 15, target dose Cycle 3 Day 8 and onwards). Optional glofitamab maintenance was permitted (every 2 months for >2 years; dose-escalation phase only).

R Rituximab: 375 mg/m$^2$; IV D1 for Cycle 1 and/or subsequent dosing cycles during induction Chop:

- Cyclophosphamide: 750 mg/m$^2$; IV on Day 1
- Doxorubicin: 50 mg/m$^2$; IV on Day 1
- Vincristine: 1.4 mg/m$^2$; IV push on Day 1 with a cap of 2 mg
- Prednisone: 100 mg/day orally on Days 1-5 (prednisone on Day 1 may be administered IV, with the remaining doses on Days 2-5 to be administered orally)

1 L DLBCL safety run-in: Patients (ECOG PS 0-3) received glofitamab 30 mg plus standard R-CHOP for 6-8 cycles (each 21-day). Patients received R-CHOP in C1; glofitamab step-up dosing began in C2 (2.5 mg Cycle 2 Day 8, 10 mg Cycle 2 Day 15, 30 mg Cycle 3 Day 8 and onwards).

Response rates were assessed by PET-CT (Lugano criteria; [Cheson et al. *J Clin Oncol* 2014]). CRS events were graded by ASTCT criteria [Lee et al. *Biol Blood Marrow Transplant* 2019].

Results:

R/R NHL dose-escalation: At data cut-off (Jun. 10, 2021), 31 patients (23 follicular lymphoma [FL]; 6 transformed FL; 1 marginal-zone lymphoma; 1 mantle-cell lymphoma) had received glofitamab with R/G-CHOP. Median age was 62 years, median prior lines of therapy was 2 (range: 1-5). In efficacy-evaluable patients (n=31), after a median 9.0 months' (range: 0-29) follow-up, the overall response rate (ORR) was 90% (n=28) and complete response rate (CRR) was 77% (n=24). Median duration of response was not reached. Grade (Gr) ≥3 adverse events (AEs) occurred in 28 (90%) patients, serious AEs in 21 (68%) patients and CRS in 17 (55%) patients (mostly low grade; majority after the first 2.5 mg glofitamab dose; Table 18). One (3%) patient had a Gr 5 AE (COVID-19 pneumonia not related to study treatment). AEs led to glofitamab dose modification/interruption in 2 (6%) patients and glofitamab withdrawal in 1 (3%) patient. Neurologic AEs (NAEs) occurred in 20 (65%) patients: Gr 1-2 (16 pts, 52%); Gr 3 (4 pts, 13%). Immune effector cell-associated neurotoxicity syndrome (ICANS)-like AEs were uncommon; a serious AE was reported in 1 patient only (Gr 3 epilepsy during the maintenance phase; resolved in 3 days). Neutropenia occurred in 24 (77%) patients. Median dose intensity was 100% for all R-CHOP components.

1 L DLBCL safety run-in: At data cut-off, 13 patients were enrolled (safety population); of these, 4 patients received glofitamab 30 mg with R-CHOP and were efficacy-evaluable. Median age was 68 years, all pts had Ann Arbor Stage 3/4 disease. At interim assessment (C3), CRR was 100% (4/4). Of 13 patients, 1 (8%) had a CRS event (Gr 1 with fever only) after the first 2.5 mg glofitamab dose; no other CRS events observed. Gr ≥3 AEs occurred in 8 (62%) patients and Gr ≥3 AEs related to glofitamab in 1 (8%) patient only. One (8%) patient had a serious AE and 1 (8%)

patient had a Gr 5 AE (infusion-related reaction related to rituximab on C1D1). No AEs led to glofitamab or R-CHOP dose interruptions. NAEs occurred in 3 (23%) patients (all Gr 1-2; none were ICANS-like). Neutropenia occurred in 6 (46%) pts. Median dose intensity was 100% for all R-CHOP components.

Conclusions: Initial data show that glofitamab+R-CHOP has tolerable safety in R/R NHL and 1 L DLBCL. R-CHOP dose intensity was maintained in all patients. The very low CRS rate and no neurotoxicity in 1 L DLBCL may render glofitamab particularly suitable for the outpatient setting without the need for hospitalization.

TABLE 18

Summary of CRS

| | R/R NHL dose-escalation phase (N = 31) | IL DLBCL safety run-in phase (N = 13) |
|---|---|---|
| Any Grade CRS, n (%) | 17 (54.8) | 1 (7.7) |
| Grade 1 CRS | 10 (32.2) | 1 (7.7) |
| Grade 2 CRS | 4 (12.9) | 0 |
| Grade ≥3 CRS | 3 (9.7) | 0 |

Example 11—Tolerability of Glofitamab in Combination with Rituximab in Combination with Cyclophosphamide (C), Doxorubicin (H), Vincristine (O), and Prednisone (P) (R-CHOP) in Patients with Previously Untreated Diffuse Large B-Cell Lymphoma (DLBCL)

An overview of safety and efficacy data from Part 2 of Study NP40126 which is currently being conducted, including 13 patients with treatment naïve DLBCL (all treated in the safety run-in group) who have received glofitamab in combination with R-CHOP at the proposed step-up dose (SUD) of 2.5/10/30 mg for at least four combination cycles, is presented.

The 2.5/10/30 mg dose regimen was selected in Part 1 of Study NP40126, which explored escalating doses of glofitamab in combination with standard-of-care doses of obinutuzumab (obinutuzumab pre-treatment [Gpt])/rituximab in combination with CHOP (G/R-CHOP) in patients with relapsed/refractory (R/R) non-Hodgkin's lymphoma (NHL). This dose regimen was utilized in a safety run-in in Part 2 of Study NP40126, prior to the dose expansion cohort being fully opened to recruitment.

13 patients with treatment-naïve DLBCL have received R-CHOP in combination with glofitamab for at least four combination cycles (i.e., at least two cycles at the 30 mg target glofitamab dose) and are beyond Cycle 4, Day 8. At the time point of data analysis, 4 of these patients have reached the end of 6 cycles, and 9 of these patients have completed 5 cycles of glofitamab in combination with R-CHOP with the SUD of 2.5/10/30 mg. This example includes an overview of the study population, in; dose information; safety in terms of CRS, SAEs, and Grade 4 neutropenia; as well as preliminary efficacy data from patients with treatment-naïve DLBCL.

In terms of exposure, all 13 patients have received at least 4 cycles of R-CHOP and the corresponding glofitamab 2.5/10 mg (Cycle 2, Day 8/Day 15) step-up doses followed by two 30 mg target doses on Cycle 3, Day 8 and Cycle 4, Day 8, respectively. No doses of R-CHOP or glofitamab have been reported as missed. Four of these patients have reached the end of 6 cycles, and 9 of these patients have completed 5 cycles of glofitamab in combination with R-CHOP with the SUD of 2.5/10/30 mg. The median dose intensity was 100% of the planned dose for each component of the R-CHOP plus glofitamab regimen. One patient had a vincristine dose reduction in Cycle 5 due to peripheral neuropathy.

In terms of the rates and grades of CRS per glofitamab dose, only a single American Society for Transplantation and Cell Therapy (ASTCT) Grade 1 CRS event has been reported to date.

CONCLUSION

In spite of the progress made in the treatment of patients with DLBCL with the addition of rituximab to CHOP chemotherapy, a significant number of patients are not cured, especially those who present with one or more disease risk factors at diagnosis. Once patients progress, after first line treatment, salvage regimens can induce a second remission, but less than half of patients experience prolonged progression-free survival (PFS) with second-line regimens without autologous stem-cell transplant. Even if patients are eligible for high-dose chemotherapy and autologous stem-cell transplant, less than half will be cured. Therefore, obtaining the best outcome with first-line therapy is critically important for patients with DLBCL.

The proposed target population for Part 2 excludes participants with good prognostic factors (international prognostics indicator [IPI] 0-1), while including participants who may not be adequately treated with standard-of-care therapy (IPI 2-5). Overall the incidence and nature of AEs in the 13 patients with treatment naïve DLBCL who received at least 4 cycles of glofitamab in combination with R-CHOP is in line with the expected safety profile following R-CHOP alone. The addition of glofitamab to R-CHOP appears to have a positive benefit-risk profile in patients with treatment-naïve DLBCL and only a single Grade 1 CRS event has occurred to date. The available data supports continued investigation of glofitamab 2.5/10/30 mg SUD in combination with R-CHOP in patients with treatment naïve DLBCL.

TABLE 19

International Prognostic Index

| Risk Factors | |
|---|---|
| Ann-Arbor Stage III or IV | |
| Age >60 years | |
| Serum LDH > 1 × ULN | |
| ECOG performance score ≥2 | |
| Extranodal involvement ≥2 | |
| **IPI Risk Group** | **Number of IPI Risk Factors** |
| Low | |
| Low-intermediate | |
| High-intermediate | |
| High | |

IPI = International Prognostic Index; ECOG = Eastern Cooperative Oncology Group. ULN = upper limit of normal.
Note:
The results of FDG-PET should not be taken into account for calculation of IPI as this prognostic score was established without FDG-PET
Adapted from Shipp et al. 1993.
REFERENCES: Shipp MA, Harrington DP, Anderson JR, et al. A predictive model for aggressive Non-Hodgkin's Lymphoma. *N Engl J Med* 1993; 329:987-94

TABLE 20

| Eastern Cooperative Oncology Group (ECOG) Performance Status | |
|---|---|
| Grade | ECOG Performance Status |
| 0 | Fully active, able to carry on all pre-disease performance without restriction |
| 1 | Restricted in physical strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of only limited self-care, confined to bed or chair more than 50% of waking hours |
| 4 | Completely disabled. Cannot carry on any self-care. Totally confined to bed or chair |
| 5 | Dead |

Example 12—Glofitamab Monotherapy in Relapsed/Refractory (R/R) Diffuse Large B Cell Lymphoma (DLBCL) Patients (Pts)

Here, we present updated data from the glofitamab monotherapy SUD cohort of study NP30179 in pts with R/R DLBCL. Step-up dosing (SUD) of glofitamab, in addition to Gpt, allowed dose escalation up to 30 mg to maximize efficacy, while mitigating cytokine release syndrome (CRS).

Methods: Pts received 1000 mg obinutuzumab seven days prior to first glofitamab administration. Glofitamab was administered intravenously with SUD (2.5/10/16 mg or 2.5/10/30 mg) on Cycle (C) 1 Day 1 and 8, and then at the target dose from C2 Day 1 q3w, for up to 12 cycles. Response rates reported are based on Lugano criteria (Cheson et al. *J Clin Oncol.* 2014, 32(27): 3059-3067).

Results: As of Sep. 14, 2021, a total of 102 R/R DLBCL pts were efficacy-evaluable. The median age was 67 (range, 21-90) years, and 58 (56.9%) of the pts were 65 or older. Of the 102 patients, 76 (74.5%) pts had de novo DLBCL, 6 (5.9%) pts had high grade B cell lymphoma (HGBCL), 6 (5.9%) had primary mediastinal large B cell lymphoma (PMBCL), and 15 (14.7%) had transformed follicular lymphoma (trFL). 49 patients (48%) had an ECOG score of 0 and 53 patients (52%) had an ECOG score of 1. 15 patients (14.7%) had bulky disease (≥10 cm). 44 patients (43.1%) had bulky disease (≥6 cm). All 102 pts had relapsed after or were refractory to two or more prior lines of therapy, including 86 (84.3%) who were refractory to prior therapy comprising an anti-CD20 antibody. 30 (29.4%) patients were R/R to three prior lines of therapy, 18 (17.6%) were R/R to four prior lines of therapy, and 11 (10.8%) were R/R to five or more prior lines of therapy. 25 (24.5%) patients completed prior therapy >6 months ago, 20 (19.6%) completed prior therapy 3-6 months ago, and 57 (55.9%) patients completed prior therapy <3 months ago. 10 (9.8%) patients were Ann Arbor stage I, 16 (15.7%) patients were Ann Arbor stage II, 18 (17.6%) patients were Ann Arbor stage III, and 58 (56.9%) patients were Ann Arbor stage IV. In efficacy-evaluable patients with R/R DLBCL (n=102), the overall response rate (ORR) was 53.9% and the CR rate was 34.3%.

In safety-evaluable patients (N=107), 68.2% experienced cytokine release syndrome (CRS) of any grade, including 12.1% Grade 2 CRS and 2.8% Grade 3+ CRS. Other AEs of interest included 40 patients (37.4%) with neutropenia (including 28 patients (26.2%) with Grade 3-4 neutropenia), one patient (0.9%) with febrile neutropenia, 22 patients (20.6%) with thrombocytopenia all Grades (including six patients (5.6%) with Grade 3-4 thrombocytopenia), 42 patients (39.3%) with infections all Grades (including 18 patients (16.8%) with Grade 3-5 infections), and 2 patients (1.9%) with peripheral neuropathy all Grade (including none with Grade 3 peripheral neuropathy).

Example 13—Glofitamab Plus R-CHOP in Previously Untreated (1 L) Diffuse Large B Cell Lymphoma (DLBCL) Patients (Pts)—Updated Data Here, we present updated data from the glofitamab+R-CHOP SUD cohort of study NP40126 in pts with 1 L DLBCL. All pts described in this example received glofitamab in combination with R-CHOP at the proposed step-up dose (SUD) of 2.5/10/30 mg.

Methods: R/R NHL dose-escalation: Patients (Eastern Cooperative Oncology Group performance status [ECOG PS]0-2) received increasing glofitamab doses in separate cohorts (70 μg, 1800 μg, 10 mg and 30 mg) plus standard R-CHOP for 6-8 cycles (each 21-day). To mitigate CRS risk, R- or obinutuzumab (G)-CHOP was given in Cycle (C)1, with the aim of tumor debulking. Glofitamab was given from C2 onwards. For 70 μg and 1800 μg cohorts, fixed-dose glofitamab was given on C2 Day 8 and onwards. For 10 mg and 30 mg cohorts, step-up dosing was used to further mitigate CRS risk (2.5 mg on day 8 of dosing cycle 2, 10 mg on day 15 of dosing cycle 2, and target dose on day 8 of dosing cycle 3 and onwards). Optional glofitamab maintenance was permitted (every 2 months for <2 years; dose-escalation phase only).

R Rituximab; 375 mg/m$^2$; IV D1 for Cycle 1 and/or subsequent dosing cycles during induction Chop:

- Cyclophosphamide 750 mg/m$^2$; IV on day 1
- Doxorubicin 50 mg/m$^2$; IV on Day 1
- Vincristine 1.4 mg/m$^2$; IV push on Day 1 with a cap of 2 mg
- Prednisone 100 mg/day orally on Days 1-5 (prednisone on Day 1 may be administered IV, with the remaining doses on Days 2-5 to be administered orally)

1 L DLBCL safety run-in: Patients (ECOG PS 0-3) received glofitamab 30 mg plus standard R-CHOP for 6-8 cycles (each 21-day). Patients received R-CHOP in C1; glofitamab step-up dosing began in C2 (2.5 mg on day 8 of cycle 2, 10 mg on day 15 of cycle 2, 30 mg day 8 of cycles and onwards).

Response rates were assessed by PET-CT (Lugano criteria; [Cheson et al. *J Clin Oncol* 2014]). CRS events were graded by ASTCT criteria [Lee et al. *Biol Blood Marrow Transplant* 2019].

Results: As of Feb. 21, 2022, a total of 55 1 L DLBCL pts (13 pts in Safety run-in cohort described above in Examples 10 and 11 and 42 pts in single-arm dose expansion phase cohort) were treated with glofitamab+R-CHOP. The observed treatment-emergent adverse events in the 53 safety-evaluable patients are summarized below in Table 21.

TABLE 21

Treatment-Emergent Adverse Events (TEAEs) Observed in 1 L DLBCL Patients Treated with Glofitamab SUD Plus R-CHOP

| TEAEs | Patients (N = 53) |
|---|---|
| Median treatment cycle of glofitamab (range) | 5 (1-7) |
| AEs | 46 (86.8%) |
| Glofitamab-related | 25 (47.2%) |
| Grade 3-5 AEs | 29 (54.7%) |
| Glofitamab-related | 9 (17.0%) |
| SAEs | 14 (26.4%) |
| Glofitamab-related | 3 (5.7%) |
| Grade 5 AEs | 2 (3.8%)[a] |
| Glofitamab-related | 0 |
| AEs leading to withdrawal from glofitamab | 1 (1.9%)[b] |
| Glofitamab-related | 0 |
| AEs leading to withdrawal from R-CHOP | 2 (3.8%)[c] |
| AEs leading to dose interruption of R-CHOP | 6 (11.3%)[d] |
| AEs leading to dose reduction of R-CHOP | 6 (11.3%) |

AE = adverse event; SAE = serious adverse event

[a]Gr5 AEs: IRR during rituximab infusion at C1D1 and Gr5 COVID-19 pneumonia (Study Day 320-340);

[b]AEs leading to withdrawal from glofitamab: Gr3 cerebrovascular accident occurred at C3D22 and recovered in 4 days

[c]AEs leading to withdrawal from R-CHOP: Gr5 IRR during rituximab infusion at C1D1 and Gr4 thrombosis on C2D1 (both occurred without glofitamab exposure);

[d]AEs leading to dose interruption of R-CHOP: glofitamab-related: Gr3 herpes zoster in 1 pt; glofitamab-unrelated neutropenia in 2 pts (Gr4 in Ipt, Gr3 in Ipt), IRR (during rituximab infusion) in 2 pts (Gr3 in 1 pt and Gr2 in 1 pt), Gr3 anemia in 1 pt, Gr5 COVID-19 pneumonia in 1 pt), Gr2 venous thrombosis in 1 pt (unrelated to glofitamab)

No patient withdrew from glofitamab+R-CHOP treatment because of a glofitamab-related AE. No Grade 5 glofitamab-related AEs were observed. Majority of AEs that led to dose interruption of R-CHOP were unrelated to glofitamab.

In particular, very low rates and levels of CRS were observed. Of the 53 safety-evaluable 1L DLBCL patients, only four (7.5%) patients experienced CRS of any Grade. Of these, three (5.7%) experienced Grade 1 CRS and one (1.9%) experienced Grade 2 CRS. All CRS occurred in dosing cycles 2 or 3 (i.e., first two cycles of glofitamab administration). More than 40 patients in the expansion cohort were treated without mandating hospitalization.

Grade 4 neutropenia was reported in 14 (26.4%) patients. No serious neutropenia was reported. Febrile neutropenia was reported in five (9.4%) patients, with four (7.5%) patients experiencing serious febrile neutropenia. Infections were reported in 13 (24.5%) patients: seven (13.2%) patients Grade 1-2; five (9.4%) patients Grade 3-4; one (1.9%) patient Grade 5 (COVID-19 pneumonia). Serious infection was reported in five (9.4%) patients. The incidence rate of Grade 4 neutropenia, febrile neutropenia, and infections appear low with glofitamab based on the preliminary data, with the caveat of shorter follow-up/less treatment exposure. Only one Grade 4 neutropenia event led to dose delay.

As of the CCOD (Feb. 21, 2022), 28 of the 1 L DLBCL patients were efficacy-evaluable. Complete metabolic response was observed in 21/28 (75%) of patients. Partial metabolic response was observed in 3/28 (10.7%) of patients. Overall response rate was 85.7%. 1/28 (3.6%) patient had stable metabolic disease, and 1/28 (3.6%) patient had progressive metabolic disease. Of the 28 patients reported in the efficacy-evaluable group, two patients (7.1%) were withdrawn from the study prior to receiving glofitamab.

Conclusion: 1 L DLBCL patients treated with glofitamab (SUD)+R-CHOP exhibited a well tolerated safety profile. In particular, of the 53 safety-evaluable patients, only 7.5% exhibited CRS of any grade. In addition, in the 28 efficacy-evaluable patients evaluated via PET/CT by the Lugano criteria, the observed CR rate was 75%.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a CD20-positive B cell proliferative disorder comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of either 16 or 30 mg of the anti-CD20/anti-CD3 bispecific antibody, wherein the anti-CD20/anti-CD3 bispecific antibody comprises:

(a) at least one antigen binding domain that specifically binds to CD20, comprising a heavy chain variable region comprising:

(i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising:

(i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and (b) at least one antigen binding domain that specifically binds to CD3, comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11;

and a light chain variable region comprising:

(i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14:

wherein (i) the first dose (C1D1) is administered on day 1 of the first dosing cycle and the second dose (C1D2) is administered on day 8 of the first dosing cycle;

(ii) the single dose of the second dosing cycle (C2D1) is administered on day 1 of the second dosing cycle; and (iii) one dosing cycle comprises 14 days or 21 days; and wherein the method further comprising administering to the subject obinutuzumab, wherein:

(iv) obinutuzumab is administered 7 days before the first dose of the anti-CD20/anti-CD3 bispecific antibody (C1D1); and (v) obinutuzumab is administered at one single dose of 1000 ma or a first and a second dose of each 1000 ma obinutuzumab.

2. The method of claim 1, wherein:

(a) the method comprises 1 to 10 additional dosing cycles (C3 to C12);

(b) the anti-CD20/anti-CD3 bispecific antibody is administered intravenously;

(c) the subject is human; and/or (d) the subject is a high-risk subject.

3. The method of claim 2, wherein the 1 to 10 additional dosing cycles (C3 to C12) each comprises a single dose (C3D1 to C12D1) of either 16 or 30 mg of the anti-CD20/anti-CD3 bispecific antibody.

4. The method of claim 3, wherein the single dose of the additional dosing cycles (C3D1 to C12D1) is administered on day 1 of the respective additional dosing cycle.

5. The method of claim 1, comprising 12 dosing cycles in total.

6. The method of claim 1, wherein the CD20-positive B cell proliferative disorder is a non-Hodgkin's lymphoma (NHL).

7. The method of claim 6, wherein the NHL is:

(a) relapsed or refractory NHL;

(b) indolent NHL (iNHL) or aggressive NHL (aNHL); and/or (c) a diffuse large B cell lymphoma (DLBCL), high grade B cell lymphoma (HGBCL), primary mediastinal large B-cell lymphoma (PMBCL), marginal zone lymphoma (MZL), mantle cell lymphoma (MCL), or follicular lymphoma (FL).

8. The method of claim 7, wherein:

(a) the DLBCL is a Richter's transformation;

(b) the DLBCL is a previously untreated DLBCL;

(c) the MCL is a relapsed or refractory (R/R) MCL;

(d) the FL is Grade 1, 2, or 3a FL;

(e) the FL is a transformed FL; or (f) the FL is an R/R FL.

9. The method of claim 7, wherein:

(a) the subject has an MCL, and the subject has received at least one prior systemic treatment regimen comprising a Bruton tyrosine kinase inhibitor (BTKi); or (b) the subject has an FL, and the subject is a high-risk subject who:

(i) has relapsed after or is refractory to at least two prior therapies;

(ii) has relapsed after or is refractory to treatment with a phosphoinositide 3-kinase (PI3K) inhibitor;

(iii) experiences progression of disease within 24 months of frontline treatment; and/or (iv) has lesions, wherein the sum of the product of the lesion diameters is ≥3,000 $mm^2$.

10. The method of claim 9, wherein the BTKi comprises ibrutinib, acalabrutinib, or zanubrutinib.

11. The method of claim 1, wherein a population of subjects having the CD20-positive B cell proliferative disorder exhibits cytokine release syndrome after being administered the anti-CD20/anti-CD3 bispecific antibody, and wherein the rate of the cytokine release syndrome of a grade of 3 or greater (as defined by the American Society for Transplantation and Cellular Therapy, 2019; ASTCT) is less than or about 5%.

12. The method of claim 1, wherein:

(a) administration of the anti-CD20/anti-CD3 bispecific antibody to a plurality of subjects having CD20-positive B cell proliferative disorder results in a complete response rate of at least about 70%;

(b) administration of the anti-CD20/anti-CD3 bispecific antibody to a plurality of subjects having MCL results in an overall response rate of at least about 80%;

(c) administration of the anti-CD20/anti-CD3 bispecific antibody to a plurality of subjects having MCL results in a complete response rate of at least about 65%;

(d) administration of the anti-CD20/anti-CD3 bispecific antibody to a plurality of subjects having FL results in an overall response rate of at least about 80%; and/or (e) administration of the anti-CD20/anti-CD3 bispecific antibody to a plurality of subjects having FL results in a complete metabolic response rate of at least about 40%.

13. The method of claim 1, wherein the first and second dose of obinutuzumab are administered on the same day.

14. The method of claim 1, wherein the subject has an MCL and has received at least two prior systemic therapies.

15. The method of claim 1, wherein obinutuzumab is administered on the first day of the second dosing cycle (C2) and on the first day of any subsequent dosing cycle.

16. The method of claim 15, wherein obinutuzumab is administered at a dose of 1000 mg.

17. The method of claim 1, wherein the subject receives corticosteroid premedication prior to the anti-CD20/anti-CD3 bispecific antibody.

18. The method of claim 17, wherein the corticosteroid premedication comprises prednisolone and methylprednisolone, and/or dexamethasone; and/or the corticosteroid premedication is given prior to the first dose (C1D1) of the anti-CD20/anti-CD3 bispecific antibody.

19. The method of claim 1, wherein the anti-CD20/anti-CD3 bispecific antibody comprises:

(a) at least one antigen binding domain that specifically binds to CD20 comprising a VH domain comprising an amino acid sequence of SEQ ID NO: 7 and a VL domain comprising an amino acid sequence of SEQ ID NO: 8; and (b) at least one antigen binding domain that specifically binds to CD3 comprising a VH domain comprising an amino acid sequence of SEQ ID NO: 15 and a VL domain comprising an amino acid sequence of SEQ ID NO: 16.

20. The method of claim 1, wherein the anti-CD20/anti-CD3 bispecific antibody comprises:

(a) an antigen binding domain that specifically binds to CD3 and is a cross-Fab molecule wherein the variable domains or the constant domains of the Fab heavy and light chain are exchanged;

(b) an IgG1 Fc domain comprising one or more amino acid substitutions that reduce binding to an Fc receptor and/or effector function;

(c) an IgG1 Fc domain comprising the amino acid substitutions L234A, L235A, and P329G (numbering according to Kabat EU index);

(d) at least one Fab molecule comprising an antigen binding domain that specifically binds to CD20, wherein in the constant domain CL of the Fab molecule the amino acid at position 124 is substituted by lysine (K) (numbering according to Kabat) and the amino acid at position 123 is substituted by arginine (R) or lysine (K) (numbering according to Kabat), and wherein in the constant domain CH1 of the Fab molecule the amino acid at position 147 is substituted by glutamic acid (E) (numbering according to Kabat EU index) and the amino acid at position 213 is substituted by glutamic acid (E) (numbering according to Kabat EU index); and/or (e) two antigen binding domains that specifically bind to CD20 and one antigen binding domain that specifically binds to CD3.

21. The method of claim 1, wherein:

(a) the anti-CD20/anti-CD3 bispecific antibody is bivalent for CD20 and monovalent for CD3;

(b) the anti-CD20/anti-CD3 bispecific antibody comprises (i) an antigen binding domain that specifically binds to CD3 which is fused at the C-terminus of the Fab heavy chain to the N-terminus of the first subunit of the Fc domain;

(ii) a first antigen binding domain that specifically binds to CD20 which is fused at the C-terminus of the Fab heavy chain to the N-terminus of the Fab heavy chain of the antigen binding domain that specifically binds to CD3; and (iii) a second antigen binding domain that specifically binds to CD20 which is fused at the C-terminus of the Fab heavy chain to the N-terminus of the second subunit of the Fc domain; and/or (c) the anti-CD20/anti-CD3 bispecific antibody is glofitamab.

22. A method of treating a subject having a non-Hodgkin lymphoma comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of 30 mg of the anti-CD20/anti-CD3 bispecific antibody, wherein the anti-CD20/anti-CD3 bispecific antibody comprises:

(a) at least one antigen binding domain that specifically binds to CD20, comprising a heavy chain variable region comprising:

(i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising:

(i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and (b) at least one antigen binding domain that specifically binds to CD3, comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11;

and a light chain variable region comprising:

(i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14; and wherein (i) the first dose (C1D1) is administered on day 1 of the first dosing cycle and the second dose (C1D2) is administered on day 8 of the first dosing cycle;

(ii) the single dose of the second dosing cycle (C2D1) is administered on day 1 of the second dosing cycle; and (iii) one dosing cycle comprises 14 days or 21 days; and wherein the method further comprising administering to the subject obinutuzumab, wherein:

(iv) obinutuzumab is administered 7 days before the first dose of the anti-CD20/anti-CD3 bispecific antibody (C1D1); and (v) obinutuzumab is administered at one single dose of 1000 mg or a first and a second dose of each 1000 mg obinutuzumab.

23. A method of treating a subject having a diffuse large B cell lymphoma comprising administering to the subject an anti-CD20/anti-CD3 bispecific antibody in a dosing regimen comprising at least a first dosing cycle and a second dosing cycle, wherein: (a) the first dosing cycle comprises a first dose (C1D1) and a second dose (C1D2) of the anti-CD20/anti-CD3 bispecific antibody, wherein the C1D1 is 2.5 mg, and the C1D2 is 10 mg; and (b) the second dosing cycle comprises a single dose (C2D1) of 30 mg of the anti-CD20/anti-CD3 bispecific antibody, wherein the anti-CD20/anti-CD3 bispecific antibody comprises:

(a) a first antigen binding domain that specifically binds to CD20, comprising a heavy chain variable region comprising:

(i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising:

(i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6;

(b) second antigen binding domain that specifically binds to CD3, comprising a heavy chain variable region comprising:

(i) an HVR-H1 comprising the amino acid sequence of SEQ ID NO: 9;

(ii) an HVR-H2 comprising the amino acid sequence of SEQ ID NO: 10; and (iii) an HVR-H3 comprising the amino acid sequence of SEQ ID NO:11;

and a light chain variable region comprising:

(i) an HVR-L1 comprising the amino acid sequence of SEQ ID NO: 12;

(ii) an HVR-L2 comprising the amino acid sequence of SEQ ID NO: 13; and (iii) an HVR-L3 comprising the amino acid sequence of SEQ ID NO: 14; and (c) a third antigen binding domain that specifically binds to CD20, comprising a heavy chain variable region comprising:

(i) an HVR-H1 comprising the amino acid sequence of SEQ ID NO: 1;

(ii) an HVR-H2 comprising the amino acid sequence of SEQ ID NO: 2; and (iii) an HVR-H3 comprising the amino acid sequence of SEQ ID NO:3;

and a light chain variable region comprising:

(i) an HVR-L1 comprising the amino acid sequence of SEQ ID NO: 4;

(ii) an HVR-L2 comprising the amino acid sequence of SEQ ID NO: 5; and (iii) an HVR-L3 comprising the amino acid sequence of SEQ ID NO: 6; and wherein (i) the first dose (C1D1) is administered on day 1 of the first dosing cycle and the second dose (C1D2) is administered on day 8 of the first dosing cycle;

(ii) the single dose of the second dosing cycle (C2D1) is administered on day 1 of the second dosing cycle; and (iii) one dosing cycle comprises 14 days or 21 days; and wherein the method further comprising administering to the subject obinutuzumab, wherein obinutuzumab is administered 7 days before the first dose of the anti-CD20/anti-CD3 bispecific antibody (C1D1); and obinutuzumab is administered at one single dose of 1000 mg.

24. A method of treating a subject having a diffuse large B cell lymphoma comprising administering to the subject glofitamab in a dosing regimen comprising at least a first dosing cycle and a second dosing cycle, wherein: (a) the first dosing cycle comprises a first dose (C1D1) and a second dose (C1D2) of glofitamab, wherein the C1D1 is 2.5 mg, and the C1D2 is 10 mg; and (b) the second dosing cycle comprises a single dose (C2D1) of 30 mg of glofitamab; wherein (a) the first dose (C1D1) is administered on day 1 of the first dosing cycle and the second dose (C1D2) is administered on day 8 of the first dosing cycle;

(b) the single dose of the second dosing cycle (C2D1) is administered on day 1 of the second dosing cycle;

(c) the method comprises 10 additional dosing cycles (C3 to C12), wherein the 10 additional dosing cycles (C3 to C12) each comprises a single dose (C3D1 to C12D1) of 30 mg of glofitamab, and wherein the single dose of the additional dosing cycles (C3D1 to C12D1) is administered on day 1 of the respective additional dosing cycle;

(d) one dosing cycle comprises 14 days or 21 days; and (e) glofitamab is administered intravenously; and wherein the method further comprising administering to the subject obinutuzumab, wherein obinutuzumab is administered 7 days before the first dose of glofitamab (C1D1); and obinutuzumab is administered at one single dose of 1000 mg.

* * * * *

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Tyr Ser Trp Ile Asn
1               5


<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Arg Ile Phe Pro Gly Asp Gly Asp Thr Asp Tyr Asn Gly Lys Phe Lys
1               5                   10                  15

Gly
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asn Val Phe Asp Gly Tyr Trp Leu Val Tyr
1               5                   10


<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Arg Ser Ser Lys Ser Leu Leu His Ser Asn Gly Ile Thr Tyr Leu Tyr
1               5                   10                  15


<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gln Met Ser Asn Leu Val Ser
1               5


<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ala Gln Asn Leu Glu Leu Pro Tyr Thr
1               5


<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asn Val Phe Asp Gly Tyr Trp Leu Val Tyr Trp Gly Gln Gly
100 105 110

Thr Leu Val Thr Val Ser Ser
115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Thr Gln Thr Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Val Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ala Gln Asn
85 90 95

Leu Glu Leu Pro Tyr Thr Phe Gly Gly Gly Thr Lys Val Glu Ile Lys
100 105 110

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Thr Tyr Ala Met Asn
1 5

<210> SEQ ID NO 10
<211> LENGTH: 19
<212> TYPE: PRT
<213> ORGANISM: Artificial Sequence
<220> FEATURE:
<223> OTHER INFORMATION: Synthetic Construct

<400> SEQUENCE: 10

Arg Ile Arg Ser Lys Tyr Asn Asn Tyr Ala Thr Tyr Tyr Ala Asp Ser
1 5 10 15

Val Lys Gly

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

His Gly Asn Phe Gly Asn Ser Tyr Val Ser Trp Phe Ala Tyr
1 5 10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

```
Gly Ser Ser Thr Gly Ala Val Thr Thr Ser Asn Tyr Ala Asn
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

```
Gly Thr Asn Lys Arg Ala Pro
1               5
```

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

```
Ala Leu Trp Tyr Ser Asn Leu Trp Val
1               5
```

<210> SEQ ID NO 15
<211> LENGTH: 127
<212> TYPE: PRT
<213> ORGANISM: Artificial Sequence
<220> FEATURE:
<223> OTHER INFORMATION: Synthetic Construct

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser
        115                 120                 125
```

<210> SEQ ID NO 16
<211> LENGTH: 111
<212> TYPE: PRT
<213> ORGANISM: Artificial Sequence
<220> FEATURE:
<223> OTHER INFORMATION: Synthetic Construct

<400> SEQUENCE: 16

Gln Ala Val Val Thr Gln Glu Pro Ser Leu Thr Val Ser Pro Gly Gly
1 5 10 15

Thr Val Thr Leu Thr Cys Gly Ser Ser Thr Gly Ala Val Thr Thr Ser
20 25 30

Asn Tyr Ala Asn Trp Val Gln Glu Lys Pro Gly Gln Ala Phe Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu Ser Ser
100 105 110

<210> SEQ ID NO 17
<211> LENGTH: 672
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Ser Tyr Ser
20 25 30

Trp Ile Asn Trp Val Arg Gln Ala Pro Gly Gln Gly Leu Glu Trp Met
35 40 45

Gly Arg Ile Phe Pro Gly Asp Gly Asp Thr Asp Tyr Asn Gly Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asn Val Phe Asp Gly Tyr Trp Leu Val Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Glu Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Glu Lys Val Glu Pro Lys Ser Cys Asp Gly
210 215 220

Gly Gly Gly Ser Gly Gly Gly Gly Ser Gln Ala Val Val Thr Gln Glu
225 230 235 240

```
Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
    370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
```

660 665 670

<210> SEQ ID NO 18
<211> LENGTH: 447
<212> TYPE: PRT
<213> ORGANISM: Artificial Sequence
<220> FEATURE:
<223> OTHER INFORMATION: Synthetic Construct

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
```

```
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 19
<211> LENGTH: 232
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 20
<211> LENGTH: 219
<212> TYPE: PRT
<213> ORGANISM: Artificial Sequence
<220> FEATURE:
<223> OTHER INFORMATION: Synthetic Construct
```

```
<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Gly Gly Gly Gly Ser
1               5


<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Ser Gly Gly Gly Gly
1               5


<210> SEQ ID NO 23
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 23

Gly Gly Gly Gly Ser Gly Gly Gly Gly
1 5

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Gly Gly Gly Gly Ser Gly Gly Gly Gly Ser
1 5 10

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Asp Gly Gly Gly Gly Ser Gly Gly Gly Gly Ser
1 5 10

<210> SEQ ID NO 26
<211> LENGTH: 20
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser Gly Gly Gly Gly Ser Gly Gly Gly Gly Ser Gly
1 5 10 15

Gly Gly Gly Ser
20

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Gly Gly Gly Ser Gly Gly Gly Ser Gly Gly Gly Ser
1 5 10

<210> SEQ ID NO 28
<211> LENGTH: 16
<212> TYPE: PRT
<213> ORGANISM: Artificial Sequence
<220> FEATURE:
<223> OTHER INFORMATION: Synthetic Construct

<400> SEQUENCE: 28

Gly Gly Gly Ser Gly Gly Gly Ser Gly Gly Gly Ser Gly Gly Gly Ser
1 5 10 15

<210> SEQ ID NO 29
<211> LENGTH: 20
<212> TYPE: PRT
<213> ORGANISM: Artificial Sequence
<220> FEATURE:

```
<223> OTHER INFORMATION: Synthetic Construct

<400> SEQUENCE: 29

Gly Gly Gly Ser Gly Gly Gly Ser Gly Gly Gly Ser Gly Gly Gly Ser
1               5                   10                  15

Gly Gly Gly Ser
            20


<210> SEQ ID NO 30
<211> LENGTH: 24
<212> TYPE: PRT
<213> ORGANISM: Artificial Sequence
<220> FEATURE:
<223> OTHER INFORMATION: Synthetic Construct

<400> SEQUENCE: 30

Gly Gly Gly Ser Gly Gly Gly Ser Gly Gly Gly Ser Gly Gly Gly Ser
1               5                   10                  15

Gly Gly Gly Ser Gly Gly Gly Ser
            20


<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Gly Gly Gly Gly Ser Gly Gly Gly Gly Ser
1               5                   10


<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Gly Gly Gly Gly Ser Gly Gly Gly Gly Ser Gly Gly Gly Gly Ser
1               5                   10                  15


<210> SEQ ID NO 33
<211> LENGTH: 20
<212> TYPE: PRT
<213> ORGANISM: Artificial Sequence
<220> FEATURE:
<223> OTHER INFORMATION: Synthetic Construct

<400> SEQUENCE: 33

Gly Gly Gly Gly Ser Gly Gly Gly Gly Ser Gly Gly Gly Gly Ser Gly
1               5                   10                  15

Gly Gly Gly Ser
            20


<210> SEQ ID NO 34
<211> LENGTH: 25
<212> TYPE: PRT
<213> ORGANISM: Artificial Sequence
<220> FEATURE:
<223> OTHER INFORMATION: Synthetic Construct

<400> SEQUENCE: 34

Gly Gly Gly Gly Ser Gly Gly Gly Gly Ser Gly Gly Gly Gly Ser Gly
```

```
1               5                   10                  15

Gly Gly Gly Ser Gly Gly Gly Gly Ser
            20                  25


<210> SEQ ID NO 35
<211> LENGTH: 13
<212> TYPE: PRT
<213> ORGANISM: Artificial Sequence
<220> FEATURE:
<223> OTHER INFORMATION: Synthetic Construct

<400> SEQUENCE: 35

Gly Gly Gly Ser Gly Gly Gly Ser Gly Gly Gly Ser Gly
1               5                   10


<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Gly Gly Gly Ser Gly Gly Gly Ser Gly Gly Gly Ser Gly Gly Gly Ser
1               5                   10                  15

Gly


<210> SEQ ID NO 37
<211> LENGTH: 21
<212> TYPE: PRT
<213> ORGANISM: Artificial Sequence
<220> FEATURE:
<223> OTHER INFORMATION: Synthetic Construct

<400> SEQUENCE: 37

Gly Gly Gly Ser Gly Gly Gly Ser Gly Gly Gly Ser Gly Gly Gly Ser
1               5                   10                  15

Gly Gly Gly Ser Gly
            20


<210> SEQ ID NO 38
<211> LENGTH: 25
<212> TYPE: PRT
<213> ORGANISM: Artificial Sequence
<220> FEATURE:
<223> OTHER INFORMATION: Synthetic Construct

<400> SEQUENCE: 38

Gly Gly Gly Ser Gly Gly Gly Ser Gly Gly Gly Ser Gly Gly Gly Ser
1               5                   10                  15

Gly Gly Gly Ser Gly Gly Gly Ser Gly
            20                  25


<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Gly Gly Gly Gly Ser Gly Gly Gly Gly Ser Gly
1               5                   10
```

```
<210> SEQ ID NO 40
<211> LENGTH: 16
<212> TYPE: PRT
<213> ORGANISM: Artificial Sequence
<220> FEATURE:
<223> OTHER INFORMATION: Synthetic Construct

<400> SEQUENCE: 40

Gly Gly Gly Gly Ser Gly Gly Gly Gly Ser Gly Gly Gly Gly Ser Gly
1               5                   10                  15


<210> SEQ ID NO 41
<211> LENGTH: 21
<212> TYPE: PRT
<213> ORGANISM: Artificial Sequence
<220> FEATURE:
<223> OTHER INFORMATION: Synthetic Construct

<400> SEQUENCE: 41

Gly Gly Gly Gly Ser Gly Gly Gly Gly Ser Gly Gly Gly Gly Ser Gly
1               5                   10                  15

Gly Gly Gly Ser Gly
            20


<210> SEQ ID NO 42
<211> LENGTH: 26
<212> TYPE: PRT
<213> ORGANISM: Artificial Sequence
<220> FEATURE:
<223> OTHER INFORMATION: Synthetic Construct

<400> SEQUENCE: 42

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25


<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Gly Gly Ser Gly Gly Gly Ser Gly Gly Gly Ser Gly Gly
1               5                   10


<210> SEQ ID NO 44
<211> LENGTH: 18
<212> TYPE: PRT
<213> ORGANISM: Artificial Sequence
<220> FEATURE:
<223> OTHER INFORMATION: Synthetic Construct

<400> SEQUENCE: 44

Gly Gly Gly Ser Gly Gly Gly Ser Gly Gly Gly Ser Gly Gly Gly Ser
1               5                   10                  15

Gly Gly


<210> SEQ ID NO 45
<211> LENGTH: 22
<212> TYPE: PRT
<213> ORGANISM: Artificial Sequence
<220> FEATURE:
<223> OTHER INFORMATION: Synthetic Construct
```

<400> SEQUENCE: 45

```
Gly Gly Gly Ser Gly Gly Gly Ser Gly Gly Gly Ser Gly Gly Gly Ser
1               5                   10                  15

Gly Gly Gly Ser Gly Gly
            20
```

<210> SEQ ID NO 46
<211> LENGTH: 26
<212> TYPE: PRT
<213> ORGANISM: Artificial Sequence
<220> FEATURE:
<223> OTHER INFORMATION: Synthetic Construct

<400> SEQUENCE: 46

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly
            20                  25
```

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

```
Gly Gly Gly Gly Ser Gly Gly Gly Gly Ser Gly Gly
1               5                   10
```

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

```
Gly Gly Gly Gly Ser Gly Gly Gly Gly Ser Gly Gly Gly Gly Ser Gly
1               5                   10                  15

Gly
```

<210> SEQ ID NO 49
<211> LENGTH: 22
<212> TYPE: PRT
<213> ORGANISM: Artificial Sequence
<220> FEATURE:
<223> OTHER INFORMATION: Synthetic Construct

<400> SEQUENCE: 49

```
Gly Gly Gly Gly Ser Gly Gly Gly Gly Ser Gly Gly Gly Gly Ser Gly
1               5                   10                  15

Gly Gly Gly Ser Gly Gly
            20
```

<210> SEQ ID NO 50
<211> LENGTH: 27
<212> TYPE: PRT
<213> ORGANISM: Artificial Sequence
<220> FEATURE:
<223> OTHER INFORMATION: Synthetic Construct

<400> SEQUENCE: 50

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly
20 25

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Gly Gly Gly Ser Gly Gly Gly Ser Gly Gly Gly Ser Gly Gly Gly
1 5 10 15

<210> SEQ ID NO 52
<211> LENGTH: 19
<212> TYPE: PRT
<213> ORGANISM: Artificial Sequence
<220> FEATURE:
<223> OTHER INFORMATION: Synthetic Construct

<400> SEQUENCE: 52

Gly Gly Gly Ser Gly Gly Gly Ser Gly Gly Gly Ser Gly Gly Gly Ser
1 5 10 15

Gly Gly Gly

<210> SEQ ID NO 53
<211> LENGTH: 23
<212> TYPE: PRT
<213> ORGANISM: Artificial Sequence
<220> FEATURE:
<223> OTHER INFORMATION: Synthetic Construct

<400> SEQUENCE: 53

Gly Gly Gly Ser Gly Gly Gly Ser Gly Gly Gly Ser Gly Gly Gly Ser
1 5 10 15

Gly Gly Gly Ser Gly Gly Gly
20

<210> SEQ ID NO 54
<211> LENGTH: 27
<212> TYPE: PRT
<213> ORGANISM: Artificial Sequence
<220> FEATURE:
<223> OTHER INFORMATION: Synthetic Construct

<400> SEQUENCE: 54

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly
20 25

<210> SEQ ID NO 55
<211> LENGTH: 13
<212> TYPE: PRT
<213> ORGANISM: Artificial Sequence
<220> FEATURE:
<223> OTHER INFORMATION: Synthetic Construct

<400> SEQUENCE: 55

Gly Gly Gly Gly Ser Gly Gly Gly Gly Ser Gly Gly Gly
1 5 10

-continued

```
<210> SEQ ID NO 56
<211> LENGTH: 18
<212> TYPE: PRT
<213> ORGANISM: Artificial Sequence
<220> FEATURE:
<223> OTHER INFORMATION: Synthetic Construct

<400> SEQUENCE: 56

Gly Gly Gly Gly Ser Gly Gly Gly Gly Ser Gly Gly Gly Gly Ser Gly
1               5                   10                  15

Gly Gly


<210> SEQ ID NO 57
<211> LENGTH: 23
<212> TYPE: PRT
<213> ORGANISM: Artificial Sequence
<220> FEATURE:
<223> OTHER INFORMATION: Synthetic Construct

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly
            20


<210> SEQ ID NO 58
<211> LENGTH: 28
<212> TYPE: PRT
<213> ORGANISM: Artificial Sequence
<220> FEATURE:
<223> OTHER INFORMATION: Synthetic Construct

<400> SEQUENCE: 58

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly
            20                  25
```